(12) United States Patent
Jiang et al.

(10) Patent No.: US 11,827,664 B2
(45) Date of Patent: Nov. 28, 2023

(54) BIARYL AMIDES WITH MODIFIED SUGAR GROUPS FOR TREATMENT OF DISEASES ASSOCIATED WITH HEAT SHOCK PROTEIN PATHWAY

(71) Applicant: REATA PHARMACEUTICALS, INC., Irving, TX (US)

(72) Inventors: Xin Jiang, Coppell, TX (US); Melean Visnick, Irving, TX (US); Christopher F. Bender, Garland, TX (US); Gary Bolton, Ann Arbor, MI (US); Bradley Caprathe, Livonia, MI (US); Chitase Lee, Ann Arbor, MI (US)

(73) Assignee: REATA PHARMACEUTICALS, INC, Irving, TX (US)

( * ) Notice: Subject to any disclaimer, the term of this patent is extended or adjusted under 35 U.S.C. 154(b) by 0 days.

(21) Appl. No.: 17/055,331

(22) PCT Filed: May 14, 2019

(86) PCT No.: PCT/US2019/032292
§ 371 (c)(1),
(2) Date: Nov. 13, 2020

(87) PCT Pub. No.: WO2019/222269
PCT Pub. Date: Nov. 21, 2019

(65) Prior Publication Data
US 2021/0261592 A1 Aug. 26, 2021

Related U.S. Application Data

(60) Provisional application No. 62/671,047, filed on May 14, 2018.

(51) Int. Cl.
*C07H 15/203* (2006.01)
*A61P 25/02* (2006.01)
*C07H 1/00* (2006.01)

(52) U.S. Cl.
CPC ............ *C07H 15/203* (2013.01); *A61P 25/02* (2018.01); *C07H 1/00* (2013.01)

(58) Field of Classification Search
CPC .............................. C07H 15/203; C07H 15/22
See application file for complete search history.

(56) References Cited

U.S. PATENT DOCUMENTS

| | | | |
|---|---|---|---|
| 5,382,572 | A | 1/1995 | Alfonso et al. |
| 6,579,902 | B1 | 6/2003 | Demassy et al. |

(Continued)

FOREIGN PATENT DOCUMENTS

| | | |
|---|---|---|
| WO | WO 2006/050501 | 5/2006 |
| WO | WO 2007/025943 | 3/2007 |

(Continued)

OTHER PUBLICATIONS

Ferroud, D. et al., Bioorganic & Medicinal Chemistry Letters, "Synthesis and Biological Evaluation of Coumarin Carboxylic Acids as Inhibitors of Gyrase B. L-rhamnose as an effective substitute for L-novobiose", 1999, vol. 9, pp. 2881-2886 (Year: 1999).*

(Continued)

*Primary Examiner* — Bahar Craigo
(74) *Attorney, Agent, or Firm* — Parker Highlander PLLC

(57) ABSTRACT

Provided are biaryl amides and coumarin-based compounds with modified sugar groups for treatment of diseases associated with heat shock protein pathway. The compounds having the following formulas, wherein variables are as defined herein. Formulae (I), (II), (III), (IV), and (V), Pharmaceutical compositions of the compounds are also provided. These biaryl amides and coumarin-based derivatives with modified sugar groups are useful for treatment and prevention of diseases and disorders, including neurological disorders, such as neurodegenerative diseases and nerve damaging disorders, for example, diabetic peripheral neuropathy.

(I)

(II)

(III)

(Continued)

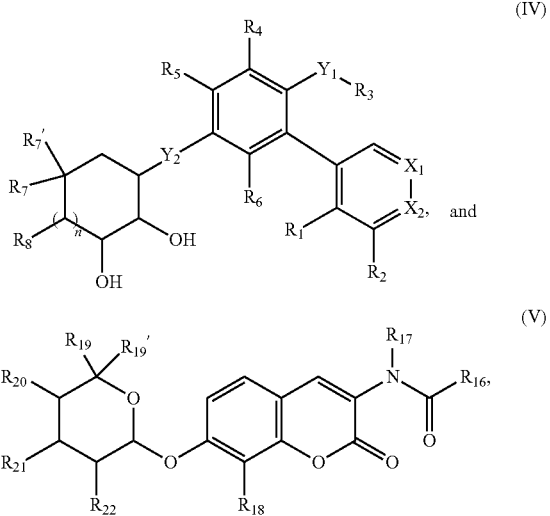

17 Claims, 2 Drawing Sheets

Specification includes a Sequence Listing.

(56) References Cited

U.S. PATENT DOCUMENTS

| | | | |
|---|---|---|---|
| 7,208,630 B2 | 4/2007 | Blagg et al. |
| 7,608,594 B2 | 10/2009 | Blagg et al. |
| 7,622,451 B2 | 11/2009 | Blagg et al. |
| 7,811,998 B2 | 10/2010 | Blagg et al. |
| 7,960,353 B2 | 6/2011 | Blagg |
| 8,212,011 B2 | 7/2012 | Blagg |
| 8,212,012 B2 | 7/2012 | Blagg |
| 9,056,104 B2 | 6/2015 | Blagg et al. |
| 9,120,774 B2 | 9/2015 | Blagg et al. |
| 9,422,320 B2 | 8/2016 | Blagg et al. |
| 9,994,556 B2 | 6/2018 | Zhao et al. |
| 10,030,006 B2 | 7/2018 | Blagg et al. |
| 10,030,041 B2 | 7/2018 | Blagg et al. |
| 10,590,065 B2 | 3/2020 | Blagg et al. |
| 10,590,157 B2 | 3/2020 | Blagg et al. |
| 10,689,344 B2 | 6/2020 | Blagg et al. |
| 10,745,386 B2 | 8/2020 | Blagg et al. |
| 2004/0063170 A1 | 4/2004 | Fujikura et al. |
| 2006/0199776 A1 | 9/2006 | Blagg et al. |
| 2007/0270452 A1 | 11/2007 | Blagg et al. |
| 2008/0146547 A1 | 6/2008 | Araldi et al. |
| 2009/0163709 A1 | 6/2009 | Blagg |
| 2009/0187014 A1 | 7/2009 | Blagg |
| 2010/0022635 A1 | 1/2010 | Rajewski |
| 2010/0048882 A1 | 2/2010 | Blagg et al. |
| 2010/0105630 A1 | 4/2010 | Blagg |
| 2011/0082098 A1 | 4/2011 | Calvet et al. |
| 2012/0252745 A1 | 10/2012 | Blagg et al. |
| 2012/0309702 A1 | 12/2012 | Blagg et al. |
| 2013/0116227 A1 | 5/2013 | Katayama et al. |
| 2015/0057240 A1 | 2/2015 | Blagg et al. |
| 2016/0272584 A1 | 9/2016 | Blagg et al. |
| 2016/0289217 A1 | 10/2016 | Blagg et al. |
| 2017/0051000 A1 | 2/2017 | Blagg et al. |
| 2017/0253582 A1 | 9/2017 | Zhao et al. |
| 2018/0057446 A1 | 3/2018 | Blagg et al. |
| 2019/0023730 A1 | 1/2019 | Blagg et al. |

FOREIGN PATENT DOCUMENTS

| | | |
|---|---|---|
| WO | WO 2008/115719 | 9/2008 |
| WO | WO 2010/096650 | 8/2010 |
| WO | WO 2011/041593 | 4/2011 |
| WO | WO 2012/138896 | 10/2012 |
| WO | WO 2012/162054 | 11/2012 |
| WO | WO 2013/119985 | 8/2013 |
| WO | WO 2015/070091 | 5/2015 |
| WO | WO 2015/070238 | 5/2015 |
| WO | WO 2015/192099 | 12/2015 |
| WO | WO 2015/200514 | 12/2015 |

OTHER PUBLICATIONS

Albermann, Christoph et al. "Substrate specificity of NovM: implications for novobiocin biosynthesis and glycorandomization." *Organic letters* 5.6 (2003): 933-936.
Alzheimer's disease, PubMed Health, Nov. 17, 2010.
Ansar et al., "A non-toxic Hsp90 inhibitor protects neurons from Aβeta-induced toxicity," *Bioorg Med Chem Lett*, 17(7):1984-90, 2007.
Anyika et al., "Development of Noviomimetics as C-Terminal Hsp90 Inhibitors", *ACS Medicinal Chemistry Letters*, 7: 67-71, 2016.
Avila et al., "High-throughput screening for Hsp90 ATPase inhibitors," *Bioorg Med. Chem. Lett.*, 16(11):3005-08, 2006.
Bosseray et al., "What's new in vaccines against herpes simplex infections?", *Pathol. Biol.*, 50(8):483-492, 2002.
Burlison and Blagg, "Synthesis and Evaluation of Coumermycin A1 Analogues that Inhibit the Hsp90 Protein Folding Machinery," *J. Org. Chem.*, 8:4855, 2006.
Burlison et al., "Development of Novobiocin Analogues That Manifest Anti-proliferative Activity against Several Cancer Cell Lines," *J. Org. Chem.*, 73:2130, 2008.
Burlison et al., "Novobiocin: Redesigning a DNA Gyrase Inhibitor for Selective Inhibition of Hsp90," *J. Am. Chem. Soc.*, 128:15529, 2006.
Calkins et al., "The Nrf2/ARE Pathway as a Potential Therapeutic Target in Neurodegenerative Disease," *Antioxid. Redox Signal.*, 11(3):497-508, 2009.
Cohen et al., "Novel C-Terminal Hsp90 Inhibitor for Head and Neck Squamous Cell Cancer (HNSCC) with in vivo Efficacy and Improved Toxicity Profiles Compared with Standard Agents," *Ann. Surg. Oncol.*, 19(Suppl. 3):S483, 2012.
Comer et al., "Characterization of a novel novobiocin analogue as a putative C-terminal inhibitor of heat shock protein 90 in prostate cancer cells," *Prostate*, 70(1):27-36, 2010.
Damasio, "Alzheimer's Disease and related dementias", In: Cecil Textbook of Medicine, 20th Edition, 2:1992-1996, 1996.
Donnelly and Blagg, "Novobiocin and additional inhibitors of the Hsp90 C-terminal nucleotide-binding pocket," *Curr. Med. Chem.*, 15(26):2702-17, 2008.
Donnelly et al., "Cytotoxic sugar analogues of an optimized novobiocin scaffold," *MedChemComm*, 1(2):165-170, 2010.
Donnelly et al., "The Design, Synthesis, and Evaluation of Coumarin Ring Derivatives of the Novobiocin Scaffold that Exhibit Antiproliferative Activity," *J. Org. Chem.*, 73:8901, 2008.
Douglas, Jr., "Introduction to Viral Diseases", In: Cecil Textbook of Medicine, 20th Edition, 2:1739-1747, 1996.
Eikelenboom et al., "Inflammatory mechanisms in Alzheimer's disease," *Trend. Pharmacol. Sci.*, 15(12):447-450, 1994.
Farmer et al., "KU-32, a novel drug for diabetic neuropathy, is safe for human islets and improves in vitro insulin secretion and viability," *Experimental Diabetes Research*, 671-673, 2012.
Forsberg et al., "Development of noviomimetics that modulate molecular chaperones and manifest neuroprotective effects", *Eur. J. Med. Chem.*, 143:1428-1435, 2018.
Forsberg et al., "Modified biphenyl Hsp90 C-terminal inhibitors for the treatment of cancer," *Bioorg. Med. Chem. Lett.*, Article in Press, 2017.

(56) References Cited

OTHER PUBLICATIONS

Goff, "Intracellular trafficking of retroviral genomes during the early phase of infection: viral exploitation of cellular pathways", *J. Gene Med.*, 3(6):517-528), 2001.
Gura et al., "Systems for identifying new drugs are often faulty", *Science*, 278:1041-1042, 1997.
Hadden et al., "Synthesis and evaluation of Hsp90 inhibitors that contain the 1,4-naphthoquinone scaffold," *Bioorg Med Chem.*, 17(2):634-40, 2009.
Huang and Blagg, "A library of noviosylated coumarin analogues," *J. Org. Chem.*, 72(10):3609-3613, 2007.
Huang et al., "Molecular Design of Anticancer Drug Leads Based on Three-Dimensional Quantitative Structure-Activity Relationship," *J. Chem. Info. Modeling*, 51(8):1999-2006, 2011.
International Preliminary Report on Patentability issued in International Application No. PCT/US2013/025387, dated Aug. 12, 2014.
International Preliminary Report on Patentability issued in International Application No. PCT/US2019/032292, dated Nov. 26, 2020.
International Search Report and Written Opinion issued in International Application No. PCT/US2013/025387, dated Apr. 2, 2013.
International Search Report and Written Opinion issued in International Application No. PCT/US2019/032292, dated Oct. 17, 2019.
International Search Report for PCT Application No. PCT/US2015/037478, dated Jan. 14, 2016.
Johnson et al., "Relationships between dmg activity in NCI preclinical in vitro and in vivo models and early clinical trials", *Br. J. Cancer*, 84(10):1424-1431, 2001.
Kusuma et al., "Synthesis and Evaluation of Novologues as C-Terminal Hsp90 Inhibitors with Cytoprotective Activity against Sensory Neuron Glucotoxicity," *J. Med. Chem.*, 55:5797, 2012.
Kusuma et al., "Targeting the Heat Shock Protein 90 Dimer with Dimeric Inhibitors", *Journal of Medicinal Chemistry*,54(18):6234-6253, 2011.
Layzer, "Degenerative diseases of the nervous system", Cecil Textbook of Medicine, 20th Edition, vol. 2, pp. 2050-2057, 1996.
Lu et al., "Neuroprotective activity and evaluation of Hsp90 inhibitors in an immortalized neuronal cell line," *Bioorg. Med. Chem.*, 17(4):1709-15, 2009.
Ma et al., "Heat Shock Protein 70 Is Necessary to Improve Mitochondrial Bioenergetics and Reverse Diabetic Sensory Neuropathy following KU-32 Therapy," *J. Pharmacol. Exp. Ther.*, 348:281-292, 2014.
Ma et al., "Modulating Molecular Chaperones Improves Mitochondrial Bioenergetics and Decreases the Inflammatory Transcriptome in Diabetic Sensory Neurons," *ACS Chem. Neurosci.*, 6(9):1637-1648, 2015.
Marcu et al., "Novobiocin and related coumarins and depletion of heat shock protein 90-dependent signaling proteins," *J. Natl. Cancer Inst.*, 92:242-248, 2000.
Matts et al., "Elucidation of the Hsp90 C-Terminal Inhibitor Binding Site", *ACS Chem Biol.*, 6(8):800-807, 2011.
Mayer et al., "Hsp70 chaperones: cellular functions and molecular mechanism", *Cell Mol Life Sci.*, 62 (6): 670-84, 2005.
Mays et al., "The synthesis and evaluation of flavone and isoflavone chimeras of novobiocin and derrubone," *Bioorg Med. Chem.*, 18(1):249-66, 2010.
Moroni et al., "Exploiting Conformational Dynamics in Dmg Discovery: Design of C-Terminal Inhibitors of Hsp90 with Improved Activities," *J. Chem. Info. Modeling*, 54(1):195-208, 2014.
Office Communication issued in Chinese Application No. 201580033560.X, dated Aug. 3, 2018.
Office Communication issued in corresponding Chilean Application No. 201802367, dated Sep. 5, 2019.
Office Communication issued in corresponding Chinese Application No. 201380019057.X, dated Jul. 24, 2015. [English Translation].
Office Communication issued in corresponding Eurasian Application No. 201491496, dated Aug. 10, 2015. [English Translation].
Office Communication issued in corresponding European Application No. 13706822.7, dated Jun. 22, 2015.
Office Communication issued in U.S. Appl. No. 14/377,616, dated Oct. 1, 2015.
Office Communication issued in U.S. Appl. No. 14/377,616, dated Feb. 2, 2016.
Parkinson's: Overview—PubMed Health, Apr. 8, 2015.
Pearce et al., "Failure modes in anticancer drug discovery and development", In: Cancer Drug Design and Discovery, Chapter 18, pp. 424-435, 2008.
Peterson and Blagg, "Click chemistry to probe Hsp90: synthesis and evaluation of a series of triazole-containing novobiocin analogues," *Bioorg Med Chem Lett*, 20(13):3957-60, 2010.
Peterson and Blagg, "To fold or not to fold: modulation and consequences of Hsp90 inhibition", *Future Med Chem.*, 1 (2): 267-283, 2009.
Razonable et al., "Herpesvirus infections in transplant recipients: current challenges in the clinical management of cytomegalovirus and Epstein-Barr virus infections", *Herpes*, 10(3):60-65, 2003.
Roos, "Huntington's disease: a clinical review," *Orphanet J. Rare Dis.*, 5(40):1-8, 2010.
Sadikot et al., "Development of a High-Throughput Screening Cancer Cell-Based Luciferase Refolding Assay for Identifying Hsp90 Inhibitors," *Assay and Drug Development Technologies*, 11(8):478-488, 2013.
Shelton et al., "KU135, a Novel Novobiocin-Derived C-Terminal Inhibitor of the 90-kDa Heat Shock Protein, Exerts Potent Antiproliferative Effects in Human Leukemic Cells," *Mol. Pharmacol.*, 76:1314, 2009.
Shen et al., "Synthesis of photolabile novobiocin analogues," *Bioorg Med Chem Lett.*, 14(23):5903-5906, 2004.
Simone, "Oncology: Introduction", In: Cecil Textbook of Medicine, 20th Edition, 1:1004-1010, 1996.
Urban et al., "Inhibiting Heat Shock Protein 90 Reverses Sensory Hypoalgesia in Diabetic Mice", *ASN Neuro.*, 2(4): 189-199, 2010.
Urban et al., "Modulating Molecular Chaperones Improves Sensory Fiber Recovery and Mitochondrial Function in Diabetic Peripheral Neuropathy," *Experimental Neurology*, 235(1):388-396, 2012.
Vincent et al., "Cell culture modeling to test therapies against hyperglycemia-mediated oxidative stress and injury", *Antioxid Redox Signal*, 7:(11-12):1494-1506, 2005.
Vincent et al., "Sensory Neurons and Schwann Cells Respond to Oxidative Stress by Increasing Antioxidant Defense Mechanisms", *Antioxid Redox Signal*, 11:425-438, 2009.
Yu et al., "Hsp90 Inhibitors Identified from a Library of Novobiocin Analogues," *J. Am. Chem. Soc.*, 127:12778, 2005.
Yu et al., "Hyperglycemia and downregulation of caveolin-1 enhance neuregulin-induced demyelination", *Glia*, 56: 877-887, 2008.
Yu et al., "Synthesis of Mono- and Dihydroxylated Furanoses, Pyranoses, and an Oxepanose for the Preparation of Natural Product Analogue Libraries," *J. Org. Chem.*, 70:5599-5605, 2005.
Zhang et al, "Hyperglycemia alters the schwann cell mitochondrial proteome and decreases coupled respiration in the absence of superoxide production", *J Proteome Res.*, 9(1):458-71, 2010.
Zhang et al., "C-Terminal Heat Shock Protein 90 Inhibitor Decreases Hyperglycemia-induced Oxidative Stress and Improves Mitochondrial Bioenergetics in Sensory Neurons," *J. Proteome Research*, 11(4):2581-2593, 2012.
Zhang et al., "Simplified aminocoumarin analogues as anticancer agents: Amino isosteric replacement in the noviose moiety resulted in substantial enhancement of antiproliferative activity," *Chinese Chemical Letters*, 24(8):719-722, 2013.
Zhao and Blagg, "Novobiocin analogues with second-generation noviose surrogates," *Bioorg & Med. Chem. Lett.*, 23(2):552-557, 2013.
Zhao and Blagg, In: *Inhibitors of Molecular Chaperones As Therapeutic Agents*, Ed: Timothy Machajewski, RSC Publishing:London, 2014.
Zhao et al., "3-Arylcoumarin Derivatives Manifest Anti-Proliferative Activity through Hsp90 Inhibition," *ACS Med. Chem. Lett.*, 3(4):327-331, 2012.
Zhao et al., "3D-QSAR-assisted design, synthesis and evaluation of novobiocin analogues", *ACS Med Chem Lett.*, 4(1): 57-62, 2013.
Zhao et al., "Design, synthesis and biological evaluation of biphenylamide drivatives as Hsp90 C-terminal inhibitors," *European Journal of Medicinal Chemistry*, 89:442-466, 2014.

(56) References Cited

OTHER PUBLICATIONS

Zhao et al., "Engineering an Antibiotic to Fight Cancer: Optimization of the Novobiocin Scaffold to Produce Anti-proliferative Agents," *J. Med. Chem.*, 54:3839-3853, 2011.
Zhao et al., "Identification of a New Scaffold for Hsp90 C-Terminal Inhibition," *ACS Med. Chem. Lett.*, 5(1):84-88, 2014.
Zhao et al., "Novologues containing a benzamide side chain manifest anti-proliferative activity against two breast cancer cell lines", Bioorg. Med. Chem. Lett., 24:3633-3637, 2014.
Zhao et al., "Synthesis and Evaluation of Noviose Replacements on Novobiocin that Manifest Anti-proliferative activity," *ACS Med Chem Lett.*, 1(7):311-315, 2010.
Capon, Brian. "Mechanism in carbohydrate chemistry." *Chemical reviews* 69.4 (1969): 407-498.
Mikkola, Satu, and Mikko Oivanen. "Hydrolytic decomposition of glycosides in aqueous acids." *ARKIVOC: Online Journal of Organic Chemistry* (2009).

* cited by examiner

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Lys Phe Pro Arg Gln
1               5

BIARYL AMIDES WITH MODIFIED SUGAR GROUPS FOR TREATMENT OF DISEASES ASSOCIATED WITH HEAT SHOCK PROTEIN PATHWAY

This application is a national phase application under 35 U.S.C. § 371 of International Application No. PCT/US2019/032292, filed May 14, 2019, claims the benefit of priority to United States Provisional Application No. 62/671,047, filed on May 14, 2018, the entire contents of each of which are hereby incorporated by reference.

Pursuant to 37 C.F.R. 1.821(c), a sequence listing is submitted herewith as an ASCII compliant text file named "REATP0097US_ST25.txt", created on Apr. 13, 2021 and having a size of ~1 kilobytes. The content of the aforementioned file is hereby incorporated by reference in its entirety.

BACKGROUND OF THE INVENTION

I. Field of the Invention

The present invention relates generally to the fields of biology, chemistry, and medicine. More particularly, it concerns compounds, compositions and methods for the treatment and prevention of diseases and disorders, including neurological disorders, such as neurodegenerative diseases and nerve damaging disorders, for example, diabetic peripheral neuropathy.

II. Description of Related Art

The heat shock protein 90 (Hsp90) is associated with a wide variety of disorders which result from the misfolding of one or more proteins. These disorders include neurological diseases associated with damage, loss of function, or death of a neuron. These diseases may affect either peripheral neurons (peripheral neuropathy) or central neurons (central neuropathy) and result from systemic diseases or conditions such as diabetes, leprosy, vitamin deficiencies, medication, or diseases of the immune system or from conditions such as a viral infection or a traumatic injury. Damage to peripheral neurons due to diabetes is known as diabetic peripheral neuropathy and can result in nerve damage to any organ of the body. This condition can lead to a variety of different symptoms, but the hallmark symptom is chronic pain, numbness, and tingling, particularly in the distal extremities. In 2010, approximately 132 million people are believed to have diabetic peripheral neuropathy, which is the most common complication from diabetes and leading source of morbidity and mortality in diabetes.

Neckers and coworkers reported that the DNA gyrase inhibitor, novobiocin, and related natural products bind to the Hsp90 C-terminus nucleotide binding pocket with low affinity ($IC_{50}$~700 μM) (Marcu, et al., 2000), while retaining similar biological activity. Previous studies have shown that the coumarin core of novobiocin can be replaced with a biphenyl core (Kusuma, et al., 2012). While the initial biphenyl analogs contained a noviose sugar moiety, this sugar group is synthetically challenging, requiring as many as ten steps to obtain (Yu, et al., 2005b; Beaver, et al., 2008; Zhao, et al., 2011). Moreover, the glycosylation of activated noviose sugar with the biphenyl moiety produced a mixture of anomers, which increased the difficulty of obtaining a single anomer. Thus, replacing this group without sacrificing activity or other pharmacological properties is of commercial interest. Additionally, a replacement group which shows other beneficial properties such as improved activity, stability, solubility, or any subset of these and/or other properties is important for developing compounds with the potential for treating and/or preventing diseases or disorders, including those associated with Hsp90. Binding to the C-terminus of Hsp90 may have therapeutic advantages in comparison to inhibitors that bind to the N-terminus (Kusuma, 2012). In particular, there remains a need for additional compounds with unique biological and pharmacological profiles for use in the treatment of diseases and disorders associated with the heat shock protein pathway, including inhibition of Hsp90 and/or induction of Hsp70.

SUMMARY OF THE INVENTION

The present disclosure provides biaryl Hsp90 inhibitors with modified ether groups with therapeutic properties, pharmaceutical compositions thereof, methods for their manufacture, and methods for their use.

In some aspects, the present disclosure provides compounds of the formula:

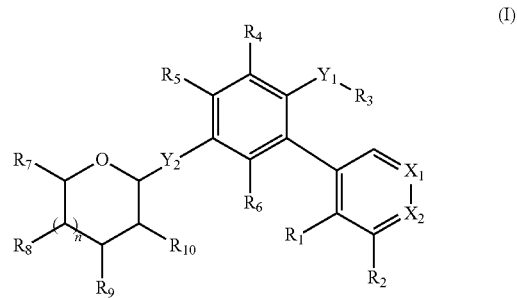

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —$NR_{11}R_{11}'$ or —$C(O)NR_{12}R_{12}'$, wherein:
  $R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}'$ are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ is carboxy or alkyl$_{(C \leq 6)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-$OR_{13}$, or a substituted version of any of these groups wherein:

$R_{13}$ is alkyl$_{(C≤12)}$, substituted alkyl$_{(C≤12)}$, aralkyl$_{(C≤12)}$, or substituted aralkyl$_{(C≤12)}$;

$R_8$, $R_9$, and $R_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$X_1$ is $CR_{14}$ or N, wherein:

$R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and $X_2$ is $CR_{15}$ or N, wherein:

$R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;

$R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

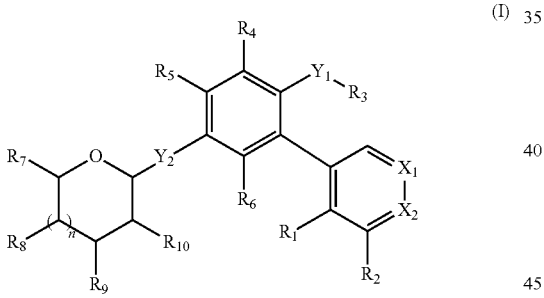

(I)

wherein:

n is 0, 1, or 2;

$Y_1$ is -alkanediyl$_{(C≤6)}$-, —C(O)-alkanediyl$_{(C≤6)}$-, or a substituted version of any of these groups;

$Y_2$ is $CH_2$, O, or S;

$R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;

$R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;

$R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;

$R_3$ is —$NR_{11}R_{11}'$ or —$C(O)NR_{12}R_{12}'$, wherein:

$R_{11}$ and $R_{11}'$ are each independently hydrogen, alkyl$_{(C≤6)}$, substituted alkyl$_{(C≤6)}$, acyl$_{(C≤6)}$, or substituted acyl$_{(C≤6)}$;

$R_{12}$ and $R_{12}'$ are each independently hydrogen, alkyl$_{(C≤6)}$, or substituted alkyl$_{(C≤6)}$;

$R_4$, $R_5$, and $R_6$ are each independently hydrogen, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;

$R_7$ is hydrogen, carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-$OR_{13}$, or a substituted version of any of these groups wherein:

$R_{13}$ is alkyl$_{(C≤12)}$, substituted alkyl$_{(C≤12)}$, aralkyl$_{(C≤12)}$, or substituted aralkyl$_{(C≤12)}$;

$R_8$ and $R_9$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$R_{10}$ is amino or alkylamino$_{(C≤6)}$, dialkylamino$_{(C≤12)}$, amido$_{(C≤12)}$, or a substituted version of any of these three groups;

$X_1$ is $CR_{14}$ or N, wherein:

$R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and $X_2$ is $CR_{15}$ or N, wherein:

$R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;

$R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

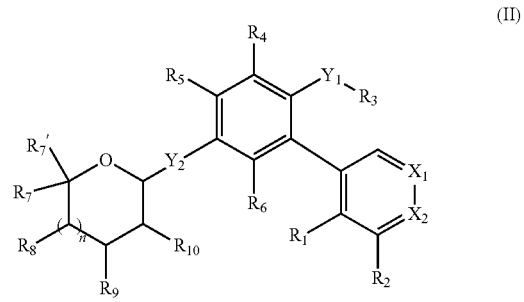

(II)

wherein:

n is 0, 1, or 2;

$Y_1$ is -alkanediyl$_{(C≤6)}$-, —C(O)-alkanediyl$_{(C≤6)}$-, or a substituted version of any of these groups;

5

$Y_2$ is $CH_2$, O, or S;

$R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;

$R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;

$R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;

$R_3$ is —$NR_{11}R_{11}'$ or —$C(O)NR_{12}R_{12}'$, wherein:

$R_{11}$ and $R_{11}'$ are each independently hydrogen, alkyl$_{(C\leq 6)}$, substituted alkyl$_{(C\leq 6)}$, acyl$_{(C\leq 6)}$, or substituted acyl$_{(C\leq 6)}$;

$R_{12}$ and $R_{12}'$ are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ is carboxy or alkyl$_{(C3-8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:

$R_{13}$ is aralkyl$_{(C\leq 12)}$ or substituted aralkyl$_{(C\leq 12)}$;

$R_7'$ is hydrogen, carboxy, or alkyl$_{(C3-8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:

$R_{13}$ is aralkyl$_{(C\leq 12)}$ or substituted aralkyl$_{(C\leq 12)}$; or $R_7$ and $R_7'$ are taken together and are -alkanediyl$_{(C\leq 7)}$-, -alkenediyl$_{(C\leq 7)}$-, or a substituted version of either of these groups;

$R_8$, $R_9$, and $R_{10}$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

$X_1$ is $CR_{14}$ or N, wherein:

$R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or $R_{14}$ and $R_{15}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; and $X_2$ is $CR_{15}$ or N, wherein:

$R_{15}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups;

$R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

6 or a compound of the formula:

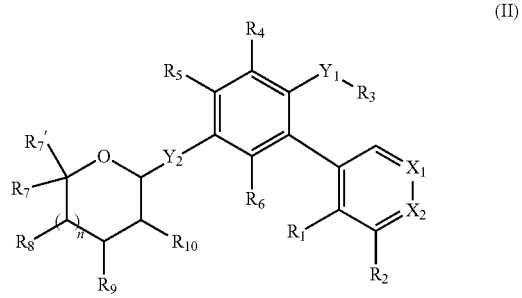

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is $CH_2$ or S;

$R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;

$R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;

$R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;

$R_3$ is —$NR_{11}R_{11}'$ or —$C(O)NR_{12}R_{12}'$, wherein:

$R_{11}$ and $R_{11}'$ are each independently hydrogen, alkyl$_{(C\leq 6)}$, substituted alkyl$_{(C\leq 6)}$, acyl$_{(C\leq 6)}$, or substituted acyl$_{(C\leq 6)}$;

$R_{12}$ and $R_{12}'$ are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ and $R_7'$ are each independently hydrogen, carboxy, or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, hetero aryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:

$R_{13}$ is aralkyl$_{(C\leq 12)}$ or substituted aralkyl$_{(C\leq 12)}$;

$R_7$ and $R_7'$ are taken together and are -alkanediyl$_{(C\leq 7)}$-, -alkenediyl$_{(C\leq 7)}$-, or a substituted version of either of these groups;

$R_8$, $R_9$, and $R_{10}$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

$X_1$ is $CR_{14}$ or N, wherein:

$R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is $CR_{15}$ or N, wherein:
$R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;

$R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a compound of the formula:

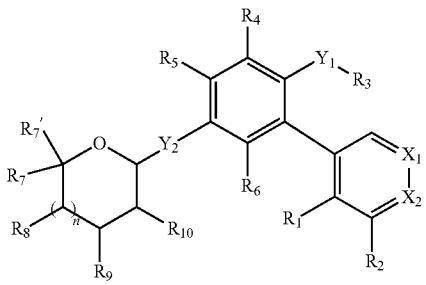

(II)

wherein:
n is 0, 1, or 2;
$Y_1$ is substituted -alkanediyl$_{(C \leq 6)}$-, —C(O)-alkanediyl$_{(C \leq 6)}$-, or substituted —C(O)-alkanediyl$_{(C \leq 6)}$-;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —$NR_{11}R_{11}'$ or —$C(O)NR_{12}R_{12}'$, wherein:
$R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}'$ are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ and $R_7'$ are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-$OR_{13}$, or a substituted version of any of these groups wherein:
$R_{13}$ is aralkyl$_{(C \leq 12)}$ or substituted aralkyl$_{(C \leq 12)}$; or
$R_7$ and $R_7'$ are taken together and are -alkanediyl$_{(C \leq 7)}$-, -alkenediyl$_{(C \leq 7)}$-, or a substituted version of any of these groups;
$R_8$, $R_9$, and $R_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;
$X_1$ is $CR_{14}$ or N, wherein:
$R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
$R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is $CR_{15}$ or N, wherein:
$R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
$R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
$R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a compound of the formula:

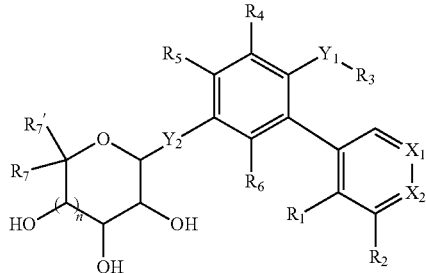

(III)

wherein:
n is 1 or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;

$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;

$R_3$ is —NR$_{11}$R$_{11}$' or —C(O)NR$_{12}$R$_{12}$', wherein:
  $R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}$' are each independently hydrogen, alkyl$_{(C \leq 6)}$, or substituted alkyl$_{(C \leq 6)}$;

$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 8)}$;

$R_7$ and $R_7$' are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, alkanediyl$_{(C \leq 6)}$-OR$_{13}$, or a substituted version of any of these groups wherein:
  $R_{13}$ is aralkyl$_{(C \leq 12)}$ or substituted aralkyl$_{(C \leq 12)}$; or $R_7$ and $R_7$' are taken together and are -alkanediyl$_{(C \leq 7)}$-, -alkenediyl$_{(C \leq 7)}$-, or a substituted version of either of these groups;

$X_1$ is CR$_{14}$ or N, wherein:
  $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
  $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is CR$_{15}$ or N, wherein:
  $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
  $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
  $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a compound of the formula:

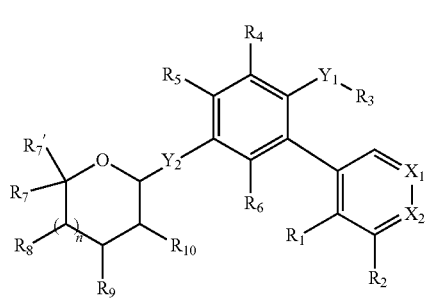

(II)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;

$Y_2$ is CH$_2$, O, or S;

$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;

$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;

$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;

$R_3$ is —NR$_{11}$R$_{11}$' or —C(O)NR$_{12}$R$_{12}$', wherein:
  $R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}$' are each independently hydrogen, alkyl$_{(C \leq 6)}$, or substituted alkyl$_{(C \leq 6)}$;

$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;

$R_7$ is carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is aralkyl$_{(C \leq 12)}$ or substituted aralkyl$_{(C \leq 12)}$;

$R_7$' is hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is aralkyl$_{(C \leq 12)}$ or substituted aralkyl$_{(C \leq 12)}$; or $R_7$ and $R_7$' are taken together and are -alkanediyl$_{(C \leq 7)}$-, -alkenediyl$_{(C \leq 7)}$-, or a substituted version of either of these groups;

$R_8$ is halo, alkoxy$_{(C3-6)}$, acyloxy$_{(C \leq 6)}$, aralkoxy$_{(C \leq 12)}$, or a substituted version of any of these groups;

$R_9$ and $R_{10}$ are each independently halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

$X_1$ is CR$_{14}$ or N, wherein:
  $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
  $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is CR$_{15}$ or N, wherein:
  $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
  $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

or a compound of the formula:

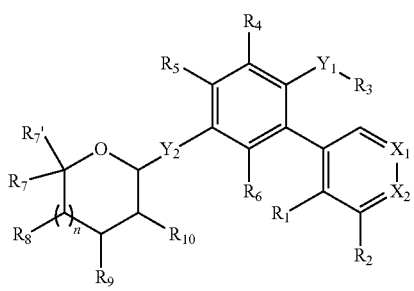

(II)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is CH$_2$, O, or S;

$R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;

$R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;

$R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;

$R_3$ is —NR$_{11}$R$_{11}$' or —C(O)NR$_{12}$R$_{12}$', wherein:
$R_{11}$ and $R_{11}$' are each independently hydrogen, alkyl$_{(C\leq 6)}$, substituted alkyl$_{(C\leq 6)}$;
$R_{12}$ and $R_{12}$' are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ and $R_7$' are each independently hydrogen, carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:
$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_7$ and $R_7$' are taken together and are -alkanediyl$_{(C\leq 7)}$-, -alkenediyl$_{(C\leq 7)}$-, or a substituted version of either of these groups;

$R_8$, $R_9$, and $R_{10}$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

$X_1$ is CR$_{14}$ or N, wherein:
$R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or $R_{14}$ and $R_{15}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; and $X_2$ is CR$_{15}$ or N, wherein:
$R_{15}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups;

$R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

or a compound of the formula:

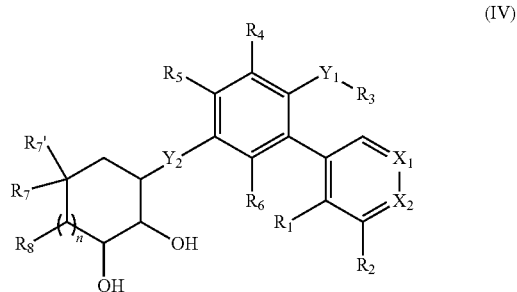

(IV)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is CH$_2$, O, or S;

$R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;

$R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;

$R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;

$R_3$ is —NR$_{11}$R$_{11}$' or —C(O)NR$_{12}$R$_{12}$', wherein:
$R_{11}$ and $R_{11}$' are each independently hydrogen, alkyl$_{(C\leq 6)}$, substituted alkyl$_{(C\leq 6)}$, acyl$_{(C\leq 6)}$, or substituted acyl$_{(C\leq 6)}$;
$R_{12}$ and $R_{12}$' are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ is carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:

$R_{13}$ is alkyl$_{(C≤12)}$, substituted alkyl$_{(C≤12)}$, aralkyl$_{(C≤12)}$, or substituted aralkyl$_{(C≤12)}$;

$R_7'$ is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

$R_{13}$ is alkyl$_{(C≤12)}$, substituted alkyl$_{(C≤12)}$, aralkyl$_{(C≤12)}$, or substituted aralkyl$_{(C≤12)}$;

$R_7$ and $R_7'$ are taken together and are -alkanediyl$_{(C≤7)}$-, -alkenediyl$_{(C≤7)}$-, or a substituted version of either of these groups;

$R_8$ is halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$X_1$ is CR$_{14}$ or N, wherein:
 $R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
 $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and $X_2$ is CR$_{15}$ or N, wherein:
 $R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
 $R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
 $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

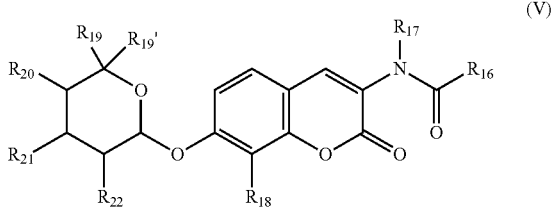

(V)

wherein:
 $R_{16}$ is alkyl$_{(C≤12)}$, cycloalkyl$_{(C≤12)}$, aryl$_{(C≤18)}$, heteroaryl$_{(C≤18)}$, or a substituted version thereof;
 $R_{17}$ and $R_{18}$ are each independently hydrogen, alkyl$_{(C≤8)}$, or substituted alkyl$_{(C≤8)}$;
 $R_{19}$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  $R_{13}$ is alkyl$_{(C≤12)}$, substituted alkyl$_{(C≤12)}$, aralkyl$_{(C≤12)}$, or substituted
 $R_{19}'$ is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  $R_{13}$ is alkyl$_{(C≤12)}$, substituted alkyl$_{(C≤12)}$, aralkyl$_{(C≤12)}$, or substituted aralkyl$_{(C≤12)}$;
 $R_{20}$, $R_{21}$, and $R_{22}$ are each independently halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups, or a protected hydroxy group;

or a pharmaceutically acceptable salt of any of the above formulas.

In some embodiments, the compounds are further defined as:

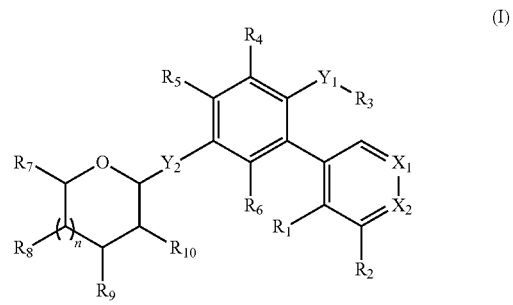

(I)

wherein:
 n is 0, 1, or 2;
 $Y_1$ is -alkanediyl$_{(C≤6)}$-, —C(O)-alkanediyl$_{(C≤6)}$-, or a substituted version of any of these groups;
 $Y_2$ is CH$_2$, O, or S;
 $R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
 $R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;
 $R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;
 $R_3$ is —NR$_{11}$R$_{11}'$ or —C(O)NR$_{12}$R$_{12}'$, wherein:
  $R_{11}$ and $R_{11}'$ are each independently hydrogen, alkyl$_{(C≤6)}$, substituted alkyl$_{(C≤6)}$, acyl$_{(C≤6)}$, or substituted acyl$_{(C≤6)}$;
  $R_{12}$ and $R_{12}'$ are each independently hydrogen, alkyl$_{(C≤6)}$, or substituted alkyl$_{(C≤6)}$;
 $R_4$, $R_5$, and $R_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
 $R_7$ is carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  $R_{13}$ is aralkyl$_{(C≤12)}$ or substituted aralkyl$_{(C≤12)}$;
 $R_8$, $R_9$, and $R_{10}$ are each independently hydrogen, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$X_1$ is $CR_{14}$ or N, wherein:
  $R_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or
  $R_{14}$ and $R_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and
$X_2$ is $CR_{15}$ or N, wherein:
  $R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
  $R_{15}$ and $R_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
  $R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;
or a compound of the formula:

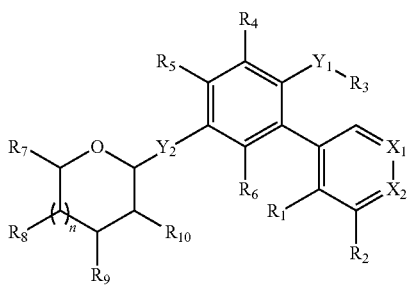

(I)

wherein:
n is 0, 1, or 2;
$Y_1$ is -alkanediyl$_{(C\leq6)}$-, —C(O)-alkanediyl$_{(C\leq6)}$-, or a substituted version of any of these groups;
$Y_2$ is $CH_2$, O, or S;
$R_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;
$R_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;
$R_2$ and $R_{15}$ are taken together and are alkanediyl$_{(C\leq6)}$, alkoxydiyl$_{(C\leq6)}$, alkylaminodiyl$_{(C\leq6)}$, or a substituted version of any of these groups;
$R_3$ is —$NR_{11}R_{11}'$ or —$C(O)NR_{12}R_{12}'$, wherein:
  $R_{11}$ and $R_{11}'$ are each independently hydrogen, alkyl$_{(C\leq6)}$, substituted alkyl$_{(C\leq6)}$, acyl$_{(C\leq6)}$, or substituted acyl$_{(C\leq6)}$;
  $R_{12}$ and $R_{12}'$ are each independently hydrogen, alkyl$_{(C\leq6)}$, or substituted alkyl$_{(C\leq6)}$;
$R_4$, $R_5$, and $R_6$ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;

$R_7$ is hydrogen, carboxy or alkyl$_{(C\leq6)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-$OR_{13}$, or a substituted version of any of these groups wherein:
  $R_{13}$ is aralkyl$_{(C\leq12)}$ or substituted aralkyl$_{(C\leq12)}$;
$R_8$ and $R_9$ are each independently hydrogen, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;
$R_{10}$ is amino or alkylamino$_{(C\leq6)}$, dialkylamino$_{(C\leq12)}$, amido$_{(C\leq12)}$, or a substituted version of any of these three groups;
$X_1$ is $CR_{14}$ or N, wherein:
  $R_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or
  $R_{14}$ and $R_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and
$X_2$ is $CR_{15}$ or N, wherein:
  $R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
  $R_{15}$ and $R_{10}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
  $R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;
or a compound of the formula:

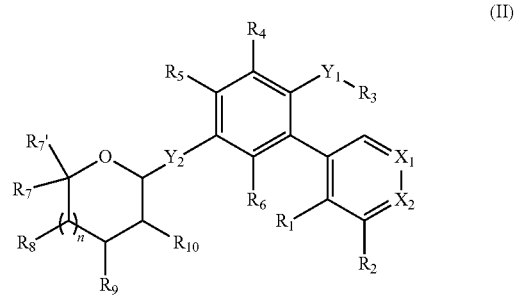

(II)

wherein:
n is 0, 1, or 2;
$Y_1$ is -alkanediyl$_{(C\leq6)}$-, —C(O)-alkanediyl$_{(C\leq6)}$-, or a substituted version of any of these groups;
$Y_2$ is $CH_2$, O, or S;
$R_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;
$R_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C≤6)}$, alkoxy$_{(C≤6)}$, alkylthio$_{(C≤6)}$, alkylsulfonyl$_{(C≤6)}$, or a substituted version of any of these groups;

$R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;

$R_3$ is —NR$_{11}$R$_{11}$' or —C(O)NR$_{12}$R$_{12}$', wherein:

$R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;

$R_{12}$ and $R_{12}$' are each independently hydrogen, alkyl$_{(C≤6)}$, or substituted alkyl$_{(C≤6)}$;

$R_4$, $R_5$, and $R_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;

$R_7$ is carboxy or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

$R_{13}$ is aralkyl$_{(C≤12)}$ or substituted aralkyl$_{(C≤12)}$;

$R_7$' is hydrogen, carboxy, or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

$R_{13}$ is aralkyl$_{(C≤12)}$ or substituted aralkyl$_{(C≤12)}$; or $R_7$ and $R_7$' are taken together and are -alkanediyl$_{(C≤7)}$-, -alkenediyl$_{(C≤7)}$-, or a substituted version of either of these groups;

$R_8$, $R_9$, and $R_{10}$ are each independently hydrogen, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$X_1$ is CR$_{14}$ or N, wherein:

$R_{10}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and $X_2$ is CR$_{15}$ or N, wherein:

$R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;

$R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

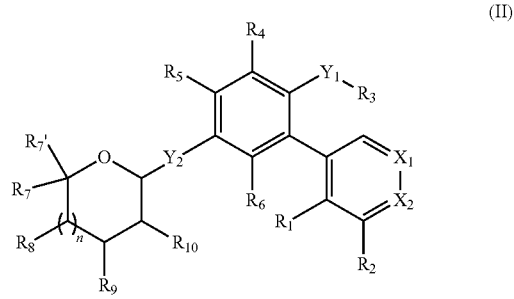

(II)

wherein:

n is 0, 1, or 2;

$Y_1$ is -alkanediyl$_{(C≤6)}$-, —C(O)-alkanediyl$_{(C≤6)}$-, or a substituted version of any of these groups;

$Y_2$ is CH$_2$ or S;

$R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;

$R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;

$R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;

$R_3$ is —NR$_{11}$R$_{11}$' or —C(O)NR$_{12}$R$_{12}$', wherein:

$R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;

$R_{12}$ and $R_{12}$' are each independently hydrogen, alkyl$_{(C≤6)}$, or substituted alkyl$_{(C≤6)}$;

$R_4$, $R_5$, and $R_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;

$R_7$ and $R_7$' are each independently hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

$R_{13}$ is aralkyl$_{(C≤12)}$ or substituted aralkyl$_{(C≤12)}$;

$R_7$ and $R_7$' are taken together and are -alkanediyl$_{(C≤7)}$-, -alkenediyl$_{(C≤7)}$-, or a substituted version of either of these groups;

$R_8$, $R_9$, and $R_{10}$ are each independently hydrogen, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

$X_1$ is CR$_{14}$ or N, wherein:

$R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and $X_2$ is $CR_{15}$ or N, wherein:
  $R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
  $R_{15}$ and $R_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
  $R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;
or a compound of the formula:

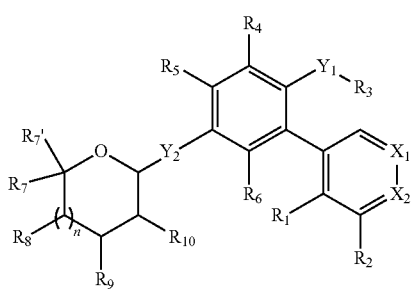

(II)

wherein:
  n is 0, 1, or 2;
  $Y_1$ is substituted -alkanediyl$_{(C\leq6)}$-, —C(O)-alkanediyl$_{(C\leq6)}$-, or substituted —C(O)-alkanediyl$_{(C\leq6)}$-;
  $Y_2$ is $CH_2$, O, or S;
  $R_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;
  $R_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;
  $R_2$ and $R_{15}$ are taken together and are alkanediyl$_{(C\leq6)}$, alkoxydiyl$_{(C\leq6)}$, alkylaminodiyl$_{(C\leq6)}$, or a substituted version of any of these groups;
  $R_3$ is —$NR_{11}R_{11}'$ or —$C(O)NR_{12}R_{12}'$, wherein:
    $R_{11}$ and $R_{11}'$ are each independently hydrogen, alkyl$_{(C\leq6)}$, substituted alkyl$_{(C\leq6)}$, acyl$_{(C\leq6)}$, or substituted acyl$_{(C\leq6)}$;
    $R_{12}$ and $R_{12}'$ are each independently hydrogen, alkyl$_{(C\leq6)}$, or substituted alkyl$_{(C\leq6)}$;
  $R_4$, $R_5$, and $R_6$ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;
  $R_7$ and $R_7'$ are each independently hydrogen, carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-$OR_{13}$, or a substituted version of any of these groups wherein:
    $R_{13}$ is aralkyl$_{(C\leq12)}$ or substituted aralkyl$_{(C\leq12)}$; or $R_7$ and $R_7'$ are taken together and are -alkanediyl$_{(C\leq7)}$-, -alkenediyl$_{(C\leq7)}$-, or a substituted version of any of these groups;
  $R_8$, $R_9$, and $R_{10}$ are each independently hydrogen, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;
$X_1$ is $CR_{14}$ or N, wherein:
  $R_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or
  $R_{14}$ and $R_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and
$X_2$ is $CR_{15}$ or N, wherein:
  $R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
  $R_{15}$ and $R_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
  $R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;
or a compound of the formula:

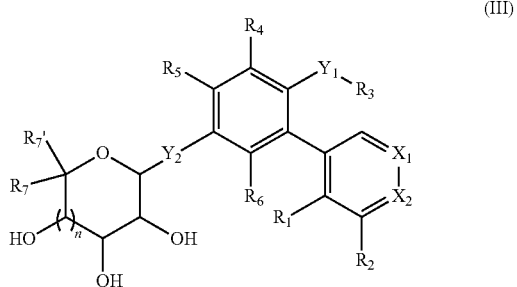

(III)

wherein:
  n is 1 or 2;
  $Y_1$ is -alkanediyl$_{(C\leq6)}$-, —C(O)-alkanediyl$_{(C\leq6)}$-, or a substituted version of any of these groups;
  $Y_2$ is $CH_2$, O, or S;
  $R_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;
  $R_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;
  $R_2$ and $R_{15}$ are taken together and are alkanediyl$_{(C\leq6)}$, alkoxydiyl$_{(C\leq6)}$, alkylaminodiyl$_{(C\leq6)}$, or a substituted version of any of these groups;

$R_3$ is —$NR_{11}R_{11}'$ or —$C(O)NR_{12}R_{12}'$, wherein:
  $R_{11}$ and $R_{11}'$ are each independently hydrogen, alkyl$_{(C\leq 6)}$, substituted alkyl$_{(C\leq 6)}$, acyl$_{(C\leq 6)}$, or substituted acyl$_{(C\leq 6)}$;
  $R_{12}$ and $R_{12}'$ are each independently hydrogen, alkyl$_{(C\leq 6)}$, or substituted alkyl$_{(C\leq 6)}$;
$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;
$R_7$ and $R_7'$ are each independently hydrogen, carboxy, or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:
  $R_{13}$ is aralkyl$_{(C\leq 12)}$ or substituted aralkyl$_{(C\leq 12)}$; or
$R_7$ and $R_7'$ are taken together and are -alkanediyl$_{(C\leq 7)}$-, -alkenediyl$_{(C\leq 7)}$-, or a substituted version of either of these groups;
$X_1$ is $CR_{14}$ or N, wherein:
  $R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or
  $R_{14}$ and $R_{15}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; and
$X_2$ is $CR_{15}$ or N, wherein:
  $R_{15}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups;
  $R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or
  $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;
or a compound of the formula:

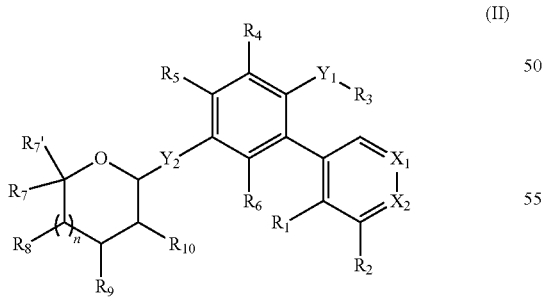

(II)

wherein:
  n is 0, 1, or 2;
  $Y_1$ is -alkanediyl$_{(C\leq 6)}$-, —C(O)-alkanediyl$_{(C\leq 6)}$-, or a substituted version of any of these groups;
  $Y_2$ is $CH_2$, O, or S;
  $R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;
  $R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;
  $R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;
  $R_3$ is —$NR_{11}R_{11}'$ or —$C(O)NR_{12}R_{12}'$, wherein:
    $R_{11}$ and $R_{11}'$ are each independently hydrogen, alkyl$_{(C\leq 6)}$, substituted alkyl$_{(C\leq 6)}$, acyl$_{(C\leq 6)}$, or substituted acyl$_{(C\leq 6)}$;
    $R_{12}$ and $R_{12}'$ are each independently hydrogen, alkyl$_{(C\leq 6)}$, or substituted alkyl$_{(C\leq 6)}$;
  $R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;
  $R_7$ is carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:
    $R_{13}$ is aralkyl$_{(C\leq 12)}$ or substituted aralkyl$_{(C\leq 12)}$;
  $R_7'$ is hydrogen, carboxy, or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-$OR_{13}$, or a substituted version of any of these groups wherein:
    $R_{13}$ is aralkyl$_{(C\leq 12)}$ or substituted aralkyl$_{(C\leq 12)}$; or
  $R_7$ and $R_7'$ are taken together and are -alkanediyl$_{(C\leq 7)}$-, -alkenediyl$_{(C\leq 7)}$-, or a substituted version of either of these groups;
  $R_8$ is alkoxy$_{(C3-6)}$, acyloxy$_{(C\leq 6)}$, aralkoxy$_{(C\leq 12)}$, or a substituted version of any of these groups;
  $R_9$ and $R_{10}$ are each independently hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;
  $X_1$ is $CR_{14}$ or N, wherein:
    $R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or
    $R_{14}$ and $R_{15}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; and
  $X_2$ is $CR_{15}$ or N, wherein:
    $R_{15}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups;
    $R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or
    $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

or a compound of the formula:

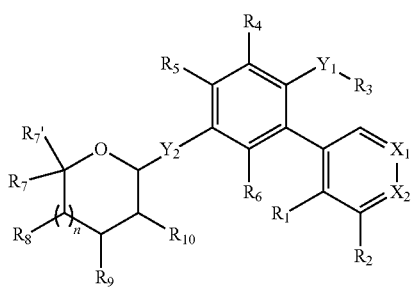

(II)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —NR$_{11}$R$_{11}$' or —C(O)NR$_{12}$R$_{12}$', wherein:
 $R_{11}$ and $R_{11}$' are each independently hydrogen, alkyl$_{(C \leq 6)}$, substituted alkyl$_{(C \leq 6)}$;
 $R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ and $R_7$' are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
 $R_{13}$ is aralkyl$_{(C \leq 12)}$ or substituted aralkyl$_{(C \leq 12)}$;
$R_7$ and $R_7$' are taken together and are -alkanediyl$_{(C \leq 7)}$-, -alkenediyl$_{(C \leq 7)}$-, or a substituted version of either of these groups;
$R_8$, $R_9$, and $R_{10}$ are each independently hydrogen, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;
$X_1$ is CR$_{14}$ or N, wherein:
 $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
 $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is CR$_{15}$ or N, wherein:
 $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
 $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
 $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;
or a compound of the formula:

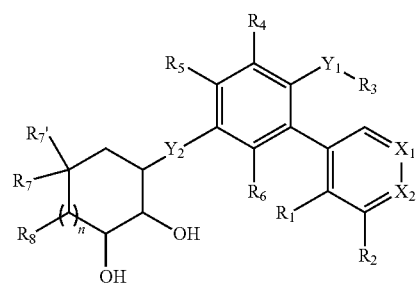

(IV)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —NR$_{11}$R$_{11}$' or —C(O)NR$_{12}$R$_{12}$', wherein:
 $R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
 $R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ is carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
 $R_{13}$ is alkyl$_{(C \leq 12)}$, substituted alkyl$_{(C \leq 12)}$, aralkyl$_{(C \leq 12)}$, or substituted aralkyl$_{(C \leq 12)}$;
$R_7$' is hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R$_7$ and R$_7$' are taken together and are -alkanediyl$_{(C\leq7)}$-, -alkenediyl$_{(C\leq7)}$-, or a substituted version of either of these groups;

R$_8$ is halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

X$_1$ is CR$_{14}$ or N, wherein:

R$_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or R$_{14}$ and R$_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and X$_2$ is CR$_{15}$ or N, wherein:

R$_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;

R$_{15}$ and R$_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or R$_{15}$ and R$_2$ are taken together and are alkanediyl$_{(C\leq6)}$, alkoxydiyl$_{(C\leq6)}$, alkylaminodiyl$_{(C\leq6)}$, or a substituted version of any of these groups;

or a compound of the formula:

(V)

wherein:

R$_{16}$ is alkyl$_{(C\leq12)}$, cycloalkyl$_{(C\leq12)}$, aryl$_{(C\leq18)}$, heteroaryl$_{(C\leq18)}$, or a substituted version thereof;

R$_{17}$ and R$_{18}$ are each independently hydrogen, alkyl$_{(C\leq8)}$, or substituted alkyl$_{(C\leq8)}$;

R$_{19}$ is alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, or a substituted version of any of these groups R$_{20}$, R$_{21}$, and R$_{22}$ are each independently hydroxy, alkoxy$_{(C\leq12)}$, substituted alkoxy$_{(C\leq12)}$, or a protected hydroxy group;

or a pharmaceutically acceptable salt of any of the above formulas.

In some embodiments, the compounds are further defined as:

(I)

wherein:

n is 0, 1, or 2;

Y$_1$ is -alkanediyl$_{(C\leq6)}$-, —C(O)-alkanediyl$_{(C\leq6)}$-, or a substituted version of any of these groups;

Y$_2$ is CH$_2$, O, or S;

R$_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;

R$_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;

R$_2$ and R$_{15}$ are taken together and are alkanediyl$_{(C\leq6)}$, alkoxydiyl$_{(C\leq6)}$, alkylaminodiyl$_{(C\leq6)}$, or a substituted version of any of these groups;

R$_3$ is —NR$_{11}$R$_{11}$' or —C(O)NR$_{12}$R$_{12}$', wherein:

R$_{11}$ and R$_{11}$' are each independently hydrogen, alkyl$_{(C\leq6)}$, substituted alkyl$_{(C\leq6)}$, acyl$_{(C\leq6)}$, or substituted acyl$_{(C\leq6)}$;

R$_{12}$ and R$_{12}$' are each independently hydrogen, alkyl$_{(C\leq6)}$, or substituted alkyl$_{(C\leq6)}$;

R$_4$, R$_5$, and R$_6$ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;

R$_7$ is carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is aralkyl$_{(C\leq12)}$ or substituted aralkyl$_{(C\leq12)}$;

R$_8$, R$_9$, and R$_{10}$ are each independently hydrogen, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

X$_1$ is CR$_{14}$ or N, wherein:

R$_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or R$_{14}$ and R$_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and $X_2$ is $CR_{15}$ or N, wherein:
  $R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
  $R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
  $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

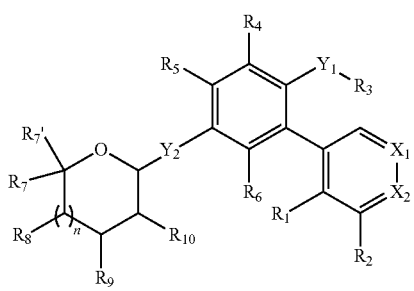

(II)

wherein:
  n is 0, 1, or 2;
  $Y_1$ is -alkanediyl$_{(C≤6)}$-, —C(O)-alkanediyl$_{(C≤6)}$-, or a substituted version of any of these groups;
  $Y_2$ is $CH_2$, O, or S;
  $R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
  $R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;
  $R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;
  $R_3$ is —NR$_{11}$R$_{11}$' or —C(O)NR$_{12}$R$_{12}$', wherein:
    $R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;
    $R_{12}$ and $R_{12}$' are each independently hydrogen, alkyl$_{(C≤6)}$, or substituted alkyl$_{(C≤6)}$;
  $R_4$, $R_5$, and $R_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
  $R_7$ is carboxy or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
    $R_{13}$ is aralkyl$_{(C≤12)}$ or substituted aralkyl$_{(C≤12)}$;
  $R_7$' is hydrogen, carboxy, or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
    $R_{13}$ is aralkyl$_{(C≤12)}$ or substituted aralkyl$_{(C≤12)}$; or
  $R_7$ and $R_7$' are taken together and are -alkanediyl$_{(C≤7)}$-, -alkenediyl$_{(C≤7)}$-, or a substituted version of either of these groups;
  $R_8$, $R_9$, and $R_{10}$ are each independently hydrogen, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
  $X_1$ is $CR_{14}$ or N, wherein:
    $R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
    $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and
  $X_2$ is $CR_{15}$ or N, wherein:
    $R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
    $R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
    $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

or a compound of the formula:

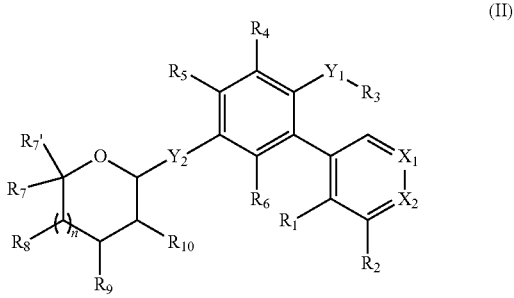

(II)

wherein:
  n is 0, 1, or 2;
  $Y_1$ is -alkanediyl$_{(C≤6)}$-, —C(O)-alkanediyl$_{(C≤6)}$-, or a substituted version of any of these groups;
  $Y_2$ is $CH_2$ or S;
  $R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
  $R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;

$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;

$R_3$ is $-NR_{11}R_{11}'$ or $-C(O)NR_{12}R_{12}'$, wherein:
  $R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}'$ are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ and $R_7'$ are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is aralkyl$_{(C \leq 12)}$ or substituted aralkyl$_{(C \leq 12)}$;
$R_7$ and $R_7'$ are taken together and are -alkanediyl$_{(C \leq 7)}$-, -alkenediyl$_{(C \leq 7)}$-, or a substituted version of either of these groups;
$R_8$, $R_9$, and $R_{10}$ are each independently hydrogen, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;
$X_1$ is $CR_{14}$ or N, wherein:
  $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
  $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is $CR_{15}$ or N, wherein:
  $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
  $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
  $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;
or a compound of the formula:

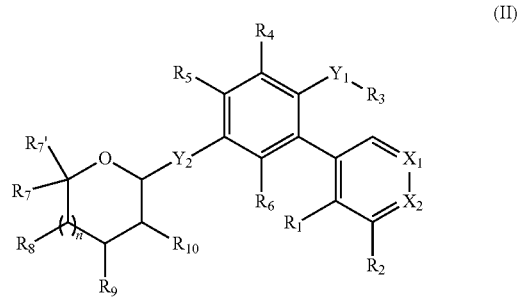

(II)

wherein:
n is 0, 1, or 2;
$Y_1$ is substituted -alkanediyl$_{(C \leq 6)}$-, $-C(O)$-alkanediyl$_{(C \leq 6)}$-, or substituted $-C(O)$-alkanediyl$_{(C \leq 6)}$-;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is $-NR_{11}R_{11}'$ or $-C(O)NR_{12}R_{12}'$, wherein:
  $R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}'$ are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ and $R_7'$ are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is aralkyl$_{(C \leq 12)}$ or substituted aralkyl$_{(C \leq 12)}$; or
$R_7$ and $R_7'$ are taken together and are -alkanediyl$_{(C \leq 7)}$-, -alkenediyl$_{(C \leq 7)}$-, or a substituted version of any of these groups;
$R_8$, $R_9$, and $R_{10}$ are each independently hydrogen, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;
$X_1$ is $CR_{14}$ or N, wherein:
  $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
  $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is $CR_{15}$ or N, wherein:
  $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
  $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
  $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a compound of the formula:

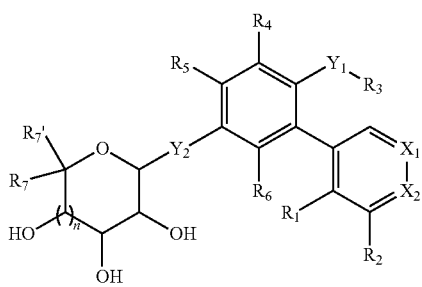

(III)

wherein:
n is 1 or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —NR$_{11}$R$_{11}$' or —C(O)NR$_{12}$R$_{12}$', wherein:
$R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ and $R_7$' are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
$R_{13}$ is aralkyl$_{(C \leq 12)}$ or substituted aralkyl$_{(C \leq 12)}$; or
$R_7$ and $R_7$' are taken together and are -alkanediyl$_{(C \leq 7)}$-, -alkenediyl$_{(C \leq 7)}$-, or a substituted version of either of these groups;
$X_1$ is CR$_{14}$ or N, wherein:
$R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
$R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is CR$_{15}$ or N, wherein:
$R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
$R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
$R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;
or a compound of the formula:

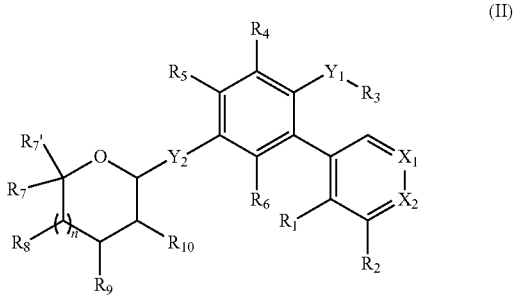

(II)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —NR$_{11}$R$_{11}$' or —C(O)NR$_{12}$R$_{12}$', wherein:
$R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ is carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
$R_{13}$ is aralkyl$_{(C \leq 12)}$ or substituted aralkyl$_{(C \leq 12)}$;
$R_7$' is hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:

$R_{13}$ is aralkyl$_{(C\leq12)}$ or substituted aralkyl$_{(C\leq12)}$; or $R_7$ and $R_7'$ are taken together and are -alkanediyl$_{(C\leq7)}$-, -alkenediyl$_{(C\leq7)}$-, or a substituted version of either of these groups;

$R_8$ is alkoxy$_{(C3-6)}$, acyloxy$_{(C\leq6)}$, aralkoxy$_{(C\leq12)}$, or a substituted version of any of these groups;

$R_9$ and $R_{10}$ are each independently hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

$X_1$ is $CR_{14}$ or N, wherein:
$R_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or
$R_{14}$ and $R_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and $X_2$ is $CR_{15}$ or N, wherein:
$R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
$R_{15}$ and $R_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
$R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;

or a compound of the formula:

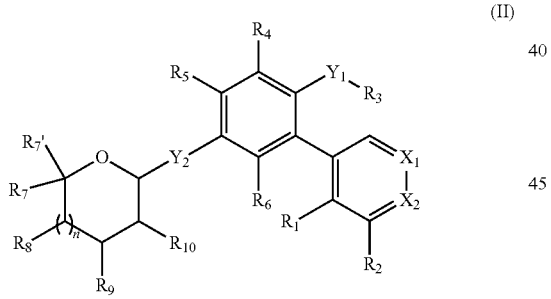

(II)

wherein:
n is 0, 1, or 2;
$Y_1$ is -alkanediyl$_{(C\leq6)}$-, —C(O)-alkanediyl$_{(C\leq6)}$-, or a substituted version of any of these groups;
$Y_2$ is $CH_2$, O, or S;
$R_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;
$R_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;

$R_2$ and $R_{15}$ are taken together and are alkanediyl$_{(C\leq6)}$, alkoxydiyl$_{(C\leq6)}$, alkylaminodiyl$_{(C\leq6)}$, or a substituted version of any of these groups;

$R_3$ is —NR$_{11}$R$_{11}'$ or —C(O)NR$_{12}$R$_{12}'$, wherein:
$R_{11}$ and $R_{11}'$ are each independently hydrogen, alkyl$_{(C\leq6)}$, substituted alkyl$_{(C\leq6)}$;
$R_{12}$ and $R_{12}'$ are each independently hydrogen, alkyl$_{(C\leq6)}$, or substituted alkyl$_{(C\leq6)}$;

$R_4$, $R_5$, and $R_6$ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;

$R_7$ and $R_7'$ are each independently hydrogen, carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
$R_{13}$ is aralkyl$_{(C\leq12)}$ or substituted aralkyl$_{(C\leq12)}$;

$R_7$ and $R_7'$ are taken together and are -alkanediyl$_{(C\leq7)}$-, -alkenediyl$_{(C\leq7)}$-, or a substituted version of either of these groups;

$R_8$, $R_9$, and $R_{10}$ are each independently hydrogen, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

$X_1$ is $CR_{14}$ or N, wherein:
$R_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or
$R_{14}$ and $R_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and $X_2$ is $CR_{15}$ or N, wherein:
$R_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;
$R_{15}$ and $R_{14}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; or
$R_{15}$ and $R_2$ are taken together and are alkanediyl$_{(C\leq6)}$, alkoxydiyl$_{(C\leq6)}$, alkylaminodiyl$_{(C\leq6)}$, or a substituted version of any of these groups;

or a compound of the formula:

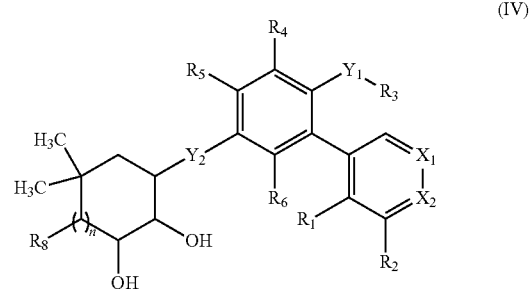

(IV)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —$NR_{11}R_{11}$' or —C(O)$NR_{12}R_{12}$', wherein:
$R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_8$ is hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;
$X_1$ is $CR_{14}$ or N, wherein:
$R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
$R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is $CR_{15}$ or N, wherein:
$R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
$R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
$R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;
or a compound of the formula:

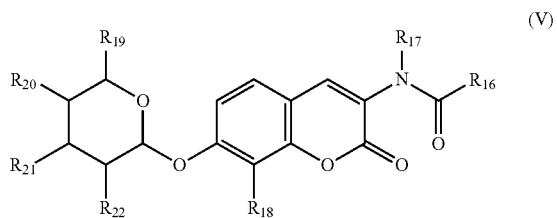

(V)

wherein:
$R_{16}$ is alkyl$_{(C \leq 12)}$, cycloalkyl$_{(C \leq 12)}$, aryl$_{(C \leq 18)}$, heteroaryl$_{(C \leq 18)}$, or a substituted version thereof;
$R_{17}$ and $R_{18}$ are each independently hydrogen, alkyl$_{(C \leq 8)}$, or substituted alkyl$_{(C \leq 8)}$;
$R_{19}$ is alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, or a substituted version of any of these groups
$R_{20}$, $R_{21}$, and $R_{22}$ are each independently hydroxy, alkoxy$_{(C \leq 12)}$, substituted alkoxy$_{(C \leq 12)}$, or a protected hydroxy group;
or a pharmaceutically acceptable salt of any of the above formulas.

In some embodiments, the compounds are further defined as:

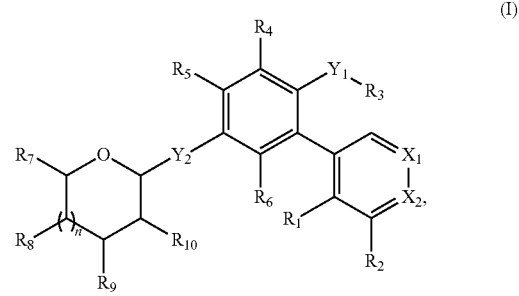

(I)

wherein:
n is 0, 1, or 2;
$Y_1$ is -alkanediyl$_{(C \leq 6)}$-, —C(O)-alkanediyl$_{(C \leq 6)}$-, or a substituted version of any of these groups;
$Y_2$ is $CH_2$, O, or S;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is —$NR_{11}R_{11}$' or —C(O)$NR_{12}R_{12}$', wherein:
$R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
$R_7$ is carboxy or alkyl$_{(C \leq 6)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-$OR_{13}$, or a substituted version of any of these groups wherein:
$R_{13}$ is alkyl$_{(C \leq 12)}$, substituted alkyl$_{(C \leq 12)}$, aralkyl$_{(C \leq 12)}$, or substituted aralkyl$_{(C \leq 12)}$;

R$_8$, R$_9$, and R$_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

X$_1$ is CR$_{14}$ or N, wherein:
R$_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
R$_{14}$ and R$_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and X$_2$ is CR$_{15}$ or N, wherein:
R$_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
R$_{15}$ and R$_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
R$_{15}$ and R$_2$ are taken together and are alkanediyl$_{(C≤6)}$, alkoxydiyl$_{(C≤6)}$, alkylaminodiyl$_{(C≤6)}$, or a substituted version of any of these groups;

or a pharmaceutically acceptable salt of the formula.

In some embodiments, the compounds are further defined as:

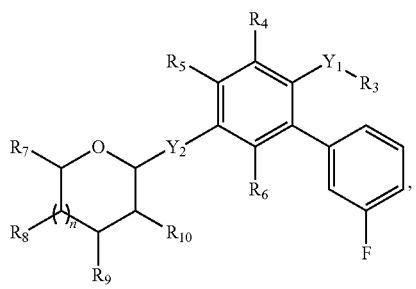

(VI)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_4$, R$_5$, and R$_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
R$_7$ is carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$—OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; and R$_8$, R$_9$, and R$_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

or a pharmaceutically acceptable salt of the formula.

In some embodiments, the compounds further defined as:

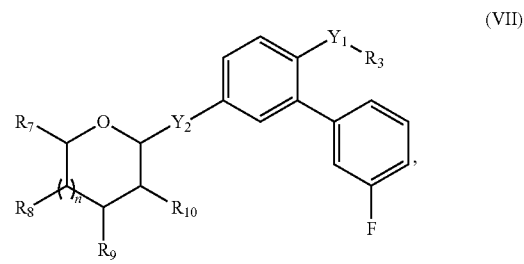

(VII)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_7$ is carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; and
R$_8$, R$_9$, and R$_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

or a pharmaceutically acceptable salt of the formula.

In some embodiments, the compounds are further defined as:

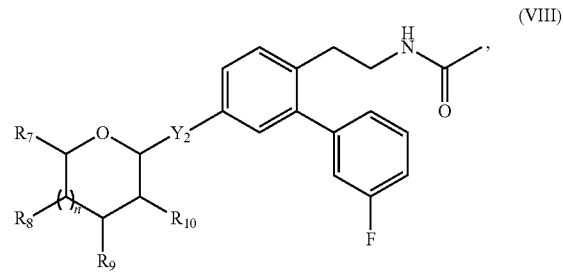

(VIII)

wherein:
n is 0, 1, or 2;
R$_7$ is carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; and $R_8$, $R_9$, and $R_{10}$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

or a pharmaceutically acceptable salt of the formula.

In other embodiments, the compounds are further defined as:

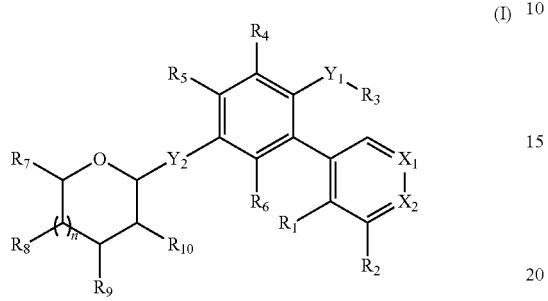

(I)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is $CH_2$, O, or S;

$R_1$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, amido$_{(C\leq 6)}$, alkoxy$_{(C\leq 6)}$, alkylsulfonyl$_{(C\leq 6)}$, or a substituted version of any of these groups;

$R_2$ is hydrogen, amino, halo, hydroxy, carboxy, or alkyl$_{(C\leq 6)}$, alkenyl$_{(C\leq 6)}$, alkynyl$_{(C\leq 6)}$, cycloalkyl$_{(C\leq 8)}$, heterocycloalkyl$_{(C\leq 8)}$, aryl$_{(C\leq 12)}$, aralkyl$_{(C\leq 12)}$, amido$_{(C\leq 6)}$, alkoxy$_{(C\leq 6)}$, alkylthio$_{(C\leq 6)}$, alkylsulfonyl$_{(C\leq 6)}$, or a substituted version of any of these groups;

$R_2$ and $R_{15}$ are taken together and are alkanediyl$_{(C\leq 6)}$, alkoxydiyl$_{(C\leq 6)}$, alkylaminodiyl$_{(C\leq 6)}$, or a substituted version of any of these groups;

$R_3$ is —NR$_{11}$R$_{11}$' or —C(O)NR$_{12}$R$_{12}$', wherein:
$R_{11}$ and $R_{11}$' are each independently hydrogen, alkyl$_{(C\leq 6)}$, substituted alkyl$_{(C\leq 6)}$, acyl$_{(C\leq 6)}$, or substituted acyl$_{(C\leq 6)}$;
$R_{12}$ and $R_{12}$' are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ is hydrogen, carboxy or alkyl$_{(C\leq 6)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:
$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_8$ and $R_9$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

$R_{10}$ is amino or alkylamino$_{(C\leq 6)}$, dialkylamino$_{(C\leq 12)}$, amido$_{(C\leq 12)}$, or a substituted version of any of these three groups;

$X_1$ is CR$_{14}$ or N, wherein:
$R_{14}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups; or
$R_{14}$ and $R_{15}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; and $X_2$ is CR$_{15}$ or N, wherein:
$R_{15}$ is hydrogen, halo, hydroxy, or alkyl$_{(C\leq 6)}$, alkenyl$_{(C\leq 6)}$, alkynyl$_{(C\leq 6)}$, alkoxy$_{(C\leq 6)}$, alkylamino$_{(C\leq 6)}$, -alkanediyl$_{(C\leq 6)}$-heterocycloalkyl$_{(C\leq 8)}$, or a substituted version of any of these groups;
$R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or
$R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

or a pharmaceutically acceptable salt of the formula.

In some embodiments, the compounds are further defined as:

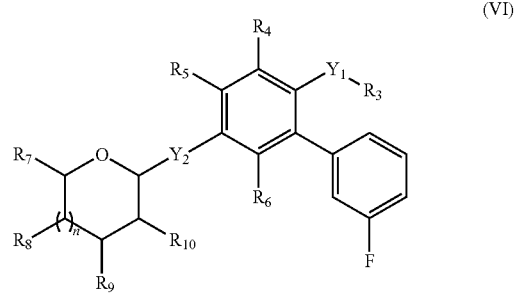

(VI)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is $CH_2$, O, or S;

$R_3$ is —NR$_{11}$R$_{11}$' or —C(O)NR$_{12}$R$_{12}$', wherein:
$R_{11}$ and $R_{11}$' are each independently hydrogen, alkyl$_{(C\leq 6)}$, substituted alkyl$_{(C\leq 6)}$, acyl$_{(C\leq 6)}$, or substituted acyl$_{(C\leq 6)}$;
$R_{12}$ and $R_{12}$' are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ is hydrogen, carboxy or alkyl$_{(C\leq 6)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$—OR$_{13}$, or a substituted version of any of these groups wherein:
$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_8$ and $R_9$ are each independently hydrogen, halo, hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

$R_{10}$ is amino or alkylamino$_{(C≤6)}$, dialkylamino$_{(C≤12)}$, amido$_{(C≤12)}$, or a substituted version of any of these three groups;

or a pharmaceutically acceptable salt thereof.

In some embodiments, the compounds are further defined as:

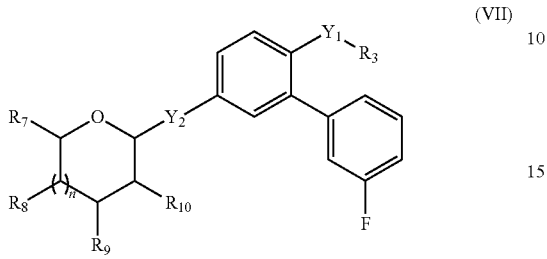

(VII)

wherein:
n is 0, 1, or 2;
$Y_1$ is -alkanediyl$_{(C≤6)}$-, —C(O)-alkanediyl$_{(C≤6)}$-, or a substituted version of any of these groups;
$Y_2$ is $CH_2$, O, or S;
$R_3$ is —NR$_{11}$R$_{11}$' or —C(O)NR$_{12}$R$_{12}$', wherein:
  $R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;
  $R_{12}$ and $R_{12}$' are each independently hydrogen, alkyl$_{(C≤6)}$, or substituted alkyl$_{(C≤6)}$;
$R_7$ is hydrogen, carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  $R_{13}$ is alkyl$_{(C≤12)}$, substituted alkyl$_{(C≤12)}$, aralkyl$_{(C≤12)}$, or substituted aralkyl$_{(C≤12)}$;
$R_8$ and $R_9$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
$R_{10}$ is amino or alkylamino$_{(C≤6)}$, dialkylamino$_{(C≤12)}$, amido$_{(C≤12)}$, or a substituted version of any of these three groups;

or a pharmaceutically acceptable salt thereof.

In some embodiments, the compounds are further defined as:

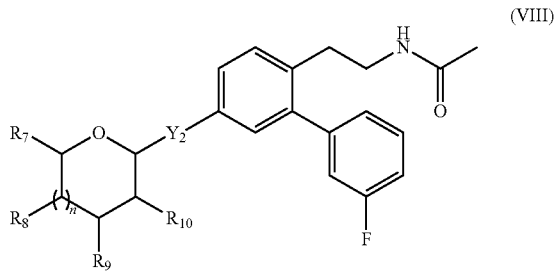

(VIII)

wherein:
n is 0, 1, or 2;
$Y_1$ is -alkanediyl$_{(C≤6)}$-, —C(O)-alkanediyl$_{(C≤6)}$-, or a substituted version of any of these groups;
$Y_2$ is $CH_2$, O, or S;
$R_3$ is —NR$_{11}$R$_{11}$' or —C(O)NR$_{12}$R$_{12}$', wherein:
  $R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;
  $R_{12}$ and $R_{12}$' are each independently hydrogen, alkyl$_{(C≤6)}$, or substituted alkyl$_{(C≤6)}$;
$R_7$ is hydrogen, carboxy or alkyl$_{(C≤6)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  $R_{13}$ is alkyl$_{(C≤12)}$, substituted alkyl$_{(C≤12)}$, aralkyl$_{(C≤12)}$, or substituted aralkyl$_{(C≤12)}$;
$R_8$ and $R_9$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
$R_{10}$ is amino or alkylamino$_{(C≤6)}$, dialkylamino$_{(C≤12)}$, amido$_{(C≤12)}$, or a substituted version of any of these three groups;

or a pharmaceutically acceptable salt thereof.

In other embodiments, the compounds are further defined as:

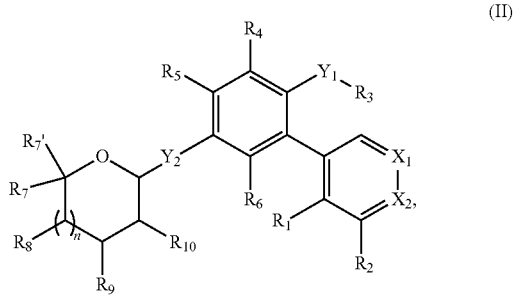

(II)

wherein:
n is 0, 1, or 2;
$Y_1$ is -alkanediyl$_{(C≤6)}$-, —C(O)-alkanediyl$_{(C≤6)}$-, or a substituted version of any of these groups;
$Y_2$ is $CH_2$, O, or S;
$R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
$R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;
$R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;
$R_3$ is —NR$_{11}$R$_{11}$' or —C(O)NR$_{12}$R$_{12}$', wherein:
  $R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;
  $R_{12}$ and $R_{12}$' are each independently hydrogen, alkyl$_{(C≤6)}$, or substituted alkyl$_{(C≤6)}$;
$R_4$, $R_5$, and $R_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
$R_7$ is carboxy or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$;
R$_7$' is hydrogen, carboxy, or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or
R$_7$ and R$_7$' are taken together and are -alkanediyl$_{(C≤7)}$-, -alkenediyl$_{(C≤7)}$-, or a substituted version of either of these groups;
R$_8$, R$_9$, and R$_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
X$_1$ is CR$_{14}$ or N, wherein:
R$_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
R$_{14}$ and R$_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and
X$_2$ is CR$_{15}$ or N, wherein:
R$_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
R$_{15}$ and R$_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
R$_{15}$ and R$_2$ are taken together and are alkanediyl$_{(C≤6)}$, alkoxydiyl$_{(C≤6)}$, alkylaminodiyl$_{(C≤6)}$, or a substituted version of any of these groups;
or a pharmaceutically acceptable salt of the formula.

In some embodiments, the compounds are further defined as:

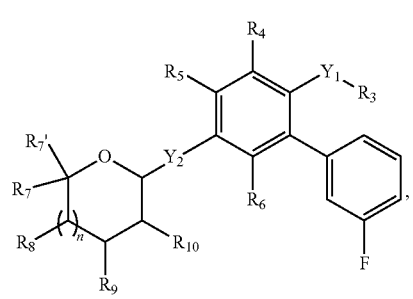

(IX)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_4$, R$_5$, and R$_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
R$_7$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$;
R$_7$' is hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or
R$_7$ and R$_7$' are taken together and are -alkanediyl$_{(C≤7)}$-, -alkenediyl$_{(C≤7)}$-, or a substituted version of either of these groups; and
R$_8$, R$_9$, and R$_{10}$ are each independently hydrogen, halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
or a pharmaceutically acceptable salt of the formula.

In some embodiments, the compounds are further defined as:

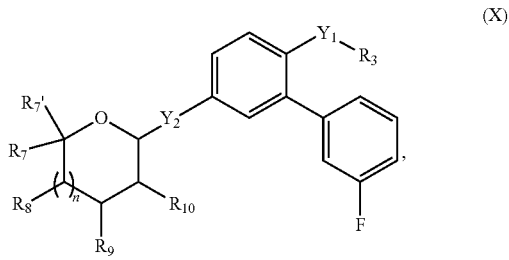

(X)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_7$ is carboxy or alkyl$_{(C3-8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$;

R₇' is hydrogen, carboxy, or alkyl$_{(C3-8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$; or R₇ and R₇' are taken together and are -alkanediyl$_{(C\leq7)}$-, -alkenediyl$_{(C\leq7)}$-, or a substituted version of either of these groups; and R₈, R₉, and R₁₀ are each independently hydrogen, halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

or a pharmaceutically acceptable salt of the formula.

In some embodiments, the compounds are further defined as:

(XI)

wherein:

n is 0, 1, or 2;

R₇ is carboxy or alkyl$_{(C3-8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R₇' is hydrogen, carboxy, or alkyl$_{(C3-8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$; or R₇ and R₇' are taken together and are -alkanediyl$_{(C\leq7)}$-, -alkenediyl$_{(C\leq7)}$-, or a substituted version of any of these groups; and R₈, R₉, and R₁₀ are each independently hydrogen, halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

or a pharmaceutically acceptable salt of the formula.

In other embodiments, the compounds are further defined as:

(II)

wherein:

n is 0, 1, or 2;

Y₁ is -alkanediyl$_{(C\leq6)}$-, —C(O)-alkanediyl$_{(C\leq6)}$-, or a substituted version of any of these groups;

Y₂ is CH₂ or S;

R₁ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, amido$_{(C\leq6)}$, alkoxy$_{(C\leq6)}$, alkylsulfonyl$_{(C\leq6)}$, or a substituted version of any of these groups;

R₂ is hydrogen, amino, halo, hydroxy, carboxy, or alkyl$_{(C\leq6)}$, alkenyl$_{(C\leq6)}$, alkynyl$_{(C\leq6)}$, cyclo alkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;

R₂ and R₁₅ are taken together and are alkanediyl$_{(C\leq6)}$, alkoxydiyl$_{(C\leq6)}$, alkylaminodiyl$_{(C\leq6)}$, or a substituted version of any of these groups;

R₃ is —NR$_{11}$R$_{11}$' or —C(O)NR$_{12}$R$_{12}$', wherein:

R$_{11}$ and R$_{11}$' are each independently hydrogen, alkyl$_{(C\leq6)}$, substituted alkyl$_{(C\leq6)}$, acyl$_{(C\leq6)}$, or substituted acyl$_{(C\leq6)}$;

R$_{12}$ and R$_{12}$' are each independently hydrogen, alkyl$_{(C\leq6)}$, or substituted alkyl$_{(C\leq6)}$;

R₄, R₅, and R₆ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;

R₇ and R₇' are each independently hydrogen, carboxy, or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$, R₇ and R₇' are taken together and are -alkanediyl$_{(C\leq7)}$-, -alkenediyl$_{(C\leq7)}$-, or a substituted version of any of these groups;

R₈, R₉, and R₁₀ are each independently hydrogen, halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

X₁ is CR$_{14}$ or N, wherein:

R$_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is $CR_{15}$ or N, wherein:
- $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
- $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
- $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a pharmaceutically acceptable salt of the formula.

In other embodiments, the compounds are further defined as:

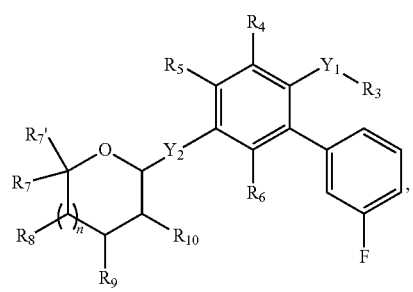

(XII)

wherein:
- n is 0, 1, or 2;
- $Y_1$ is -alkanediyl$_{(C \leq 6)}$-, —C(O)-alkanediyl$_{(C \leq 6)}$-, or a substituted version of any of these groups;
- $Y_2$ is $CH_2$ or S;
- $R_3$ is —NR$_{11}$R$_{11}$' or —C(O)NR$_{12}$R$_{12}$', wherein:
  - $R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
  - $R_{12}$ and $R_{12}$' are each independently hydrogen, alkyl$_{(C \leq 6)}$, or substituted alkyl$_{(C \leq 6)}$;
- $R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;
- $R_7$ and $R_7$' are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  - $R_{13}$ is alkyl$_{(C \leq 12)}$, substituted alkyl$_{(C \leq 12)}$, aralkyl$_{(C \leq 12)}$, or substituted aralkyl$_{(C \leq 12)}$;
- $R_7$ and $R_7$' are taken together and are -alkanediyl$_{(C \leq 7)}$-, -alkenediyl$_{(C \leq 7)}$-, or a substituted version of either of these groups; and
- $R_8$, $R_9$, and $R_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In some embodiments, the compounds are further defined as:

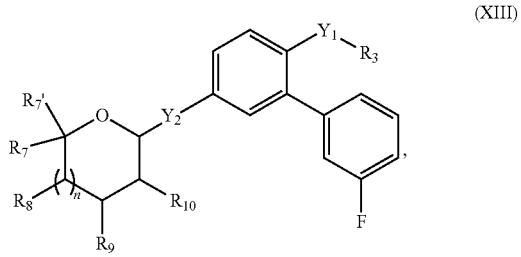

(XIII)

wherein:
- n is 0, 1, or 2;
- $Y_1$ is -alkanediyl$_{(C \leq 6)}$-, —C(O)-alkanediyl$_{(C \leq 6)}$-, or a substituted version of any of these groups;
- $Y_2$ is $CH_2$ or S;
- $R_3$ is —NR$_{11}$R$_{11}$' or —C(O)NR$_{12}$R$_{12}$', wherein:
  - $R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
  - $R_{12}$ and $R_{12}$' are each independently hydrogen, alkyl$_{(C \leq 6)}$, or substituted alkyl$_{(C \leq 6)}$;
- $R_7$ and $R_7$' are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, alkanediyl$_{(C \leq 6)}$-OR$_{13}$, or a substituted version of any of these groups wherein:
  - $R_{13}$ is alkyl$_{(C \leq 12)}$, substituted alkyl$_{(C \leq 12)}$, aralkyl$_{(C \leq 12)}$, or substituted aralkyl$_{(C \leq 12)}$;
- $R_7$ and $R_7$' are taken together and are -alkanediyl$_{(C \leq 7)}$-, -alkenediyl$_{(C \leq 7)}$-, or a substituted version of any of these groups; and
- $R_8$, $R_9$, and $R_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In some embodiments, the compounds are further defined as:

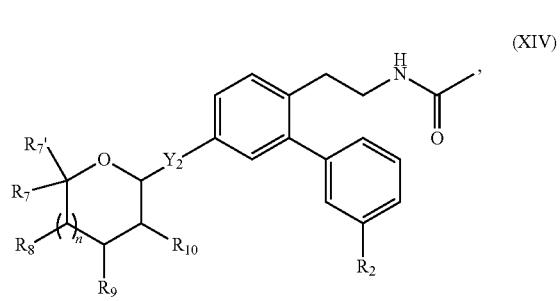

(XIV)

wherein:
- n is 0, 1, or 2;
- $Y_2$ is $CH_2$ or S;
- $R_7$ and $R_7$' are each independently hydrogen, carboxy, or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  - $R_{13}$ is alkyl$_{(C \leq 12)}$, substituted alkyl$_{(C \leq 12)}$, aralkyl$_{(C \leq 12)}$, or substituted aralkyl$_{(C \leq 12)}$, $R_7$ and $R_7'$ are taken together and are -alkanediyl$_{(C \leq 7)}$-, -alkenediyl$_{(C \leq 7)}$-, or a substituted version of either of these groups; and $R_8$, $R_9$, and $R_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In other embodiments, the compounds are further defined as:

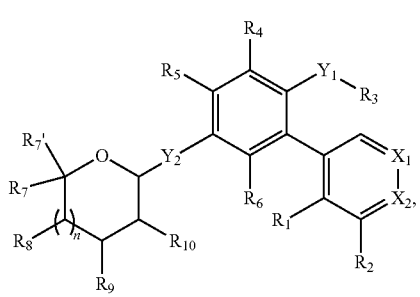

(II)

wherein:

n is 0, 1, or 2;

$Y_1$ is substituted -alkanediyl$_{(C \leq 6)}$-, —C(O)-alkanediyl$_{(C \leq 6)}$-, or substituted —C(O)-alkanediyl$_{(C \leq 6)}$-;

$Y_2$ is CH$_2$, O, or S;

$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;

$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;

$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;

$R_3$ is —NR$_{11}$R$_{11}'$ or —C(O)NR$_{12}$R$_{12}'$, wherein:
  $R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}'$ are each independently hydrogen, alkyl$_{(C \leq 6)}$, or substituted alkyl$_{(C \leq 6)}$;

$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;

$R_7$ and $R_7'$ are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is alkyl$_{(C \leq 12)}$, substituted alkyl$_{(C \leq 12)}$, aralkyl$_{(C \leq 12)}$, or substituted aralkyl$_{(C \leq 12)}$; or $R_7$ and $R_7'$ are taken together and are -alkanediyl$_{(C \leq 7)}$-, -alkenediyl$_{(C \leq 7)}$-, or a substituted version of either of these groups; and $R_8$, $R_9$, and $R_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

$X_1$ is CR$_{14}$ or N, wherein:
  $R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
  $R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and $X_2$ is CR$_{15}$ or N, wherein:
  $R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
  $R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
  $R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;

or a pharmaceutically acceptable salt of the formula.

In some embodiments, the compounds are further defined as:

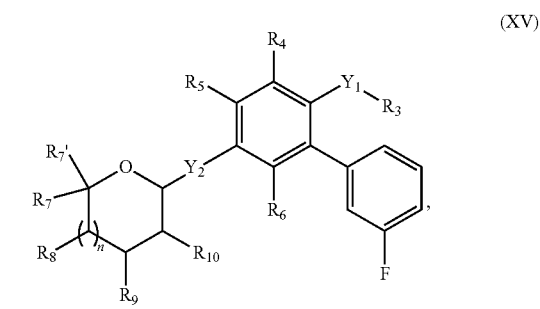

(XV)

wherein:

n is 0, 1, or 2;

$Y_1$ is substituted -alkanediyl$_{(C \leq 6)}$-, —C(O)-alkanediyl$_{(C \leq 6)}$-, or substituted —C(O)-alkanediyl$_{(C \leq 6)}$-;

$Y_2$ is CH$_2$, O, or S;

$R_3$ is —NR$_{11}$R$_{11}'$ or —C(O)NR$_{12}$R$_{12}'$, wherein:
  $R_{11}$ and $R_{11}'$ are each independently hydrogen, alkyl$_{(C \leq 6)}$, substituted alkyl$_{(C \leq 6)}$, acyl$_{(C \leq 6)}$, or substituted acyl$_{(C \leq 6)}$;
  $R_{12}$ and $R_{12}'$ are each independently hydrogen, alkyl$_{(C \leq 6)}$, or substituted alkyl$_{(C \leq 6)}$;

$R_4$, $R_5$, and $R_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;

$R_7$ and $R_7'$ are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, hetero aryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:
  $R_{13}$ is alkyl$_{(C \leq 12)}$, substituted alkyl$_{(C \leq 12)}$, aralkyl$_{(C \leq 12)}$, or substituted aralkyl$_{(C \leq 12)}$; or R$_7$ and R$_7$' are taken together and are -alkanediyl$_{(C \leq 7)}$-, -alkenediyl$_{(C \leq 7)}$-, or a substituted version of either of these groups; and R$_8$, R$_9$, and R$_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In some embodiments, the compounds are further defined as:

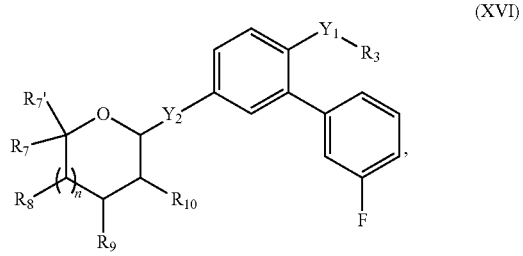

(XVI)

wherein:

n is 0, 1, or 2;

Y$_1$ is substituted -alkanediyl$_{(C \leq 6)}$-, —C(O)-alkanediyl$_{(C \leq 6)}$-, or substituted —C(O)-alkanediyl$_{(C \leq 6)}$—;

Y$_2$ is CH$_2$, O, or S;

R$_3$ is —NR$_{11}$R$_{11}$' or —C(O)NR$_{12}$R$_{12}$', wherein:

R$_{11}$ and R$_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;

R$_{12}$ and R$_{12}$' are each independently hydrogen, alkyl$_{(C \leq 6)}$, or substituted alkyl$_{(C \leq 6)}$;

R$_7$ and R$_7$' are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, alkanediyl$_{(C \leq 6)}$-OR$_{13}$, or a substituted version of any of these groups wherein:

R$_{13}$ is alkyl$_{(C \leq 12)}$, substituted alkyl$_{(C \leq 12)}$, aralkyl$_{(C \leq 12)}$, or substituted aralkyl$_{(C \leq 12)}$; or R$_7$ and R$_7$' are taken together and are -alkanediyl$_{(C \leq 7)}$-, -alkenediyl$_{(C \leq 7)}$-, or a substituted version of either of these groups; and R$_8$, R$_9$, and R$_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In some embodiments, the compounds are further defined as:

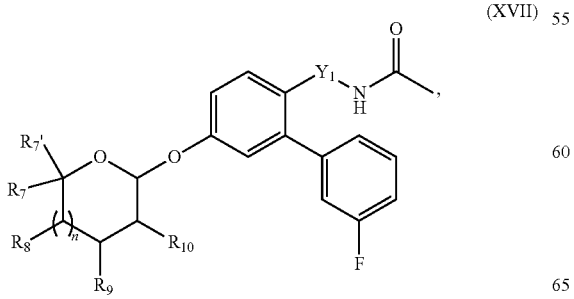

(XVII)

wherein:

n is 0, 1, or 2;

Y$_1$ is substituted -alkanediyl$_{(C \leq 6)}$-, —C(O)-alkanediyl$_{(C \leq 6)}$-, or substituted —C(O)-alkanediyl$_{(C \leq 6)}$-;

R$_7$ and R$_7$' are each independently hydrogen, carboxy or alkyl$_{(C \leq 8)}$, alkenyl$_{(C \leq 8)}$, alkynyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, aralkyl$_{(C \leq 12)}$, heteroaralkyl$_{(C \leq 12)}$, -alkanediyl$_{(C \leq 6)}$-OR$_{13}$, or a substituted version of any of these groups wherein:

R$_{13}$ is alkyl$_{(C \leq 12)}$, substituted alkyl$_{(C \leq 12)}$, aralkyl$_{(C \leq 12)}$, or substituted aralkyl$_{(C \leq 12)}$; or R$_7$ and R$_7$' are taken together and are -alkanediyl$_{(C \leq 7)}$-, -alkenediyl$_{(C \leq 7)}$-, or a substituted version of either of these groups; and R$_8$, R$_9$, and R$_{10}$ are each independently hydrogen, halo, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups;

or a pharmaceutically acceptable salt of the formula.

In other embodiments, the compounds are further defined as:

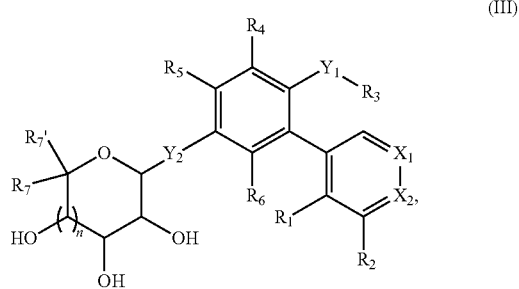

(III)

wherein:

n is 1 or 2;

Y$_1$ is -alkanediyl$_{(C \leq 6)}$-, —C(O)-alkanediyl$_{(C \leq 6)}$-, or a substituted version of any of these groups;

Y$_2$ is CH$_2$, O, or S;

R$_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;

R$_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;

R$_2$ and R$_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;

R$_3$ is —NR$_{11}$R$_{11}$' or —C(O)NR$_{12}$R$_{12}$', wherein:

R$_{11}$ and R$_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;

R$_{12}$ and R$_{12}$' are each independently hydrogen, alkyl$_{(C \leq 6)}$, or substituted alkyl$_{(C \leq 6)}$;

R$_4$, R$_5$, and R$_6$ are each independently hydrogen, halo, alkyl$_{(C \leq 6)}$, substituted alkyl$_{(C \leq 6)}$, alkoxy$_{(C \leq 6)}$, substituted alkoxy$_{(C \leq 6)}$, acyloxy$_{(C \leq 6)}$, or substituted acyloxy$_{(C \leq 6)}$;

R$_7$ and R$_7$' are each independently hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or R$_7$ and R$_7$' are taken together and are -alkanediyl$_{(C≤7)}$-, -alkenediyl$_{(C≤7)}$-, or a substituted version of either of these groups;

X$_1$ is CR$_{14}$ or N, wherein:
R$_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
R$_{14}$ and R$_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and X$_2$ is CR$_{15}$ or N, wherein:
R$_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
R$_{15}$ and R$_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
R$_{15}$ and R$_2$ are taken together and are alkanediyl$_{(C≤6)}$, alkoxydiyl$_{(C≤6)}$, alkylaminodiyl$_{(C≤6)}$, or a substituted version of any of these groups;

or a pharmaceutically acceptable salt of the formula.

In some embodiments, the compounds are further defined as:

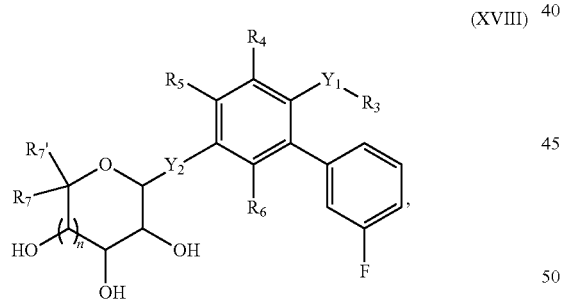
(XVIII)

wherein:
n is 1 or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_4$, R$_5$, and R$_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$; and R$_7$ and R$_7$' are each independently hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or R$_7$ and R$_7$' are taken together and are -alkanediyl$_{(C≤7)}$-, -alkenediyl$_{(C≤7)}$-, or a substituted version of either of these groups;

or a pharmaceutically acceptable salt of the formula.

In some embodiments, the compounds are further defined as:

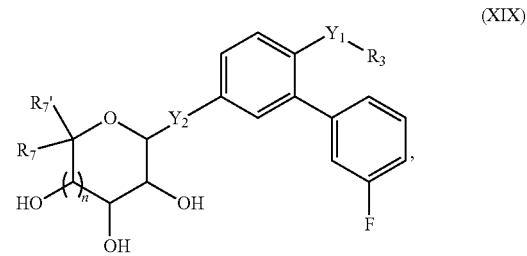
(XIX)

wherein:
n is 1 or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$; and
R$_7$ and R$_7$' are each independently hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or R$_7$ and R$_7$' are taken together and are -alkanediyl$_{(C≤7)}$-, -alkenediyl$_{(C≤7)}$-, or a substituted version of either of these groups;

or a pharmaceutically acceptable salt of the formula.

In some embodiments, the compounds further defined as:

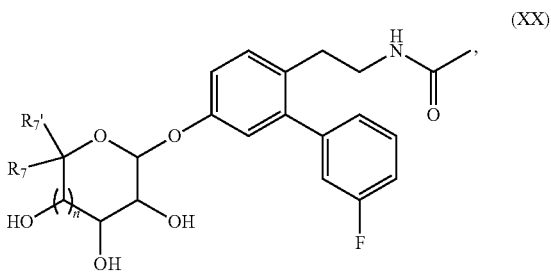
(XX)

wherein:
n is 1 or 2; and
R$_7$ and R$_7$' are each independently hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, hetero aryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or
R$_7$ and R$_7$' are taken together and are -alkanediyl$_{(C≤7)}$-, -alkenediyl$_{(C≤7)}$-, or a substituted version of either of these groups;
or a pharmaceutically acceptable salt of the formula.

In other embodiments, the compounds are further defined as:

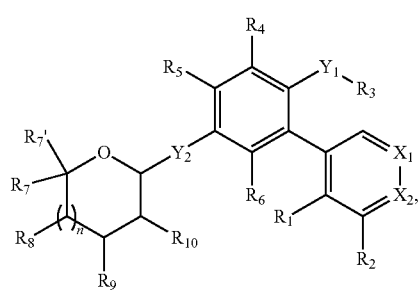

(II)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
R$_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;
R$_2$ and R$_{15}$ are taken together and are alkanediyl$_{(C≤6)}$, alkoxydiyl$_{(C≤6)}$, alkylaminodiyl$_{(C≤6)}$, or a substituted version of any of these groups;
R$_3$ is —NR$_{11}$R$_{11}$' or —C(O)NR 12R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_4$, R$_5$, and R$_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
R$_7$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$;
R$_7$' is hydrogen, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
R$_{13}$ is alkyl$_{(C≤12)}$, substituted alkyl$_{(C≤12)}$, aralkyl$_{(C≤12)}$, or substituted aralkyl$_{(C≤12)}$; or
R$_7$ and R$_7$' are taken together and are -alkanediyl$_{(C≤7)}$-, -alkenediyl$_{(C≤7)}$-, or a substituted version of either of these groups;
R$_8$ is alkoxy$_{(C3-6)}$, acyloxy$_{(C≤6)}$, aralkoxy$_{(C≤12)}$, or a substituted version of any of these groups;
R$_9$ and R$_{10}$ are each independently halo or hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;
X$_1$ is CR$_{14}$ or N, wherein:
R$_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
R$_{14}$ and R$_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; and
X$_2$ is CR$_{15}$ or N, wherein:
R$_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
R$_{15}$ and R$_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
R$_{15}$ and R$_2$ are taken together and are alkanediyl$_{(C≤6)}$, alkoxydiyl$_{(C≤6)}$, alkylaminodiyl$_{(C≤6)}$, or a substituted version of any of these groups;
or a pharmaceutically acceptable salt of the formula.

In some embodiments, the compounds are further defined as:

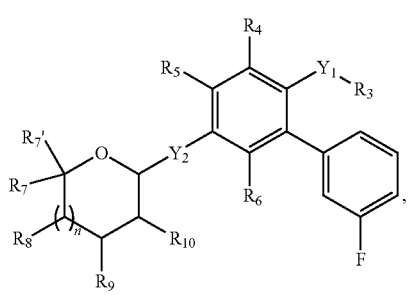

(XXI)

wherein:
n is 0, 1, or 2;
Y$_1$ is -alkanediyl$_{(C≤6)}$-, —C(O)-alkanediyl$_{(C≤6)}$-, or a substituted version of any of these groups;
Y$_2$ is CH$_2$, O, or S;
R$_3$ is —NR$_{11}$R$_{11}$' or —C(O)NR$_{12}$R$_{12}$', wherein:
R$_{11}$ and R$_{11}$' are each independently hydrogen, alkyl$_{(C≤6)}$, substituted alkyl$_{(C≤6)}$, acyl$_{(C≤6)}$, or substituted acyl$_{(C≤6)}$;
R$_{12}$ and R$_{12}$' are each independently hydrogen, alkyl$_{(C≤6)}$, or substituted alkyl$_{(C≤6)}$;
R$_4$, R$_5$, and R$_6$ are each independently hydrogen, halo, alkyl$_{(C≤6)}$, substituted alkyl$_{(C≤6)}$, alkoxy$_{(C≤6)}$, substituted alkoxy$_{(C≤6)}$, acyloxy$_{(C≤6)}$, or substituted acyloxy$_{(C≤6)}$;
R$_7$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
  R$_{13}$ is alkyl$_{(C\leq12)}$, substituted alkyl$_{(C\leq12)}$, aralkyl$_{(C\leq12)}$, or substituted aralkyl$_{(C\leq12)}$;
R$_7$' is hydrogen, carboxy, or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
  R$_{13}$ is alkyl$_{(C\leq12)}$, substituted alkyl$_{(C\leq12)}$, aralkyl$_{(C\leq12)}$, or substituted aralkyl$_{(C\leq12)}$; or
R$_7$ and R$_7$' are taken together and are -alkanediyl$_{(C\leq7)}$-, -alkenediyl$_{(C\leq7)}$-, or a substituted version of either of these groups;
R$_8$ is alkoxy$_{(C3-6)}$, acyloxy$_{(C\leq6)}$, aralkoxy$_{(C\leq12)}$, or a substituted version of any of these groups; and
R$_9$ and R$_{10}$ are each independently halo or hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;
or a pharmaceutically acceptable salt of the formula.

In some embodiments, the compounds are further defined as:

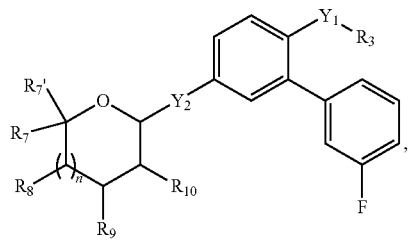

(XXII)

wherein:
  n is 0, 1, or 2;
  Y$_1$ is -alkanediyl$_{(C\leq6)}$-, —C(O)-alkanediyl$_{(C\leq6)}$-, or a substituted version of any of these groups;
  Y$_2$ is CH$_2$, O, or S;
  R$_3$ is —NR$_{11}$R$_{11}$' or —C(O)NR$_{12}$R$_{12}$', wherein:
    R$_{11}$ and R$_{11}$' are each independently hydrogen, alkyl$_{(C\leq6)}$, substituted alkyl$_{(C\leq6)}$, acyl$_{(C\leq6)}$, or substituted acyl$_{(C\leq6)}$;
    R$_{12}$ and R$_{12}$' are each independently hydrogen, alkyl$_{(C\leq6)}$, or substituted alkyl$_{(C\leq6)}$;
  R$_7$ is carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
    R$_{13}$ is alkyl$_{(C\leq12)}$, substituted alkyl$_{(C\leq12)}$, aralkyl$_{(C\leq12)}$, or substituted aralkyl$_{(C\leq12)}$;
  R$_7$' is hydrogen, carboxy, or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
    R$_{13}$ is alkyl$_{(C\leq12)}$, substituted alkyl$_{(C\leq12)}$, aralkyl$_{(C\leq12)}$, or substituted aralkyl$_{(C\leq12)}$; or
  R$_7$ and R$_7$' are taken together and are -alkanediyl$_{(C\leq7)}$-, -alkenediyl$_{(C\leq7)}$-, or a substituted version of either of these groups;
  R$_8$ is alkoxy$_{(C3-6)}$, acyloxy$_{(C\leq6)}$, aralkoxy$_{(C\leq12)}$, or a substituted version of any of these groups; and
  R$_9$ and R$_{10}$ are each independently halo or hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;
or a pharmaceutically acceptable salt of the formula.

In some embodiments, the compounds are further defined as:

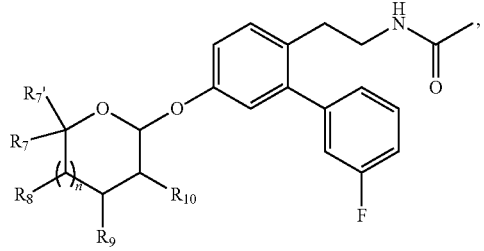

(XXIII)

wherein:
  n is 0, 1, or 2;
  R$_7$ is carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
    R$_{13}$ is alkyl$_{(C\leq12)}$, substituted alkyl$_{(C\leq12)}$, aralkyl$_{(C\leq12)}$, or substituted aralkyl$_{(C\leq12)}$;
  R$_7$' is hydrogen, carboxy, or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:
    R$_{13}$ is alkyl$_{(C\leq12)}$, substituted alkyl$_{(C\leq12)}$, aralkyl$_{(C\leq12)}$, or substituted aralkyl$_{(C\leq12)}$; or
  R$_7$ and R$_7$' are taken together and are -alkanediyl$_{(C\leq7)}$-, -alkenediyl$_{(C\leq7)}$-, or a substituted version of either of these groups;
  R$_8$ is alkoxy$_{(C3-6)}$, acyloxy$_{(C\leq6)}$, aralkoxy$_{(C\leq12)}$, or a substituted version of any of these groups; and
  R$_9$ and R$_{10}$ are each independently halo or hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;
or a pharmaceutically acceptable salt of the formula.

In other embodiments, the compounds are further defined as:

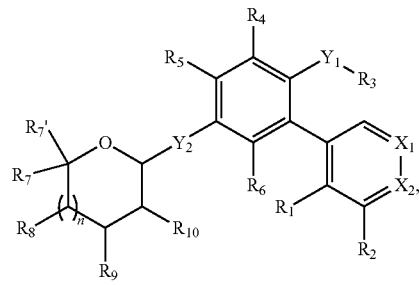

(II)

wherein:
n is 0, 1, or 2;
$Y_1$ is -alkanediyl$_{(C\le 6)}$-, —C(O)-alkanediyl$_{(C\le 6)}$-, or a substituted version of any of these groups;
$Y_2$ is $CH_2$, O, or S;
$R_1$ is hydrogen, amino, halo, hydroxy, carboxy, or alkyl$_{(C\le 6)}$, alkenyl$_{(C\le 6)}$, alkynyl$_{(C\le 6)}$, cycloalkyl$_{(C\le 8)}$, heterocycloalkyl$_{(C\le 8)}$, amido$_{(C\le 6)}$, alkoxy$_{(C\le 6)}$, alkylsulfonyl$_{(C\le 6)}$, or a substituted version of any of these groups;
$R_2$ is hydrogen, amino, halo, hydroxy, carboxy, or alkyl$_{(C\le 6)}$, alkenyl$_{(C\le 6)}$, alkynyl$_{(C\le 6)}$, cycloalkyl$_{(C\le 8)}$, heterocycloalkyl$_{(C\le 8)}$, aryl$_{(C\le 12)}$, aralkyl$_{(C\le 12)}$, amido$_{(C\le 6)}$, alkoxy$_{(C\le 6)}$, alkylthio$_{(C\le 6)}$, alkylsulfonyl$_{(C\le 6)}$, or a substituted version of any of these groups;
$R_2$ and $R_{15}$ are taken together and are alkanediyl$_{(C\le 6)}$, alkoxydiyl$_{(C\le 6)}$, alkylaminodiyl$_{(C\le 6)}$, or a substituted version of any of these groups;
$R_3$ is —$NR_{11}R_{11}'$ or —$C(O)NR_{12}R_{12}'$, wherein:
$R_{11}$ and $R_{11}'$ are each independently hydrogen, alkyl$_{(C\le 6)}$, substituted alkyl$_{(C\le 6)}$;
$R_{12}$ and $R_{12}'$ are each independently hydrogen, alkyl$_{(C\le 6)}$, or substituted alkyl$_{(C\le 6)}$;
$R_4$, $R_5$, and $R_6$ are each independently hydrogen, halo, alkyl$_{(C\le 6)}$, substituted alkyl$_{(C\le 6)}$, alkoxy$_{(C\le 6)}$, substituted alkoxy$_{(C\le 6)}$, acyloxy$_{(C\le 6)}$, or substituted acyloxy$_{(C\le 6)}$;
$R_7$ and $R_7'$ are each independently hydrogen, carboxy or alkyl$_{(C\le 8)}$, alkenyl$_{(C\le 8)}$, alkynyl$_{(C\le 8)}$, cycloalkyl$_{(C\le 8)}$, heterocycloalkyl$_{(C\le 8)}$, aryl$_{(C\le 12)}$, heteroaryl$_{(C\le 12)}$, aralkyl$_{(C\le 12)}$, heteroaralkyl$_{(C\le 12)}$, -alkanediyl$_{(C\le 6)}$-$OR_{13}$, or a substituted version of any of these groups wherein:
$R_{13}$ is alkyl$_{(C\le 12)}$, substituted alkyl$_{(C\le 12)}$, aralkyl$_{(C\le 12)}$, or substituted aralkyl$_{(C\le 12)}$,
$R_7$ and $R_7'$ are taken together and are -alkanediyl$_{(C\le 7)}$-, -alkenediyl$_{(C\le 7)}$-, or a substituted version of either of these groups;
$R_8$, $R_9$, and $R_{10}$ are each independently hydrogen, halo, hydroxy, or alkyl$_{(C\le 6)}$, alkoxy$_{(C\le 6)}$, acyl$_{(C\le 6)}$, acyloxy$_{(C\le 6)}$, aralkyl$_{(C\le 12)}$, aralkoxy$_{(C\le 12)}$, or a substituted version of any of these groups;
$X_1$ is $CR_{14}$ or N, wherein:
$R_{14}$ is hydrogen, halo, hydroxy, or alkyl$_{(C\le 6)}$, alkenyl$_{(C\le 6)}$, alkynyl$_{(C\le 6)}$, alkoxy$_{(C\le 6)}$, alkylamino$_{(C\le 6)}$, -alkanediyl$_{(C\le 6)}$-heterocycloalkyl$_{(C\le 8)}$, or a substituted version of any of these groups; or
$R_{14}$ and $R_{15}$ are taken together and are alkanediyl$_{(C\le 6)}$, alkenediyl$_{(C\le 6)}$, alkoxydiyl$_{(C\le 6)}$, alkylaminodiyl$_{(C\le 6)}$, or a substituted version of any of these groups; and
$X_2$ is $CR_{15}$ or N, wherein:
$R_{15}$ is hydrogen, halo, hydroxy, or alkyl$_{(C\le 6)}$, alkenyl$_{(C\le 6)}$, alkynyl$_{(C\le 6)}$, alkoxy$_{(C\le 6)}$, alkylamino$_{(C\le 6)}$, -alkanediyl$_{(C\le 6)}$-heterocycloalkyl$_{(C\le 8)}$, or a substituted version of any of these groups;
$R_{15}$ and $R_{14}$ are taken together and are alkanediyl$_{(C\le 6)}$, alkenediyl$_{(C\le 6)}$, alkoxydiyl$_{(C\le 6)}$, alkylaminodiyl$_{(C\le 6)}$, or a substituted version of any of these groups; or
$R_{15}$ and $R_2$ are taken together and are alkanediyl$_{(C\le 6)}$, alkoxydiyl$_{(C\le 6)}$, alkylaminodiyl$_{(C\le 6)}$, or a substituted version of any of these groups;
or a pharmaceutically acceptable salt of the formula.

In some embodiments, the compounds are further defined as:

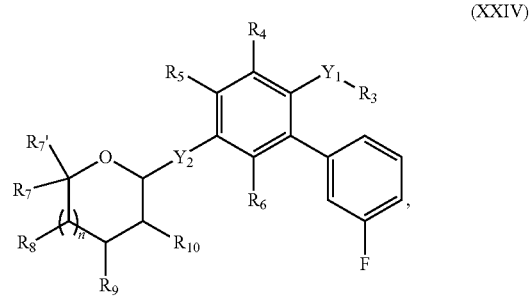

(XXIV)

wherein:
n is 0, 1, or 2;
$Y_1$ is -alkanediyl$_{(C\le 6)}$-, —C(O)-alkanediyl$_{(C\le 6)}$-, or a substituted version of any of these groups;
$Y_2$ is $CH_2$, O, or S;
$R_3$ is —$NR_{11}R_{11}'$ or —$C(O)NR_{12}R_{12}'$, wherein:
$R_{11}$ and $R_{11}'$ are each independently hydrogen, alkyl$_{(C\le 6)}$, substituted alkyl$_{(C\le 6)}$;
$R_{12}$ and $R_{12}'$ are each independently hydrogen, alkyl$_{(C\le 6)}$, or substituted alkyl$_{(C\le 6)}$;
$R_4$, $R_5$, and $R_6$ are each independently hydrogen, halo, alkyl$_{(C\le 6)}$, substituted alkyl$_{(C\le 6)}$, alkoxy$_{(C\le 6)}$, substituted alkoxy$_{(C\le 6)}$, acyloxy$_{(C\le 6)}$, or substituted acyloxy$_{(C\le 6)}$;
$R_7$ and $R_7'$ are each independently hydrogen, carboxy or alkyl$_{(C\le 8)}$, alkenyl$_{(C\le 8)}$, alkynyl$_{(C\le 8)}$, cycloalkyl$_{(C\le 8)}$, heterocycloalkyl$_{(C\le 8)}$, aryl$_{(C\le 12)}$, heteroaryl$_{(C\le 12)}$, aralkyl$_{(C\le 12)}$, heteroaralkyl$_{(C\le 12)}$, -alkanediyl$_{(C\le 6)}$-$OR_{13}$, or a substituted version of any of these groups wherein:
$R_{13}$ is alkyl$_{(C\le 12)}$, substituted alkyl$_{(C\le 12)}$, aralkyl$_{(C\le 12)}$, or substituted aralkyl$_{(C\le 12)}$,
$R_7$ and $R_7'$ are taken together and are -alkanediyl$_{(C\le 7)}$-, -alkenediyl$_{(C\le 7)}$-, or a substituted version of either of these groups; and
$R_8$, $R_9$, and $R_{10}$ are each independently hydrogen, halo, hydroxy, or alkyl$_{(C\le 6)}$, alkoxy$_{(C\le 6)}$, acyl$_{(C\le 6)}$, acyloxy$_{(C\le 6)}$, aralkyl$_{(C\le 12)}$, aralkoxy$_{(C\le 12)}$, or a substituted version of any of these groups;
or a pharmaceutically acceptable salt of the formula.

In some embodiments, the compounds are further defined as:

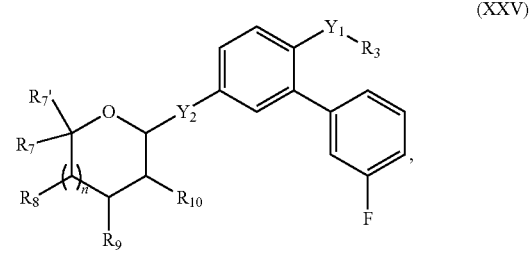

(XXV)

wherein:
n is 0, 1, or 2;
$Y_1$ is -alkanediyl$_{(C\le 6)}$-, —C(O)-alkanediyl$_{(C\le 6)}$-, or a substituted version of any of these groups;
$Y_2$ is $CH_2$, O, or S;
$R_3$ is —$NR_{11}R_{11}'$ or —$C(O)NR_{12}R_{12}'$, wherein:
$R_{11}$ and $R_{11}'$ are each independently hydrogen, alkyl$_{(C\le 6)}$, substituted alkyl$_{(C\le 6)}$;

R$_{12}$ and R$_{12}$' are each independently hydrogen, alkyl$_{(C\leq6)}$, or substituted alkyl$_{(C\leq6)}$;

R$_7$ and R$_7$' are each independently hydrogen, carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R$_7$ and R$_7$' are taken together and are -alkanediyl$_{(C\leq7)}$-, -alkenediyl$_{(C\leq7)}$-, or a substituted version of either of these groups; and R$_8$, R$_9$, and R$_{10}$ are each independently hydrogen, halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

or a pharmaceutically acceptable salt of the formula.

In some embodiments, the compounds are further defined as:

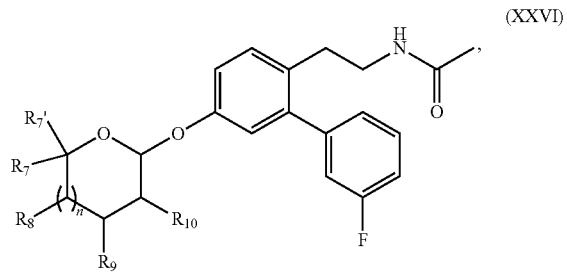

(XXVI)

wherein:
n is 0, 1, or 2;

R$_7$ and R$_7$' are each independently hydrogen, carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R$_7$ and R$_7$' are taken together and are -alkanediyl$_{(C\leq7)}$-, -alkenediyl$_{(C\leq7)}$-, or a substituted version of either of these groups; and R$_8$, R$_9$, and R$_{10}$ are each independently hydrogen, halo, hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

or a pharmaceutically acceptable salt of the formula.

In other embodiments, the compounds are further defined as:

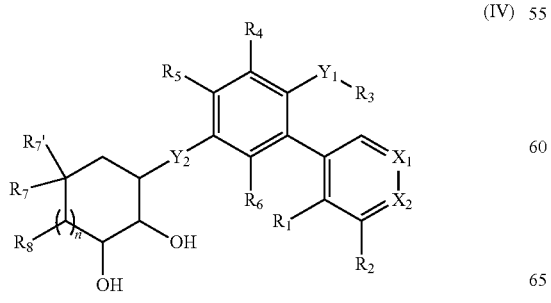

(IV)

wherein:
n is 0, 1, or 2;

Y$_1$ is -alkanediyl$_{(C\leq6)}$-, —C(O)-alkanediyl$_{(C\leq6)}$-, or a substituted version of any of these groups;

Y$_2$ is CH$_2$, O, or S;

R$_1$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkykl$_{(C\leq8)}$, amido$_{(C\leq6)}$, alkoxy$_{(C\leq6)}$, alkylsulfonyl$_{(C\leq6)}$, or a substituted version of any of these groups;

R$_2$ is hydrogen, amino, halo, hydroxy, carboxy, or alkyl$_{(C\leq6)}$, alkenyl$_{(C\leq6)}$, alkynyl$_{(C\leq6)}$, cycloalkyl$_{(C\leq8)}$, heterocycloalkyl$_{(C\leq8)}$, aryl$_{(C\leq12)}$, aralkyl$_{(C\leq12)}$, amido$_{(C\leq6)}$, alkoxy$_{(C\leq6)}$, alkylthio$_{(C\leq6)}$, alkylsulfonyl$_{(C\leq6)}$, or a substituted version of any of these groups;

R$_2$ and R$_{15}$ are taken together and are alkanediyl$_{(C\leq6)}$, alkoxydiyl$_{(C\leq6)}$, alkylaminodiyl$_{(C\leq6)}$, or a substituted version of any of these groups;

R$_3$ is —NR$_{11}$R$_{11}$' or —C(O)NR$_{12}$R$_{12}$', wherein:

R$_{11}$ and R$_{11}$' are each independently hydrogen, alkyl$_{(C\leq6)}$, substituted alkyl$_{(C\leq6)}$, acyl$_{(C\leq6)}$, or substituted acyl$_{(C\leq6)}$;

R$_{12}$ and R$_{12}$' are each independently hydrogen, alkyl$_{(C\leq6)}$, or substituted alkyl$_{(C\leq6)}$;

R$_4$, R$_5$, and R$_6$ are each independently hydrogen, halo, alkyl$_{(C\leq6)}$, substituted alkyl$_{(C\leq6)}$, alkoxy$_{(C\leq6)}$, substituted alkoxy$_{(C\leq6)}$, acyloxy$_{(C\leq6)}$, or substituted acyloxy$_{(C\leq6)}$;

R$_7$ is carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R$_7$' is hydrogen, carboxy or alkyl$_{(C\leq8)}$, alkenyl$_{(C\leq8)}$, alkynyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, aralkyl$_{(C\leq12)}$, heteroaralkyl$_{(C\leq12)}$, -alkanediyl$_{(C\leq6)}$-OR$_{13}$, or a substituted version of any of these groups wherein:

R$_{13}$ is alkyl$_{(C\leq12)}$, substituted alkyl$_{(C\leq12)}$, aralkyl$_{(C\leq12)}$, or substituted aralkyl$_{(C\leq12)}$;

R$_7$ and R$_7$' are taken together and are -alkanediyl$_{(C\leq7)}$-, -alkenediyl$_{(C\leq7)}$-, or a substituted version of either of these groups;

R$_8$ is halo or hydroxy, or alkyl$_{(C\leq6)}$, alkoxy$_{(C\leq6)}$, acyl$_{(C\leq6)}$, acyloxy$_{(C\leq6)}$, aralkyl$_{(C\leq12)}$, aralkoxy$_{(C\leq12)}$, or a substituted version of any of these groups;

X$_1$ is CR$_{14}$ or N, wherein:

R$_{14}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups; or R$_{14}$ and R$_{15}$ are taken together and are alkanediyl$_{(C\leq6)}$, alkenediyl$_{(C\leq6)}$, alkoxydiyl$_{(C\leq6)}$, alkylaminodiyl$_{(C\leq6)}$, or a substituted version of any of these groups; and X$_2$ is CR$_{15}$ or N, wherein:

R$_{15}$ is hydrogen, halo, hydroxy, or alkyl$_{(C\leq6)}$, alkenyl$_{(C\leq6)}$, alkynyl$_{(C\leq6)}$, alkoxy$_{(C\leq6)}$, alkylamino$_{(C\leq6)}$, -alkanediyl$_{(C\leq6)}$-heterocycloalkyl$_{(C\leq8)}$, or a substituted version of any of these groups;

$R_{15}$ and $R_{14}$ are taken together and are alkanediyl$_{(C\leq 6)}$, alkenediyl$_{(C\leq 6)}$, alkoxydiyl$_{(C\leq 6)}$, alkylaminodiyl$_{(C\leq 6)}$, or a substituted version of any of these groups; or $R_{15}$ and $R_2$ are taken together and are alkanediyl$_{(C\leq 6)}$, alkoxydiyl$_{(C\leq 6)}$, alkylaminodiyl$_{(C\leq 6)}$, or a substituted version of any of these groups;

or a pharmaceutically acceptable salt of the formula.

In some embodiments, the compounds are further defined as:

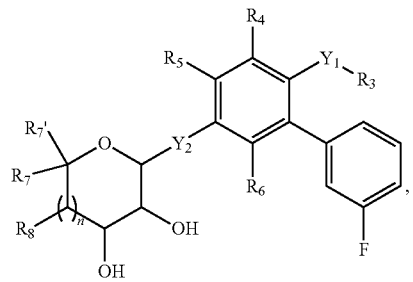
(XXVII)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is $CH_2$, O, or S;

$R_3$ is —NR$_{11}$R$_{11}$' or —C(O)NR$_{12}$R$_{12}$', wherein:

$R_{11}$ and $R_{11}$' are each independently hydrogen, alkyl$_{(C\leq 6)}$, substituted alkyl$_{(C\leq 6)}$, acyl$_{(C\leq 6)}$, or substituted acyl$_{(C\leq 6)}$;

$R_{12}$ and $R_{12}$' are each independently hydrogen, alkyl$_{(C\leq 6)}$, or substituted alkyl$_{(C\leq 6)}$;

$R_4$, $R_5$, and $R_6$ are each independently hydrogen, halo, alkyl$_{(C\leq 6)}$, substituted alkyl$_{(C\leq 6)}$, alkoxy$_{(C\leq 6)}$, substituted alkoxy$_{(C\leq 6)}$, acyloxy$_{(C\leq 6)}$, or substituted acyloxy$_{(C\leq 6)}$;

$R_7$ is carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:

$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_7$' is hydrogen, carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:

$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_7$ and $R_7$' are taken together and are -alkanediyl$_{(C\leq 7)}$-, -alkenediyl$_{(C\leq 7)}$-, or a substituted version of either of these groups; and $R_8$ is halo or hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

or a pharmaceutically acceptable salt of the formula.

In some embodiments, the compounds are further defined as:

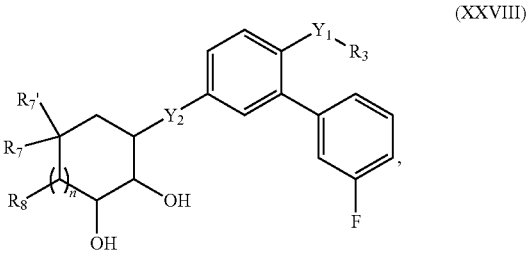
(XXVIII)

wherein:

n is 0, 1, or 2;

$Y_1$ is -alkanediyl$_{(C\leq 6)}$-, —C(O)-alkanediyl$_{(C\leq 6)}$-, or a substituted version of any of these groups;

$Y_2$ is $CH_2$, O, or S;

$R_3$ is —NR$_{11}$R$_{11}$' or —C(O)NR$_{12}$R$_{12}$', wherein:

$R_{11}$ and $R_{11}$' are each independently hydrogen, alkyl$_{(C\leq 6)}$, substituted alkyl$_{(C\leq 6)}$, acyl$_{(C\leq 6)}$, or substituted acyl$_{(C\leq 6)}$;

$R_{12}$ and $R_{12}$' are each independently hydrogen, alkyl$_{(C\leq 6)}$, or substituted alkyl$_{(C\leq 6)}$;

$R_7$ is carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:

$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_7$' is hydrogen, carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C\leq 12)}$, aralkyl$_{(C\leq 12)}$, heteroaralkyl$_{(C\leq 12)}$, -alkanediyl$_{(C\leq 6)}$-OR$_{13}$, or a substituted version of any of these groups wherein:

$R_{13}$ is alkyl$_{(C\leq 12)}$, substituted alkyl$_{(C\leq 12)}$, aralkyl$_{(C\leq 12)}$, or substituted aralkyl$_{(C\leq 12)}$;

$R_7$ and $R_7$' are taken together and are -alkanediyl$_{(C\leq 7)}$-, -alkenediyl$_{(C\leq 7)}$-, or a substituted version of either of these groups; and $R_8$ is halo or hydroxy, or alkyl$_{(C\leq 6)}$, alkoxy$_{(C\leq 6)}$, acyl$_{(C\leq 6)}$, acyloxy$_{(C\leq 6)}$, aralkyl$_{(C\leq 12)}$, aralkoxy$_{(C\leq 12)}$, or a substituted version of any of these groups;

or a pharmaceutically acceptable salt of the formula.

In some embodiments, the compounds are further defined as:

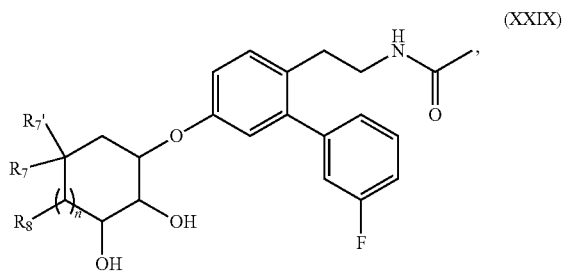
(XXIX)

wherein:

n is 0, 1, or 2;

$R_7$ is carboxy or alkyl$_{(C\leq 8)}$, alkenyl$_{(C\leq 8)}$, alkynyl$_{(C\leq 8)}$, cycloalkyl$_{(C\leq 8)}$, heterocycloalkyl$_{(C\leq 8)}$, aryl$_{(C\leq 12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted aralkyl$_{(C≤12)}$;

R$_7$' is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted aralkyl$_{(C≤12)}$;

R$_7$ and R$_7$' are taken together and are -alkanediyl$_{(C≤7)}$-, -alkenediyl$_{(C≤7)}$-, or a substituted version of either of these groups; and R$_8$ is halo or hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups;

or a pharmaceutically acceptable salt of the formula.

In other embodiments, the compounds are further defined as:

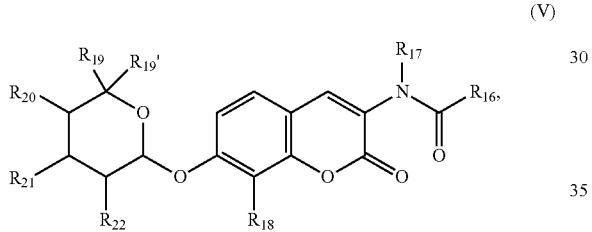

(V)

wherein:

R$_{16}$ is alkyl$_{(C≤12)}$, cycloalkyl$_{(C≤12)}$, aryl$_{(C≤18)}$, heteroaryl$_{(C≤18)}$, or a substituted version thereof;

R$_{17}$ and R$_{18}$ are each independently hydrogen, alkyl$_{(C≤8)}$, or substituted alkyl$_{(C≤8)}$;

R$_{19}$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted R$_{19}$' is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted aralkyl$_{(C≤12)}$;

R$_{20}$, R$_{21}$, and R$_{22}$ are each independently halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups, or a protected hydroxy group;

or a pharmaceutically acceptable salt of the formula.

In some embodiments, the compounds are further defined as:

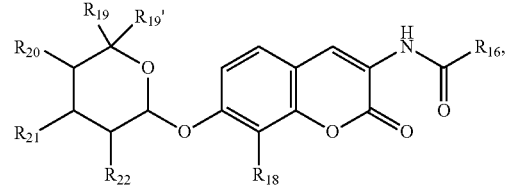

(XXX)

wherein:

R$_{16}$ is alkyl$_{(C≤12)}$, cycloalkyl$_{(C≤12)}$, aryl$_{(C≤18)}$, heteroaryl$_{(C≤18)}$, or a substituted version thereof;

R$_{16}$ is hydrogen, alkyl$_{(C≤8)}$, or substituted alkyl$_{(C≤8)}$;

R$_{19}$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted R$_{19}$' is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:

R$_{13}$ is alkyl$_{(C≤12)}$, substituted alkyl$_{(C≤12)}$, aralkyl$_{(C≤12)}$, or substituted aralkyl$_{(C≤12)}$;

R$_{20}$, R$_{21}$, and R$_{22}$ are each independently halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups, or a protected hydroxy group;

or a pharmaceutically acceptable salt of the formula.

In some embodiments, the compounds are further defined as:

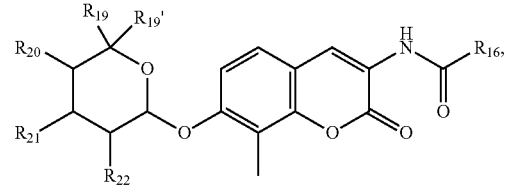

(XXXI)

wherein:

R$_{16}$ is alkyl$_{(C≤12)}$, cycloalkyl$_{(C≤12)}$, aryl$_{(C≤18)}$, heteroaryl$_{(C≤18)}$, or a substituted version thereof;

R$_{19}$ is alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, or a substituted version of any of these groups R$_{20}$, R$_{21}$, and R$_{22}$ are each independently hydroxy, alkoxy$_{(C≤12)}$, substituted alkoxy$_{(C≤12)}$, or a protected hydroxy group;

or a pharmaceutically acceptable salt of the formula.

In some embodiments, the compounds are further defined as:

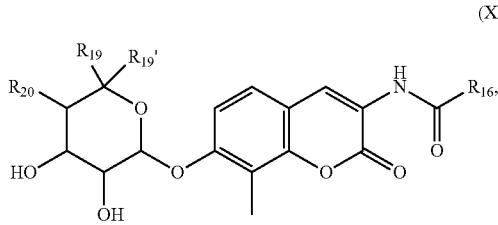

(XXXII)

wherein:
- $R_{16}$ is alkyl$_{(C≤12)}$, cycloalkyl$_{(C≤12)}$, aryl$_{(C≤18)}$, heteroaryl$_{(C≤18)}$, or a substituted version thereof;
- $R_{19}$ is carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  - $R_{13}$ is alkyl$_{(C≤12)}$, substituted alkyl$_{(C≤12)}$, aralkyl$_{(C≤12)}$, or substituted
- $R_{19}'$ is hydrogen, carboxy or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C≤12)}$, aralkyl$_{(C≤12)}$, heteroaralkyl$_{(C≤12)}$, -alkanediyl$_{(C≤6)}$-OR$_{13}$, or a substituted version of any of these groups wherein:
  - $R_{13}$ is alkyl$_{(C≤12)}$, substituted alkyl$_{(C≤12)}$, aralkyl$_{(C≤12)}$, or substituted aralkyl$_{(C≤12)}$;
- $R_{20}$ is halo, hydroxy, or alkyl$_{(C≤6)}$, alkoxy$_{(C≤6)}$, acyl$_{(C≤6)}$, acyloxy$_{(C≤6)}$, aralkyl$_{(C≤12)}$, aralkoxy$_{(C≤12)}$, or a substituted version of any of these groups, or a protected hydroxy group;

or a pharmaceutically acceptable salt of the formula.

In some embodiments, $R_1$ is hydrogen. In some embodiments, $R_2$ is halo such as fluoro. In some embodiments, $X_1$ is CR$_{14}$. In some embodiments, $R_{14}$ is hydrogen. In some embodiments, $X_2$ is CR$_{15}$. In some embodiments, $R_{15}$ is hydrogen.

In some embodiments, $Y_1$ is -alkanediyl$_{(C≤6)}$- or substituted -alkanediyl$_{(C≤6)}$-. In some embodiments, $Y_1$ is -alkanediyl$_{(C≤6)}$- such as —CH$_2$CH$_2$—. In other embodiments, $Y_1$ is substituted -alkanediyl$_{(C≤6)}$- such as —CF$_2$CH$_2$— or —CH(OH)CH$_2$—. In some embodiments, $R_3$ is —NR$_{11}$R$_{11}'$. In some embodiments, $R_{11}$ is hydrogen. In other embodiments, $R_{11}$ is alkyl$_{(C≤6)}$ or substituted alkyl$_{(C≤6)}$. In some embodiments, $R_{11}$ is alkyl$_{(C≤6)}$ such as methyl. In other embodiments, $R_{11}$ is acyl$_{(C≤6)}$ or substituted acyl$_{(C≤6)}$. In some embodiments, $R_{11}$ is acyl$_{(C≤6)}$ such as acetyl. In some embodiments, $R_{11}'$ is hydrogen. In other embodiments, $R_{11}'$ is alkyl$_{(C≤6)}$ or substituted alkyl$_{(C≤6)}$. In some embodiments, $R_{11}'$ is alkyl$_{(C≤6)}$ such as methyl. In other embodiments, $R_3$ is —C(O)NR$_{12}$R$_{12}'$. In some embodiments, $R_{12}$ is hydrogen. In some embodiments, $R_{12}'$ is hydrogen.

In some embodiments, $R_4$ is hydrogen. In other embodiments, $R_4$ is hydroxy. In some embodiments, $R_5$ is hydrogen. In other embodiments, $R_5$ is hydroxy. In some embodiments, $R_6$ is hydrogen. In other embodiments, $R_6$ is hydroxy. In some embodiments, $Y_2$ is O. In other embodiments, $Y_2$ is S. In some embodiments, $Y_2$ is CH$_2$. In some embodiments, n is 1 or 2. In other embodiments, n is 0 or 1. In some embodiments, n is 1. In other embodiments, n is 0.

In some embodiments, $R_9$ is hydroxy. In other embodiments, $R_9$ is hydrogen. In some embodiments, $R_{10}$ is hydrogen. In other embodiments, $R_{10}$ is hydroxy. In other embodiments, $R_{10}$ is amino. In other embodiments, $R_{10}$ is amido$_{(C≤12)}$ or substituted amido$_{(C≤12)}$. In some embodiments, $R_{10}$ is amido$_{(C≤12)}$ such as —NHC(O)CH$_3$.

In some embodiments, $R_8$ is hydroxy. In other embodiments, $R_8$ is alkyl$_{(C≤6)}$ or substituted alkyl$_{(C≤6)}$. In some embodiments, $R_8$ is alkyl$_{(C≤6)}$ such as methyl. In other embodiments, $R_8$ is alkoxy$_{(C≤6)}$ or substituted alkoxy$_{(C≤6)}$. In some embodiments, $R_8$ is alkoxy$_{(C≤6)}$ such as methoxy or isopropoxy. In other embodiments, $R_8$ is substituted alkoxy$_{(C≤6)}$ such as difluoromethoxy. In other embodiments, $R_8$ is aralkoxy$_{(C≤6)}$ or substituted aralkoxy$_{(C≤6)}$. In some embodiments, $R_8$ is aralkoxy$_{(C≤6)}$ such as benzyloxy.

In some embodiments, $R_7$ is hydrogen. In other embodiments, $R_7$ is carboxy. In other embodiments, $R_7$ is alkyl$_{(C≤6)}$ or substituted alkyl$_{(C≤6)}$. In some embodiments, $R_7$ is alkyl$_{(C≤6)}$ such as methyl, propyl, or isobutyl. In other embodiments, $R_7$ is substituted alkyl$_{(C≤6)}$ such as hydroxymethyl, fluoromethyl, hydoxyethyl, or fluoroisopropyl. In other embodiments, $R_7$ is alkenyl$_{(C≤8)}$ or substituted alkenyl$_{(C≤8)}$. In some embodiments, $R_7$ is alkenyl$_{(C≤8)}$ such as allyl. In other embodiments, $R_7$ is aryl$_{(C≤8)}$ or substituted aryl$_{(C≤8)}$. In some embodiments, $R_7$ is aryl$_{(C≤8)}$ such as phenyl. In other embodiments, $R_7$ is -alkanediyl$_{(C≤6)}$-OR$_{13}$. In some embodiments, $R_{13}$ is aralkyl$_{(C≤8)}$ such as benzyl.

In some embodiments, $R_7'$ is hydrogen. In other embodiments, $R_7'$ is alkyl$_{(C≤8)}$ or substituted alkyl$_{(C≤8)}$. In some embodiments, $R_7'$ is alkyl$_{(C≤8)}$ such as methyl, propyl, or isobutyl. In other embodiments, $R_7'$ is alkenyl$_{(C≤8)}$ or substituted alkenyl$_{(C≤8)}$. In some embodiments, $R_7'$ is alkenyl$_{(C≤8)}$ such as allyl. In other embodiments, $R_7'$ is aryl$_{(C≤8)}$ or substituted aryl$_{(C≤8)}$. In some embodiments, $R_7'$ is aryl$_{(C≤8)}$ such as phenyl. In other embodiments, $R_7$ and $R_7'$ are taken together and are -alkanediyl$_{(C≤7)}$-, -alkenediyl$_{(C≤7)}$-, or a substituted version of either of these groups. In some embodiments, $R_7$ and $R_7'$ are taken together and are —CH$_2$CH$_2$CH$_2$CH$_2$— and form a cyclopentyl ring. In other embodiments, $R_7$ and $R_7'$ are taken together and are -alkanediyl$_{(C≤7)}$-, -alkenediyl$_{(C≤7)}$-, or a substituted version of either of these groups. In some embodiments, $R_7$ and $R_7'$ are taken together and are —CH$_2$CH=CHCH$_2$— and form a cyclopentenyl ring.

In some embodiments, $R_{16}$ is alkyl$_{(C≤12)}$ or substituted alkyl$_{(C≤12)}$. In some embodiments, $R_{16}$ is alkyl$_{(C≤8)}$ such as methyl. In some embodiments, $R_{17}$ is hydrogen. In some embodiments, $R_{19}$ is alkyl$_{(C≤12)}$ or substituted alkyl$_{(C≤12)}$. In some embodiments, Rig is alkyl$_{(C≤8)}$ such as methyl. In some embodiments, $R_{19}$ is alkyl$_{(C≤12)}$ or substituted alkyl$_{(C≤12)}$. In some embodiments, $R_{19}$ is alkyl$_{(C≤8)}$ such as methyl. In some embodiments, Rd is hydrogen.

In some embodiments, $R_{20}$ is hydroxy. In other embodiments, $R_{20}$ is alkoxy$_{(C≤12)}$ or substituted alkoxy$_{(C≤12)}$. In some embodiments, $R_{20}$ is alkoxy$_{(C≤8)}$ such as methoxy. In some embodiments, $R_{21}$ is hydroxy. In some embodiments, $R_{22}$ is hydroxy.

In some embodiments, the compounds are further defined as:

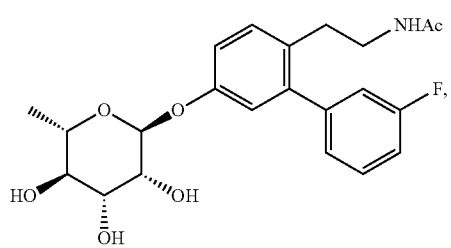

69
-continued
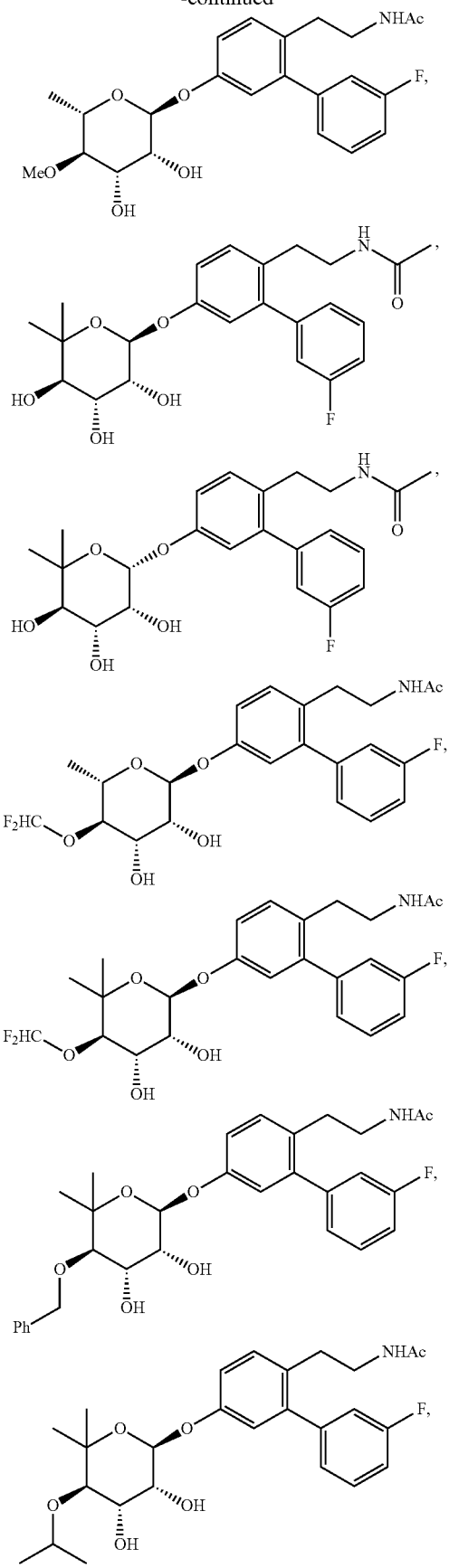
70
-continued
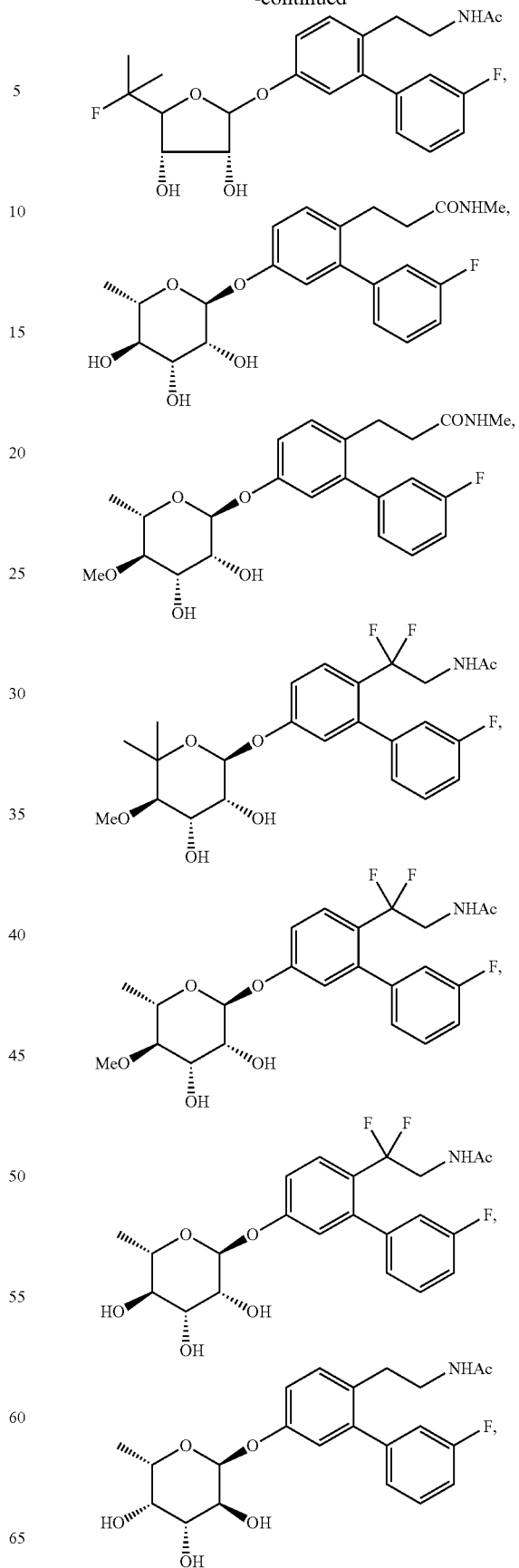

-continued
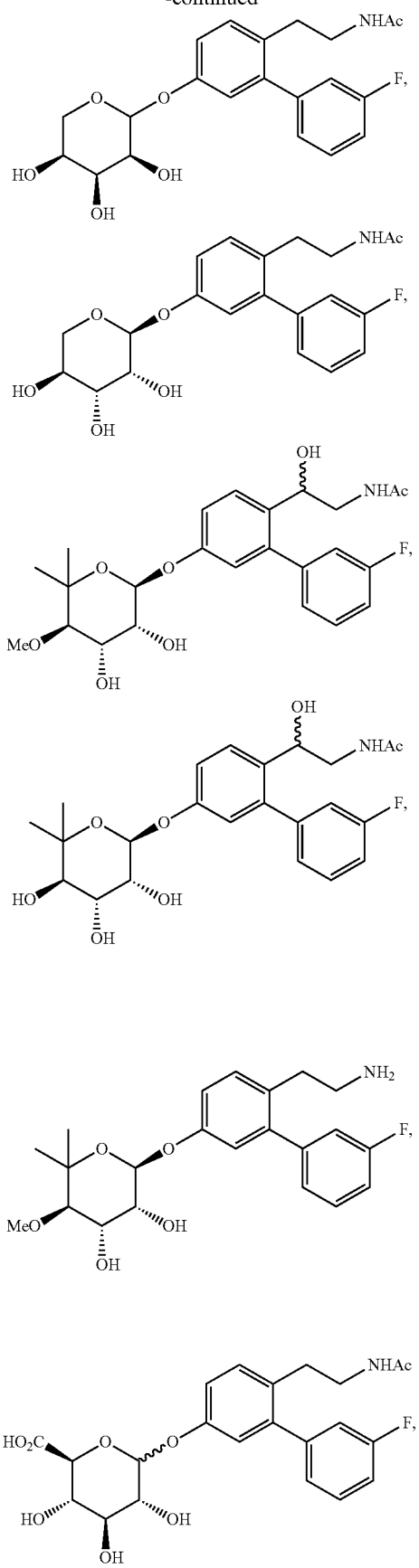
-continued
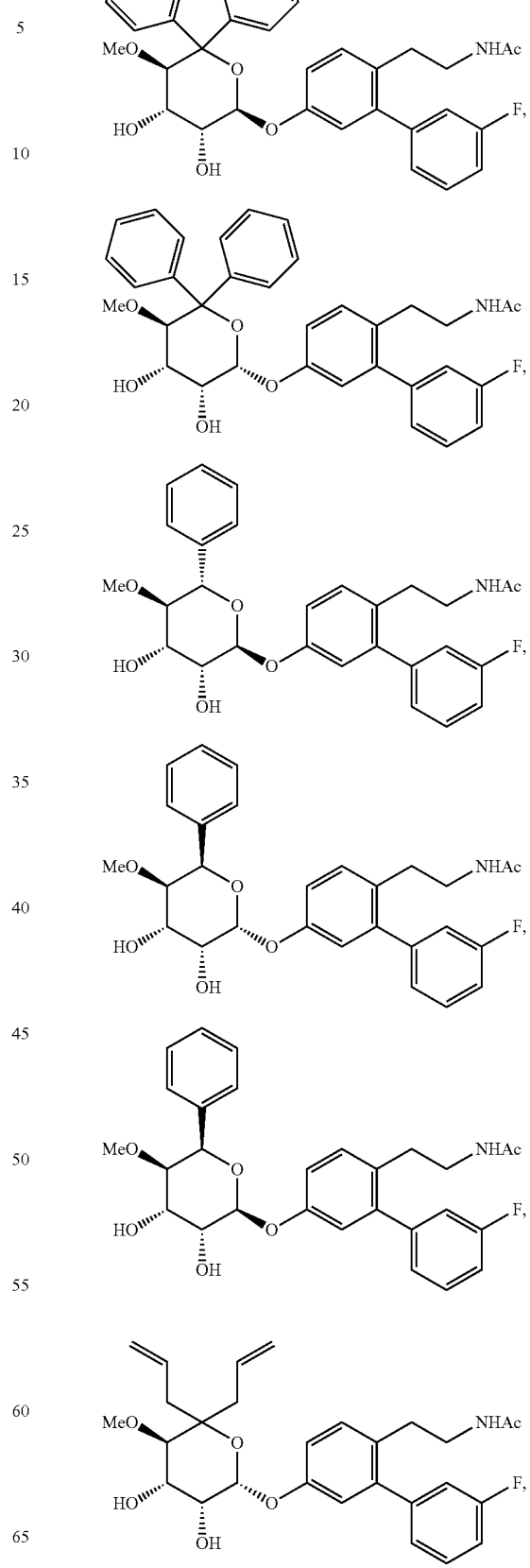

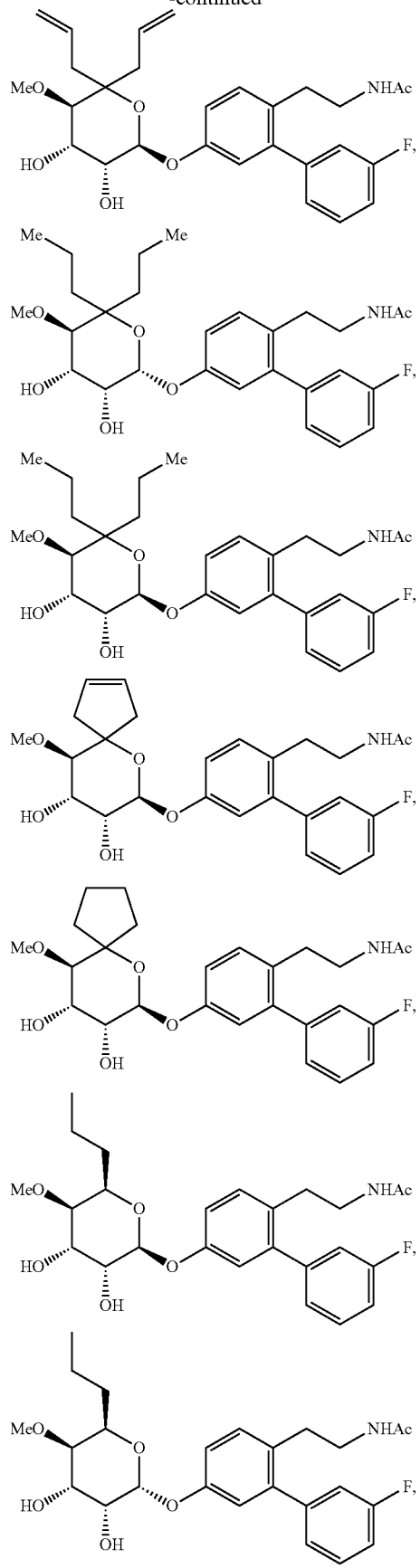
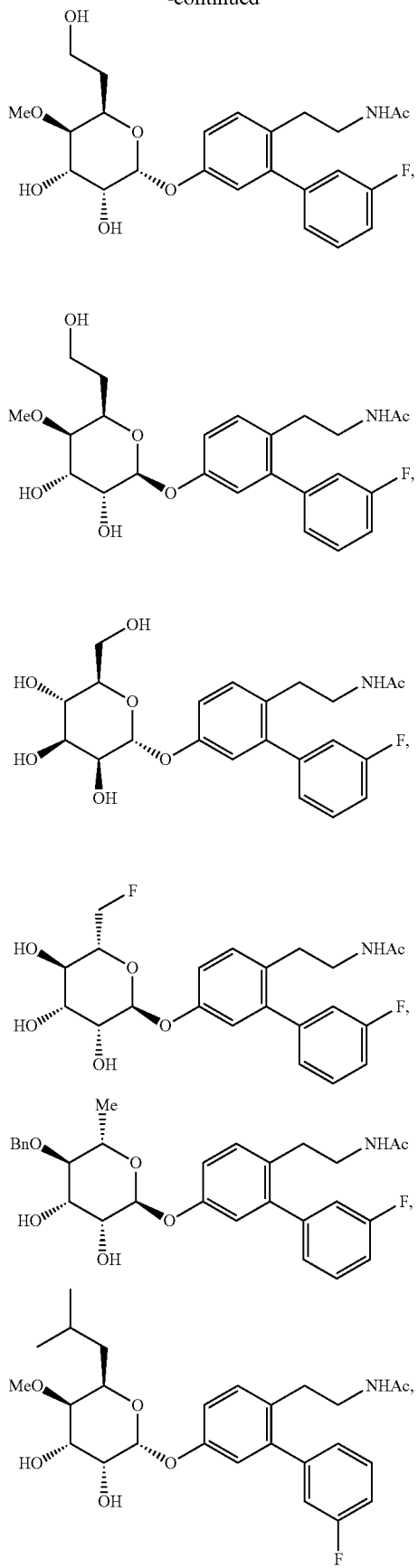

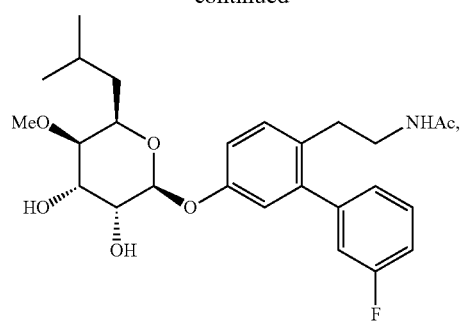
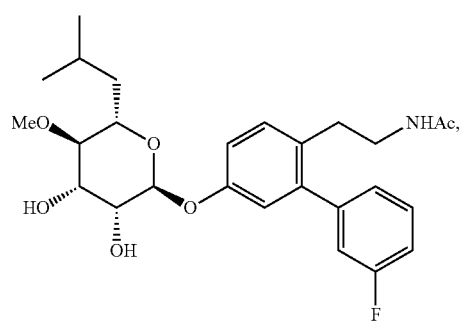
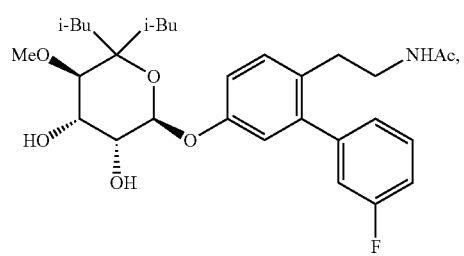
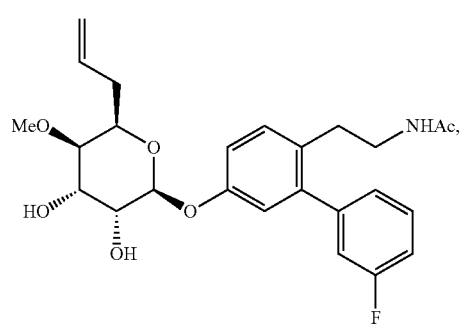
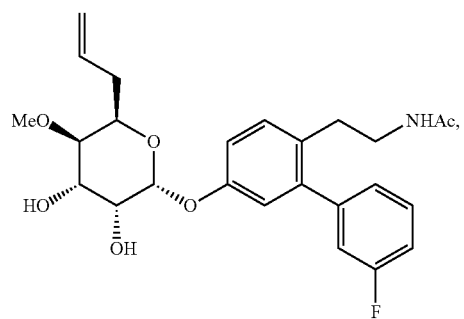
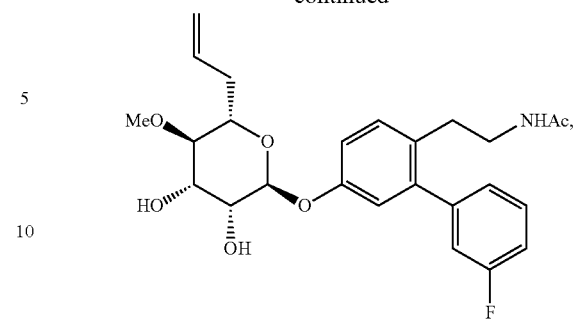
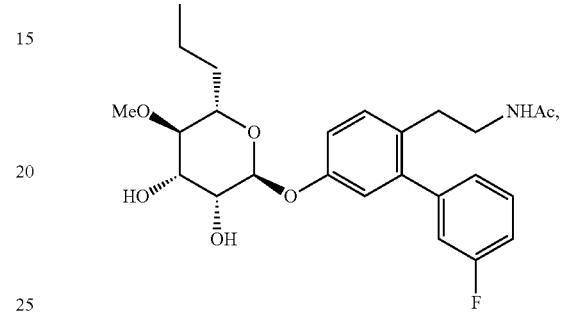
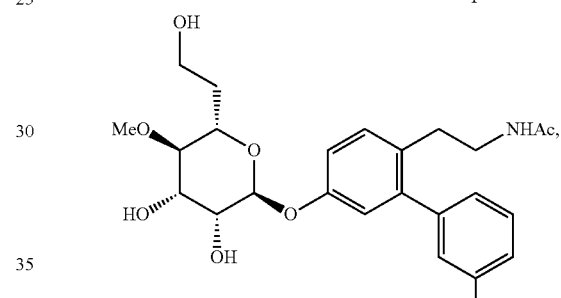
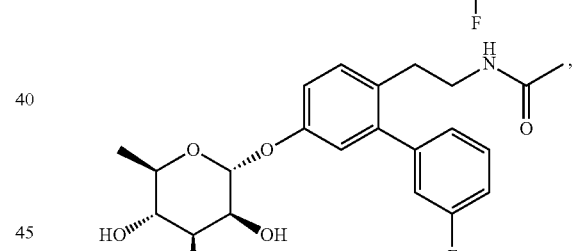
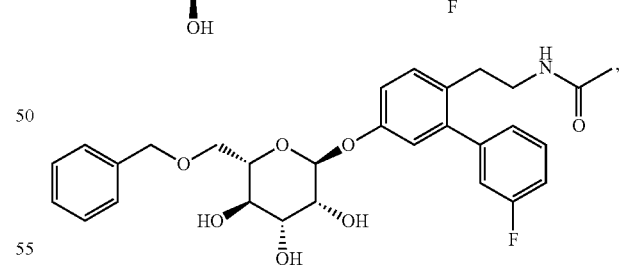
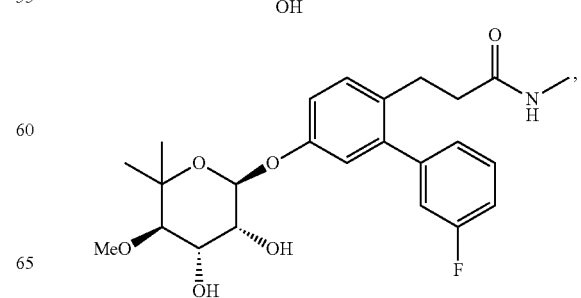

77
-continued
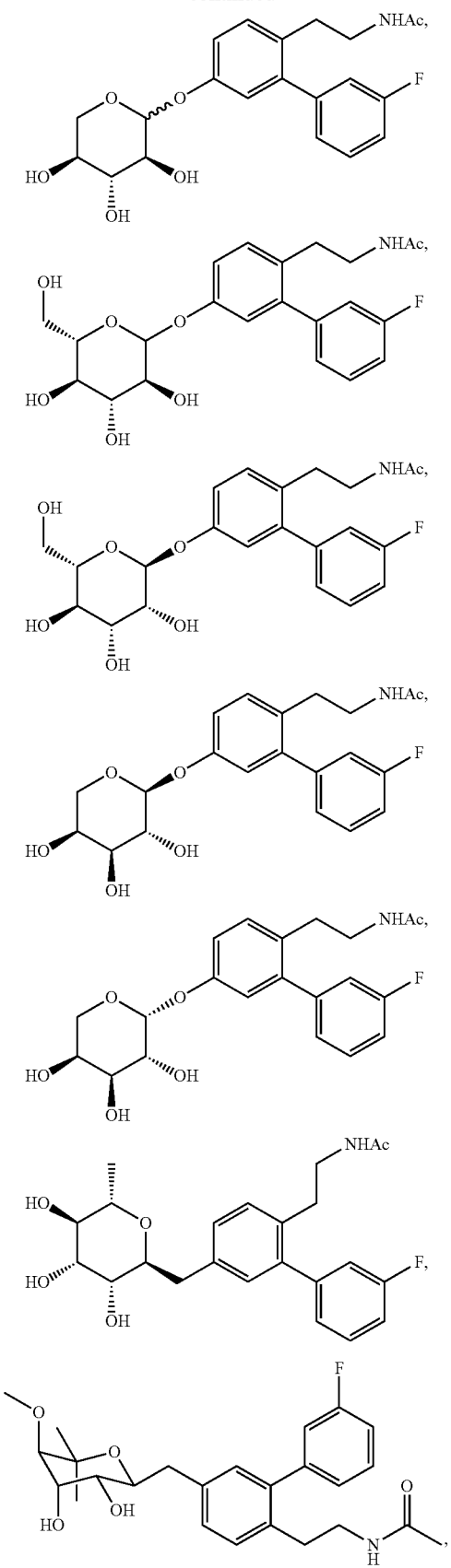
78
-continued
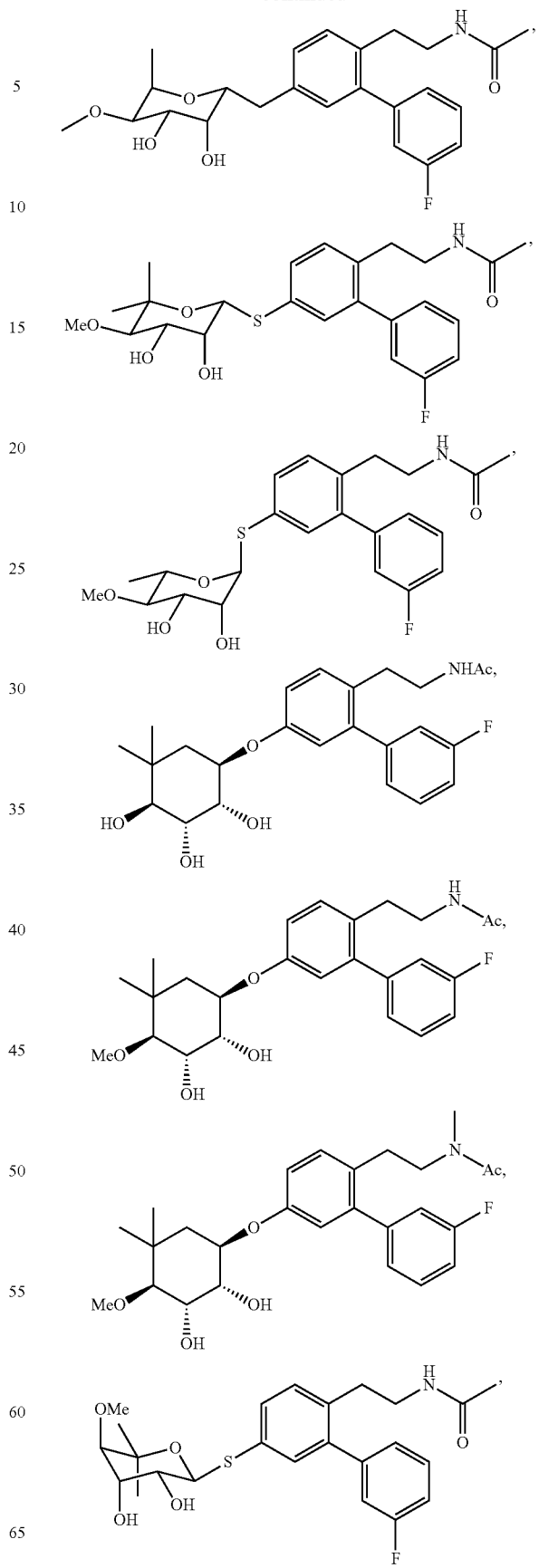

-continued
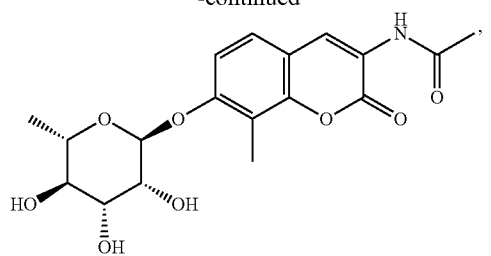
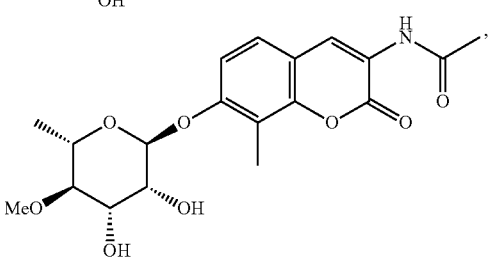
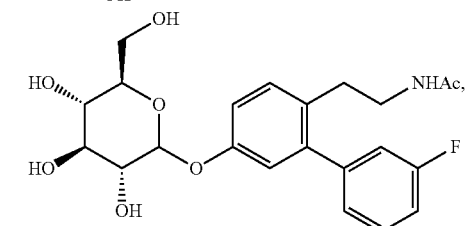
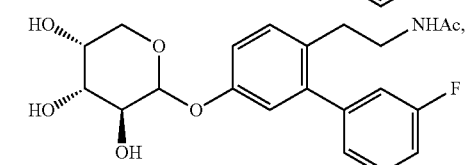
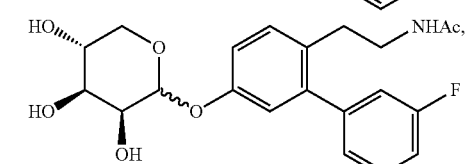
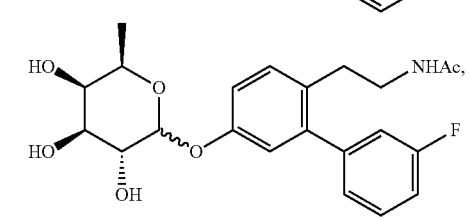
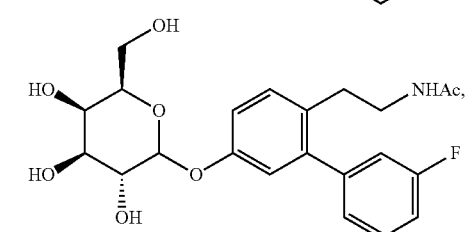
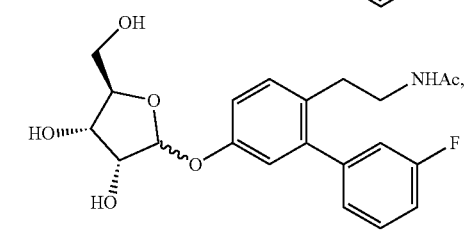
-continued
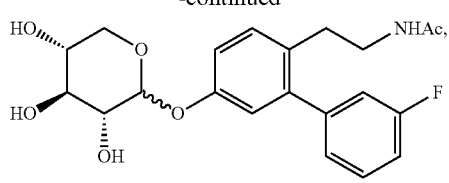
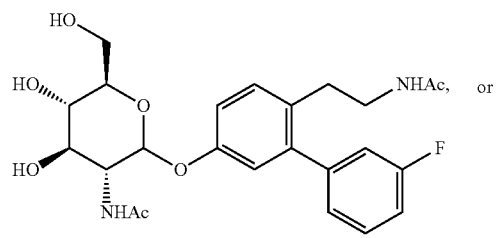
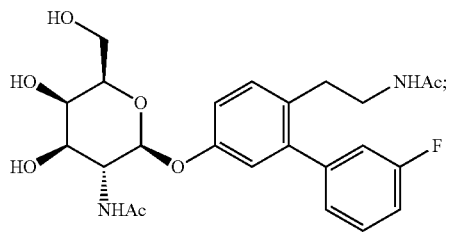
or a pharmaceutically acceptable salt of any of these formulas.
In yet another aspect, the present disclosure provides compounds of the formula:
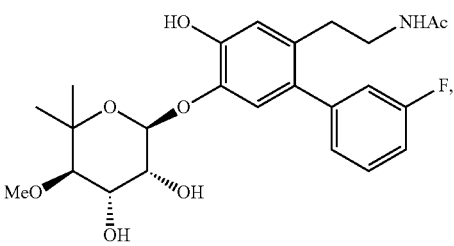
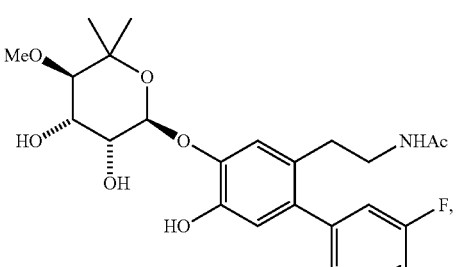
or a pharmaceutically acceptable salt of either of these formulas.

In another aspect, the present disclosure provides compounds of the formula:

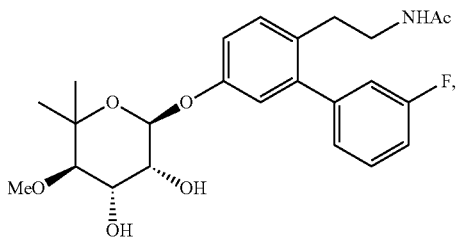 [SMILES: CO[C@@H]1[C@@H](O)[C@@H](O)[C@H](Oc2ccc(CCNC(C)=O)c(-c3cccc(F)c3)c2)OC1(C)C]

wherein the compound is essentially free of any other stereoisomers;
or a pharmaceutically acceptable salt of the formula.

In yet another aspect, the present disclosure provides compounds of the formula:

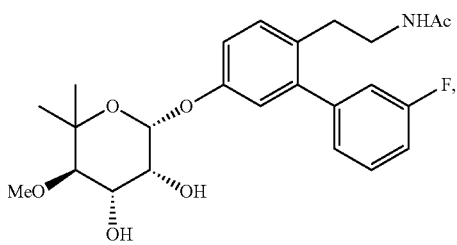 [SMILES: CO[C@@H]1[C@@H](O)[C@@H](O)[C@@H](Oc2ccc(CCNC(C)=O)c(-c3cccc(F)c3)c2)OC1(C)C]

wherein the compound is essentially free of any other stereoisomers;
or a pharmaceutically acceptable salt of the formula.

In still yet another aspect, the present disclosure provides compounds of the formula, or a pharmaceutically acceptable salt of the formula:

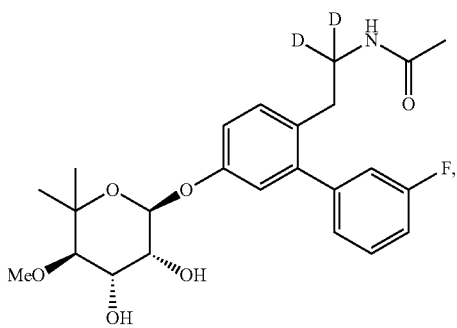 [SMILES: [2H]C([2H])(Cc1ccc(O[C@@H]2OC(C)(C)[C@H](OC)[C@@H](O)[C@H]2O)cc1-c1cccc(F)c1)NC(C)=O]

wherein the compound is greater than 90% deuterated at the positions indicated in the formula.

In another aspect, the present disclosure provides pharmaceutical compositions comprising:
(A) a compound described herein; and
(B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical compositions are formulated for oral, intraarterial, or intravenous administration. In some embodiments, the pharmaceutical compositions are formulated as a unit dose.

In still yet another aspect, the present disclosure provides methods of treating a disease or disorder in a patient comprising administering to the patient in need thereof a therapeutically effective amount of a compound or composition described herein. In some embodiments, the disease or disorder is a neurological disorder. In other embodiments, the disease or disorder is diabetes or a complication thereof. In some embodiments, the disease or disorder is a complication from diabetes such as neuropathy, nephropathy, retinopathy, or vasculopathy. In some embodiments, the complication from diabetes is neuropathy such as diabetic peripheral neuropathy. In some embodiments, the disease or disorder is associated with misregulation of the Hsp70 protein. In some embodiments, the disease or disorder is associated with misregulation of the Hsp90 protein. In some embodiments, the patient is a mammal such as human. In some embodiments, the compound is administered once to the patient. In other embodiments, the compound is administered two or more times to the patient.

In yet another aspect, the present disclosure provides methods of inducing expression of a Hsp70 protein comprising contacting the protein with an effective amount of a compound or composition described herein sufficient to induce the expression of the Hsp70 protein. In some embodiments, the protein is contacted in vitro. In other embodiments, the protein is contacted in vivo. In some embodiments, the effective amount of a compound or composition is effective enough to induce expression by at least 50% of the Hsp70 protein such as by more than 100%. In some embodiments, the induction of Hsp70 protein expression is sufficient to treat a disease or disorder. In some embodiments, the disease or disorder is a neurodegenerative disease such as a neurodegenerative disease is associated with misfolded proteins, demyelination, inflammation, and neuropathy. In some embodiments, the neurodegenerative disease is diabetic peripheral neuropathy. In other embodiments, the disease or disorder is cancer. In other embodiments, the induction of Hsp70 protein expression results in a modulation in expression of one or more downstream products. In some embodiments, the induction of Hsp70 protein expression results in a modulation in activity of one or more downstream products.

In still yet another aspect, the present disclosure provides methods of inhibiting of a Hsp90 protein comprising contacting the protein with an effective amount of a compound or composition described herein sufficient to inhibit the activity of the Hsp90 protein. In some embodiments, the protein is contacted in vitro. In other embodiments, the protein is contacted in vivo. In some embodiments, the effective amount of a compound or composition is effective enough to inhibit the expression of the Hsp90 protein by at least 50% such as when the Hsp90 protein expression is inhibited by more than 75%. In some embodiments, the inhibition of Hsp90 protein expression is sufficient to treat a disease or disorder. In some embodiments, the disease or disorder is cancer or a hyperproliferative disorder. In some embodiments, the disease or disorder is associated with a highly proliferating cell. In some embodiments, the inhibition of Hsp90 protein expression results in a modulation in expression of one or more downstream products. In other embodiments, the inhibition of Hsp90 protein expression results in a modulation in activity of one or more downstream products.

In still yet another aspect, the present disclosure provides compound of the formula:

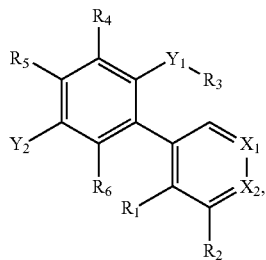

(XXXIII)

wherein:
n is 0, 1, or 2;
$Y_1$ is -alkanediyl$_{(C \leq 6)}$-, —C(O)-alkanediyl$_{(C \leq 6)}$-, -alkanediyl$_{(C \leq 6)}$-C(O)R$_{17}$, or a substituted version of any of these groups, wherein:
$R_{17}$ is alkyl$_{(C \leq 6)}$ or substituted alkyl$_{(C \leq 6)}$;
$Y_2$ is hydroxy or mercapto;
$R_1$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, amido$_{(C \leq 6)}$, alkoxy$_{(C \leq 6)}$, alkylsulfonyl$_{(C \leq 6)}$, or a substituted version of any of these groups;
$R_2$ is hydrogen, amino, halo, hydroxy, carboxy, or alkyl$_{(C \leq 6)}$, alkenyl$_{(C \leq 6)}$, alkynyl$_{(C \leq 6)}$, cycloalkyl$_{(C \leq 8)}$, heterocycloalkyl$_{(C \leq 8)}$, aryl$_{(C \leq 12)}$, aralkyl$_{(C \leq 12)}$, amido$_{(C \leq 6)}$, alkoxy$_{(C \leq 6)}$, alkylthio$_{(C \leq 6)}$, alkylsulfonyl$_{(C \leq 6)}$, or a substituted version of any of these groups;
$R_2$ and $R_{15}$ are taken together and are alkanediyl$_{(C \leq 6)}$, alkoxydiyl$_{(C \leq 6)}$, alkylaminodiyl$_{(C \leq 6)}$, or a substituted version of any of these groups;
$R_3$ is carboxy, —NR$_{11}$R$_{11}$', or —C(O)NR$_{12}$R$_{12}$', wherein:
$R_{11}$ and $R_{11}$' are each independently hydrogen, alkyl$_{(C \leq 6)}$, substituted alkyl$_{(C \leq 6)}$, acyl$_{(C \leq 6)}$, or substituted acyl$_{(C \leq 6)}$;
$R_{12}$ and $R_{12}$' are each independently hydrogen, alkyl$_{(C \leq 6)}$, or substituted alkyl$_{(C \leq 6)}$;
$R_4$, $R_5$, and $R_6$ are each independently absent, hydrogen, halo, alkyl$_{(C \leq 6)}$, substituted alkyl$_{(C \leq 6)}$, alkoxy$_{(C \leq 6)}$, substituted alkoxy$_{(C \leq 6)}$, aralkoxy$_{(C \leq 12)}$, substituted aralkoxy$_{(C \leq 12)}$, acyloxy$_{(C \leq 6)}$, or substituted acyloxy$_{(C \leq 6)}$;
$X_1$ is CR$_{14}$ or N, wherein:
$R_{14}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups; or
$R_{14}$ and $R_{15}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; and
$X_2$ is CR$_{15}$ or N, wherein:
$R_{15}$ is hydrogen, halo, hydroxy, or alkyl$_{(C \leq 6)}$, alkenyl$_{(C \leq 6)}$, alkynyl$_{(C \leq 6)}$, alkoxy$_{(C \leq 6)}$, alkylamino$_{(C \leq 6)}$, -alkanediyl$_{(C \leq 6)}$-heterocycloalkyl$_{(C \leq 8)}$, or a substituted version of any of these groups;
$R_{15}$ and $R_{14}$ are taken together and are alkanediyl$_{(C \leq 6)}$, alkenediyl$_{(C \leq 6)}$, alkoxydiyl$_{(C \leq 6)}$, alkylaminodiyl$_{(C \leq 6)}$, or a substituted version of any of these groups; or
$R_{15}$ and $R_2$ are taken together and are alkanediyl$_{(C \leq 6)}$, alkoxydiyl$_{(C \leq 6)}$, alkylaminodiyl$_{(C \leq 6)}$, or a substituted version of any of these groups;
provided that the compound is not a compound of the formula:

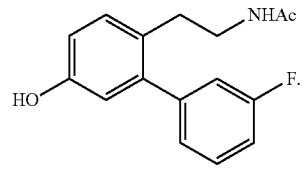 [SMILES: CC(=O)NCCc1ccc(O)cc1-c1cccc(F)c1]

In some embodiments, the compounds are further defined as:

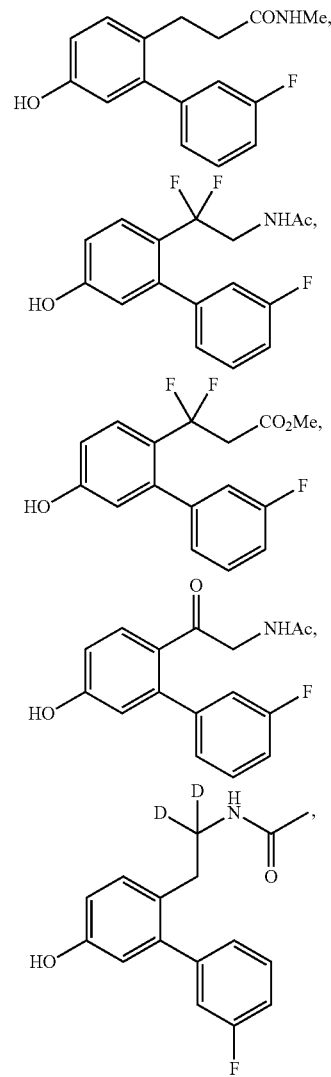

-continued

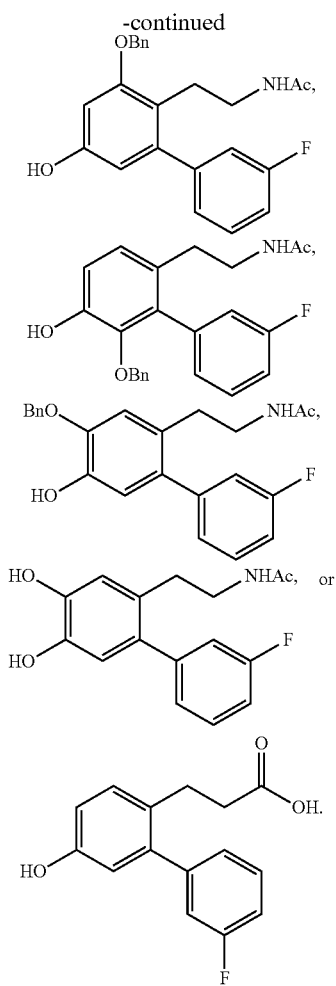

In another aspect, the present disclosure provides methods of making compounds described herein comprising reacting (a) with (b) in the presence of a coupling agent:

(a) a compound of the formula:

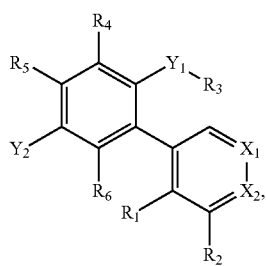

(XXXIII)

wherein:
n is 0, 1, or 2;
$Y_1$ is -alkanediyl$_{(C≤6)}$-, —C(O)-alkanediyl$_{(C≤6)}$-, -alkanediyl$_{(C≤6)}$-C(O)R$_{17}$, or a substituted version of any of these groups, wherein:
   $R_{17}$ is alkyl$_{(C≤6)}$ or substituted alkyl$_{(C≤6)}$;
$Y_2$ is hydroxy or mercapto;
$R_1$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, amido$_{(C≤6)}$, alkoxy$_{(C≤6)}$, alkylsulfonyl$_{(C≤6)}$, or a substituted version of any of these groups;
$R_2$ is hydrogen, amino, halo, hydroxy, carboxy, or alkyl$_{(C≤6)}$, alkenyl$_{(C≤6)}$, alkynyl$_{(C≤6)}$, cycloalkyl$_{(C≤8)}$, heterocycloalkyl$_{(C≤8)}$, aryl$_{(C≤12)}$, aralkyl$_{(C≤12)}$, amido$_{(C≤6)}$, alkoxy$_{(C≤6)}$, alkylthio$_{(C≤6)}$, alkylsulfonyl$_{(C≤6)}$, or a substituted version of any of these groups;
$R_2$ and $R_{15}$ are taken together and are alkanediyl$_{(C≤6)}$, alkoxydiyl$_{(C≤6)}$, alkylaminodiyl$_{(C≤6)}$, or a substituted version of any of these groups;
$R_3$ is carboxy, —NR$_{11}$R$_{11}$', or —C(O)NR$_{12}$R$_{12}$', wherein:
   $R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;
   $R_{12}$ and $R_{12}$' are each independently hydrogen, alkyl$_{(C≤6)}$, or substituted alkyl$_{(C≤6)}$;
$R_4$, $R_5$, and $R_6$ are each independently absent, hydrogen, halo, alkyl$_{(C≤6)}$, substituted alkyl$_{(C≤6)}$, alkoxy$_{(C≤6)}$, substituted alkoxy$_{(C≤6)}$, aralkoxy$_{(C≤12)}$, substituted aralkoxy$_{(C≤12)}$, acyloxy$_{(C≤6)}$, or substituted acyloxy$_{(C≤6)}$;
$X_1$ is CR$_{14}$ or N, wherein:
   $R_{14}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups; or
   $R_{14}$ and $R_{15}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups;
$X_2$ is CR$_{15}$ or N, wherein:
   $R_{15}$ is hydrogen, halo, hydroxy, or alkyl$_{(C≤6)}$, alkenyl$_{(C≤6)}$, alkynyl$_{(C≤6)}$, alkoxy$_{(C≤6)}$, alkylamino$_{(C≤6)}$, -alkanediyl$_{(C≤6)}$-heterocycloalkyl$_{(C≤8)}$, or a substituted version of any of these groups;
   $R_{15}$ and $R_{14}$ are taken together and are alkanediyl$_{(C≤6)}$, alkenediyl$_{(C≤6)}$, alkoxydiyl$_{(C≤6)}$, alkylaminodiyl$_{(C≤6)}$, or a substituted version of any of these groups; or
   $R_{15}$ and $R_2$ are taken together and are alkanediyl$_{(C≤6)}$, alkoxydiyl$_{(C≤6)}$, alkylaminodiyl$_{(C≤6)}$, or a substituted version of any of these groups;

(b) a compound of the formula:

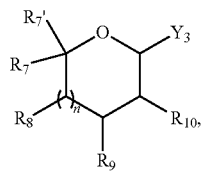

(XXXIV)

wherein:
n is 0, 1, or 2;
$Y_3$ is hydroxy, halo, acyloxy$_{(C≤8)}$, iminooxy$_{(C≤8)}$, or a substituted version of either of these groups;
$R_7$ and $R_7$' are each independently hydrogen, hydroxy, carboxy, or alkyl$_{(C≤8)}$, alkenyl$_{(C≤8)}$, alkynyl$_{(C≤8)}$, cycloalkyl$_{(C≤8)}$, heterocycloalkyl$_{(C≤8)}$, aryl$_{(C≤12)}$, heteroaryl$_{(C \leq 12)}$, aralkyl$_{(C \leq 12)}$, heteroaralkyl$_{(C \leq 12)}$, alkanediyl$_{(C \leq 6)}$-OR$_{13}$, or a substituted version of any of these groups wherein:

R$_{13}$ is aralkyl$_{(C \leq 12)}$ or substituted aralkyl$_{(C \leq 12)}$;

R$_7$ and R$_7$' are taken together and are -alkanediyl$_{(C \leq 7)}$-, -alkenediyl$_{(C \leq 7)}$-, or a substituted version of either of these groups; and R$_8$, R$_9$, and R$_{10}$ are each independently hydrogen, hydroxy, or alkyl$_{(C \leq 6)}$, alkoxy$_{(C \leq 6)}$, acyl$_{(C \leq 6)}$, acyloxy$_{(C \leq 6)}$, aralkyl$_{(C \leq 12)}$, aralkoxy$_{(C \leq 12)}$, or a substituted version of any of these groups.

In some embodiments, the coupling agent is a Lewis acid. In some embodiments, the Lewis acid comprises a boron reagent such as BF$_3$, or more specifically BF$_3 \cdot$Et$_2$O. In some embodiments, the methods further comprise a solvent. In other embodiments, the methods do not comprise a solvent.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1A:
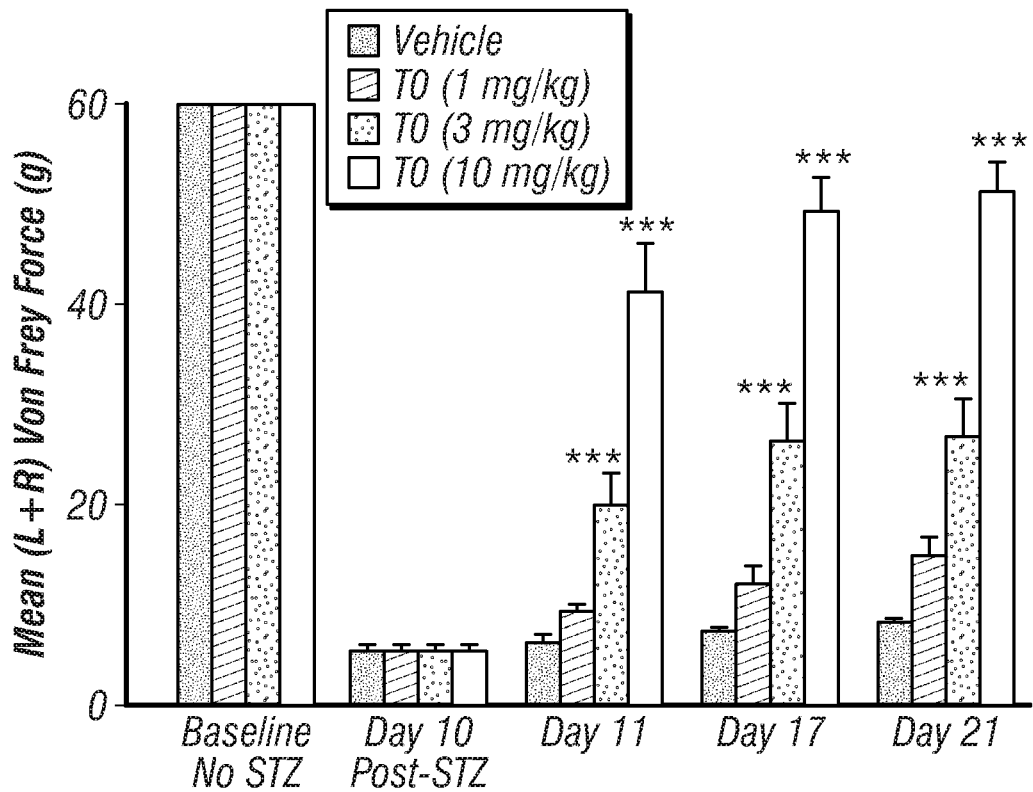
FIGS. 1A-1C show the results of a rat streptozotocin induced diabetes model for painful diabetic neuropathy for compounds T0 (KU-596) (FIG. 1A), T2 (FIG. 1B), and T1 (FIG. 1C). Streptozotocin was injected into rats to induce diabetes after a baseline von Frey measurement for allodynia was collected. Oral administration of each test drug was started on Day 10 after another von Frey measurement. Compounds T1 and T2 both demonstrated comparable to slightly better activity to compound T0 (KU-596).

In some aspects, the present disclosure provides biaryl amide compounds with modified sugar groups that are useful for treatment and prevention of diseases and disorders, including neurological disorders, such as neurodegenerative diseases and nerve damaging disorders, for example, diabetic peripheral neuropathy.

I. Compounds of the Present Invention

The compounds of the present invention (also referred to as "compounds of the present disclosure" or "compounds disclosed herein") are shown, for example, above in the summary of the invention section, the preceding paragraphs, in the claims below, and in the formulas provided in Table 1 below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

TABLE 1

Examples of Biaryl- and Coumarin-Based Compounds with Modified Sugar Groups

| Compound Reference Number | Structure |
|---|---|
| T0 (KU-596) | 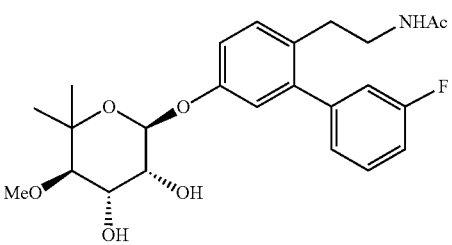 [SMILES: CO[C@@H]1[C@@H](O)[C@@H](O)[C@H](Oc2ccc(CCNC(C)=O)c(-c3cccc(F)c3)c2)OC1(C)C] |

TABLE 1-continued

Examples of Biaryl- and Coumarin-Based Compounds with Modified Sugar Groups

| Compound Reference Number | Structure |
|---|---|
| T1 | 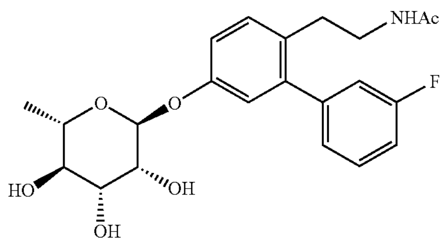 [SMILES: CC(=O)NCCc1ccc(O[C@@H]2O[C@@H](C)[C@H](O)[C@@H](O)[C@H]2O)cc1-c1cccc(F)c1] |
| T2 | 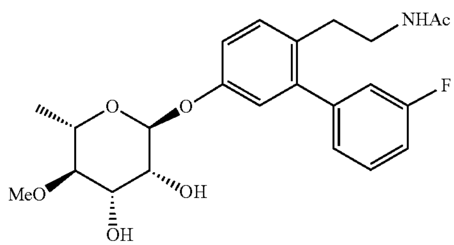 [SMILES: CO[C@@H]1[C@@H](O)[C@@H](O)[C@H](Oc2ccc(CCNC(C)=O)c(-c3cccc(F)c3)c2)O[C@H]1C] |
| T3 | 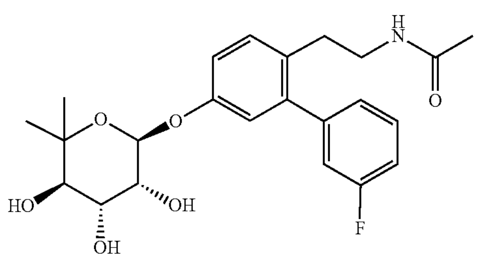 [SMILES: CC(=O)NCCc1ccc(O[C@@H]2OC(C)(C)[C@H](O)[C@@H](O)[C@H]2O)cc1-c1cccc(F)c1] |
| T4 | 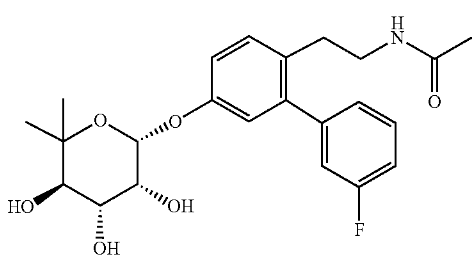 [SMILES: CC(=O)NCCc1ccc(O[C@H]2OC(C)(C)[C@H](O)[C@@H](O)[C@H]2O)cc1-c1cccc(F)c1] |
| T5 | 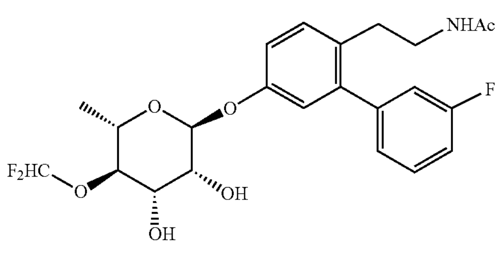 [SMILES: CC(=O)NCCc1ccc(O[C@@H]2O[C@@H](C)[C@H](OC(F)F)[C@@H](O)[C@H]2O)cc1-c1cccc(F)c1] |
| T6 | 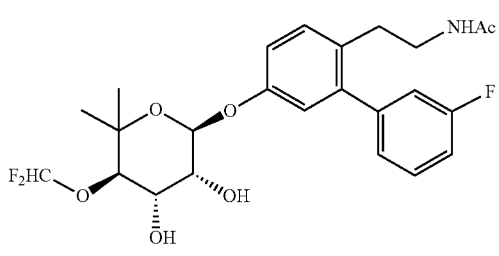 [SMILES: CC(=O)NCCc1ccc(O[C@@H]2OC(C)(C)[C@H](OC(F)F)[C@@H](O)[C@H]2O)cc1-c1cccc(F)c1] |

TABLE 1-continued

Examples of Biaryl- and Coumarin-Based Compounds with Modified Sugar Groups

| Compound Reference Number | Structure |
|---|---|
| T7 | 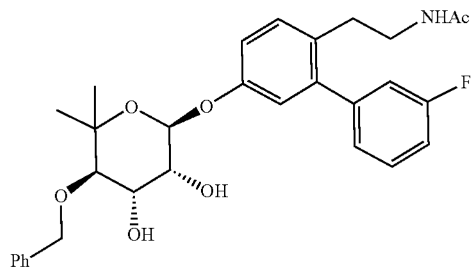 [SMILES: CC(=O)NCCc1ccc(O[C@@H]2OC(C)(C)[C@H](OCc3ccccc3)[C@@H](O)[C@H]2O)cc1-c1cccc(F)c1] |
| T8 | 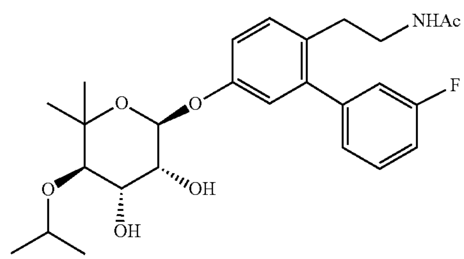 [SMILES: CC(=O)NCCc1ccc(O[C@@H]2OC(C)(C)[C@H](OC(C)C)[C@@H](O)[C@H]2O)cc1-c1cccc(F)c1] |
| T9 | 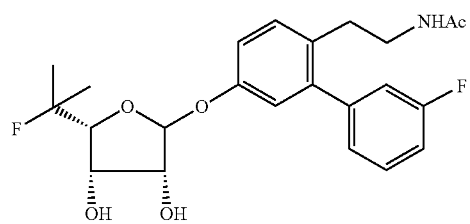 [SMILES: CC(=O)NCCc1ccc(OC2O[C@@H](C(C)(C)F)[C@@H](O)[C@H]2O)cc1-c1cccc(F)c1] |
| T10 | 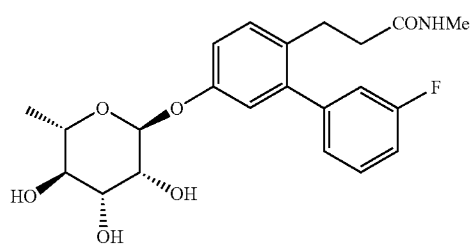 |
| T11 | 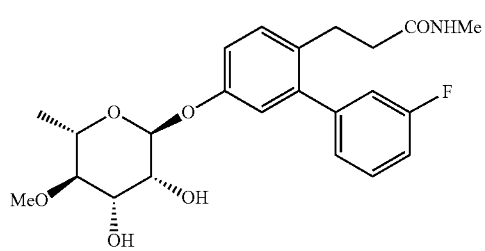 |
| T12 | 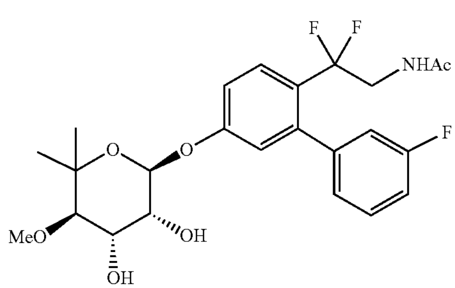 [SMILES: CO[C@@H]1[C@@H](O)[C@@H](O)[C@H](Oc2ccc(C(F)(F)CNC(C)=O)c(-c3cccc(F)c3)c2)OC1(C)C] |

TABLE 1-continued

Examples of Biaryl- and Coumarin-Based Compounds with Modified Sugar Groups

| Compound Reference Number | Structure |
|---|---|
| T13 | 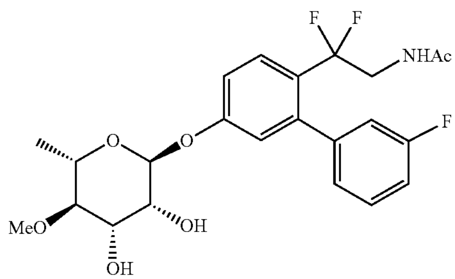 [SMILES: CO[C@@H]1[C@@H](O)[C@@H](O)[C@H](Oc2ccc(C(F)(F)CNC(C)=O)c(-c3cccc(F)c3)c2)O[C@H]1C] |
| T14 | 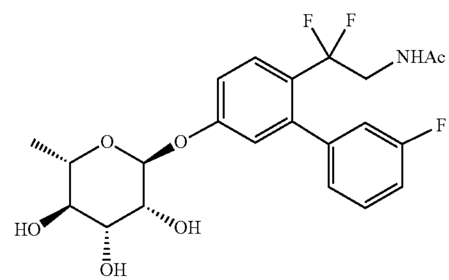 [SMILES: CC(=O)NCC(F)(F)c1ccc(O[C@@H]2O[C@@H](C)[C@H](O)[C@@H](O)[C@H]2O)cc1-c1cccc(F)c1] |
| T15 | 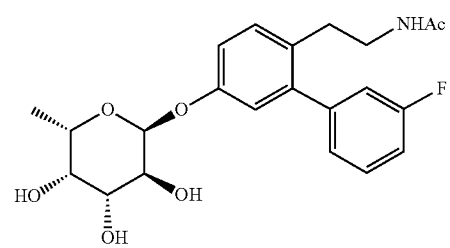 [SMILES: CC(=O)NCCc1ccc(O[C@@H]2O[C@@H](C)[C@@H](O)[C@@H](O)[C@@H]2O)cc1-c1cccc(F)c1] |
| T16 | 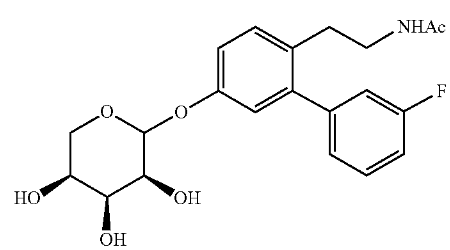 [SMILES: CC(=O)NCCc1ccc(OC2OC[C@H](O)[C@H](O)[C@@H]2O)cc1-c1cccc(F)c1] |
| T17 | 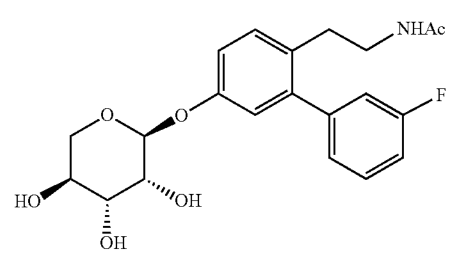 [SMILES: CC(=O)NCCc1ccc(O[C@@H]2OC[C@H](O)[C@@H](O)[C@H]2O)cc1-c1cccc(F)c1] |

TABLE 1-continued
Examples of Biaryl- and Coumarin-Based Compounds with Modified Sugar Groups
| Compound Reference Number | Structure |
|---|---|
| T18 | 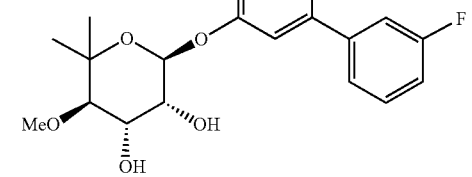 |
| T19 | 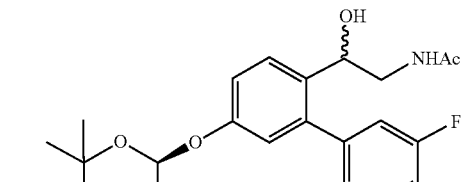 |
| T20 | 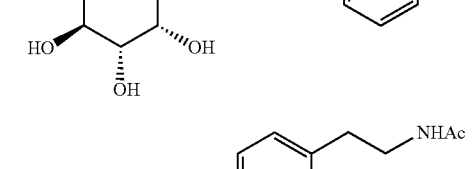 |
| T21 | 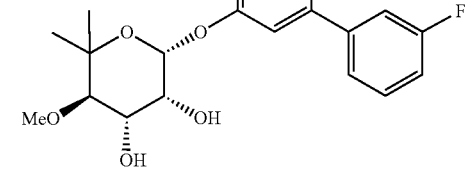 |
| T22 | 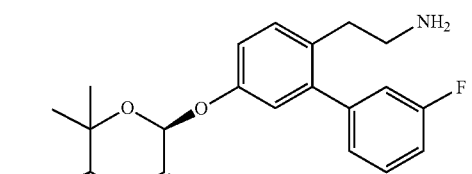 |
| T23 | 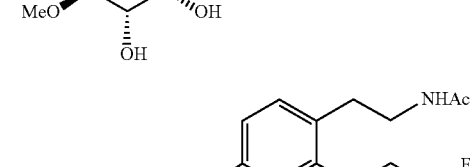 |

TABLE 1-continued

Examples of Biaryl- and Coumarin-Based Compounds with Modified Sugar Groups

| Compound Reference Number | Structure |
|---|---|
| T24 | 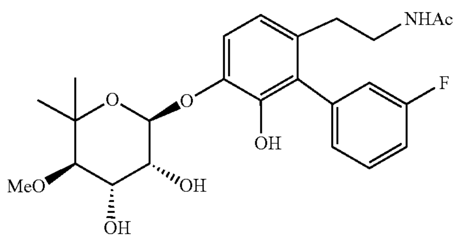 [SMILES: CO[C@@H]1[C@@H](O)[C@@H](O)[C@H](Oc2ccc(CCNC(C)=O)c(-c3cccc(F)c3)c2O)OC1(C)C] |
| T25 | 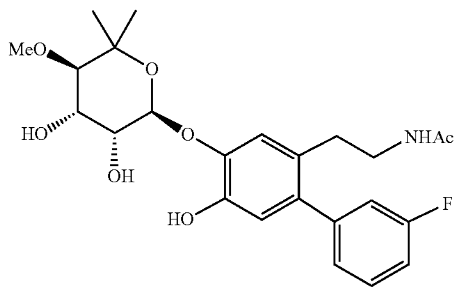 [SMILES: CO[C@@H]1[C@@H](O)[C@@H](O)[C@H](Oc2cc(CCNC(C)=O)c(-c3cccc(F)c3)cc2O)OC1(C)C] |
| T26 | 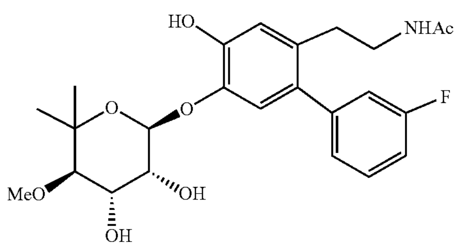 [SMILES: CO[C@@H]1[C@@H](O)[C@@H](O)[C@H](Oc2cc(-c3cccc(F)c3)c(CCNC(C)=O)cc2O)OC1(C)C] |
| T27 | 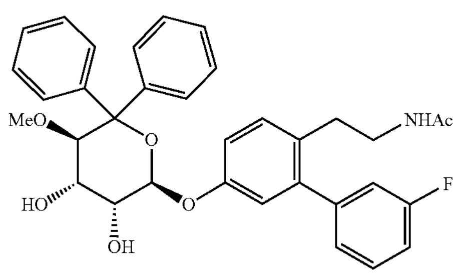 [SMILES: CO[C@@H]1[C@@H](O)[C@@H](O)[C@H](Oc2ccc(CCNC(C)=O)c(-c3cccc(F)c3)c2)OC1(c1ccccc1)c1ccccc1] |
| T28 | 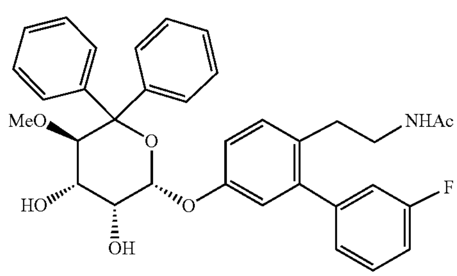 [SMILES: CO[C@@H]1[C@@H](O)[C@@H](O)[C@@H](Oc2ccc(CCNC(C)=O)c(-c3cccc(F)c3)c2)OC1(c1ccccc1)c1ccccc1] |

TABLE 1-continued

Examples of Biaryl- and Coumarin-Based Compounds with Modified Sugar Groups

| Compound Reference Number | Structure |
| --- | --- |
| T29 | 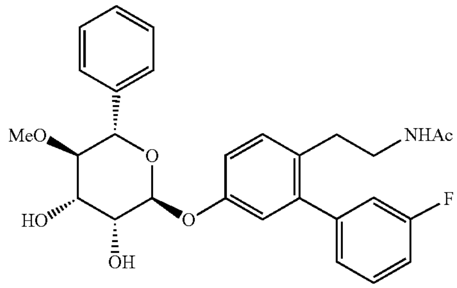 [SMILES: CO[C@@H]1[C@@H](O)[C@@H](O)[C@H](Oc2ccc(CCNC(C)=O)c(-c3cccc(F)c3)c2)O[C@H]1c1ccccc1] |
| T30 | 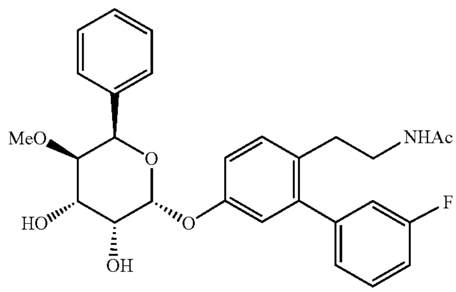 [SMILES: CO[C@@H]1[C@@H](O)[C@@H](O)[C@@H](Oc2ccc(CCNC(C)=O)c(-c3cccc(F)c3)c2)O[C@@H]1c1ccccc1] |
| T31 | 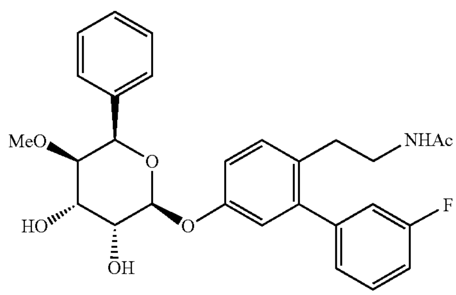 [SMILES: CO[C@@H]1[C@@H](O)[C@@H](O)[C@H](Oc2ccc(CCNC(C)=O)c(-c3cccc(F)c3)c2)O[C@@H]1c1ccccc1] |
| T32 | 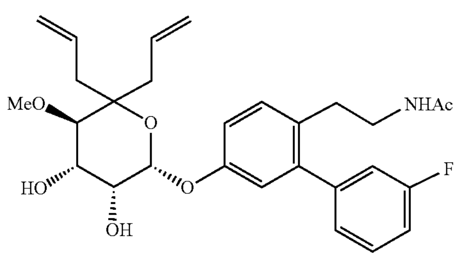 [SMILES: C=CCC1(CC=C)O[C@H](Oc2ccc(CCNC(C)=O)c(-c3cccc(F)c3)c2)[C@H](O)[C@H](O)[C@H]1OC] |
| T33 | 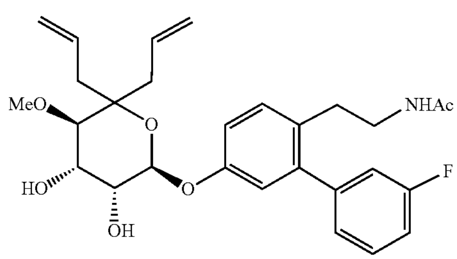 [SMILES: C=CCC1(CC=C)O[C@@H](Oc2ccc(CCNC(C)=O)c(-c3cccc(F)c3)c2)[C@H](O)[C@H](O)[C@H]1OC] |

TABLE 1-continued

Examples of Biaryl- and Coumarin-Based Compounds with Modified Sugar Groups

| Compound Reference Number | Structure |
|---|---|
| T34 | *(structure)* |
| T35 | *(structure)* |
| T36 | *(structure)* |
| T37 | *(structure)* |
| T38 | *(structure)* |

TABLE 1-continued

Examples of Biaryl- and Coumarin-Based Compounds with Modified Sugar Groups

| Compound Reference Number | Structure |
|---|---|
| T39 | 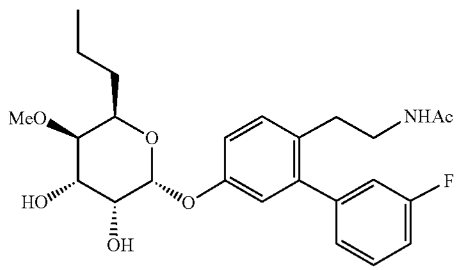 [SMILES: CCC[C@H]1O[C@H](Oc2ccc(CCNC(C)=O)c(-c3cccc(F)c3)c2)[C@H](O)[C@H](O)[C@H]1OC] |
| T40 | 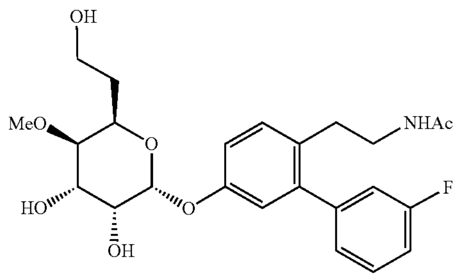 [SMILES: CO[C@@H]1[C@@H](O)[C@@H](O)[C@@H](Oc2ccc(CCNC(C)=O)c(-c3cccc(F)c3)c2)O[C@@H]1CCO] |
| T41 | 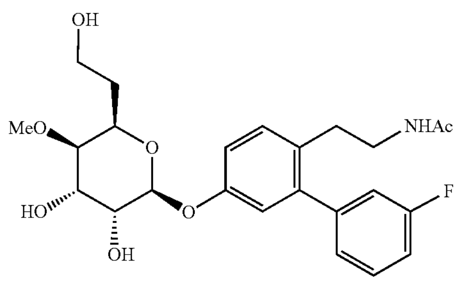 [SMILES: CO[C@@H]1[C@@H](O)[C@@H](O)[C@H](Oc2ccc(CCNC(C)=O)c(-c3cccc(F)c3)c2)O[C@@H]1CCO] |
| T42 | 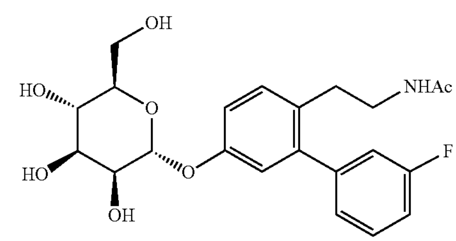 [SMILES: CC(=O)NCCc1ccc(O[C@H]2O[C@H](CO)[C@@H](O)[C@H](O)[C@@H]2O)cc1-c1cccc(F)c1] |
| T43 | 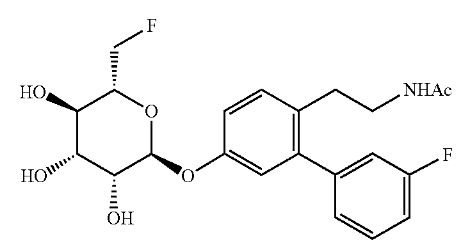 [SMILES: CC(=O)NCCc1ccc(O[C@@H]2O[C@@H](CF)[C@H](O)[C@@H](O)[C@H]2O)cc1-c1cccc(F)c1] |
| T44 | 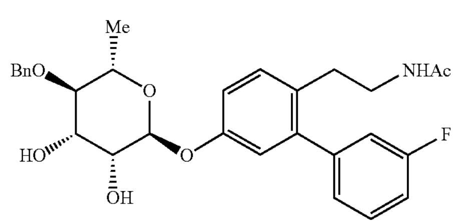 [SMILES: CC(=O)NCCc1ccc(O[C@@H]2O[C@@H](C)[C@H](OCc3ccccc3)[C@@H](O)[C@H]2O)cc1-c1cccc(F)c1] |

TABLE 1-continued

Examples of Biaryl- and Coumarin-Based Compounds with Modified Sugar Groups

| Compound Reference Number | Structure |
| --- | --- |
| T45 | 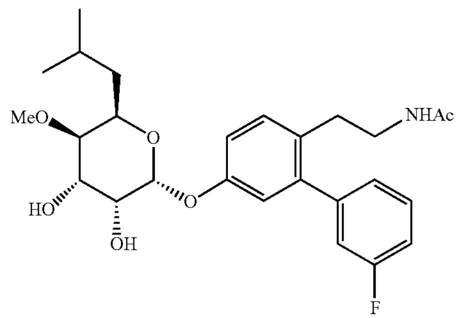 [SMILES: CO[C@@H]1[C@@H](O)[C@@H](O)[C@@H](Oc2ccc(CCNC(C)=O)c(-c3cccc(F)c3)c2)O[C@@H]1CC(C)C] |
| T46 | 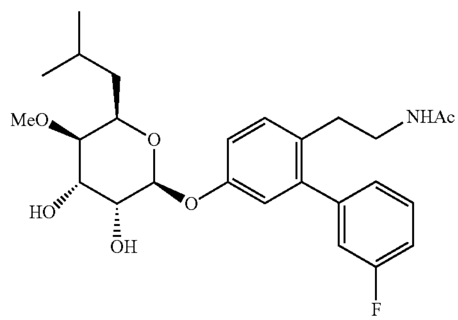 [SMILES: CO[C@@H]1[C@@H](O)[C@@H](O)[C@H](Oc2ccc(CCNC(C)=O)c(-c3cccc(F)c3)c2)O[C@@H]1CC(C)C] |
| T47 | 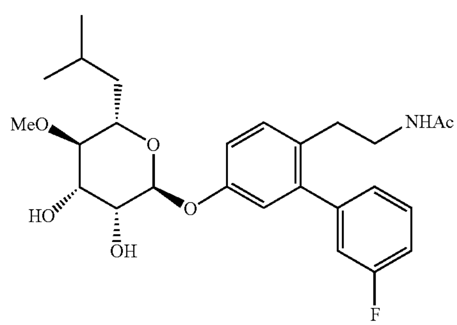 [SMILES: CO[C@@H]1[C@@H](O)[C@@H](O)[C@H](Oc2ccc(CCNC(C)=O)c(-c3cccc(F)c3)c2)O[C@H]1CC(C)C] |
| T48 | 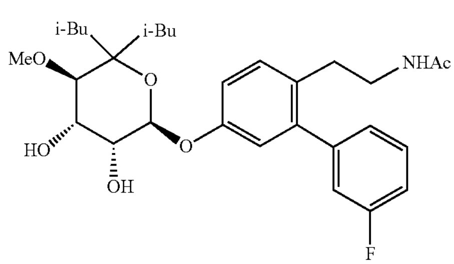 |

TABLE 1-continued
Examples of Biaryl- and Coumarin-Based Compounds with Modified Sugar Groups
| Compound Reference Number | Structure |
| --- | --- |
| T49 | 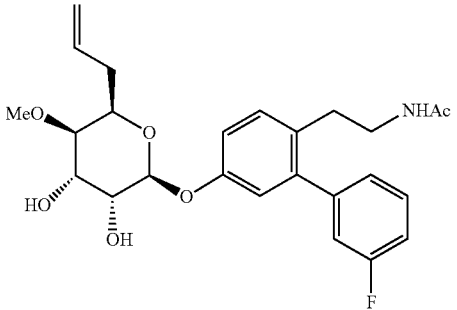 [SMILES: C=CC[C@H]1O[C@@H](Oc2ccc(CCNC(C)=O)c(-c3cccc(F)c3)c2)[C@H](O)[C@H](O)[C@H]1OC] |
| T50 | 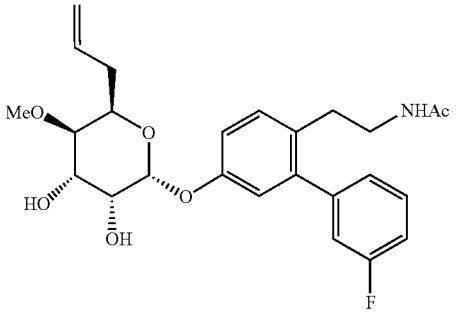 [SMILES: C=CC[C@H]1O[C@H](Oc2ccc(CCNC(C)=O)c(-c3cccc(F)c3)c2)[C@H](O)[C@H](O)[C@H]1OC] |
| T51 | 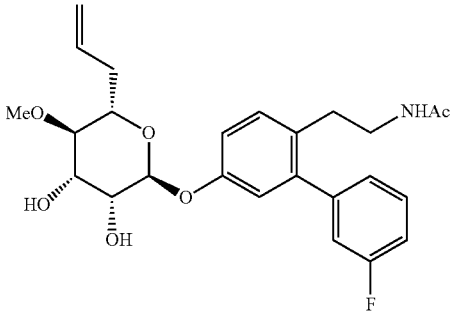 |
| T52 | 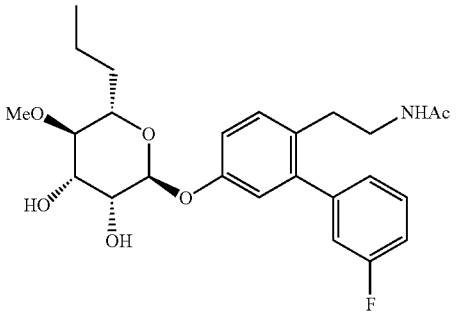 |

TABLE 1-continued

Examples of Biaryl- and Coumarin-Based Compounds with Modified Sugar Groups

| Compound Reference Number | Structure |
| --- | --- |
| T53 | 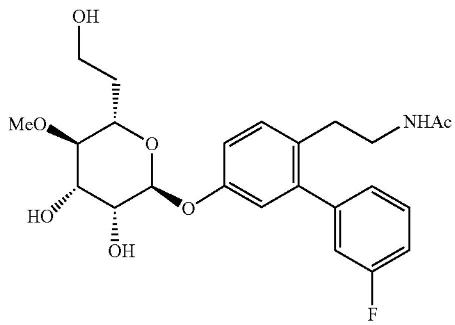 [SMILES: CO[C@@H]1[C@@H](O)[C@@H](O)[C@H](Oc2ccc(CCNC(C)=O)c(-c3cccc(F)c3)c2)O[C@H]1CCO] |
| T54 | 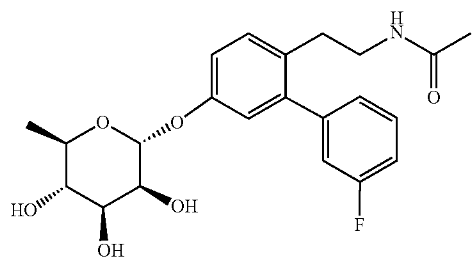 [SMILES: CC(=O)NCCc1ccc(O[C@H]2O[C@H](C)[C@@H](O)[C@H](O)[C@@H]2O)cc1-c1cccc(F)c1] |
| T55 | 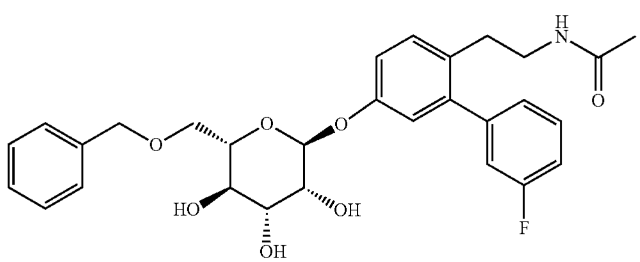 [SMILES: CC(=O)NCCc1ccc(O[C@@H]2O[C@@H](COCc3ccccc3)[C@H](O)[C@@H](O)[C@H]2O)cc1-c1cccc(F)c1] |
| T56 | 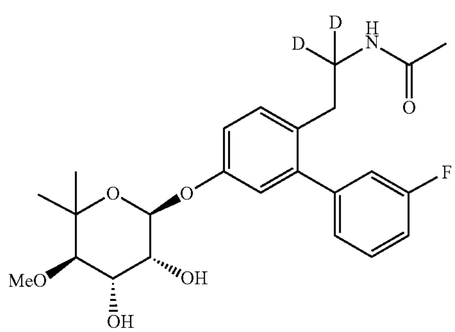 [SMILES: [2H]C([2H])(Cc1ccc(O[C@@H]2OC(C)(C)[C@H](OC)[C@@H](O)[C@H]2O)cc1-c1cccc(F)c1)NC(C)=O] |
| T57 | 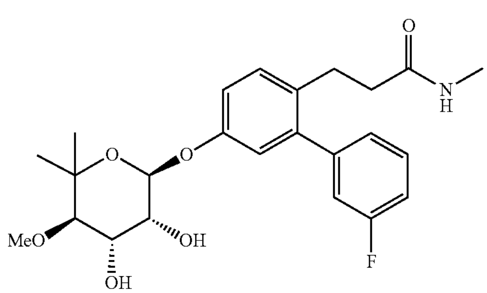 |

TABLE 1-continued

Examples of Biaryl- and Coumarin-Based Compounds with Modified Sugar Groups

| Compound Reference Number | Structure |
|---|---|
| T58 | 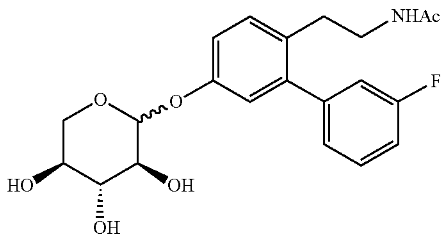 |
| T59 | 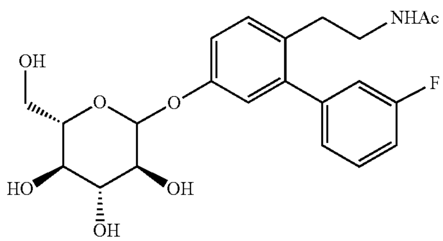 [SMILES: CC(=O)NCCc1ccc(OC2O[C@@H](CO)[C@H](O)[C@@H](O)[C@@H]2O)cc1-c1cccc(F)c1] |
| T60 | 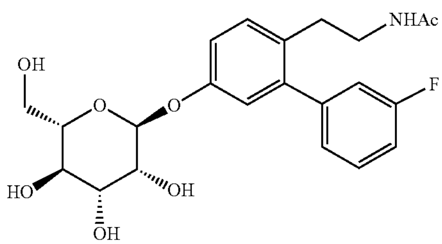 [SMILES: CC(=O)NCCc1ccc(O[C@@H]2O[C@@H](CO)[C@H](O)[C@@H](O)[C@H]2O)cc1-c1cccc(F)c1] |
| T61 | (Anomeric Isomer I) |
| T62 | (Anomeric Isomer II) |
| T63 | 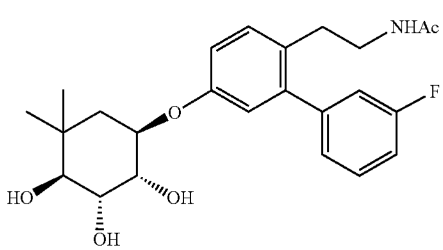 [SMILES: CC(=O)NCCc1ccc(O[C@@H]2CC(C)(C)[C@H](O)[C@@H](O)[C@H]2O)cc1-c1cccc(F)c1] |

TABLE 1-continued

Examples of Biaryl- and Coumarin-Based Compounds with Modified Sugar Groups

| Compound Reference Number | Structure |
|---|---|
| T64 | 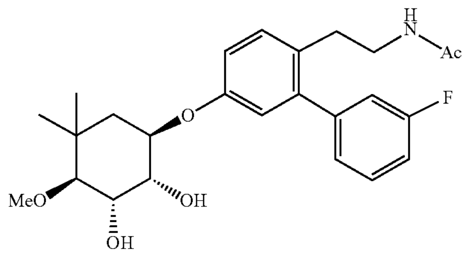 |
| T65 | 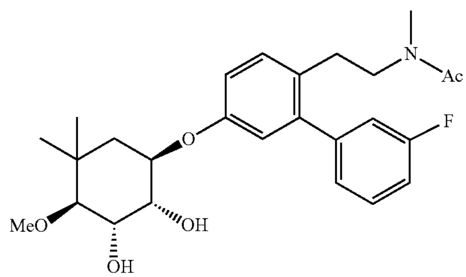 [SMILES: CO[C@@H]1[C@@H](O)[C@@H](O)[C@H](Oc2ccc(CCN(C)C(C)=O)c(-c3cccc(F)c3)c2)CC1(C)C] |
| T66 | 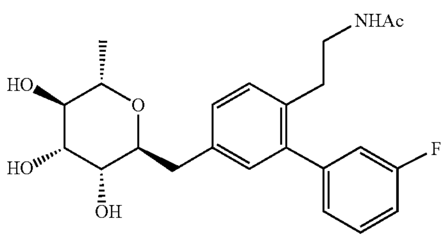 [SMILES: CC(=O)NCCc1ccc(C[C@@H]2O[C@@H](C)[C@H](O)[C@@H](O)[C@H]2O)cc1-c1cccc(F)c1] |
| T67 | 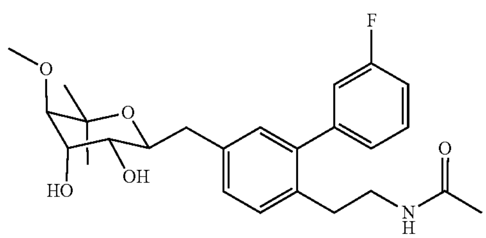 [SMILES: COC1C(O)C(O)C(Cc2ccc(CCNC(C)=O)c(-c3cccc(F)c3)c2)OC1(C)C] |
| T68 | 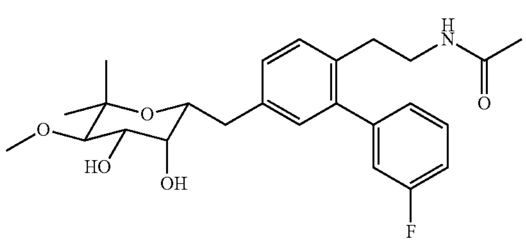 [SMILES: COC1C(O)C(O)C(Cc2ccc(CCNC(C)=O)c(-c3cccc(F)c3)c2)OC1(C)C] |
| T69 | 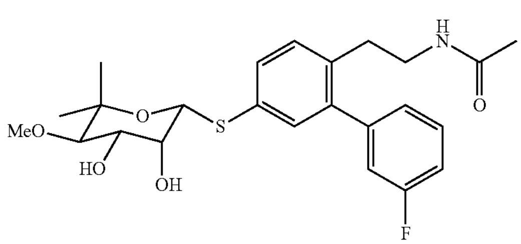 [SMILES: COC1C(O)C(O)C(Sc2ccc(CCNC(C)=O)c(-c3cccc(F)c3)c2)OC1(C)C] |

TABLE 1-continued

Examples of Biaryl- and Coumarin-Based Compounds with Modified Sugar Groups

| Compound Reference Number | Structure |
|---|---|
| T70 | 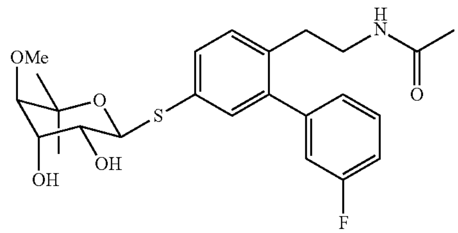 [SMILES: COC1C(O)C(O)C(Sc2ccc(CCNC(C)=O)c(-c3cccc(F)c3)c2)OC1(C)C] |
| T71 | 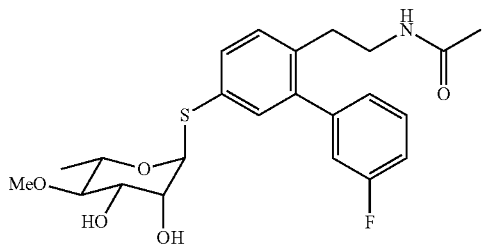 [SMILES: COC1C(C)OC(Sc2ccc(CCNC(C)=O)c(-c3cccc(F)c3)c2)C(O)C1O] |
| T72 | 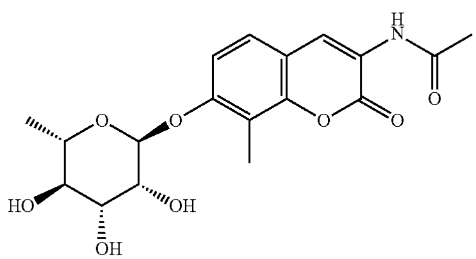 [SMILES: CC(=O)Nc1cc2ccc(O[C@@H]3O[C@@H](C)[C@H](O)[C@@H](O)[C@H]3O)c(C)c2oc1=O] |
| T73 | 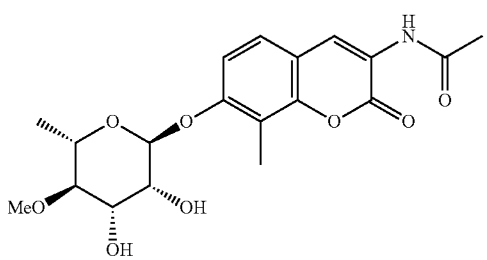 [SMILES: CO[C@@H]1[C@@H](O)[C@@H](O)[C@H](Oc2ccc3cc(NC(C)=O)c(=O)oc3c2C)O[C@H]1C] |
| T74 | 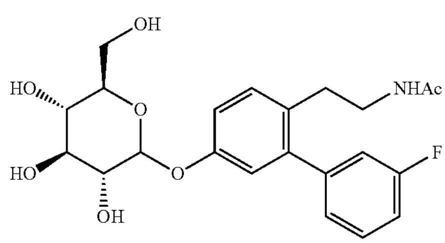 [SMILES: CC(=O)NCCc1ccc(OC2O[C@H](CO)[C@@H](O)[C@H](O)[C@H]2O)cc1-c1cccc(F)c1] |
| T75 | 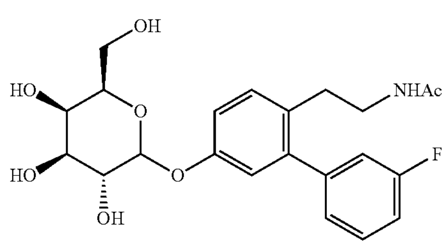 [SMILES: CC(=O)NCCc1ccc(OC2O[C@H](CO)[C@H](O)[C@H](O)[C@H]2O)cc1-c1cccc(F)c1] |

TABLE 1-continued

Examples of Biaryl- and Coumarin-Based Compounds with Modified Sugar Groups

| Compound Reference Number | Structure |
| --- | --- |
| T76 | 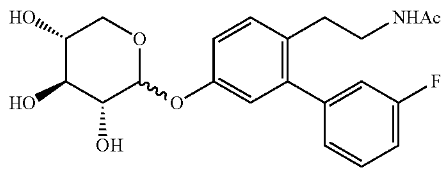 [SMILES: CC(=O)NCCc1ccc(OC2OC[C@@H](O)[C@H](O)[C@H]2O)cc1-c1cccc(F)c1] |
| T77 | 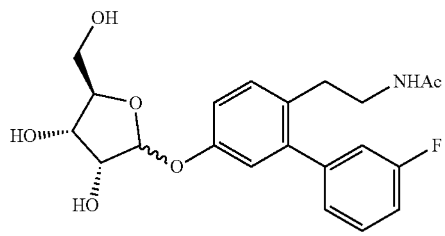 [SMILES: CC(=O)NCCc1ccc(OC2O[C@H](CO)[C@@H](O)[C@H]2O)cc1-c1cccc(F)c1] |
| T78 | 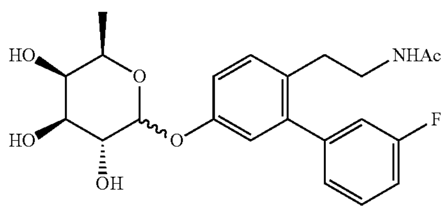 [SMILES: CC(=O)NCCc1ccc(OC2O[C@H](C)[C@H](O)[C@H](O)[C@H]2O)cc1-c1cccc(F)c1] |
| T79 | 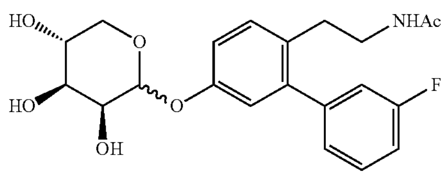 [SMILES: CC(=O)NCCc1ccc(OC2OC[C@@H](O)[C@H](O)[C@@H]2O)cc1-c1cccc(F)c1] |
| T80 | 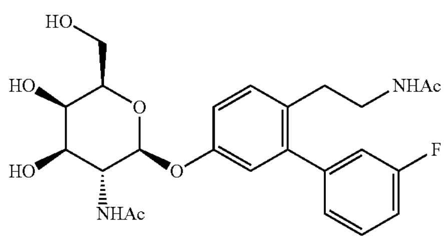 [SMILES: CC(=O)NCCc1ccc(O[C@@H]2O[C@H](CO)[C@H](O)[C@H](O)[C@H]2NC(C)=O)cc1-c1cccc(F)c1] |
| T81 | 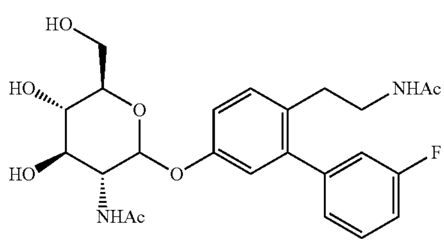 [SMILES: CC(=O)NCCc1ccc(OC2O[C@H](CO)[C@@H](O)[C@H](O)[C@H]2NC(C)=O)cc1-c1cccc(F)c1] |
| T82 | 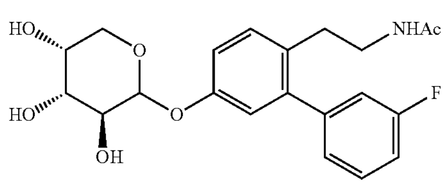 [SMILES: CC(=O)NCCc1ccc(OC2OC[C@@H](O)[C@@H](O)[C@@H]2O)cc1-c1cccc(F)c1] |

In some embodiments, the compounds listed may be used for the prevention and treatment of one or more diseases or disorders discussed herein or otherwise. In some embodiments, biaryl- and coumarin-based compounds with modified sugar derivatives covered by the claims or otherwise disclosed herein may be used. All such compounds are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

Also disclosed herein are compounds that are synthetic intermediates useful for the preparation and manufacture of the disclosed and claimed biaryls and coumarin-based compounds with modified sugar groups. Such synthetic intermediates are disclosed throughout the application, including, for example, in the synthetic schemes presented in the Examples section below.

In some embodiments, the compounds of the present invention have the advantage that they may be more efficacious than, be less toxic than, be longer acting than, be more potent than, produce fewer side effects than, be more easily absorbed than, more stable than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures, and individual diastereomers. In some embodiments, a single diastereomer is obtained. The chiral centers of the compounds of the present invention can have the S or the R configuration.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present invention function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present invention exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Indications

Approximately 26 million Americans are afflicted with either Type 1 or Type 2 diabetes. Despite the use of insulin and oral anti-diabetic medications to help maintain euglycemia, about 60-70% of these individuals develop diabetic peripheral neuropathy (DPN). (Veves et al., 2008).

Diabetic peripheral neuropathy may manifest first as a neuropathic pain syndrome, in which patients feel significant pain in the absence of a painful stimulus (allodynia) or have an exaggerated sensation of pain in response to a stimulus that would only be perceived as mildly noxious under normal circumstances (hyperalgesia). Hyperalgesia can be thermal (in response to moderate temperature change, whether heat or cold) or mechanical (in response to pressure or some other physical stimulus). Furthermore, both allodynia and hyperalgesia may be experienced by a given patient at various times.

Some patients who develop painful diabetic neuropathy go on to develop insensate neuropathy in which patients have an impaired ability to perceive pressure, temperature changes, or even significant injuries in the affected areas. Insensate neuropathy is most often present in the extremities, particularly the distal extremities in a classic "stocking and glove" distribution. It is a significant contributing factor to overall morbidity, since diabetes patients often suffer from impaired wound healing and failure to perceive an injury can significantly impair response and treatment. Some patients do not develop painful diabetic neuropathy, but instead first present with insensate neuropathy. Other patients may display both numbness and hypersensitivity. Some classifications of DPN identify typical and atypical forms of the condition. The most common form, diabetic sensorimotor polyneuropathy (DSPN) is associated with longstanding hyperglycemia and microvessel alterations, and is statistically associated with retinopathy and nephropathy. The atypical DPNs differ from DSPN in onset, course, manifestations, and possibly mechanism (Tesfaye et al., 2010; Callaghan et al., 2012).

A number of small molecules based upon the novobiocin scaffold are reported to inhibit heat shock protein 90 (Hsp90) and to have significant neuroprotective properties including being useful for reversing symptoms of DPN in animal models.

One novobiocin analog ("novologue") of this type is KU-32, the first novologue shown to have significant activity in reversing established symptoms of DPN in diabetic mice (Ma et al., 2014). Another novologue is N-(2-(5-(((3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide, also known as KU-596, which is also reported to protect neurons from hyperglycemic conditions in vitro and alleviate symptoms of neuropathy in diabetic mice (Kusuma et al., 2012; U.S. Pat. No. 9,422,230; Ma et al., 2015). Because diabetic neuropathy has many features in common with neuropathies arising from other causes, such as neuropathic pain induced by physical trauma or ischemia, or drug-induced neuropathy, compounds that inhibit Hsp90 and are capable of reversing symptoms of DPN such as the compounds described herein, may also be useful for treating neuropathy more generally. Neuropathic pain from non-diabetic origins is an area of high unmet need, since many patients do not respond to existing therapies or only achieve partial relief of their symptoms.

In addition to its effects in models of diabetic neuropathy, KU-596 has been reported to improve impaired mitochondrial function in neurons and reduce the expression of inflammatory markers in diabetic neurons (Ma et al. 2015). Because diabetic tissues undergo significant oxidative stress, these results indicate that this compound, and mechanistically related compounds such as KU-32, may be useful in treating other neurological disorders that involve oxidative stress and chronic inflammation, including neurodegenerative diseases, epilepsy, multiple sclerosis, spinal cord injury, demyelinating nerve disorders, and psychiatric disorders including schizophrenia, depression, bipolar disorder, autism and related disorders, and post-traumatic stress disorders. More generally, compounds exhibiting similar mechanistic actions such as the compounds of the present invention have potential uses in non-neurological diseases that involve mitochondrial dysfunction or chronic or acute oxidative stress and inflammation, including osteoarthritis, autoimmune diseases, and mitochondrial myopathy. These compounds may also be useful in combination with other therapies, particularly therapies that reduce oxidative stress, inflammation, and mitochondrial dysfunction by other mechanisms.

A. Hsp70 Protein

In some embodiments, the compounds and compositions provided herein may be used to modulate the expression and/or activity of Hsp70 proteins or to modulate the activity of targets or signaling pathways that are regulated by Hsp70. The Hsp70 protein functions as a chaperone protein assisting in protein folding and has a wide variety of different biological functions within normal cells. In particular, Hsp70 is associated with protein folding and transport of proteins into organelles, recognition of damaged proteins and assisting in the tagging of these proteins for destruction, and recognizes proteins carrying particular amino acid sequences and transports these proteins to specific organelles such as lysosomes. Notably, Hsp70 is an important regulator of importation of proteins into mitochondria. Without wishing to be bound by any theory, it is believed that as many as 30% of proteins interact with Hsp70 which ensures their proper folding and the Hsp70 interacts with the hydrophobic portions of proteins to prevent their degradation. Furthermore, Hsp70 also helps in the identification of irreversibly damaged proteins and sends those proteins to proteasomes for degradation. Such degradation occurs in conjunction with Bag-1 and CHIP proteins.

Additionally, the Hsp70 protein is associated with identifying and marking proteins which are degraded under fasting conditions or other low nutrient conditions. In particular, the presence of the amino acid sequence KFPRQ within a protein is known to trigger the protein for degradation under such conditions by the lysosome.

The effects of novologues in models of diabetic neuropathy have been shown to be Hsp70-dependent, as Hsp70 knockout mice are unresponsive to these compounds, at doses which were fully effective in wild-type mice.

B. Hsp90 Protein

In some embodiments, the compounds and compositions of the present disclosure may bind to the C terminus of the Hsp90 protein and thus prevent the binding of the natural substrate to the protein. Other novologues, notably KU-32 and KU-596, have been designed to bind to the C-terminus of Hsp90 using molecular modelling techniques and data derived from initial observations of novobiocin binding to the C-terminus (e.g., Kusuma et al., 2012). The Hsp90 is a molecular chaperone protein, which in addition to assisting in protein folding, protein degradation, and mitigating heat stress, is implicated in stabilizing a number of proteins associated with cancer. Inhibition of the Hsp90 protein has been shown to lead to apoptosis of the cancerous cells. Without being bound by theory, a number of different molecular pathways are implicated in the Hsp90 protein's role in cancer development and proliferation. For example, the protein is implicated in stabilizing mutant oncogenic proteins such as v-Src, Bcr/Abl, and p53, stabilizing several growth factors and signaling molecules such as EGFR, PI3K, and AKT proteins which leads to growth factor signaling pathway promotion, and promotes the induction of VEGF, nitric oxide synthase, and the matrix metalloproteinase MMP2 which promote angiogenesis and methatesis of the cancerous cells. Many different cancer types and subtypes rely on pathways mediated by the Hsp90 protein for proliferation and tumor development, and inhibitors of the highly conserved Hsp90 protein are considered to have potential as treatments for a wide variety of cancers.

C. Neurological Diseases or Disorders

In another aspect, the compounds, compositions, and methods provided herein may be used to treat neurological diseases and disorders, including those affecting the central nervous system, as well as those affecting the peripheral nervous system. In some embodiments, the compounds, compositions, and methods provided herein may be used to treat neurodegenerative diseases, such as Alzheimer's and Parkinson's diseases which are considered to primarily result from neurodegeneration in the central nervous system. In some embodiments, the compounds, compositions, and methods provided herein may be used to treat other neurological diseases and disorders, which involve central or peripheral neurodegeneration or neuron damage, such as epilepsy, psychiatric disorders, and peripheral neuropathies. Without being bound by any theory, in some embodiments, the compounds and compositions of the present disclosure provide neuroprotective effects by modulating the activity of Hsp90 and thus may be used to inhibit the progressive deterioration of neurons that leads to cell death.

Examples of neurological disorders or diseases that may be treated by the compounds, compositions, and methods disclosed herein include, but are not limited to chronic neurological diseases such as diabetic peripheral neuropathy (including third nerve palsy, mononeuropathy, mononeuropathy multiplex, diabetic amyotrophy, autonomic neuropathy and thoracoabdominal neuropathy), Alzheimer's disease, age-related memory loss, senility, age-related dementia, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis ("MS"), synucleinopathies, primary progressive aphasia, striatonigral degeneration, Machado-Joseph disease/spinocerebellar ataxia type 3 and olivopontocerebellar degenerations, spinocerebellar ataxia including types 1, 2, 3, and 12, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff's related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, Charcot-Marie-Tooth disease, Autosomal recessive spastic ataxia of Charlevoix-Saguenay, Dentatorubral-pallidoluysian atrophy, cystic fibrosis neuropathy, Frontotemporal dementia and parkinsonism linked to chromosome 17, familial amyloid polyneuropathy, trigeminal neuralgia associated with multiple sclerosis, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Degenerative diseases of the retina and optic nerve are also included within the methods of the present invention, including retinitis pigmentosa, optic neuritis, dominant optic atrophy, Leber hereditary optic neuropathy, and glaucoma. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In some embodiments, the neurodegenerative disorder is amyloidosis. Amyloidosis is observed in Alzheimer's disease, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis. In preferred embodiments, the neurodegenerative disorder treated and/or prevented using the methods and compositions of the disclosure is diabetic peripheral neuropathy.

D. Diseases Associated with Mitochondrial Dysfunction

Among its other functions, Hsp70 plays an important role in regulating the importation of nuclear-encoded mitochondrial proteins into the matrix of the mitochondria and promoting their proper processing and folding following importation (Harbauer, et al., 2014). A compound mechanistically related to the compounds of the present invention, KU-32, has been shown to improve mitochondrial bioenergetics (Ma, et al., 2014). Another novologue, KU-596, has been reported to improve impaired mitochondrial function in neurons and reduce the expression of inflammatory markers in diabetic neurons (Ma et al., 2015). Thus, in some embodiments, the compounds, compositions, and methods provided herein may be used to prevent or treat diseases or disorders involving mitochondrial dysfunction. Non-limiting examples of these include a wide variety of neurological disorders including neurodegenerative diseases, epilepsy, psychiatric diseases including depression, schizophrenia, anxiety disorders, PTSD, and bipolar disorder, neurodevelopmental disorders including autism and attention deficit disorders, neuromuscular disorders, including Friedreich's ataxia, mitochondrial myopathy, muscular dystrophy, and various forms of dystonia, chronic progressive external ophthalmoplegia, muscle wasting diseases including aging-related muscle wasting, diabetes-related muscle wasting, cancer-related cachexia, cachexia associated with dialysis, anorexia-related cachexia, and myasthenia gravis, impaired function of cardiac muscle associated with heart failure and other forms of cardiovascular disease, disorders of the retina, obesity, diabetes, and complications of diabetes.

III. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. Combination Therapy

In addition to being used as a monotherapy, the compounds of the present disclosure may also be used in combination therapies. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. Such second therapies include, but are not limited to, surgery, immunotherapy, radiotherapy, or a second chemotherapeutic agent. In some embodiments, the second chemotherapeutic agent is an N-terminus Hsp90 inhibitor such as geldanamycin, radicicol, the geldanamycin derivative 17AAG, NVP-AUY922, or gamitrinib. A variety of different Hsp90 inhibitors which may be used in combination with compounds provided herein are described in Jhaveri, et al., 2012, which is incorporated herein by reference.

V. Definitions

The definitions below supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

A. Chemical Groups

When used in the context of a chemical group: "hydrogen" means H; "hydroxy" means —OH; "oxo" means =O; "carbonyl" means —C(=O); "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⇌" represents a single bond or a double bond. Thus, the formula

covers, for example,

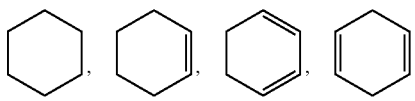

and

.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⫼" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper. Finally, a group such as —C(O)-alkanediyl$_{(C\leq6)}$- which contains a specific functional group and a chemical class is used to mean that those two elements may occur in any order such as —C(O)-alkanediyl$_{(C\leq6)}$- or -alkanediyl$_{(C\leq6)}$-C(O)—. Alternatively, groups which contain a chemical class and a variable or a second chemical class appear in the order described.

When a variable is depicted as a "floating group" on a ring system, for example, the group "R" in the formula:

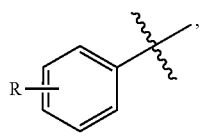

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

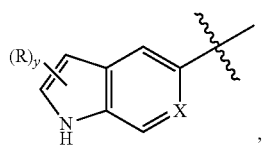

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C\leq8)}$", "cycloalkanediyl$_{(C\leq8)}$", "heteroaryl$_{(C\leq8)}$", and "acyl$_{(C\leq8)}$" is one, the minimum number of carbon atoms in the groups "alkenyl$_{(C\leq8)}$", "alkynyl$_{(C\leq8)}$", and "heterocycloalkyl$_{(C\leq8)}$" is two, the minimum number of carbon atoms in the group "cycloalkyl$_{(C\leq8)}$" is three, and the minimum number of carbon atoms in the groups "aryl$_{(C\leq8)}$" and "arenediyl(m)" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n +2 electrons in a fully conjugated cyclic π system. An aromatic compound or chemical group may be depicted as a single resonance structure; however, depiction of one resonance structure is taken to also refer to any other resonance structure. For example:

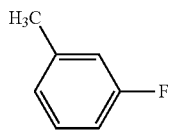

is also taken to refer to

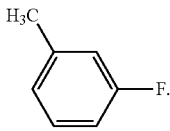

Aromatic compounds may also be depicted using a circle to represent the delocalized nature of the electrons in the fully conjugated cyclic π system, two non-limiting examples of which are shown below:

and

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H-R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H-R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CHCH═CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H-R, wherein R is alkenyl as this term is defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "cycloalkenyl" when used without the "substituted" modifier refers to a monovalent saturated aliphatic group with a carbon atom as the point of attachment, said carbon atom forming part of one or more non-aromatic ring structures, one or more carbon-carbon double bonds, provided that the group remains non-aromatic, no carbon-carbon triple bonds, and no atoms other than carbon and hydrogen. Non-limiting examples include: cyclopentenyl or cyclohexenyl. As used herein, the term does not preclude the presence of one or more alkyl groups (carbon number limitation permitting) attached to a carbon atom of the non-aromatic ring structure. The term "cycloalkenediyl" when used without the "substituted" modifier refers to a divalent saturated aliphatic group with two carbon atoms as points of attachment, one or more carbon-carbon double bonds, provided that the group remains non-aromatic, no carbon-carbon triple bonds, and no atoms other than carbon and hydrogen. A "cycloalkene" refers to the class of compounds having the formula H-R, wherein R is cycloalkenyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H-R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

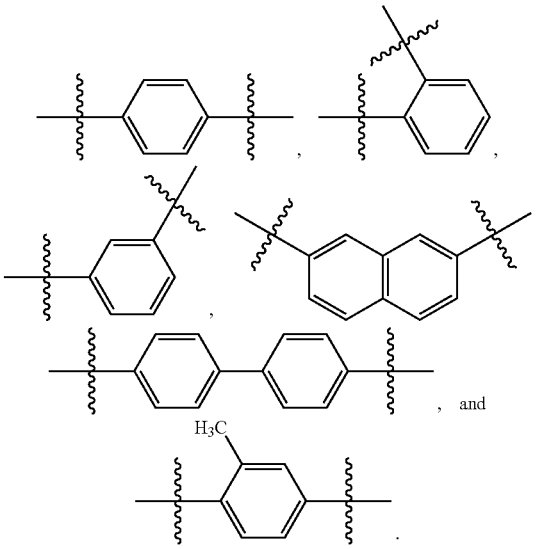

An "arene" refers to the class of compounds having the formula H-R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H-R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples are: pyridinylmethyl and 2-furanyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "imino" refers to the divalent group =NR, which is defined in an analogous manner to "acyl" or "thioacyl". The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", "acyloxy", and "iminooxy", when used without the "substituted" modifier, refers to groups, defined as —OR, in which R is cycloalkyl, alkenyl, alkynyl, aryl, aralkyl, heteroaryl, heterocycloalkyl, acyl, and imino, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)CH$_3$. The term "alkylaminodiyl" refers to the divalent group —NH-alkanediyl-, —NH-alkanediyl-NH—, or -alkanediyl-NH-alkanediyl-. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The term "alkylsulfonyl" when used without the "substituted" modifier refers to the group —S(O)$_2$R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

A "hydroxy protecting group" is well understood in the art. A hydroxy protecting group is a group which prevents the reactivity of the hydroxyl group during a reaction which modifies some other portion of the molecule and can be easily removed to generate the desired hydroxyl. Hydroxy protecting groups can be found at least in Greene and Wuts, 1999, which is incorporated herein by reference. Some non-limiting examples of hydroxy protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. A protected hydroxy group is a group of the formula: —OR$_{PGH}$, wherein R$_{PGH}$ is a hydroxy protecting group as that group is defined above.

B. Other Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. Unless the term is defined consistent with the above ways, the term "about" is used to indicate a value that is within plus or minus 5% of the listed value. In some specific embodiments, the term "about" is plus or minus 1% of the listed value.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to the patient or subject, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

Other abbreviations used herein are as follows: DMSO, dimethyl sulfoxide; OCR, oxygen consumption rate; ECAR, extracellular acidification rate; MRC, maximal respiratory capacity; FCCP, carbonyl cyanide-p-trifluoromethoxyphenylhydrazone; SDS-PAGE, sodium dodecyl sulfate polyacrylamide gel electrophoresis; PBST, phosphate buffered saline with 0.1% Tween 20; HRP, horseradish peroxidase; EDTA; ethylenediaminetetraacetic acid; DMEM, Dulbecco's Modified Eagle Medium; EtOAc, ethyl acetate; NMO, N-methylmorpholine N-oxide; THF, tetrahydrofuran, Me, methyl; NMR, nuclear magnetic resonance; DMF, N,N-dimethylformamide; TBAI, tetrabutylammonium iodide; GDA, geldanamycin; or BN or Bn, benzyl.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Compounds and Synthesis

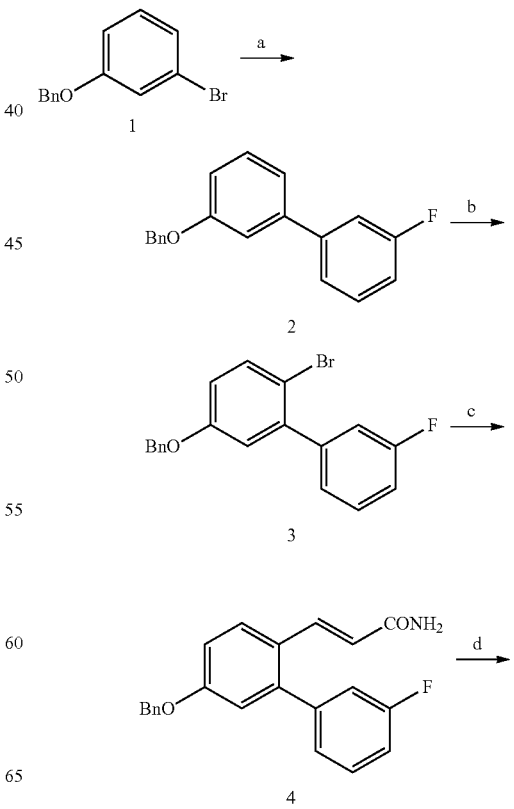

Scheme 1

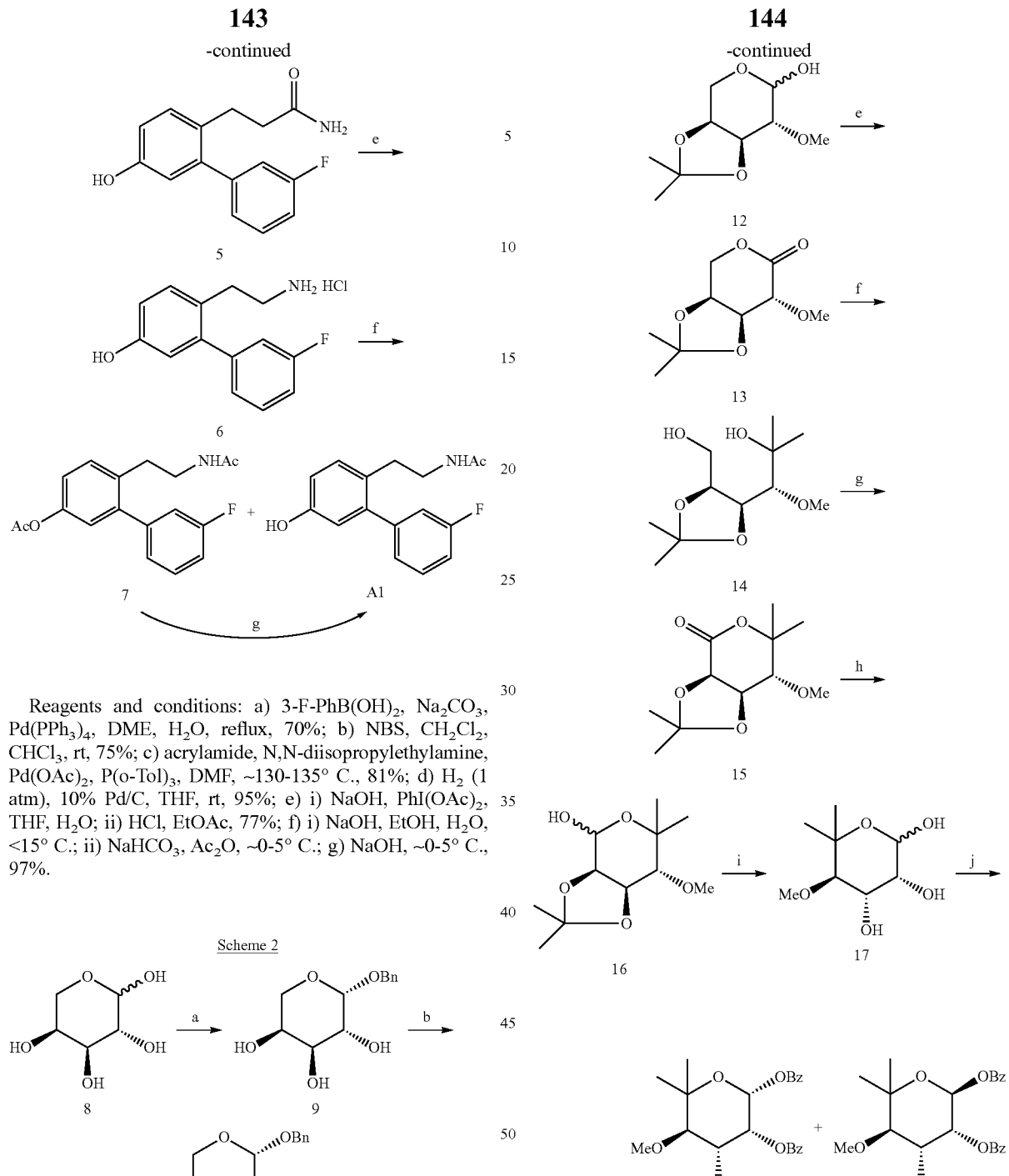

Reagents and conditions: a) 3-F-PhB(OH)$_2$, Na$_2$CO$_3$, Pd(PPh$_3$)$_4$, DME, H$_2$O, reflux, 70%; b) NBS, CH$_2$Cl$_2$, CHCl$_3$, rt, 75%; c) acrylamide, N,N-diisopropylethylamine, Pd(OAc)$_2$, P(o-Tol)$_3$, DMF, ~130-135° C., 81%; d) H$_2$ (1 atm), 10% Pd/C, THF, rt, 95%; e) i) NaOH, PhI(OAc)$_2$, THF, H$_2$O; ii) HCl, EtOAc, 77%; f) i) NaOH, EtOH, H$_2$O, <15° C.; ii) NaHCO$_3$, Ac$_2$O, ~0-5° C.; g) NaOH, ~0-5° C., 97%.

Scheme 2

Reagents and conditions: a) BnOH, AcCl, 30° C., 91%; b) 2,2-DMP, TsOH·H$_2$O, acetone, 20-25° C., 85%: c) Me$_2$SO$_4$, TBAB, 40% aq. NaOH, CPME, 20-30° C., quant.; d) H$_2$ (0.5 MPa), 10% Pd/C, CPME, 30° C., 85%; e) NaClO, NaBr, NaOAc, TEMPO, H$_2$O, CH$_2$Cl$_2$, 20-30° C., 73%; f) MeMgBr, Et$_2$O, CPME, 20-35° C., 88%; g) NaClO, NaBr, NaOAc, TEMPO, H$_2$O, CH$_2$Cl$_2$, 20-30° C., 75%; h) DIBAL-H, CH$_2$Cl$_2$, −25° C.~−5° C., 97%; i) 1) 732 ion exchange resin, H$_2$O, 40° C.; 2) Amberlite® IRA96RF, 93%; j) PhCOCl, pyridine, 0° C.-rt, 57%.

Scheme 3
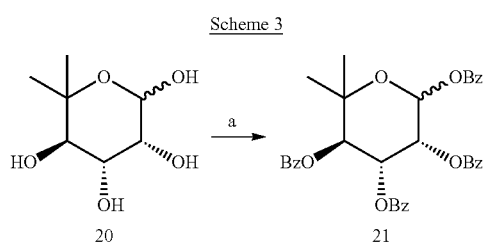
Reagents and conditions: a) PhCOCl, pyridine, 15° C., 61%.
Scheme 4
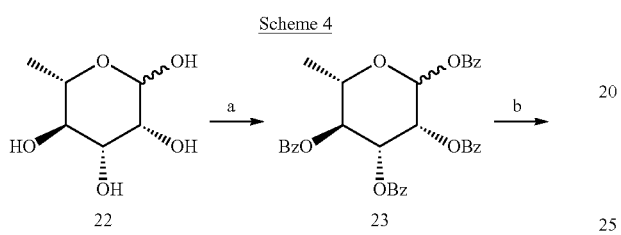
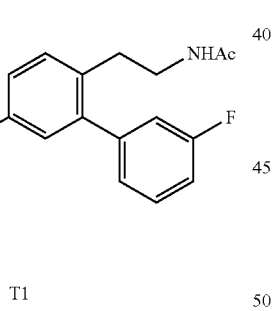
Reagents and conditions: a) BzCl, Py, 0-15° C., 93%; b) A1, BF$_3$·OEt$_2$, CH$_2$Cl$_2$, 0° C.-rt; c) NaOH, MeOH, THF, H$_2$O, rt, 81% from 23.
Scheme 5
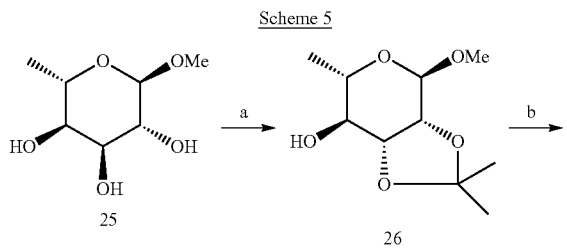
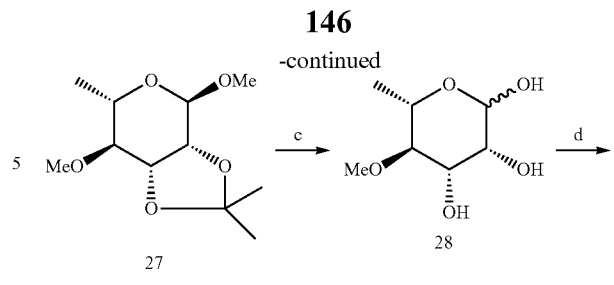
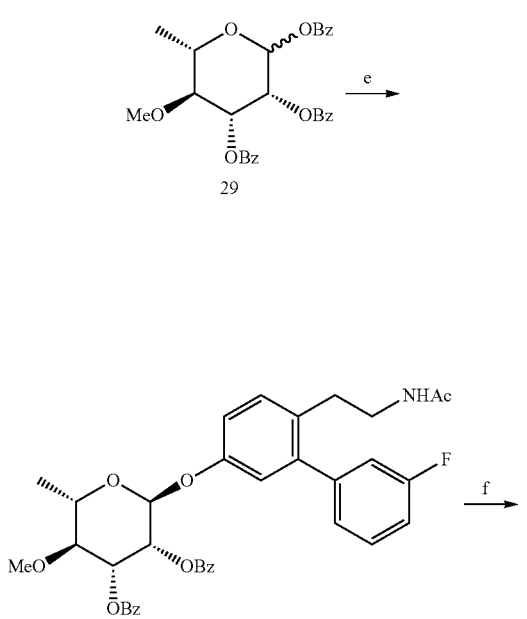
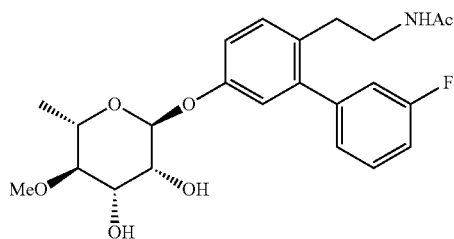
Reagents and conditions: a) 2,2-DMP, acetone, TsOH·H$_2$O, 10° C., 83%; b) NaH, THF, 0° C.; MeI, 15° C., 86%; c) 0.2 M aq. H$_2$SO$_4$, 80° C., 90%; d) BzCl, Py, 0-15° C., 68%; e) A1, BF$_3$·OEt$_2$, CH$_2$Cl$_2$, 0° C., 69%; NaOH, MeOH, THF, H$_2$O, rt, 89%.

Scheme 6
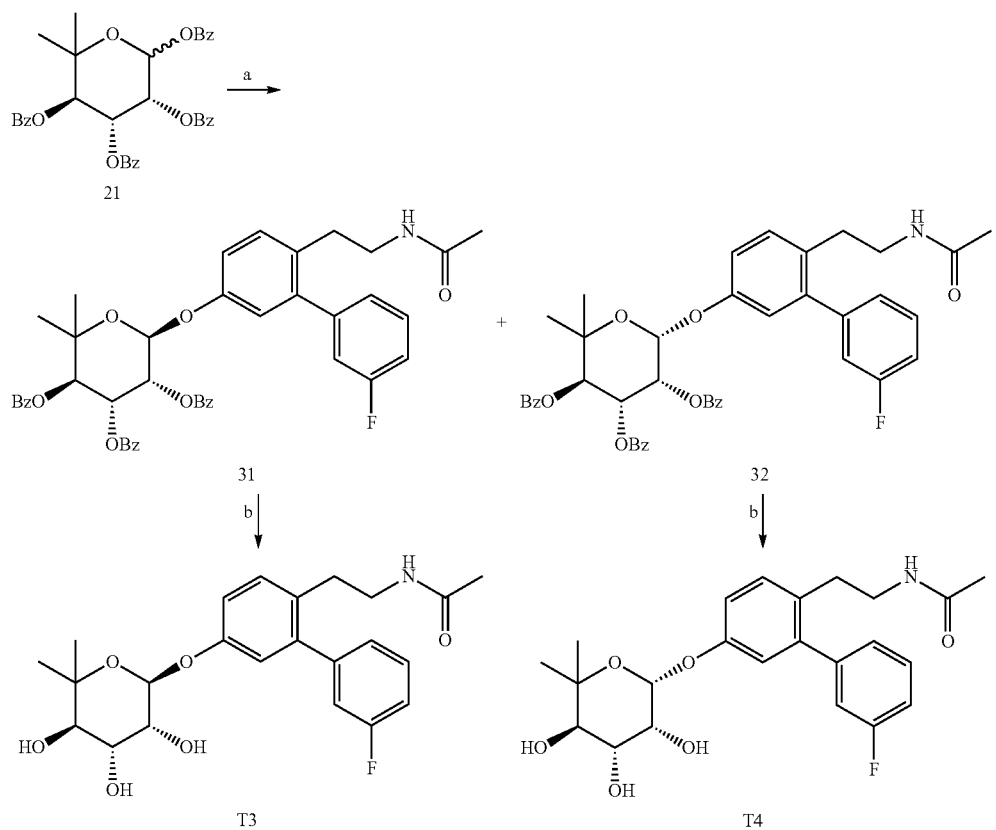
Reagents and conditions: (a) A1, BF$_3$·OEt$_2$, CH$_2$Cl$_2$, 0° C., 61% for 31; 3% for 32; (b) K$_2$CO$_3$, MeOH, rt, 98% for T3; 80% for T4.
Scheme 7
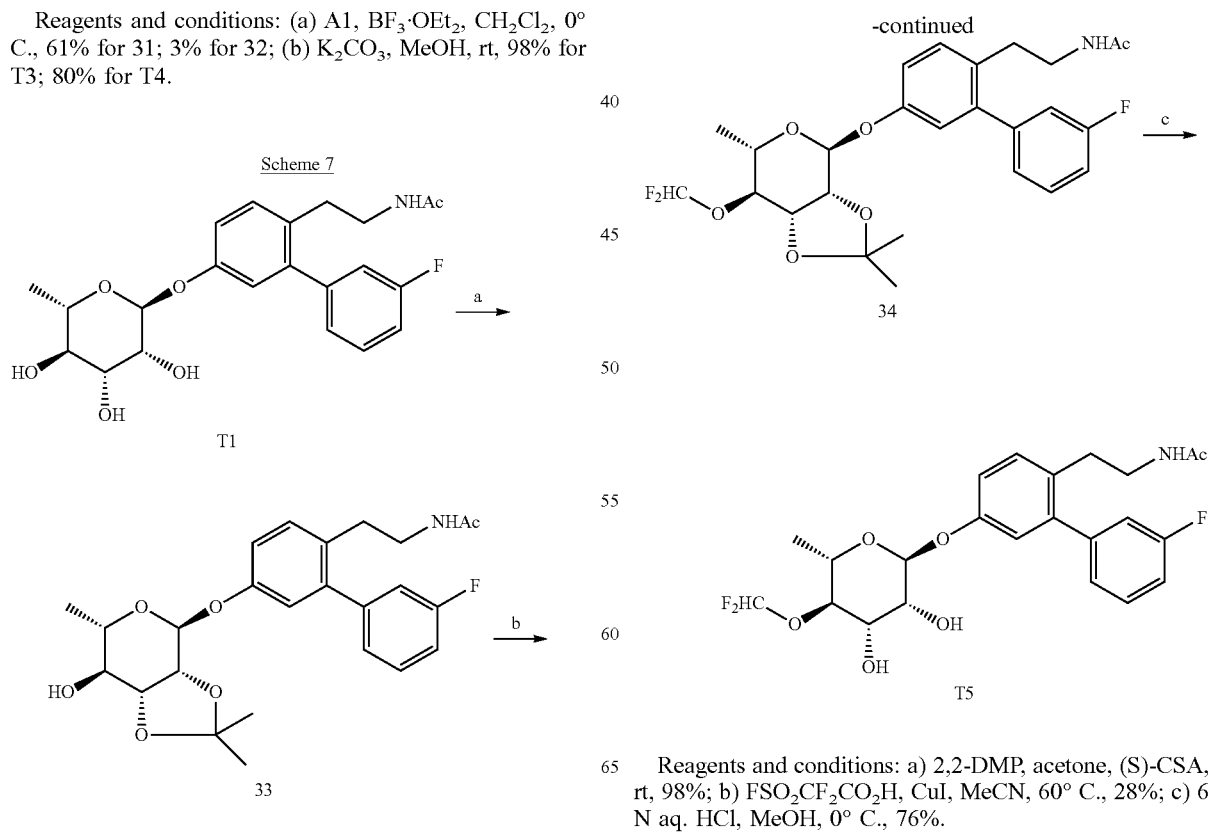
Reagents and conditions: a) 2,2-DMP, acetone, (S)-CSA, rt, 98%; b) FSO$_2$CF$_2$CO$_2$H, CuI, MeCN, 60° C., 28%; c) 6 N aq. HCl, MeOH, 0° C., 76%.

Scheme 8
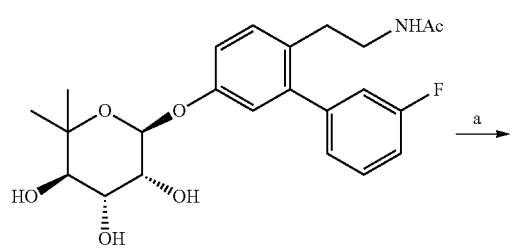
T3
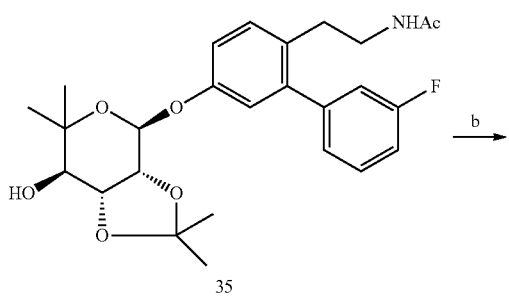
35
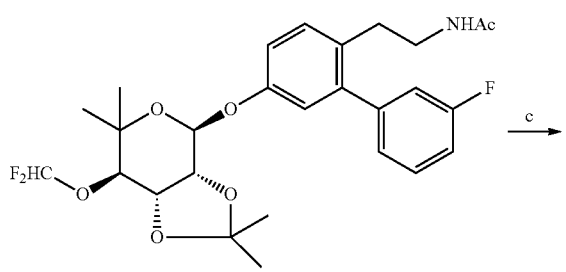
36
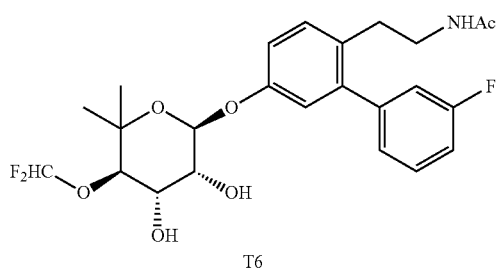
T6
Reagents and conditions: a) 2,2-DMP, acetone, (S)-CSA, rt, 97%; b) FSO$_2$CF$_2$CO$_2$H, CuI, MeCN, 60° C., 51%; c) 6 N aq. HCl, MeOH, rt, 66%.
Scheme 9
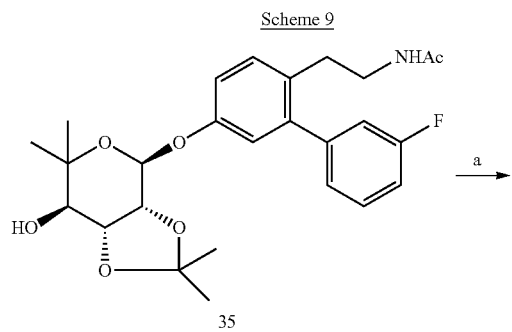
35
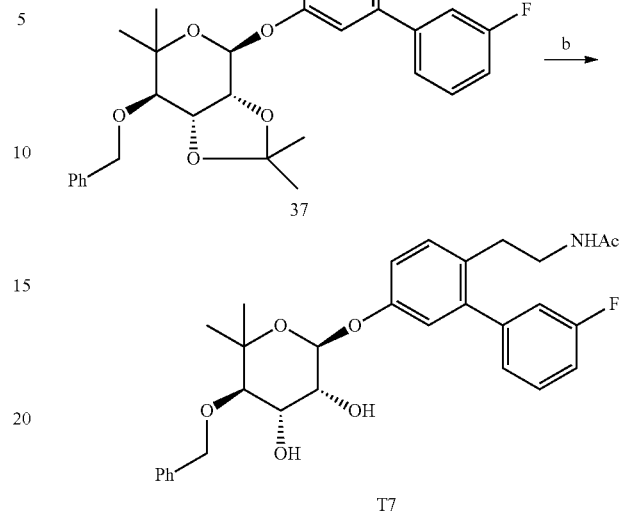
37
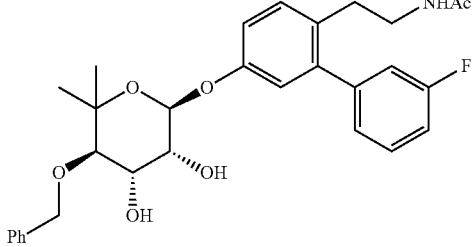
T7
Reagents and conditions: a) NaH, BnBr, DMF, 0° C.-rt, 75%; b) 6 N aq. HCl, MeOH, rt, 51%.
Scheme 10
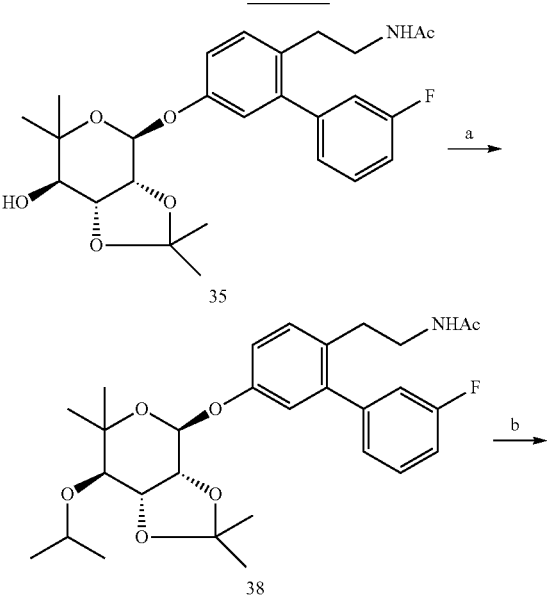
35
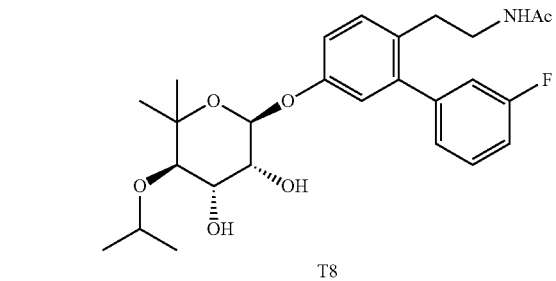
38
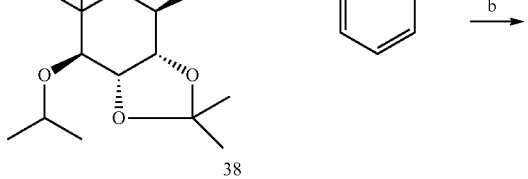
T8
Reagents and conditions: a) NaH, DMF, rt—65° C., 37%; b) 70% aq. AcOH, rt—40° C., 47%.

Scheme 11
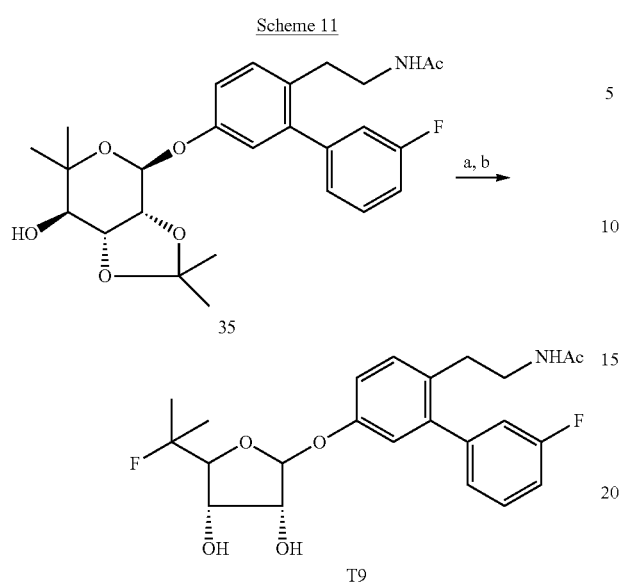
Reagents and conditions: a) DAST, CH$_2$Cl$_2$, 0° C., 23%; b) 6 N aq. HCl, MeOH, rt, 67%.
Scheme 12
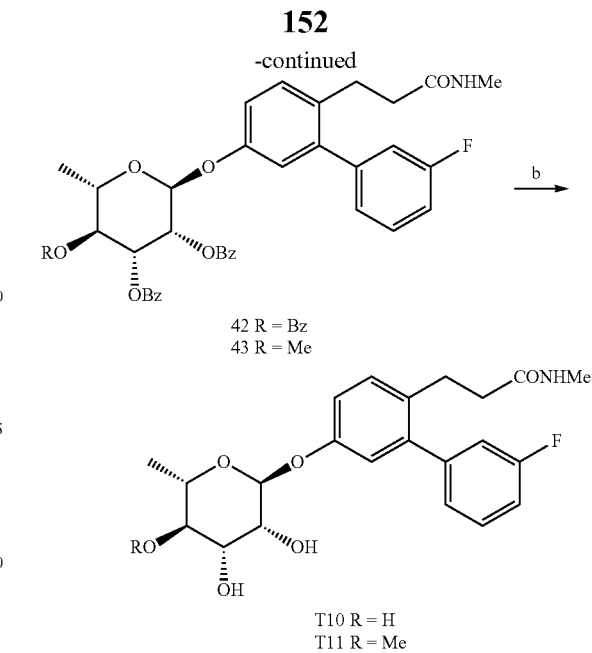
Reagents and conditions: a) MeNH$_2$·HCl, Et$_3$N, CH$_2$Cl$_2$, 0° C., 12%; b) 3, DIPEA, Pd(OAc)$_2$, tri(o-tolyl)phosphine, DMF, 135° C., 84%; c) H$_2$, 10% Pd/C, THF, rt, 93%.
Scheme 13
Reagents and conditions: a) A2, BF$_3$·OEt$_2$, CH$_2$Cl$_2$, 0° C., 62% for 43; b) 1 N aq. NaOH, THF, MeOH, rt, 60% for T10 from 23; 95% for T11.
Scheme 14

153
-continued

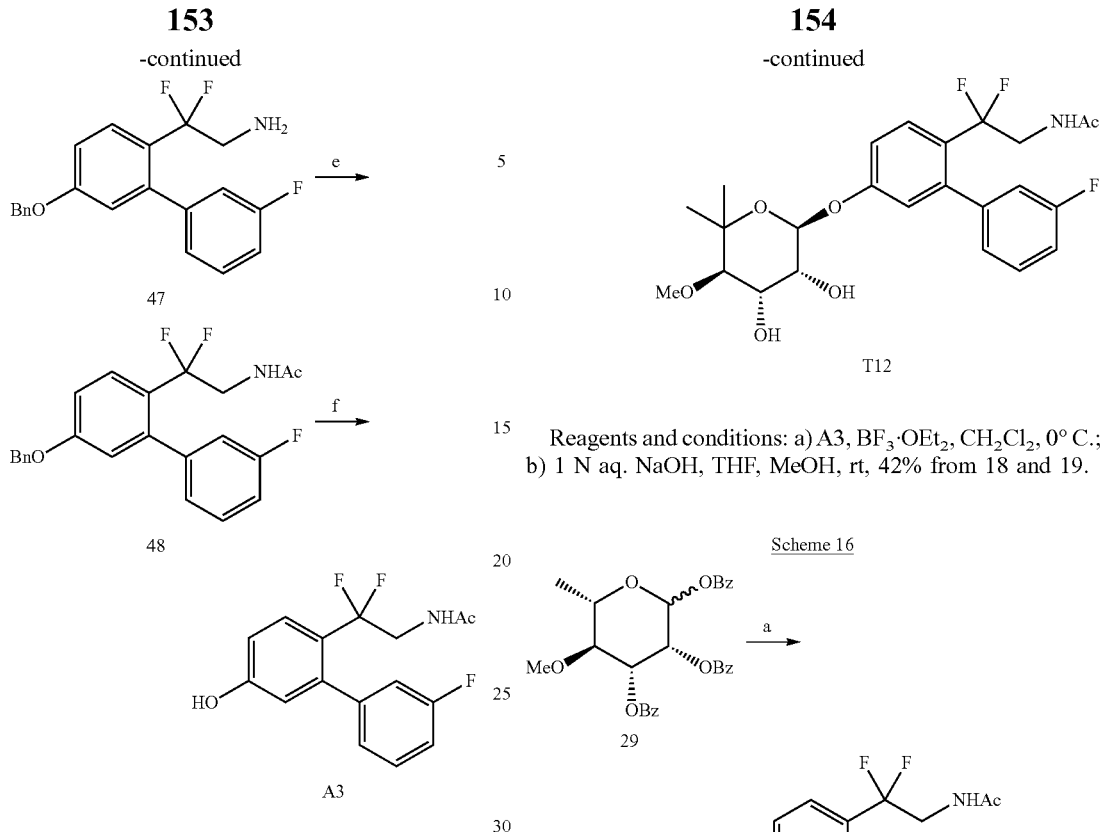

Reagents and conditions: a) n-BuLi, (CO₂Me)₂, THF, −78° C., 17%; b) DAST, 1,2-dichloroethane, 60° C., 58%; c) NaBH₄, EtOH, 0° C.-rt, 97%; d) i) Tf₂O, pyridine, MeCN, 0° C.; ii) aq. NH₄OH, rt; e) Ac₂O, Py, CH₂Cl₂, 0° C., 79% from 46; f) H₂, 10% Pd/C, THF, rt, quant.

Scheme 15

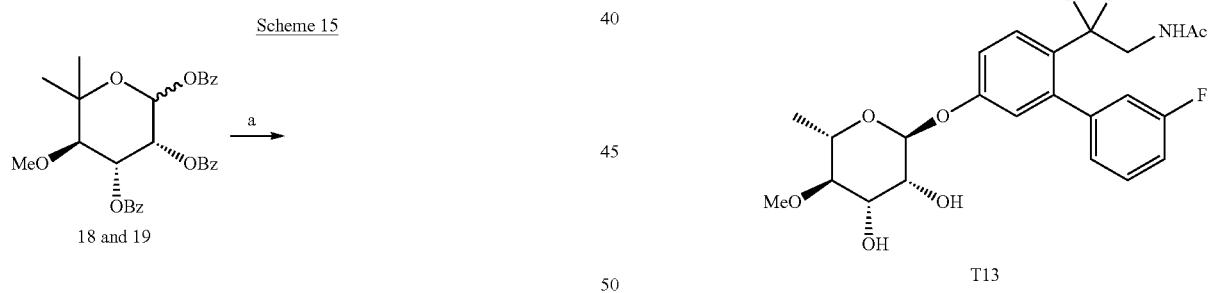

154
-continued

Reagents and conditions: a) A3, BF₃·OEt₂, CH₂Cl₂, 0° C.; b) 1 N aq. NaOH, THF, MeOH, rt, 42% from 18 and 19.

Scheme 16

Reagents and conditions: a) A3, BF₃·OEt₂, CH₂Cl₂, 0° C., 42%; b) 1 N aq. NaOH, THF, MeOH, rt, 87%.

Scheme 17

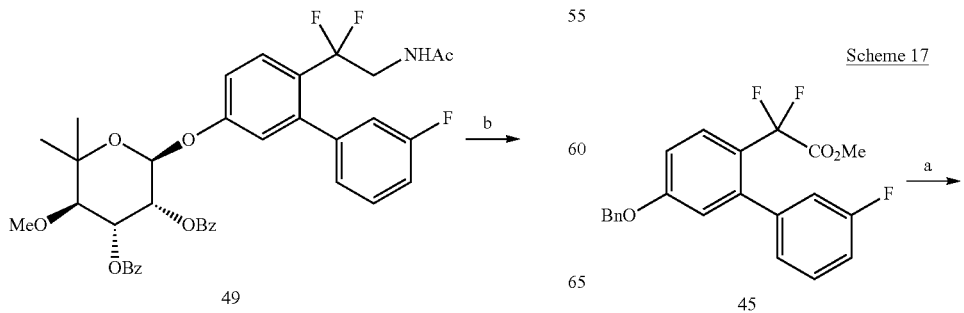

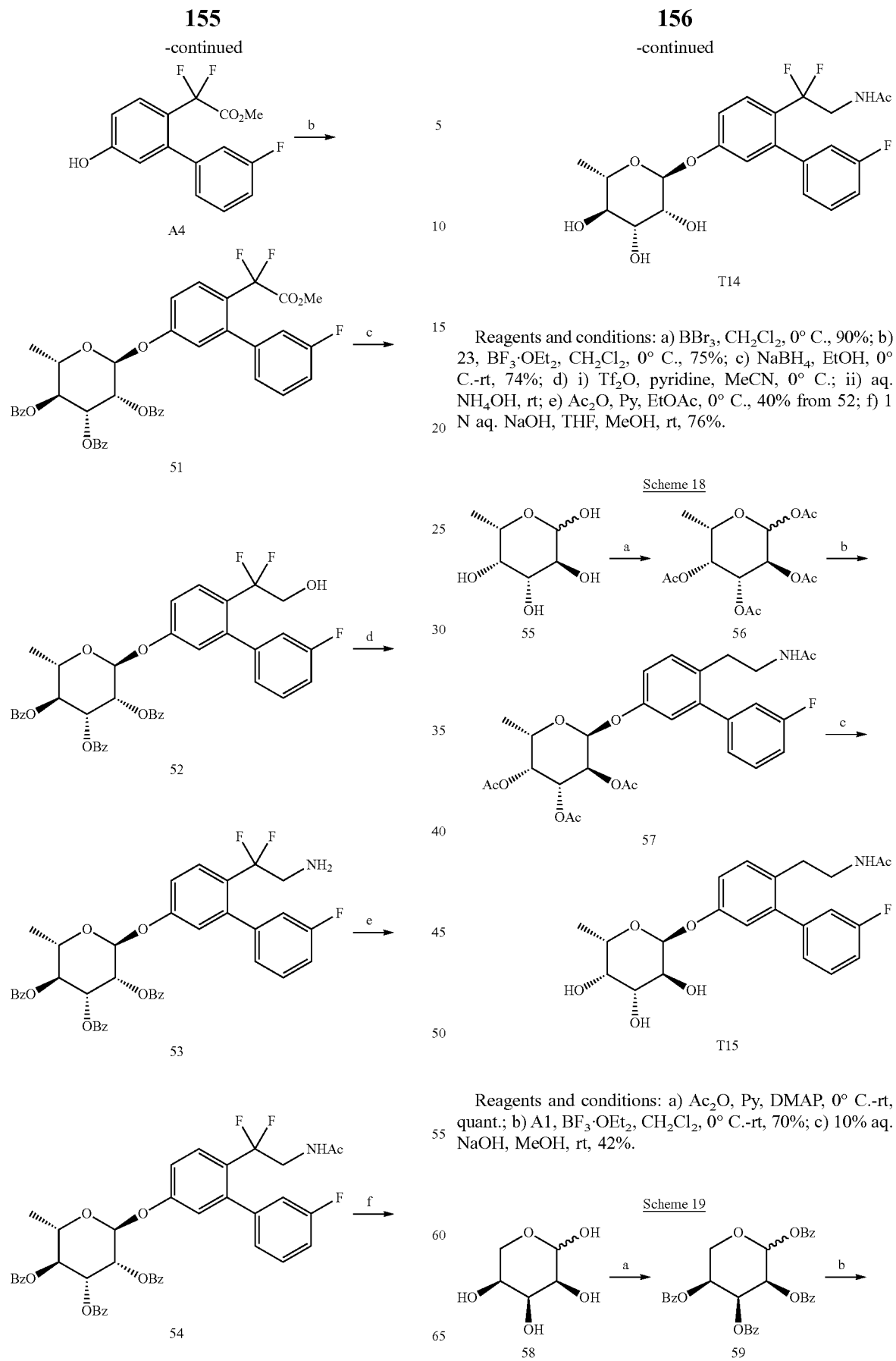
Reagents and conditions: a) BBr₃, CH₂Cl₂, 0° C., 90%; b) 23, BF₃·OEt₂, CH₂Cl₂, 0° C., 75%; c) NaBH₄, EtOH, 0° C.-rt, 74%; d) i) Tf₂O, pyridine, MeCN, 0° C.; ii) aq. NH₄OH, rt; e) Ac₂O, Py, EtOAc, 0° C., 40% from 52; f) 1 N aq. NaOH, THF, MeOH, rt, 76%.
Reagents and conditions: a) Ac₂O, Py, DMAP, 0° C.-rt, quant.; b) A1, BF₃·OEt₂, CH₂Cl₂, 0° C.-rt, 70%; c) 10% aq. NaOH, MeOH, rt, 42%.

157

-continued

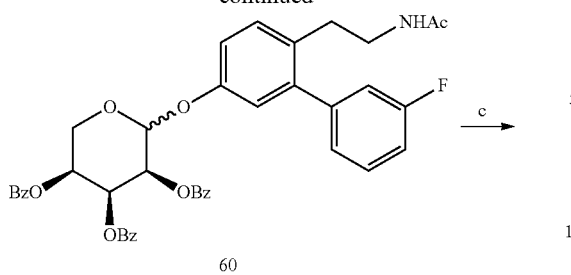

60

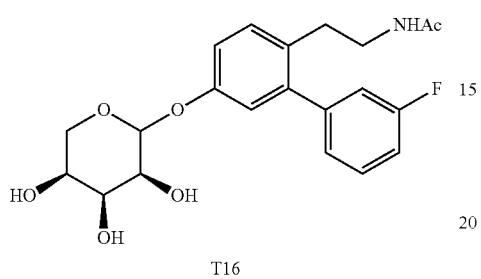

T16

Reagents and conditions: a) BzCl, Py, 0° C.-rt, 94%; b) A1, BF$_3$·OEt$_2$, CH$_2$Cl$_2$, 0° C.-rt, 57%; c) 1 N aq. NaOH, MeOH, THF, rt, 71%.

Scheme 20

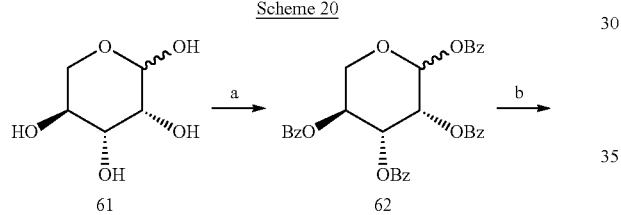

61 → 62

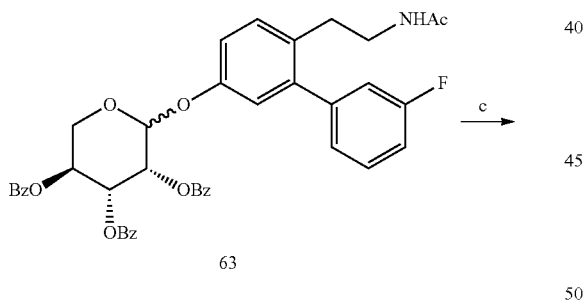

63

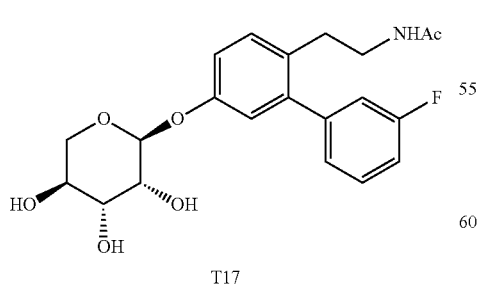

T17

Reagents and conditions: a) BzCl, Py, 0° C.-rt, 95%; b) A1, BF$_3$·OEt$_2$, CH$_2$Cl$_2$, 0° C.-rt, 50%; c) 1 N aq. NaOH, MeOH, THF, rt, 62%.

158

Scheme 21

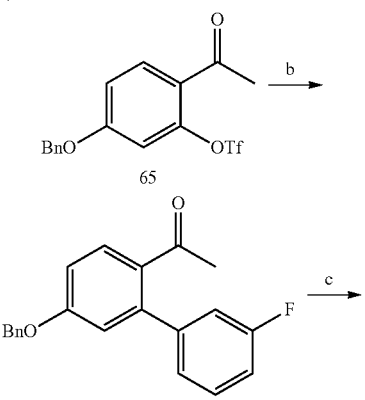

64 → 65 → 66

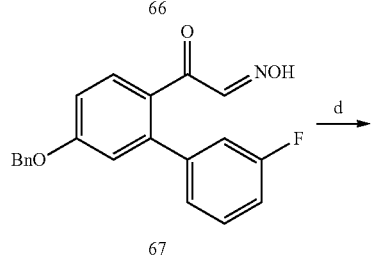

67

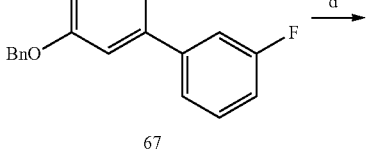

68

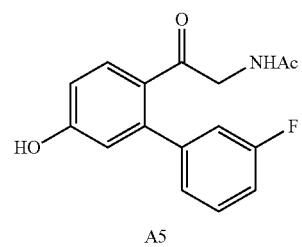

A5

Reagents and conditions: a) Tf$_2$NPh, K$_2$CO$_3$, THF, microwave, 120° C., 62%; b) 3-F-PhB(OH)$_2$, Pd(dppf)Cl$_2$, K$_2$CO$_3$, DMF, 75° C., 97%; c) t-BuOK, isopentyl nitrite, t-BuOH, THF, rt, 47%; d) In, AcOH, Ac$_2$O, THF, 70° C., 84%; e) H$_2$, 10% Pd/C, EtOAc, rt, 89%.

Scheme 22
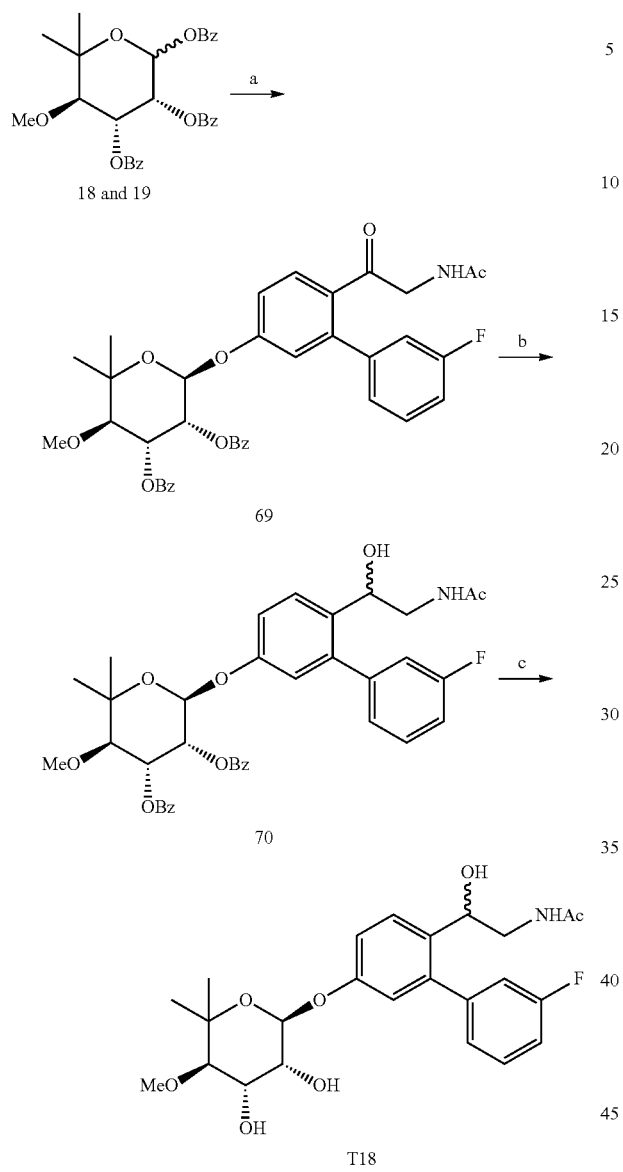
Reagents and conditions: a) A5, BF$_3$·OEt$_2$, CH$_2$Cl$_2$, rt, 46%; b) NaBH$_4$, EtOH, 0° C., 94%; c) 1 N aq. NaOH, EtOH, rt, 81%.
Scheme 23
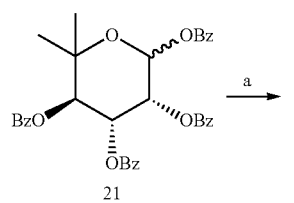
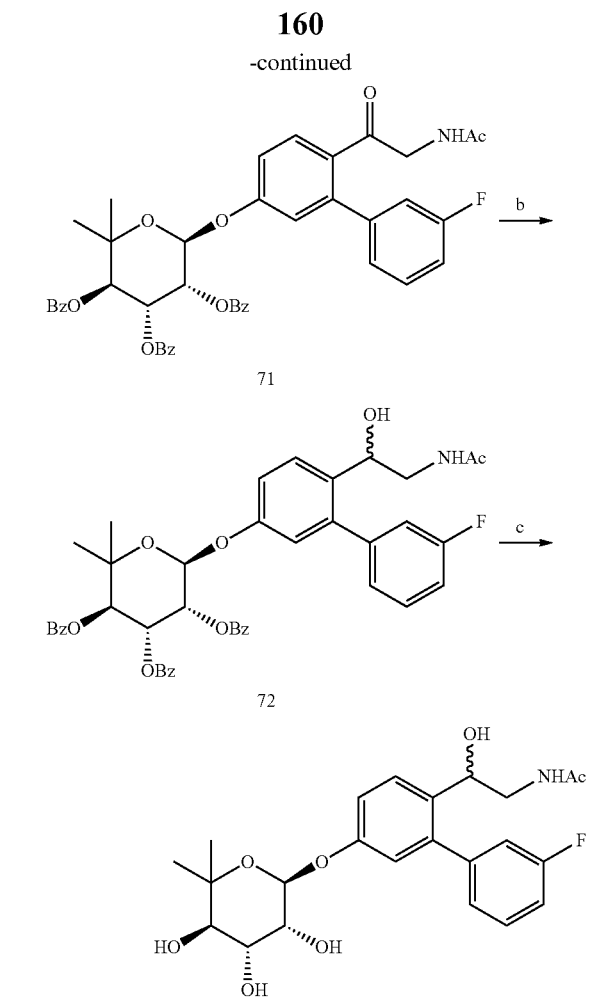
Reagents and conditions: a) A5, BF$_3$·OEt$_2$, CH$_2$Cl$_2$, 0° C., 24%; b) NaBH$_4$, MeOH, 0° C., 82%; c) 1 N aq. NaOH, MeOH, rt, 67%.
Scheme 24
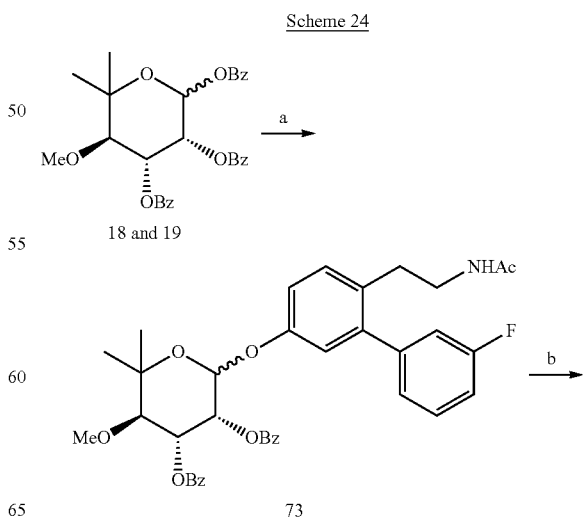

161
-continued
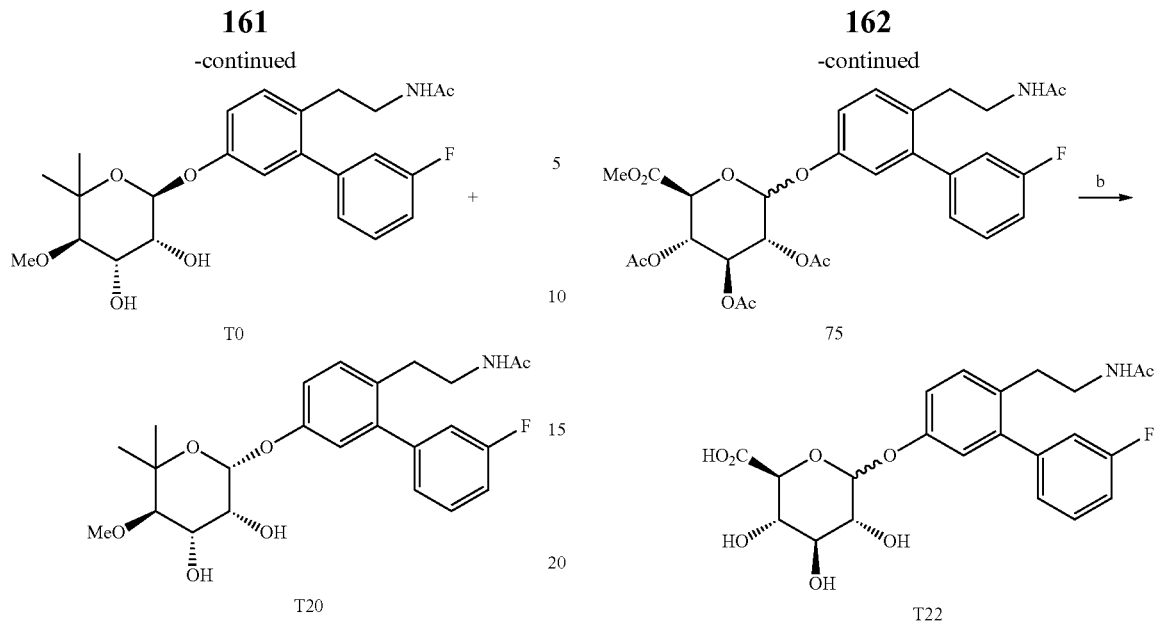
Reagents and conditions: a) A1, BF$_3$·OEt$_2$, toluene, 0° C., 79%; b) i) K$_2$CO$_3$, MeOH, rt, 64% for T0; ii) column chromatography.
Scheme 25
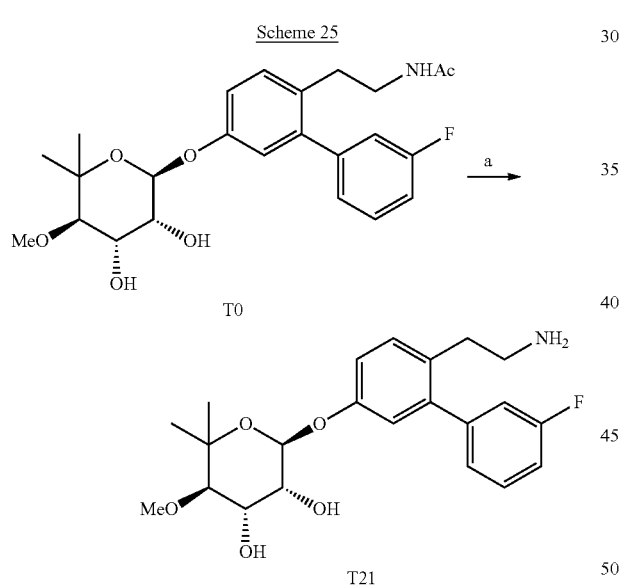
Reagents and conditions: a) NH$_4$Br, ethylenediamine, 130° C., Biotage microwave, 97%.
Scheme 26
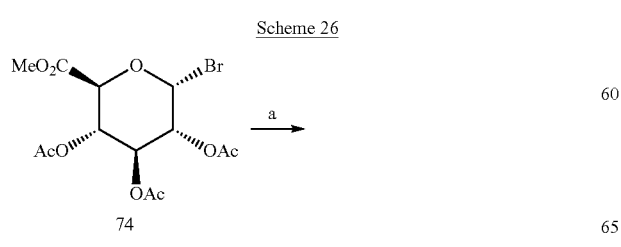
162
-continued
Reagents and conditions: a) A1, AgOTf, 4 Å MS, CH$_2$Cl$_2$, rt, quant.; b) 1 N aq. NaOH, EtOH, rt, 36%.
Scheme 27
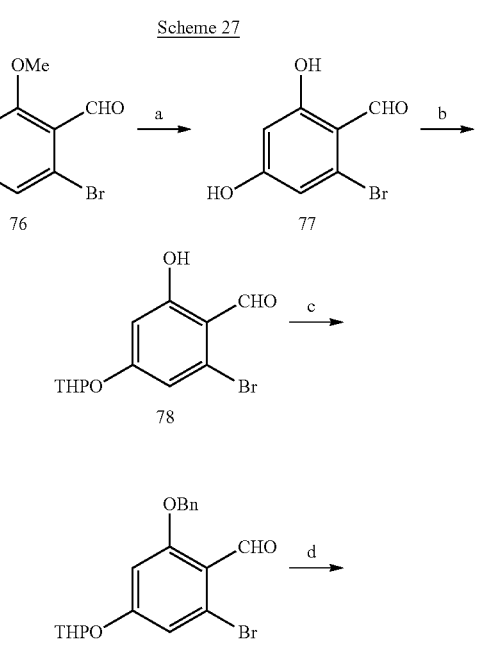
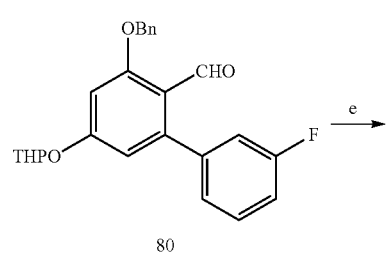

Reagents and conditions: a) BBr₃, CH₂Cl₂, 0° C.-rt, ≤85%; b) 3,4-dihydro-2H-pyran, PPTS, CH₂Cl₂, rt, 56%; c) K₂CO₃, BnBr, 0° C.-rt, 66%; d) 3-F-PhB(OH)₂, Pd(dppf)Cl₂, K₂CO₃, DMF, 90° C., 67%; e) MeNO₂, NH₄OAc, 65° C.; f) LiAlH₄, THF, 0° C.; g) NaOAc, Ac₂O, rt, 33% from 80; h) PPTS, EtOH, 65° C., 86%; i) 18 and 19, BF₃·OEt₂, CH₂Cl₂, rt, 62%; j) 1 N aq. NaOH, EtOH, 82%; k) H₂, 10% Pd/C, EtOAc, rt, 83%.
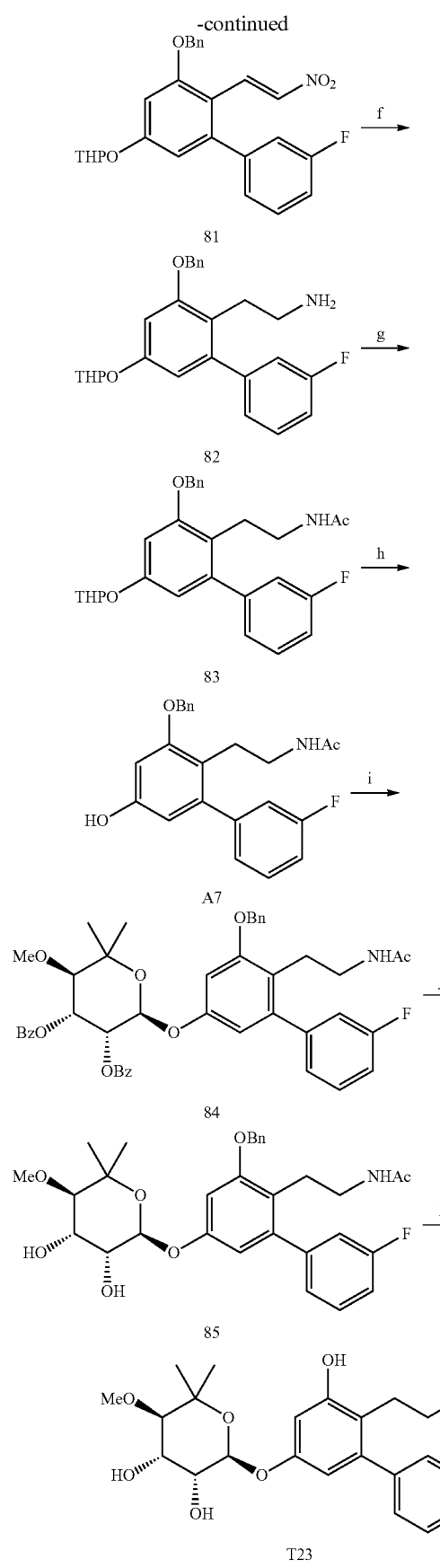
Scheme 28
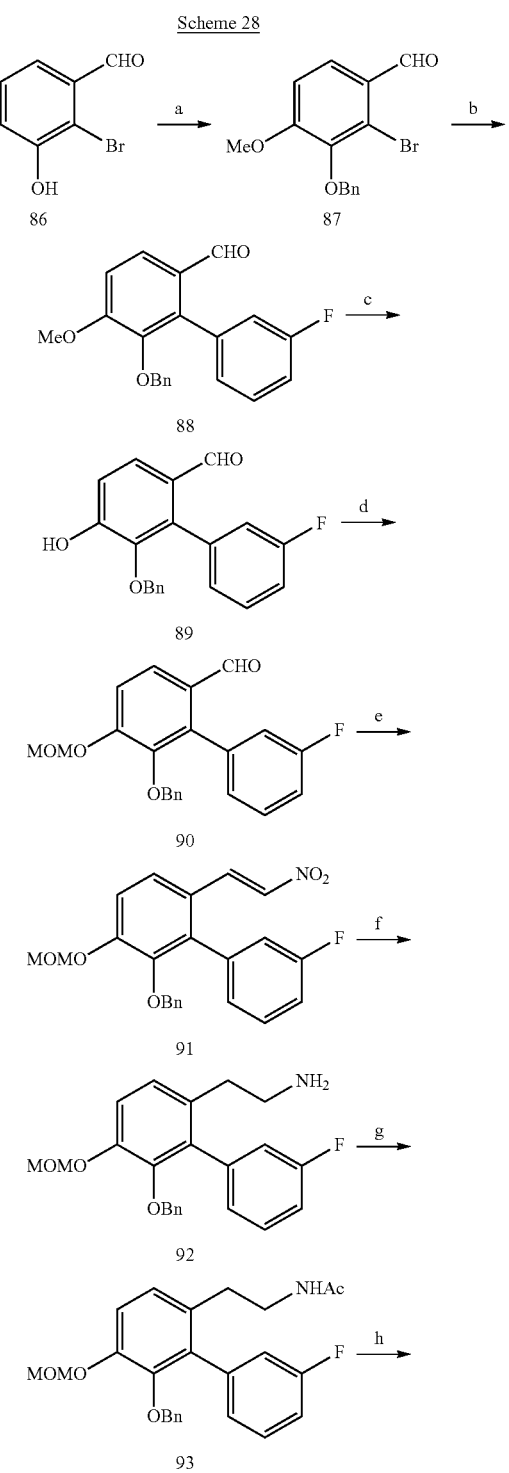

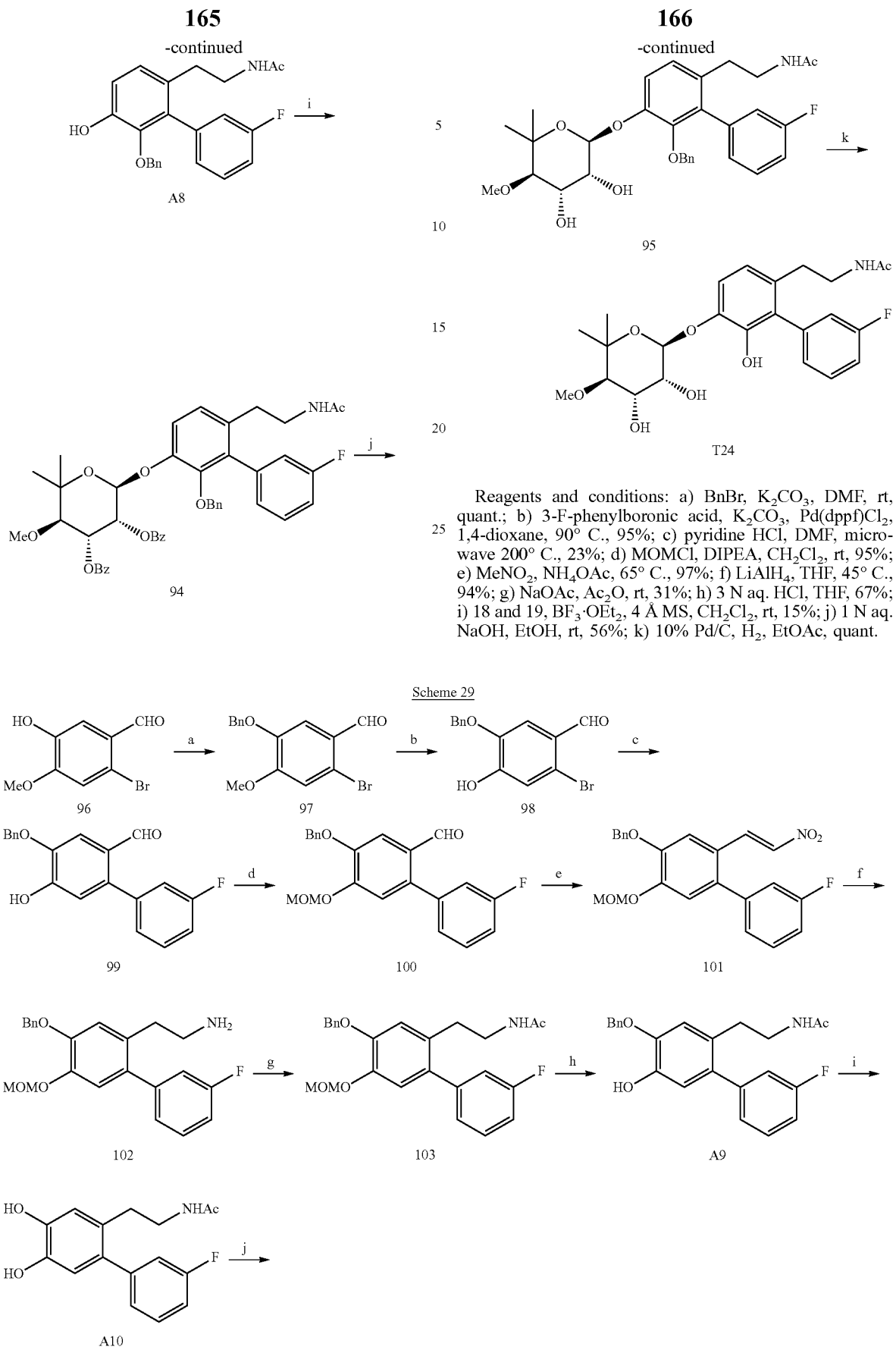
Reagents and conditions: a) BnBr, K₂CO₃, DMF, rt, quant.; b) 3-F-phenylboronic acid, K₂CO₃, Pd(dppf)Cl₂, 1,4-dioxane, 90° C., 95%; c) pyridine HCl, DMF, microwave 200° C., 23%; d) MOMCl, DIPEA, CH₂Cl₂, rt, 95%; e) MeNO₂, NH₄OAc, 65° C., 97%; f) LiAlH₄, THF, 45° C., 94%; g) NaOAc, Ac₂O, rt, 31%; h) 3 N aq. HCl, THF, 67%; i) 18 and 19, BF₃·OEt₂, 4 Å MS, CH₂Cl₂, rt, 15%; j) 1 N aq. NaOH, EtOH, rt, 56%; k) 10% Pd/C, H₂, EtOAc, quant.

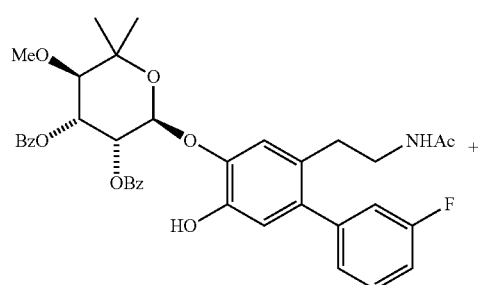
104
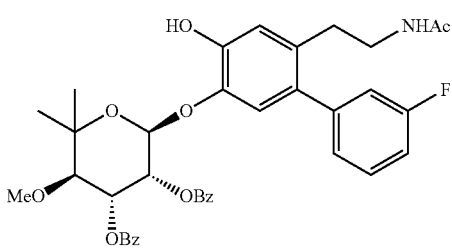
105
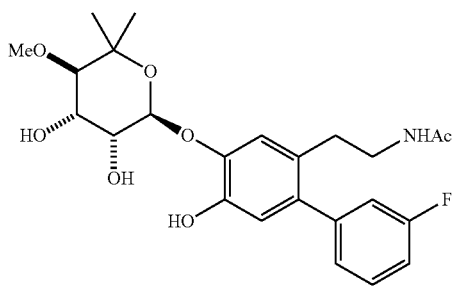
T25
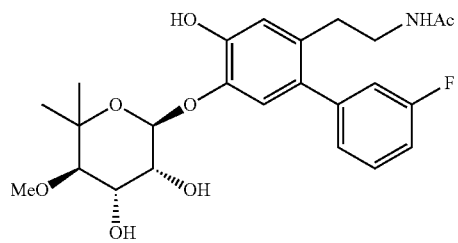
T26
Reagents and conditions: a) BnBr, K₂CO₃, DMF, rt, 50%; b) pyridine HCl, DMF, microwave 200° C., 49%; c) 3-F-PhB(OH)₂, K₂CO₃, Pd(dppf)Cl₂, 1,4-dioxane, 90° C., 79%; d) MOMCl, DIPEA, CH₂Cl₂, rt, quant.; e) MeNO₂, NH₄OAc, 65° C., 99%; f) LiAlH₄, THF, 45° C., 95%; g) NaOAc, Ac₂O, rt, 40%; h) 3 N aq. HCl, THF, 66%; i) 10% Pd/C, H₂, EtOAc, quant.; j) 18 and 19, BF₃OEt₂, 4 Å MS, CH₂Cl₂, rt, 15% for 104, 22% for 105; k) 1 N aq. NaOH, EtOH, rt, 55% for T25; 35% for T26.
Scheme 30
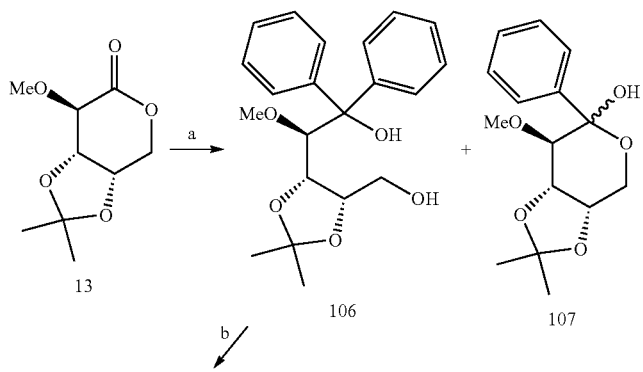

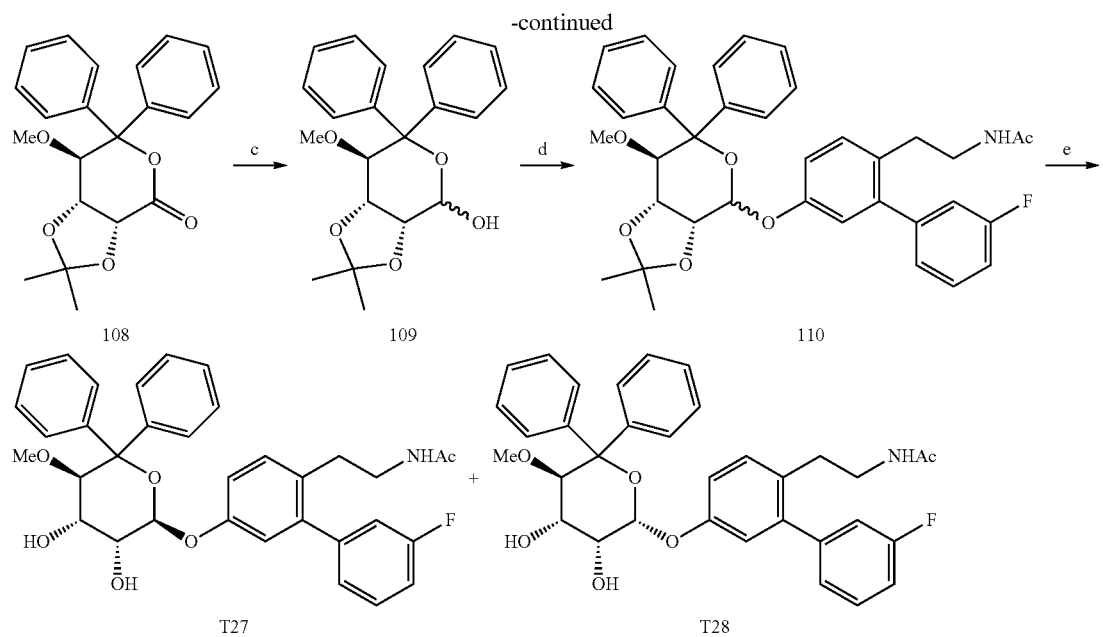
Reagents and conditions: a) PhMgBr, Et$_2$O, THF, 0° C., 37% for 106; 50% for 107; b) PDC, MgSO$_4$, CH$_2$Cl$_2$, rt, 59%; c) DIBAL-H, toluene, CH$_2$Cl$_2$, 0° C., 96%; d) A1, Ph$_3$P, DIAD, THF, rt, 55%; e) HOAc, water, 40° C., 44% for T27; 15% for T28.
Scheme 31
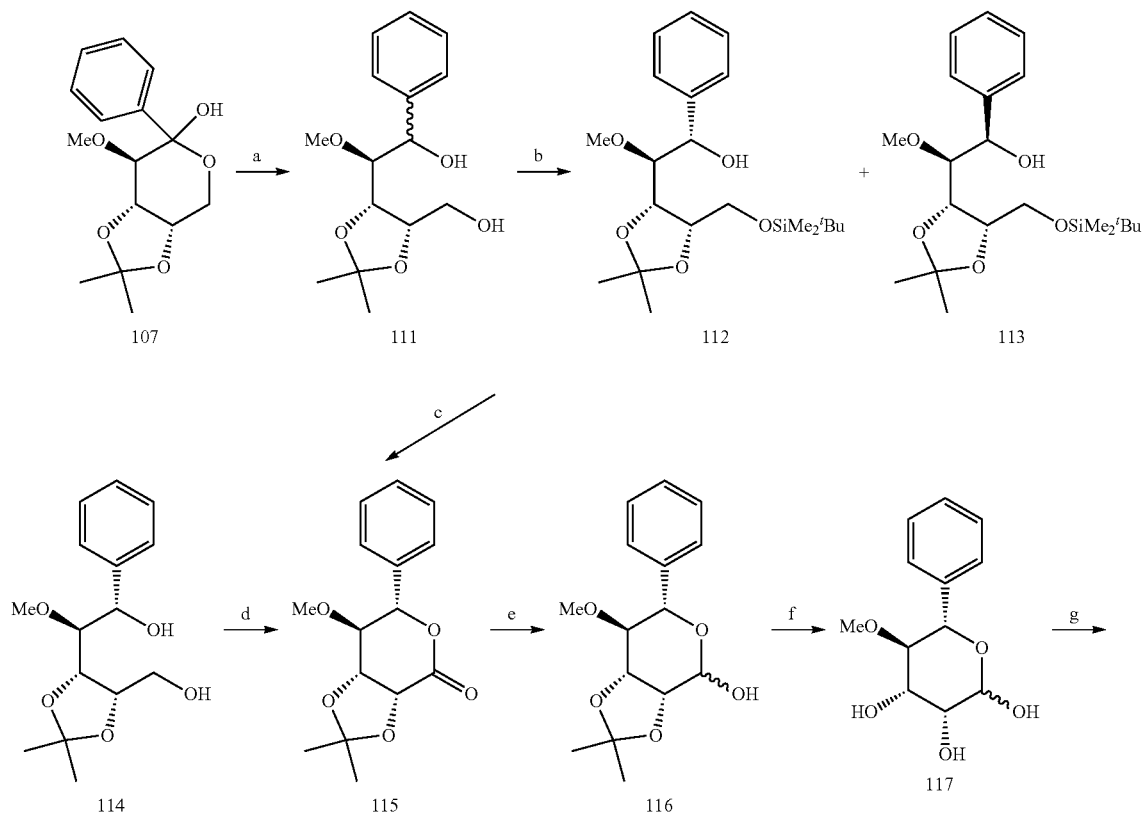

-continued
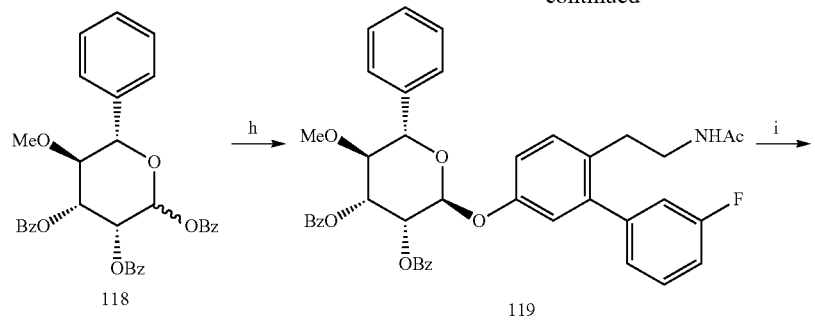
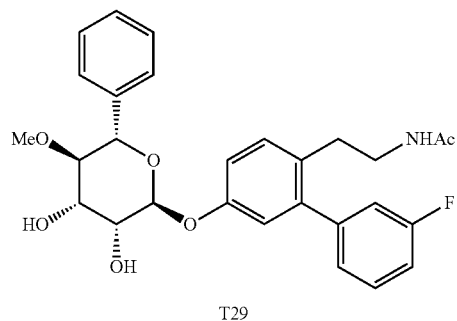
Reagents and conditions: a) NaBH₄, MeOH, 0° C.-rt, quant.; b) TBDMSCl, Et₃N, DMAP, CH₂Cl₂, rt, 36% for 112; 35% for 113; c) TBAF, THF, 0° C., 77%; d) IPh(OAc)₂, TEMPO, CH₂Cl₂, rt, 83%; e) DIBAL-H, toluene, CH₂Cl₂, 0° C., 92%; f) Dowex® 50W X2 hydrogen resin, MeCN, H₂O, 40° C., quant.; g) PhCOCl, DMAP, pyridine, rt, 70%; h) A1, BF₃OEt₂, 3 Å MS, CH₂Cl₂, rt, 65%; i) 1 N aq. NaOH, EtOH, rt, 77%.
Scheme 32
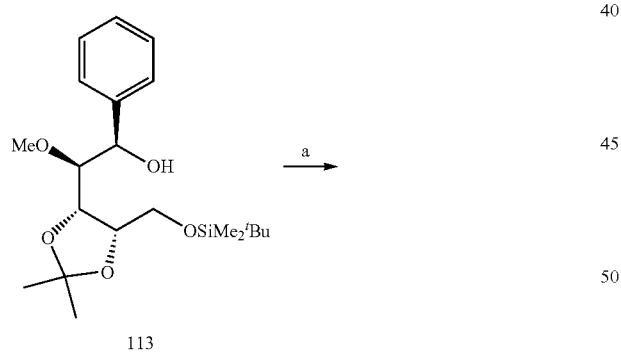
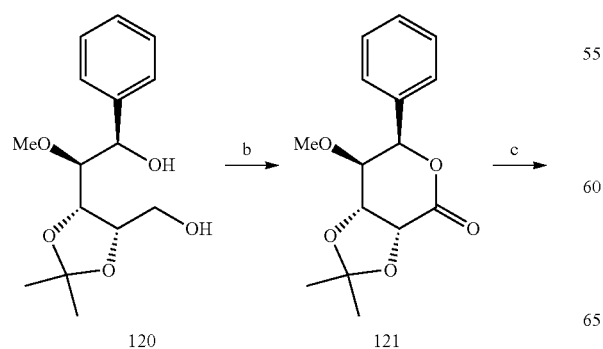
-continued
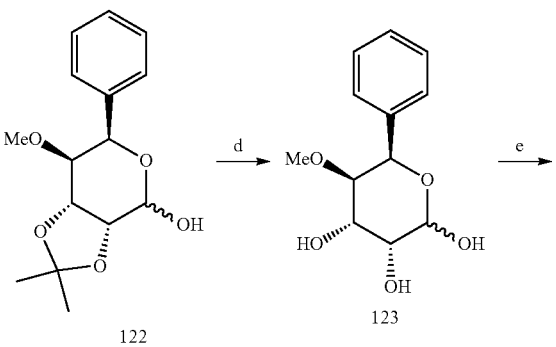
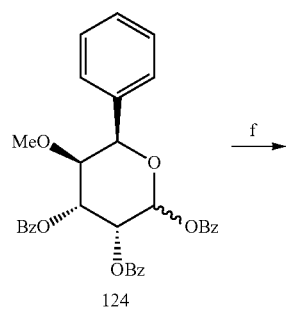

173
-continued
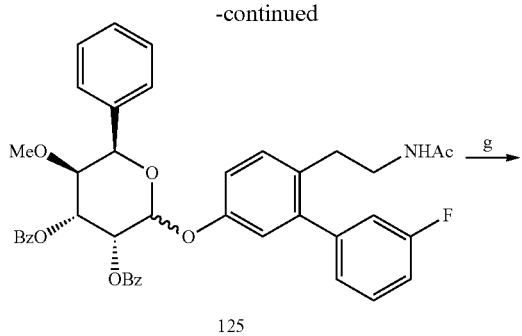
125
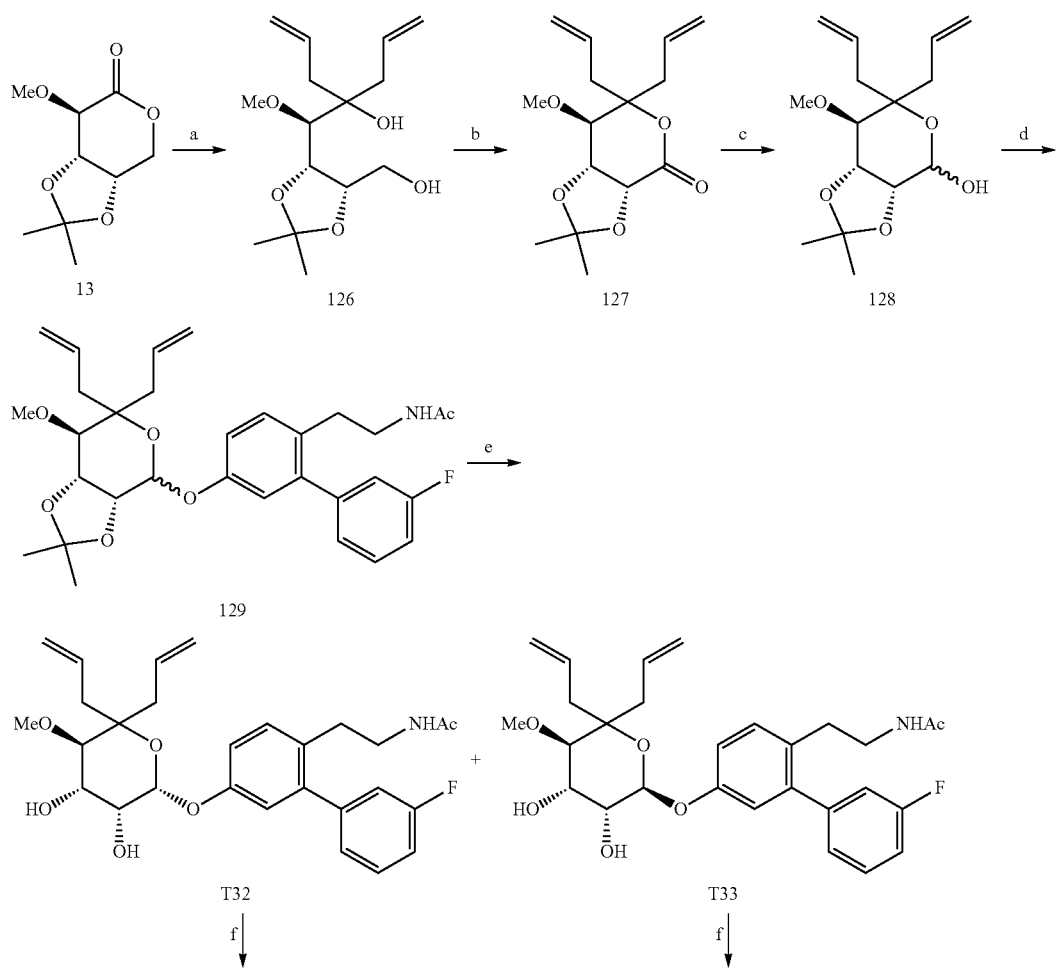
T30
174
-continued
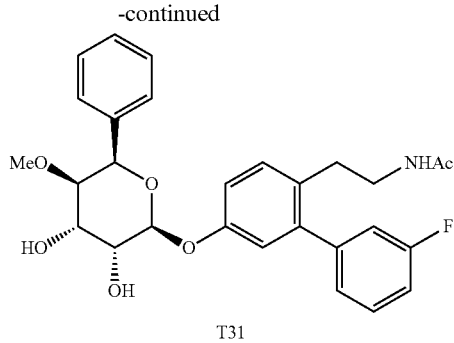
T31
Reagents and conditions: a) TBAF, THF, 0° C.; b) IPh(OAc)$_2$, TEMPO, CH$_2$Cl$_2$, rt, 74% from 113; c) DIBAL-H, toluene, CH$_2$Cl$_2$, 0° C., 93%; d) Dowex® 50W X2 hydrogen resin, MeCN, H$_2$O, 40° C., quant.; e) PhCOCl, DMAP, pyridine, rt, 77%; f) A1, BF$_3$OEt$_2$, 3 Å MS, CH$_2$Cl$_2$, rt, 65%; g) 1 N aq. NaOH, EtOH, rt, 24% for T30; 44% for T31.
Scheme 33

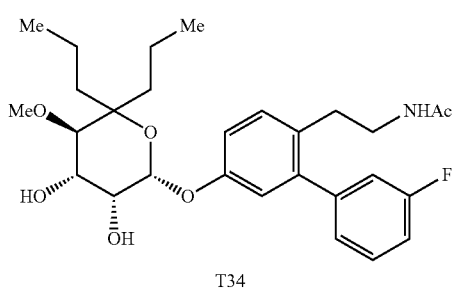

T34

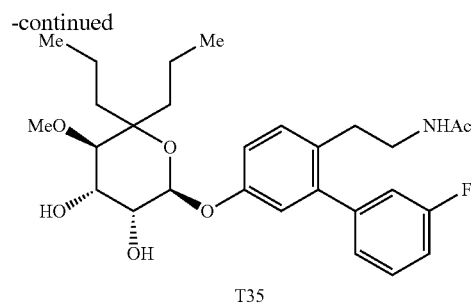

T35

Reagents and conditions: a) allylmagnesium bromide, Et₂O, MTBE, rt; b) PDC, MgSO₄, CH₂Cl₂, rt, quant.; c) DIBAL-H, toluene, CH₂Cl₂, 0° C., quant.; d) A1, Ph₃P, DIAD, THF, rt, 48%; e) HOAc, water, 40° C., 18% for T32; 15% for T33; f) 10% Pd/C, H₂, EtOAc, rt, 79% for T34; 90% for T35.

Scheme 34

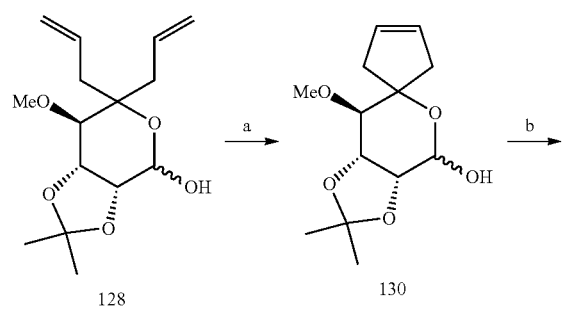

T37

Reagents and conditions: a) Grubbs Catalyst™ 2$^{nd}$ Generation, CH₂Cl₂, rt, 81%; b) Dowex® 50W X2 hydrogen resin, MeCN, H₂O, rt, 93%; c) PhCOCl, DMAP, pyridine, rt, 85%; d) A1, BF₃OEt₂, 3 Å MS, CH₂Cl₂, rt, 32%; e) 1 N aq. NaOH, EtOH, rt, 49%; f) 10% Pd/C, H₂, EtOAc, rt, 63%.

Scheme 35

177
-continued
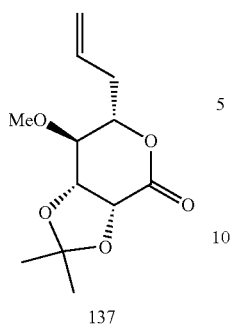
178
-continued
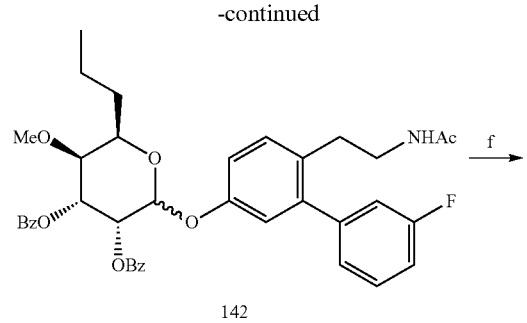
Reagents and conditions: a) allylmagnesium bromide, Et₂O, THF, 0° C.-rt, 66%; b) NaBH₄, MeOH, 0° C.-rt, quant.; c) IPh(OAc)₂, TEMPO, CH₂Cl₂, rt, 28% for 136; 24% for 137.
Scheme 36
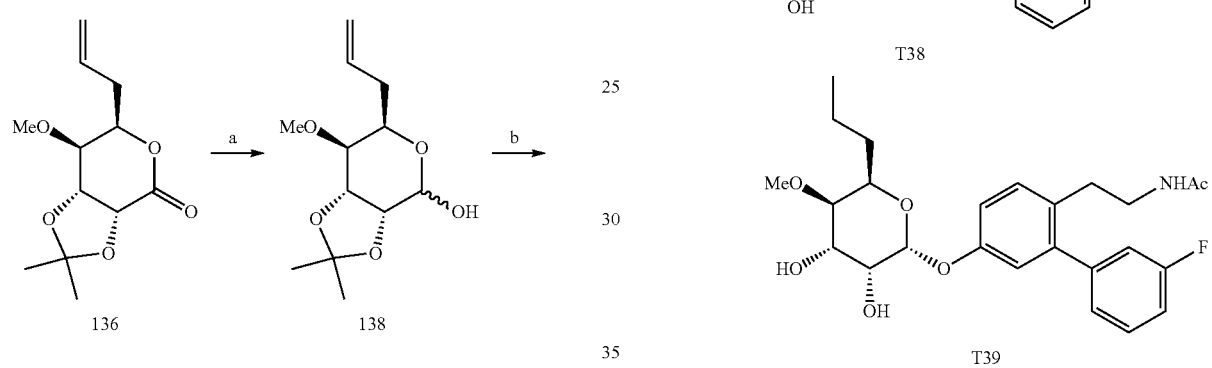
Reagents and conditions: a) DIBAL-H, toluene, CH₂Cl₂, 0° C., 92%; b) Dowex® 50W X2 hydrogen resin, MeCN, water, 40° C., 91%; c) PhCOCl, DMAP, pyridine, rt, 76%; d) H₂, 10% Pd/C, EtOAc, rt, 89%; e) A1, BF₃OEt₂, 3 Å MS, CH₂Cl₂, rt, 56%; f) 1 N aq. NaOH, EtOH, rt, 30% for T38; 12% for T39.
Scheme 37
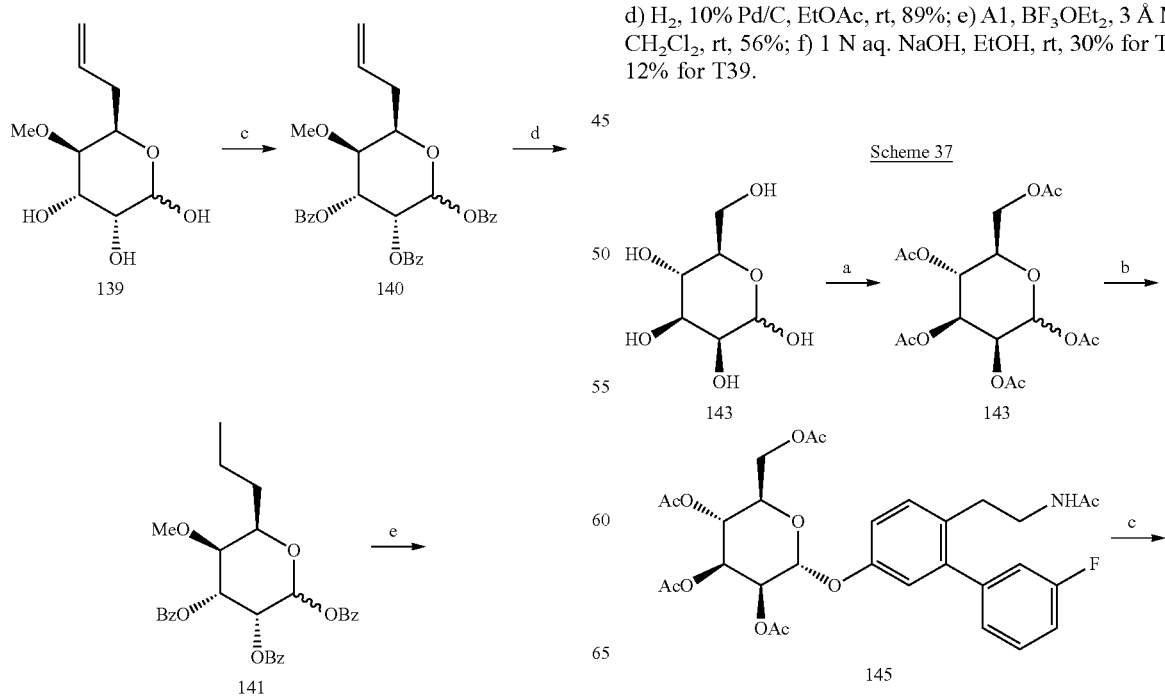

179
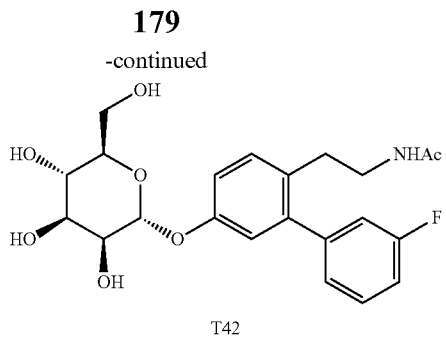
T42
Reagents and conditions: a) Ac₂O, pyridine, rt; b) A1, BF₃·OEt₂, 3 Å MS, CH₂Cl₂, rt, 66% from 143; c) NaOMe, MeOH, 50° C., 63%.
Scheme 38
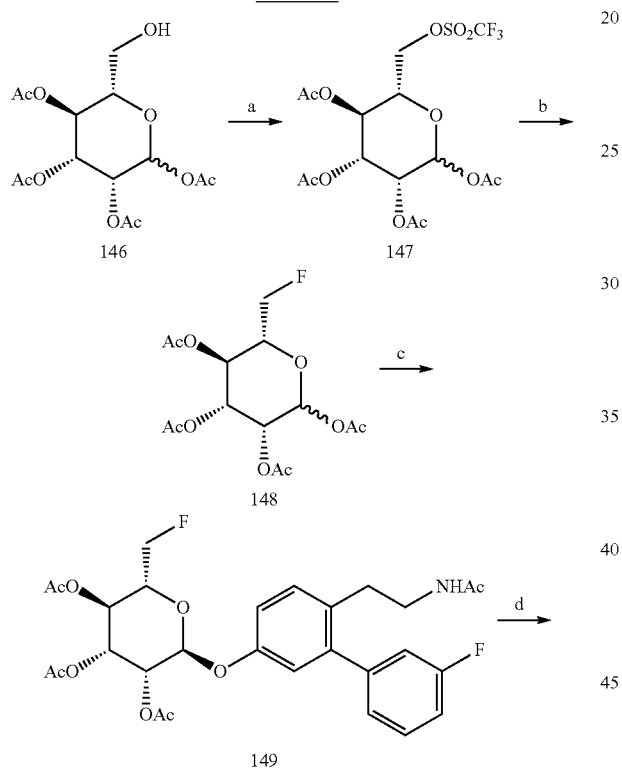
T43
Reagents and conditions: a) Tf₂O, pyridine, CH₂Cl₂, 0° C., 71%; b) CsF, t-amyl alcohol, 110° C., 57%: c) A1, BF₃·OEt₂, 3 Å MS, CH₂Cl₂, rt, 83%; d) NaOMe, MeOH, rt, 58%.
180
Scheme 39
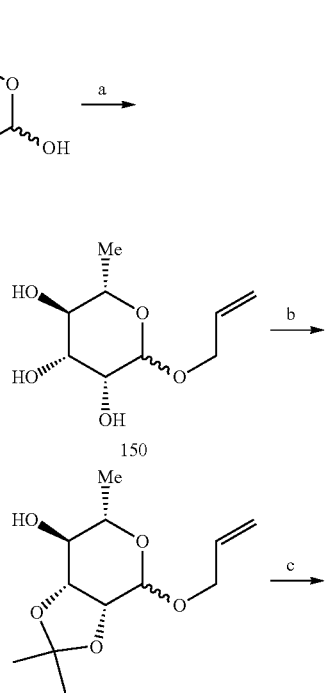
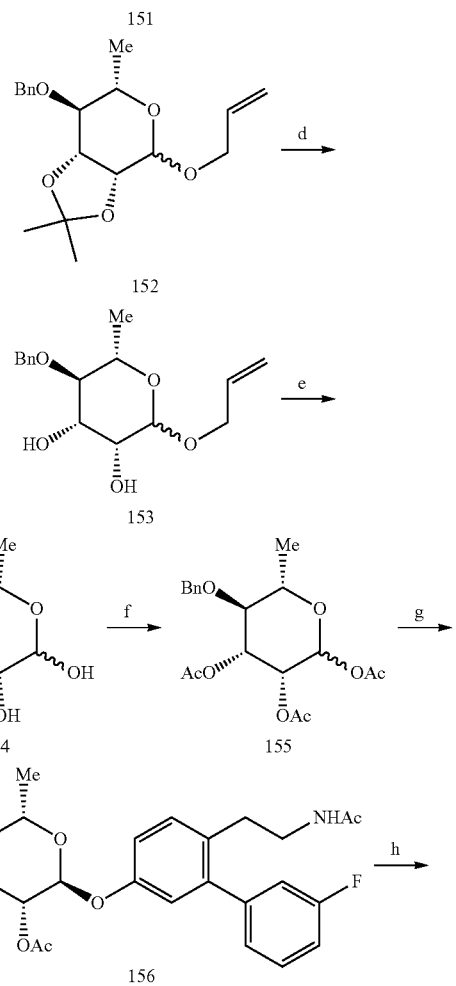

181

-continued

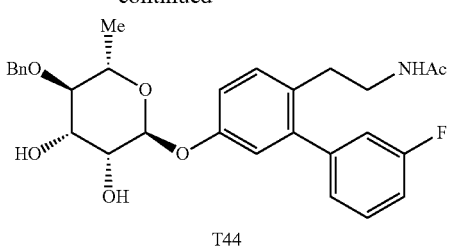

T44

Reagents and conditions: a) allyl alcohol, Sc(OTf)$_3$, 100° C., 50%; b) 2,2-DMP, acetone, CH$_2$Cl$_2$, p-TsOH·H$_2$O, rt, 95%; c) NaH, PhCH$_2$Cl, DMF, 0° C.-rt, 89%; d) Dowex® 50W X2 hydrogen resin, MeCN, H$_2$O, 45° C., 98%; e) i) Wilkinson's catalyst, 1,4-diazobicycl[2.2.2]octane, EtOH, benzene, H$_2$O, 80° C.; ii) 1 N aq. HCl, acetone, 60° C., 85%; f) Ac$_2$O, pyridine, rt, 69%; g) A1, BF$_3$·OEt$_2$, 3 Å MS, CH$_2$Cl$_2$, rt, 57%; h) NaOMe, MeOH, rt, 79%.

Scheme 40

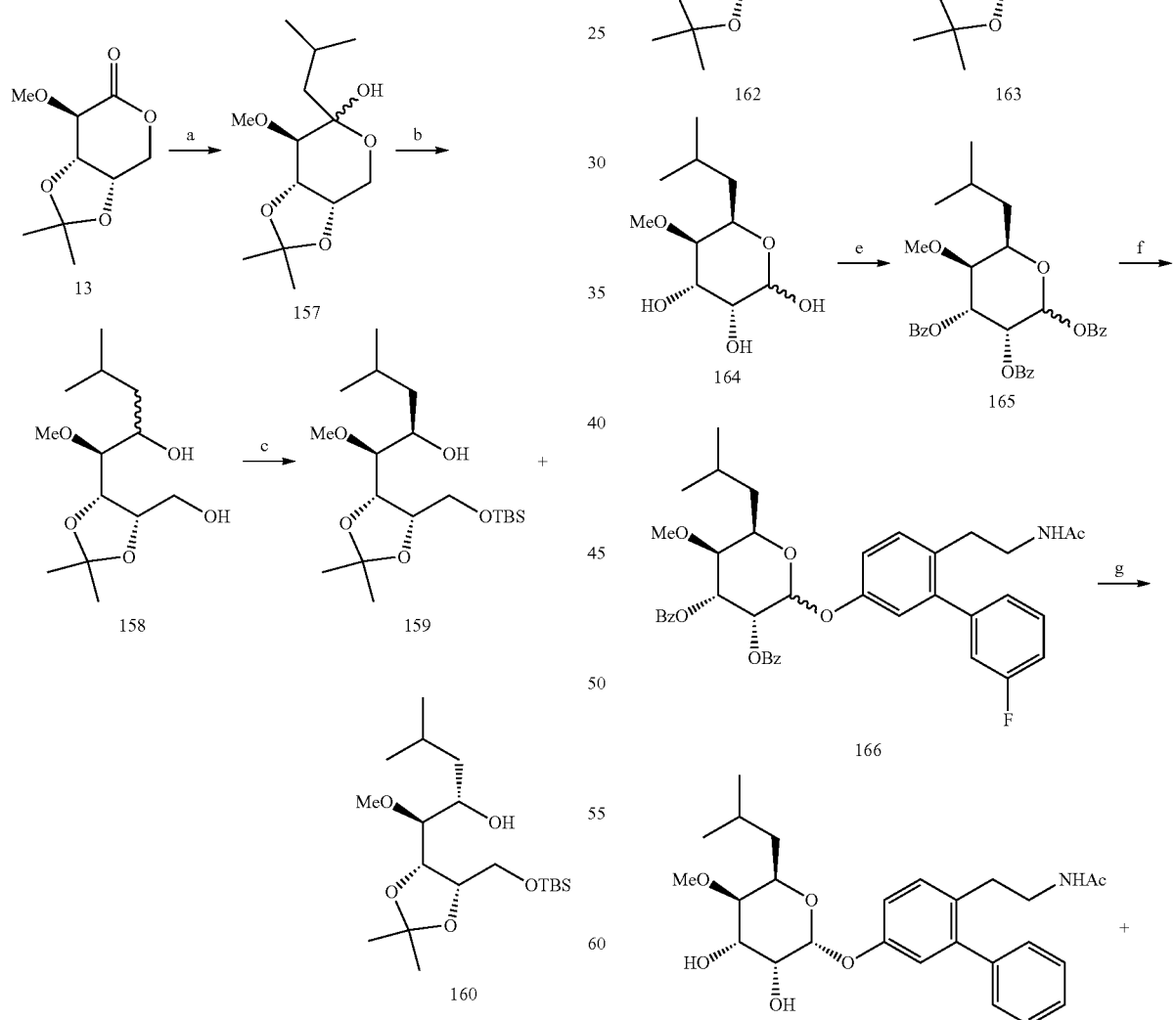

Reagents and conditions: a) Isobutyl magnesium bromide, THF, rt, 62%; b) NaBH$_4$, EtOH, 0° C.-rt, 84%; c) TBSCl, Et$_3$N, DMAP, CH$_2$Cl$_2$, rt, 39% for 159; 35% for 160.

182

Scheme 41

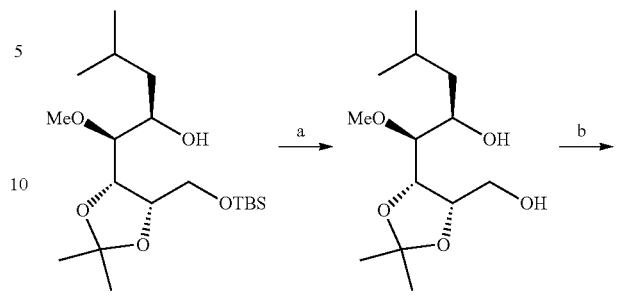

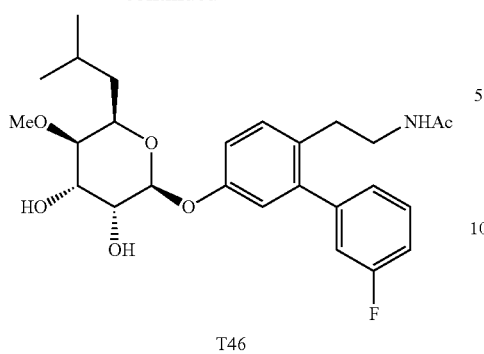

T46

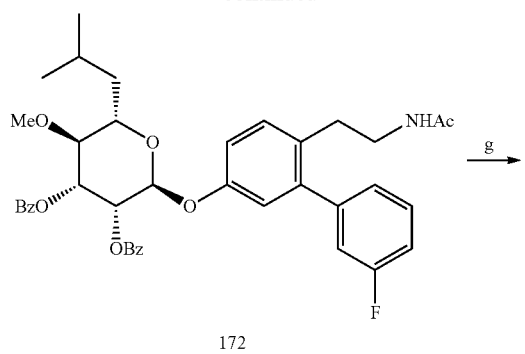

172

Reagents and conditions: a) TBAF, THF, rt, quant.; b) PhI(OAc)₂, TEMPO, CH₂Cl₂, rt, 88%; c) DIBAL-H, toluene, CH₂Cl₂, rt, 98%; d) AG50X-W2 resin, MeCN/water, 40° C., quant.; e) BzCl, pyridine, rt, 86%; f) A1, BF₃·OEt₂, 4 Å MS, rt, 62%; g) 1 N aq. NaOH, EtOH, rt, 26% for T45; 35% for T46.

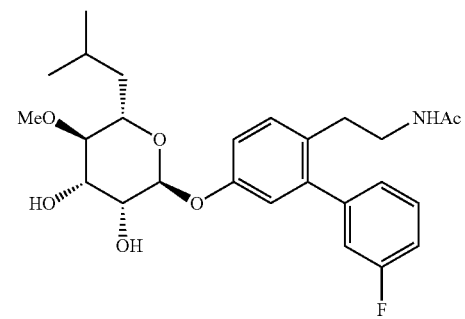

T47

Reagents and conditions: a) TBAF, THF, rt, quant.; b) PhI(OAc)₂, TEMPO, CH₂Cl₂, rt, 69%; c) DIBAL-H, toluene, CH₂Cl₂, rt, 98%; d) AG50X-W2 resin, MeCN, water, 40° C., 99%; e) BzCl, pyridine, rt, 93%; f) A1, BF₃·OEt₂, 4 Å MS, rt, 61%; g) 1 N aq. NaOH, EtOH, rt, 86%.

Scheme 42

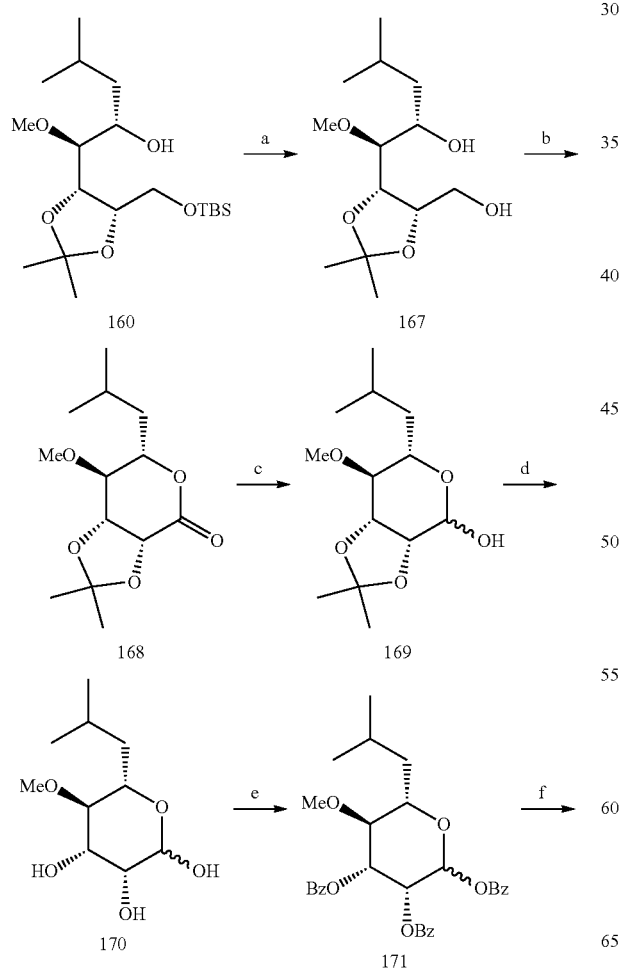

Scheme 43

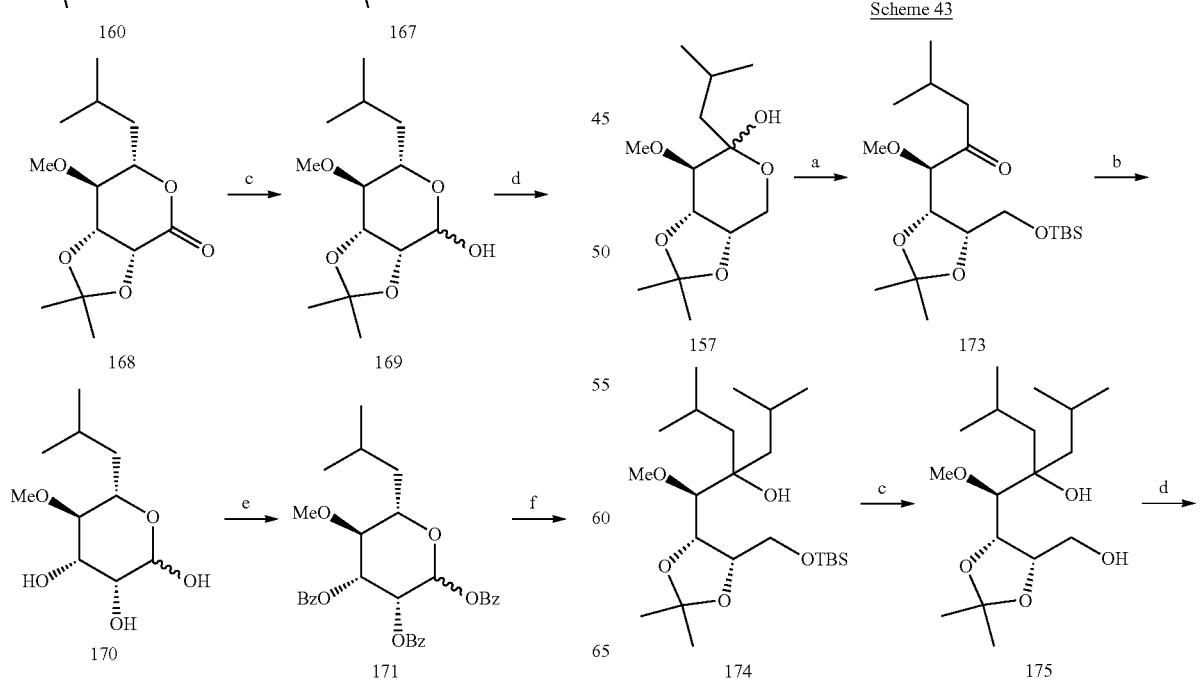

185
-continued

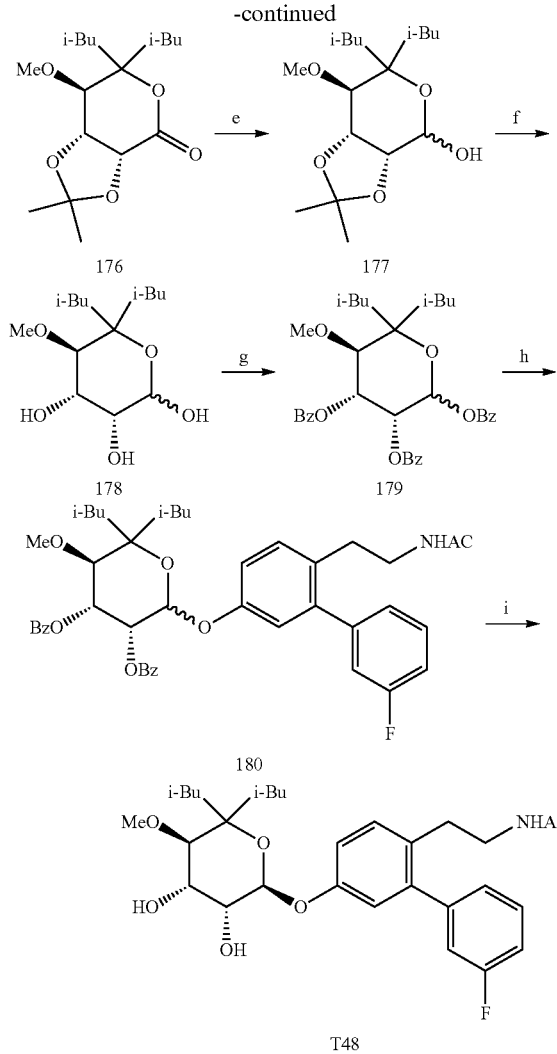

Reagents and conditions: a) TBDMSCl, Et₃N, DMAP, CH₂Cl₂, 61%; b) i-BuMgBr, THF, rt, 92%; c) TBAF, THF, rt, 67%; d) PhI(OAc)₂, TEMPO, CH₂Cl₂, rt, 74%; e) DIBAL-H, toluene, CH₂Cl₂, rt, quant.; f) AG50X-W2 resin, MeCN, water, 40° C., quant.; g) BzCl, pyridine, rt, 93%; h) A1, BF₃·OEt₂, 4 Å MS, rt, 20%; i) 1 N aq. NaOH, EtOH, rt, 34%.

186

Scheme 44

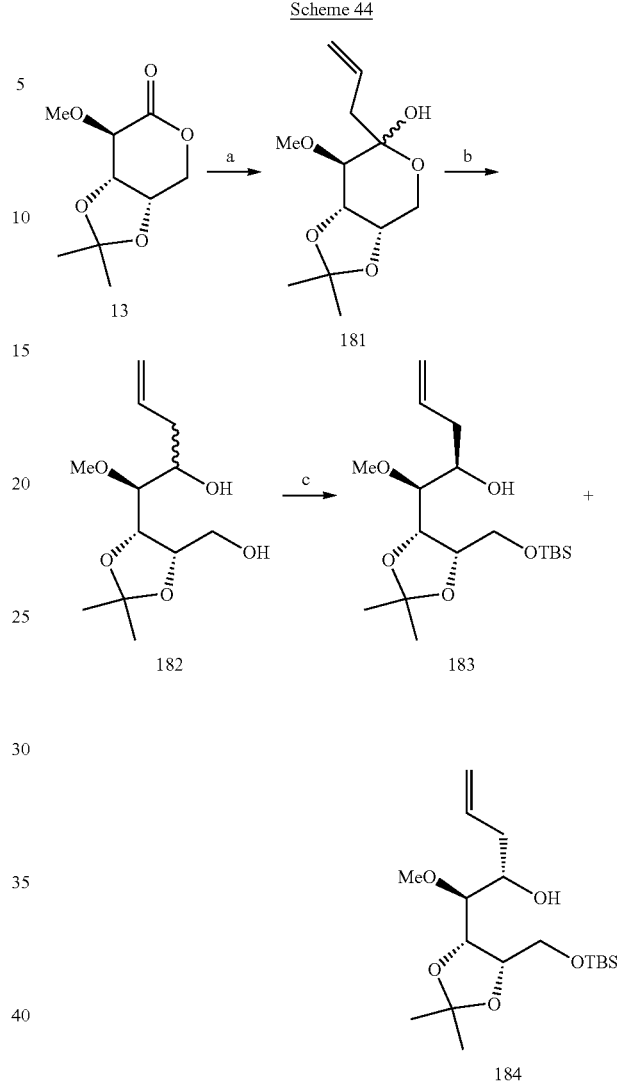

Reagents and conditions: a) allyl magnesium bromide, THF, rt, 93%; b) NaBH₄, EtOH, MeOH, 0° C.-rt, quant.; c) TBSCl, Et₃N, DMAP, CH₂Cl₂, rt, 33% for 183; 42% for 184.

Scheme 45

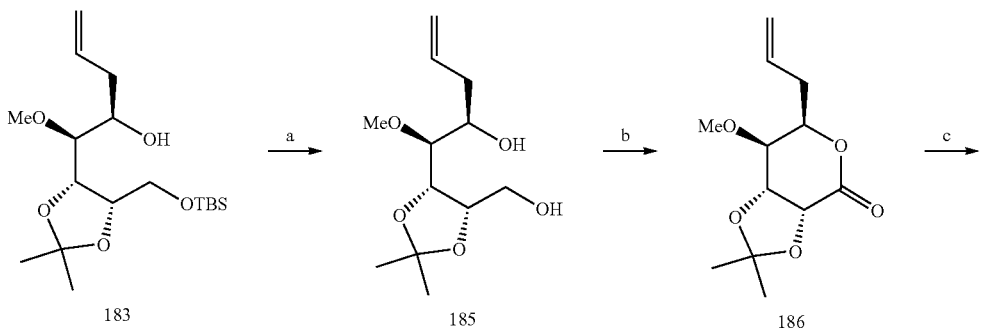

187 188
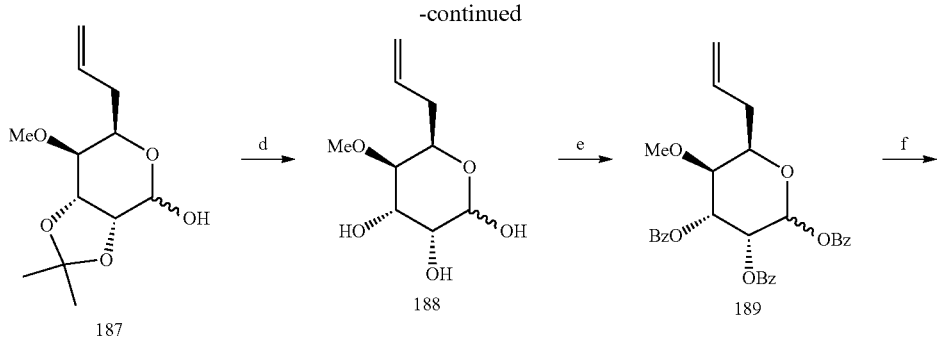
-continued
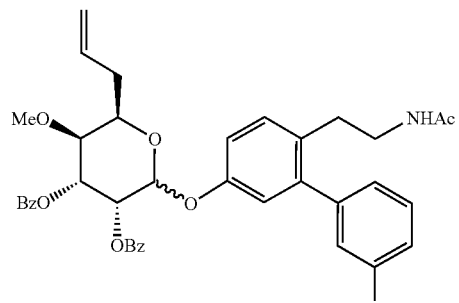
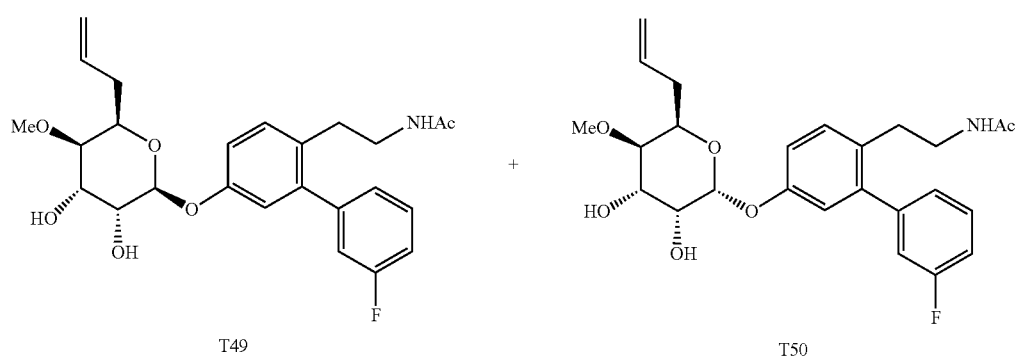
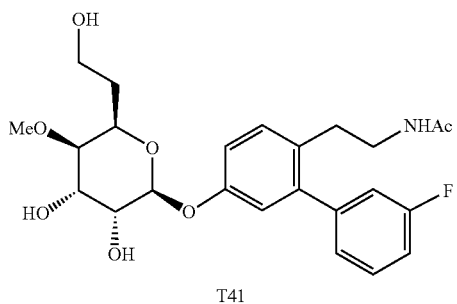
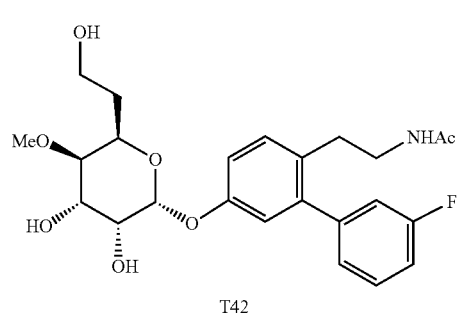

189

Reagents and conditions: a) TBAF, THF, rt, quant.; b) PhI(OAc)₂, TEMPO, CH₂Cl₂, rt, 66%; c) DIBAL-H, toluene, CH₂Cl₂, rt, 97%; d) AG50X-W2 resin, MeCN/water, 40° C., 87%; e) BzCl, pyridine, rt, 70%; f) A1, BF₃·OEt₂, 4 Å MS, rt, 39%; g) 1N aq. NaOH, EtOH, rt, 29% for T49; 20% for T50; h) O₃/O₂, CH₂Cl₂:MeOH, −78° C.; NaBH₄, −78° C.-rt, 45% for T40; 47% for T41.

Scheme 46

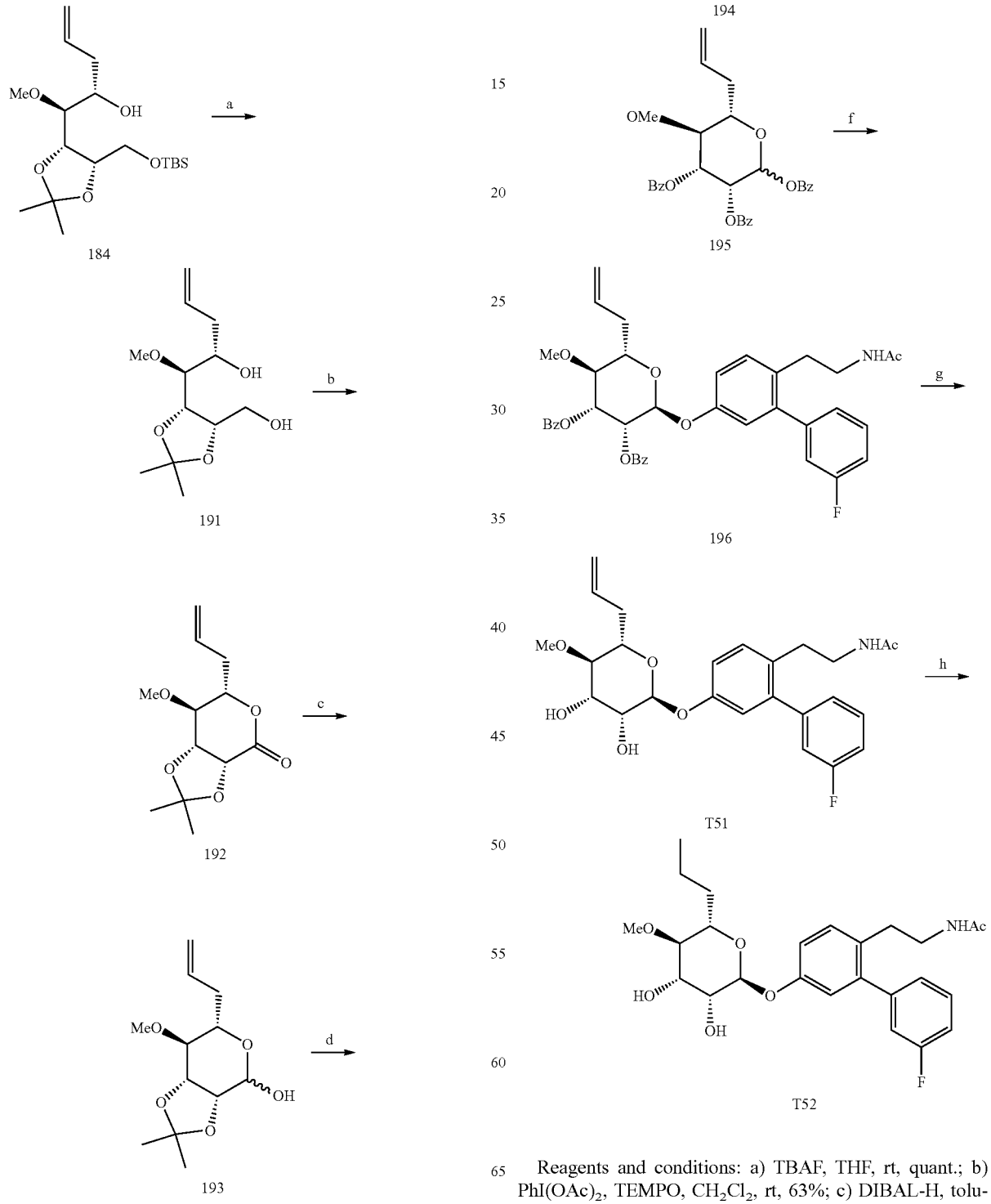

Reagents and conditions: a) TBAF, THF, rt, quant.; b) PhI(OAc)₂, TEMPO, CH₂Cl₂, rt, 63%; c) DIBAL-H, toluene, CH₂Cl₂, rt, quant.; d) AG50X-W2 resin, MeCN/water, 40° C., 93%; e) BzCl, pyridine, rt, 78%; f) A1, BF$_3$·OEt$_2$, 4 Å MS, rt, 59%; g) 1 N aq. NaOH, EtOH, rt, 98%; h) H$_2$, 10% Pd/C, EtOAc, rt, 92%.
Scheme 47
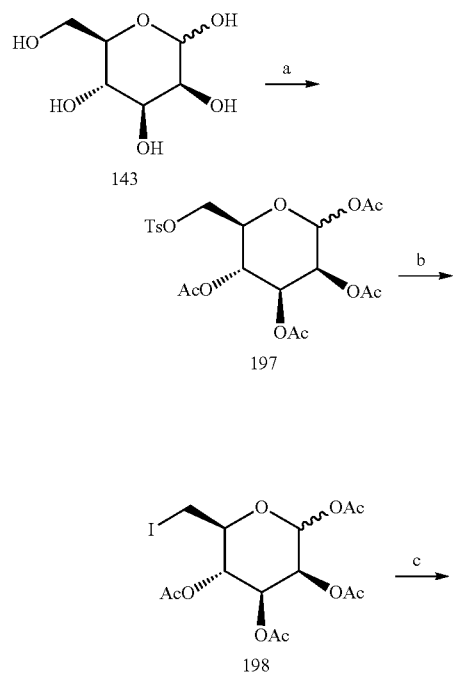
Reagents and conditions: a) O$_3$/O$_2$, CH$_2$Cl$_2$, MeOH, −78° C.; NaBH$_4$, −78° C.-rt, 44%.
Scheme 48
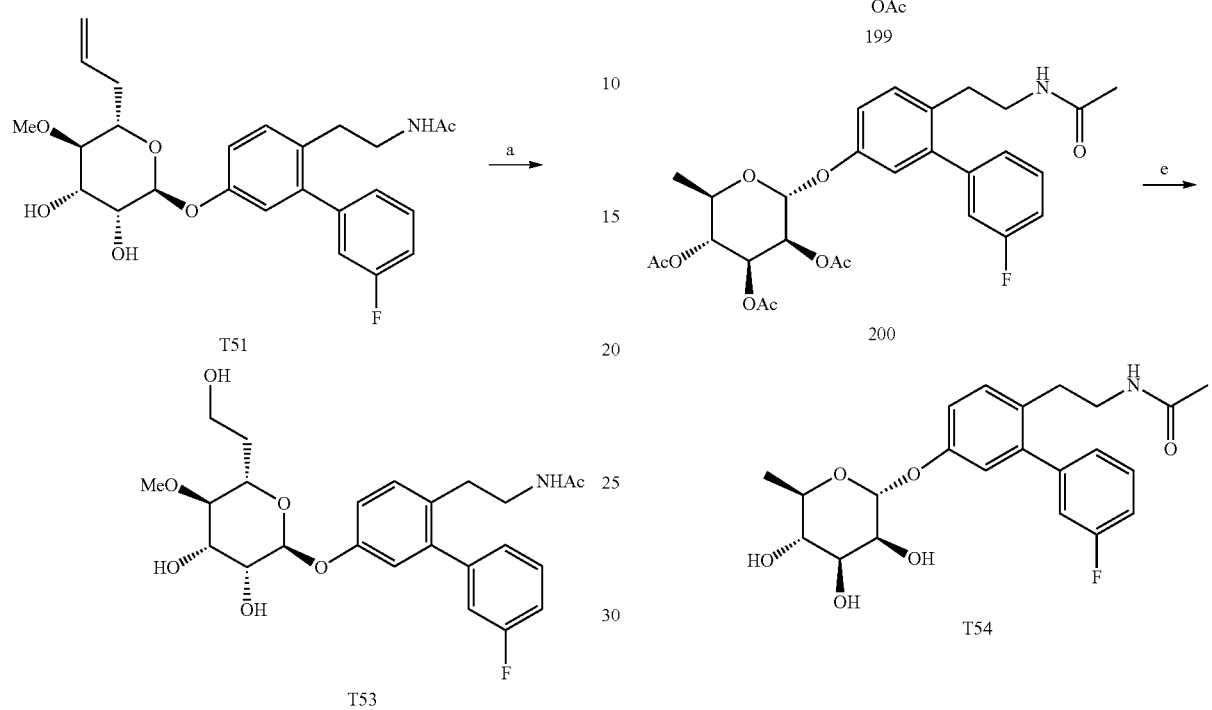
Reagents and conditions: a) i) TsCl, pyridine, 0° C.-rt; ii) Ac$_2$O, rt, 97%; b) NaI, acetone, reflux, 92%; c) H$_2$, 10% Pd/C, MeOH, rt; Ac$_2$O, pyridine, rt, 31%; d) A1, BF$_3$OEt$_2$, 4 Å MS, CH$_2$Cl$_2$, rt, 69%; e) NaOMe, MeOH, rt, 71%.
Scheme 49
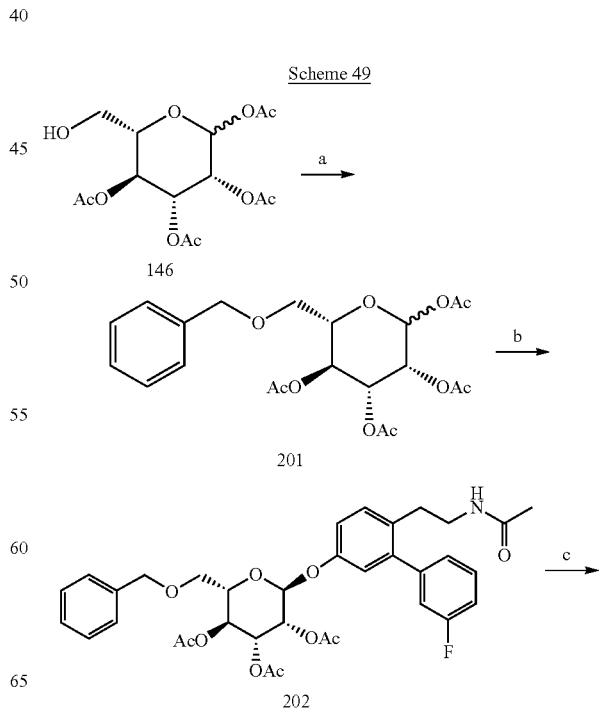

-continued
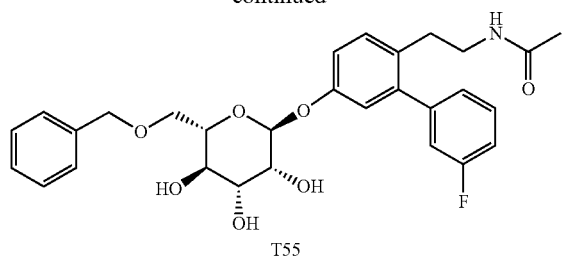
T55
Reagents and conditions: a) PhCH₂Br, Ag₂O, benzene, rt, 24%; b) A1, BF₃OEt₂, 4 Å MS, CH₂Cl₂, rt, 76%; c) NaOMe, MeOH, rt, 51%.
Scheme 50
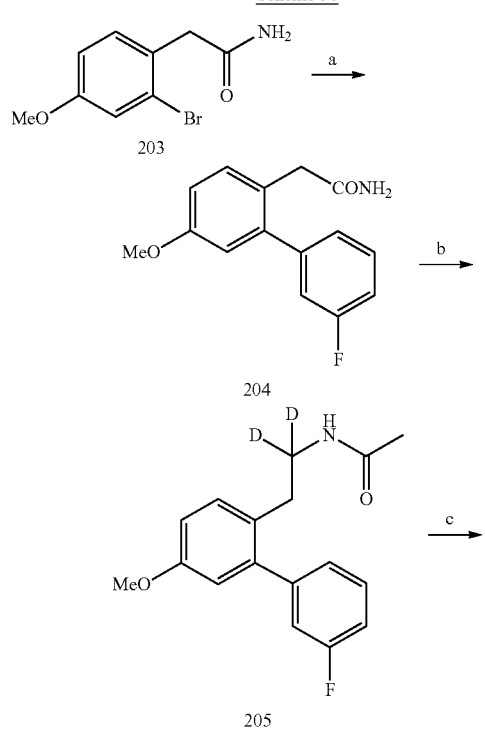
Reagents and conditions: a) 3-F-PhB(OH)₂, Ba(OH)₂·8H₂O, Pd(dppf)Cl₂, 1,4-dioxane, H₂O, 80° C., 27%; b) i) Zn(BD₄)₂, THF, toluene, reflux; ii) sat. aq. NaHCO₃, Ac₂O, EtOAc, 0° C., 50%; c) BBr₃, CH₂Cl₂, 0° C., 76%.
Scheme 51
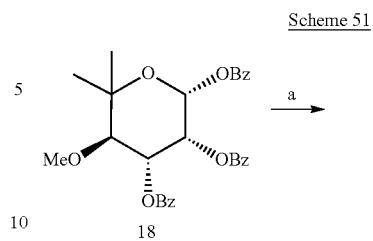
18
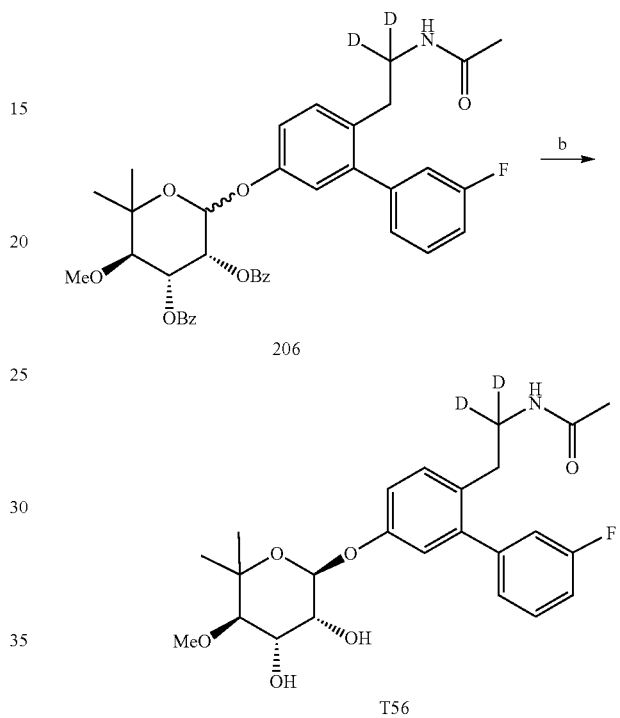
T56
Reagents and conditions: a) A6, BF₃·OEt₂, CH₂Cl₂, 0° C., 74%; c) K₂CO₃, MeOH, rt, 76%.
Scheme 52
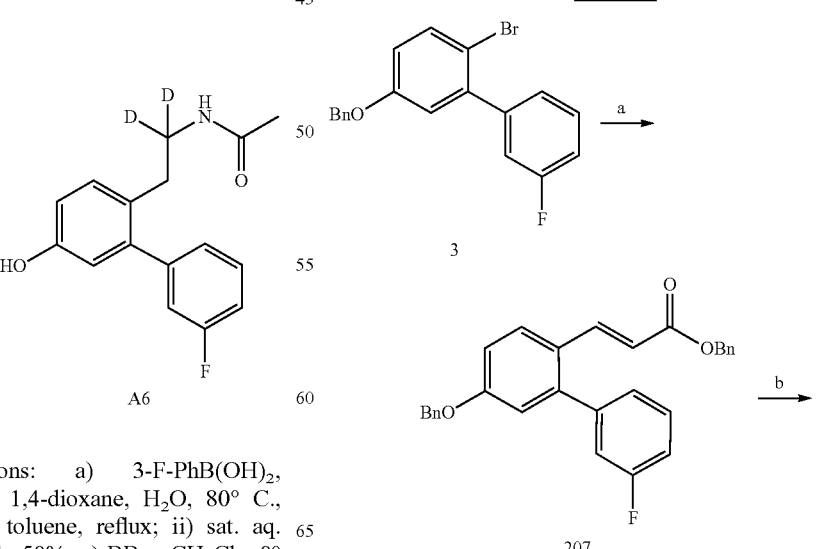

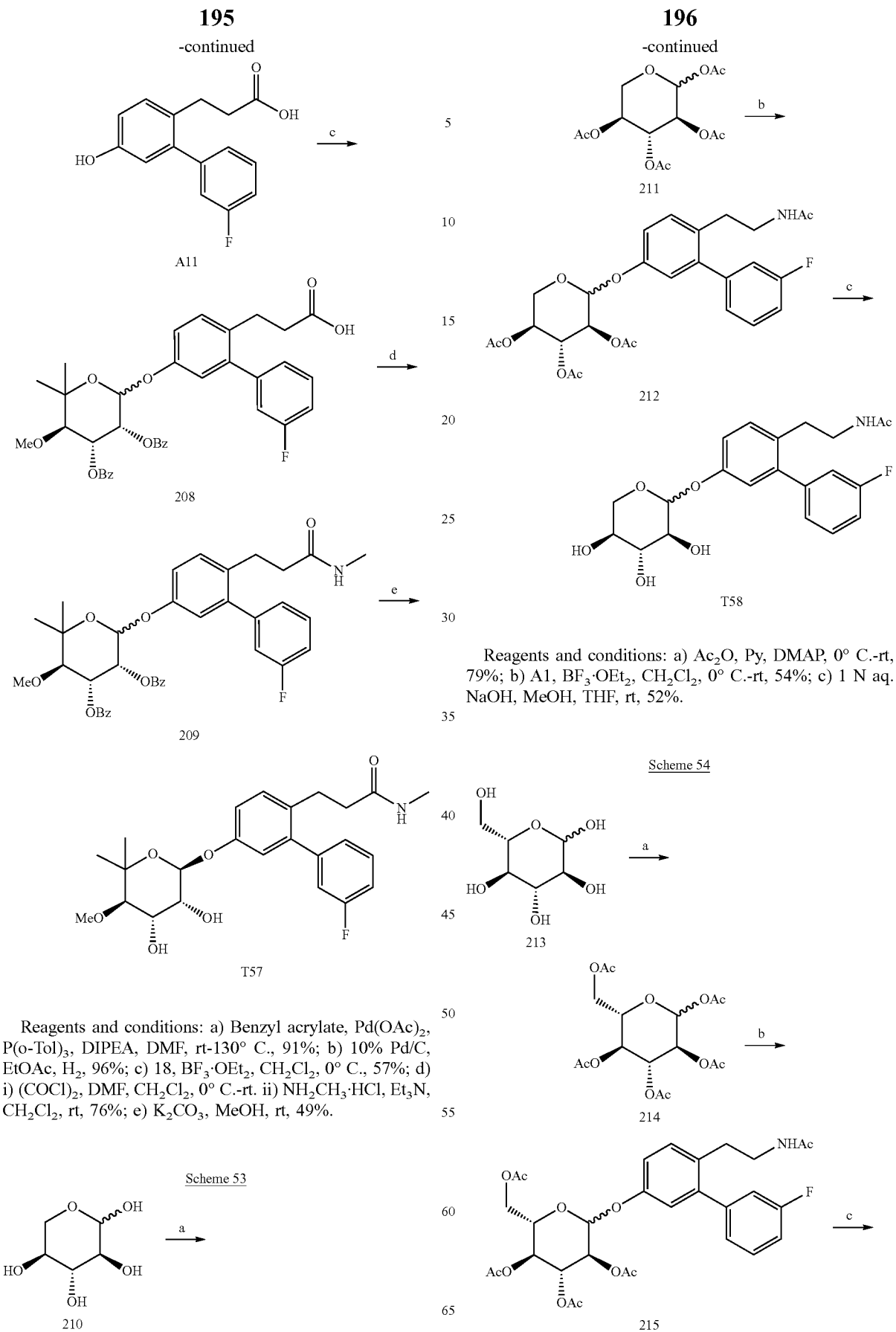
Reagents and conditions: a) Ac₂O, Py, DMAP, 0° C.-rt, 79%; b) A1, BF₃·OEt₂, CH₂Cl₂, 0° C.-rt, 54%; c) 1 N aq. NaOH, MeOH, THF, rt, 52%.
Reagents and conditions: a) Benzyl acrylate, Pd(OAc)₂, P(o-Tol)₃, DIPEA, DMF, rt-130° C., 91%; b) 10% Pd/C, EtOAc, H₂, 96%; c) 18, BF₃·OEt₂, CH₂Cl₂, 0° C., 57%; d) i) (COCl)₂, DMF, CH₂Cl₂, 0° C.-rt. ii) NH₂CH₃·HCl, Et₃N, CH₂Cl₂, rt, 76%; e) K₂CO₃, MeOH, rt, 49%.

197
-continued
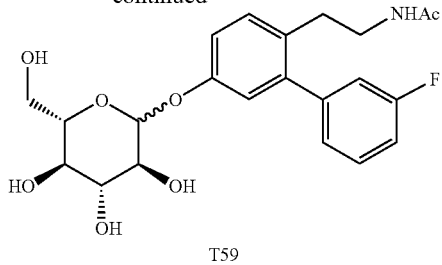
T59
Reagents and conditions: a) Ac₂O, Py, DMAP, 0° C.-rt, 84%; b) A1, BF₃·OEt₂, CH₂Cl₂, 0° C.-rt, 45%; c) 1 N aq. NaOH, MeOH, THF, rt, 61%.
198
-continued
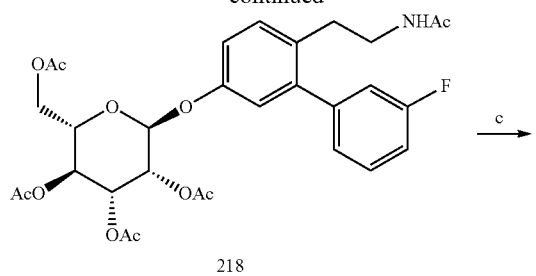
218
T60
Reagents and conditions: a) Ac₂O, Py, DMAP, 0° C.-rt, 94%.; b) A1, BF₃·OEt₂, CH₂Cl₂, 0° C.-rt, 67%; c) 1 N aq. NaOH, MeOH, rt, 75%.
Scheme 55
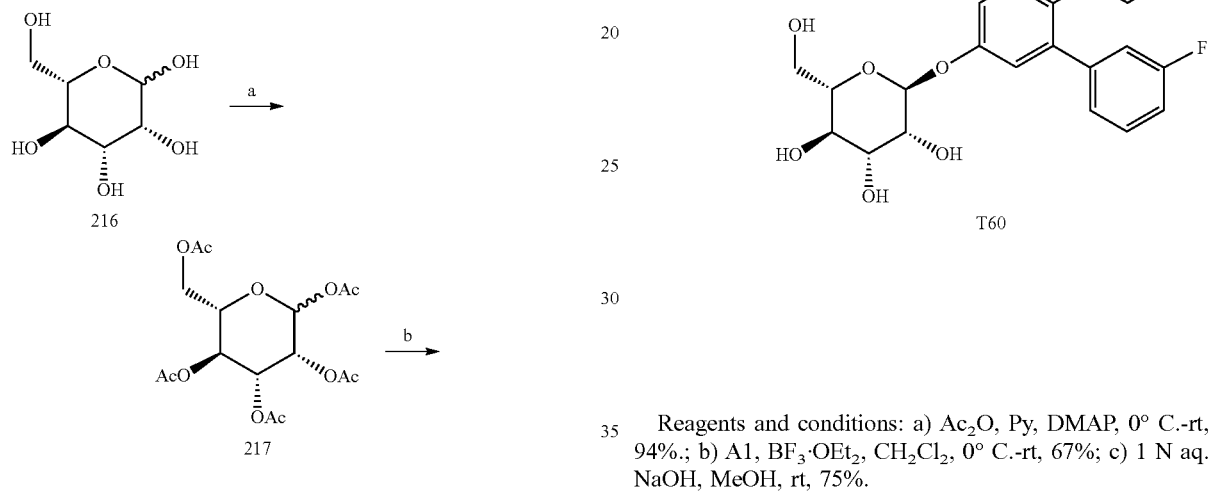
216
217
Scheme 56
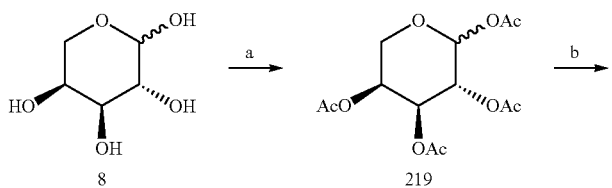
8
219
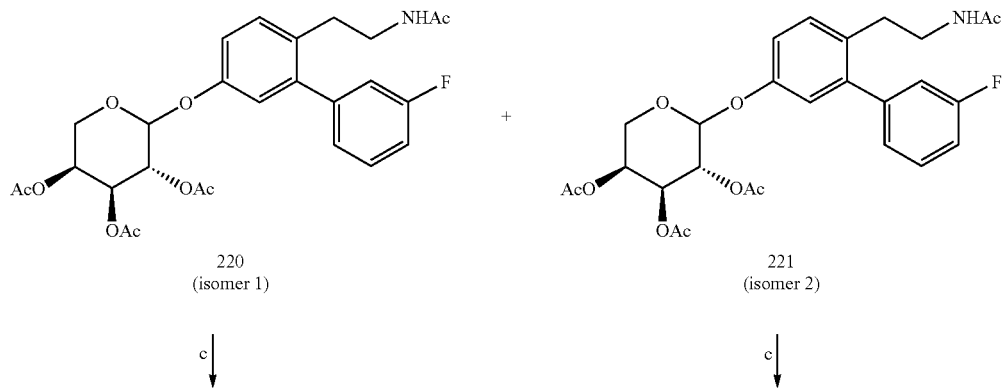
220
(isomer 1)
221
(isomer 2)

199
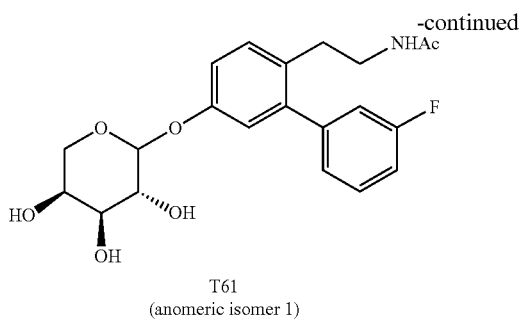
T61
(anomeric isomer 1)
200
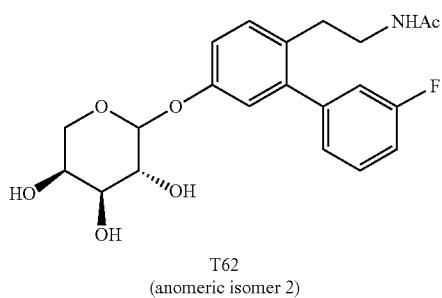
T62
(anomeric isomer 2)
Reagents and conditions: a) Ac₂O, Py, DMAP, 0° C.-rt, 94%.; b) A1, BF₃·OEt₂, CH₂Cl₂, 0° C.-rt, 24% for 220; 20% for 221; c) 1 N aq. NaOH, MeOH, THF, rt, 68% for T61; 80% for T62.
Scheme 57
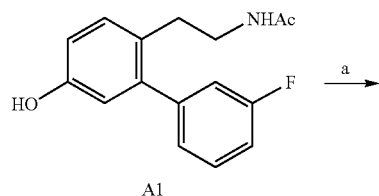
A1
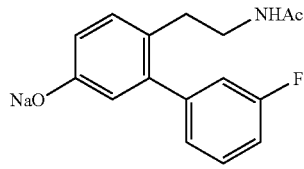
222
Reagents and conditions: a) NaOMe, MeOH, THF, 0° C., quant.
Scheme 58
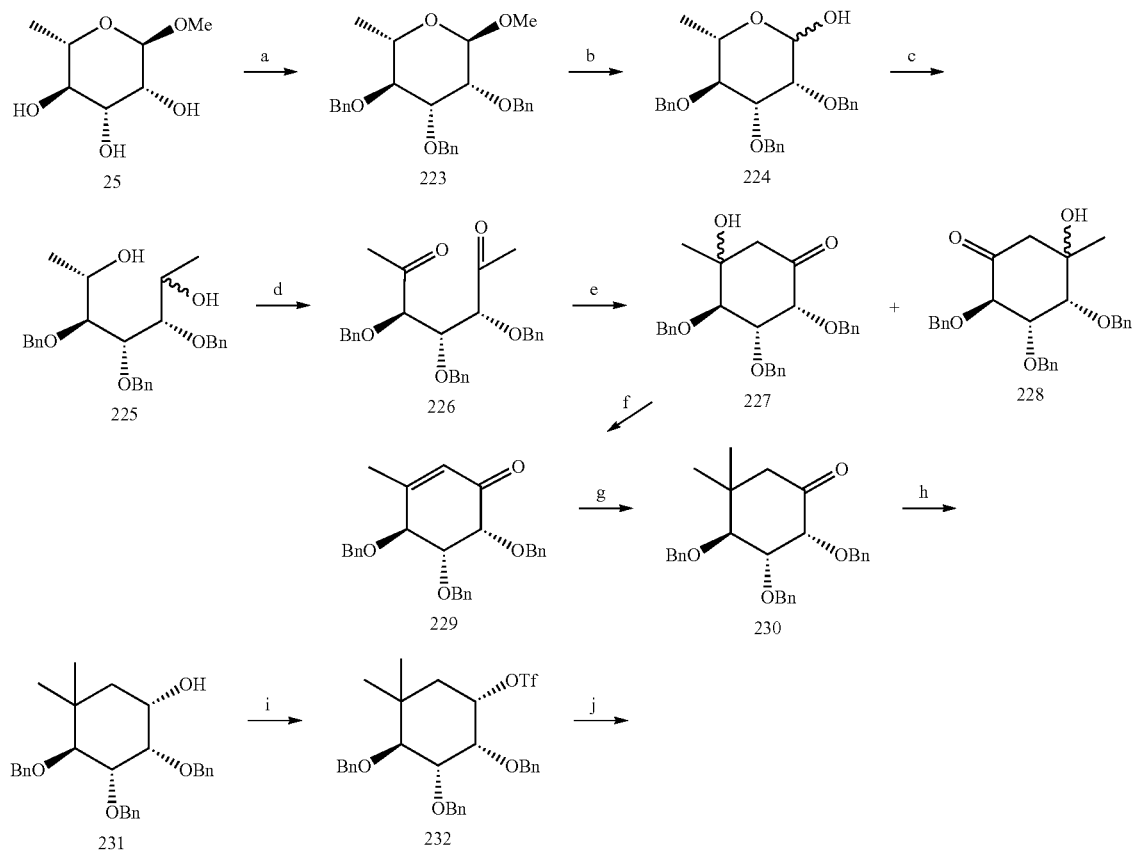

201
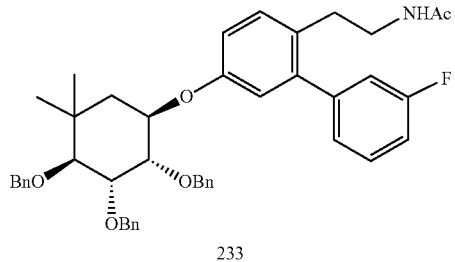
233
202
-continued
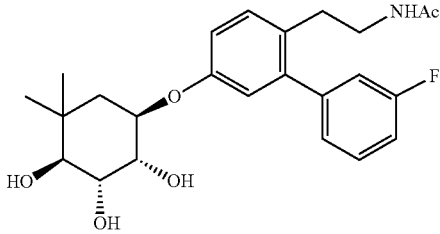
T63
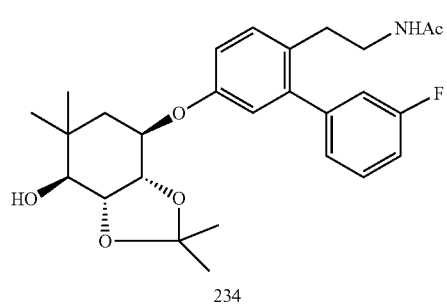
234
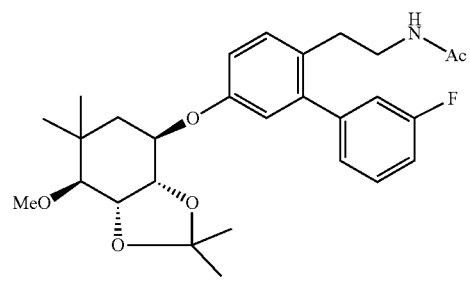
235
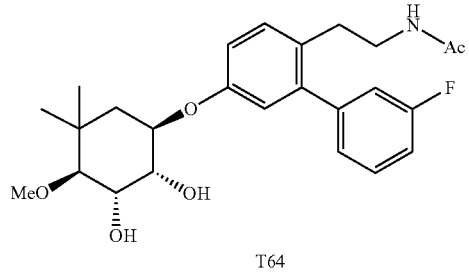
T64
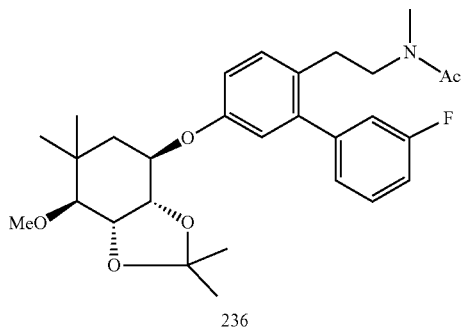
236
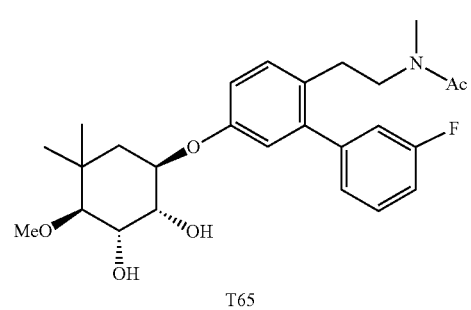
T65

Reagents and conditions: a) NaH, DMF, BnBr, 0° C.-rt, quant.; b) 2 N aq. HCl, AcOH, H₂O, 95° C., 78%; c) MeMgCl, Et₂O, THF, 0° C.-rt, 97%; d) DMSO, (COCl)₂, CH₂Cl₂, −78° C.; Et₃N, −78° C.-rt, quant.; e) LDA, THF, hexanes, −78° C., 37% for 227; f) POCl₃, Py, 0° C.-rt, 67%; g) CuBrMe₂S, AlMe₃, THF, 0° C.-rt, 92%; h) Zn(BH₄)₂, Et₂O, 0° C., 96%; i) Tf₂O, Py, CH₂Cl₂, 0° C., 88%; j) 222, 18-crown-6, DMF, 0° C., 24%; k) H₂, 10% Pd/C, THF, rt, 91%; l) 2,2-DMP, acetone, (S)-CSA, rt, 87%; m) NaH, MeI, DMF, 0° C.; n) NaH, MeI, DMF, rt, 99%; o) 6 N aq. HCl, MeOH, rt, 37% for T64 from 234; 84% for T65 from 236.

Scheme 59

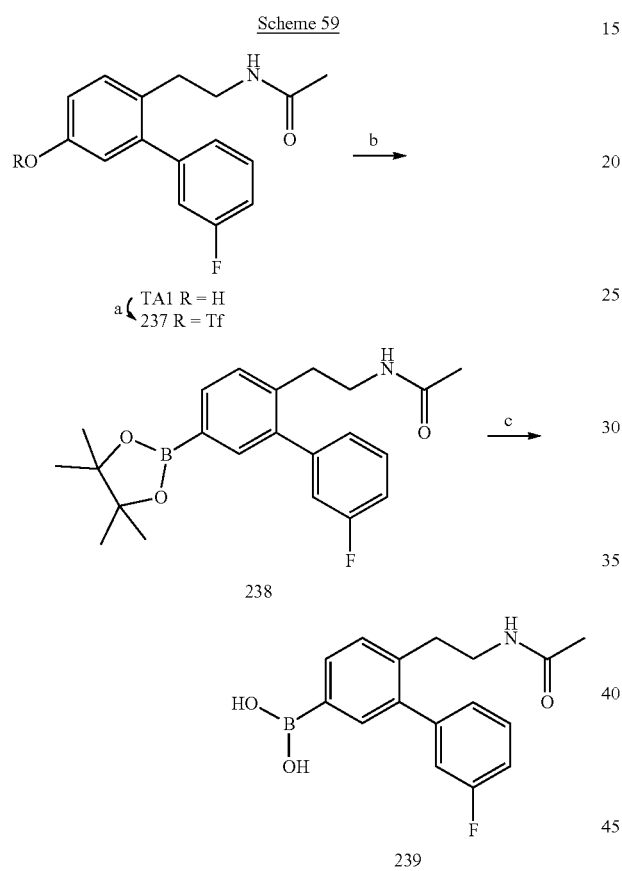

Reagents and conditions: a) Tf₂NPh, Et₃N, CH₂Cl₂, 0° C.-rt, quant.; b) bis(pinacolato)diboron, KOAc, Pd(dppf)Cl₂, DMF, 130° C., 61%; c) NaIO₄, THF, water, 1 N aq. HCl, rt, 83%.

Scheme 60

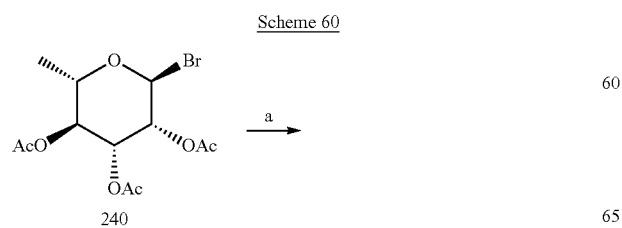

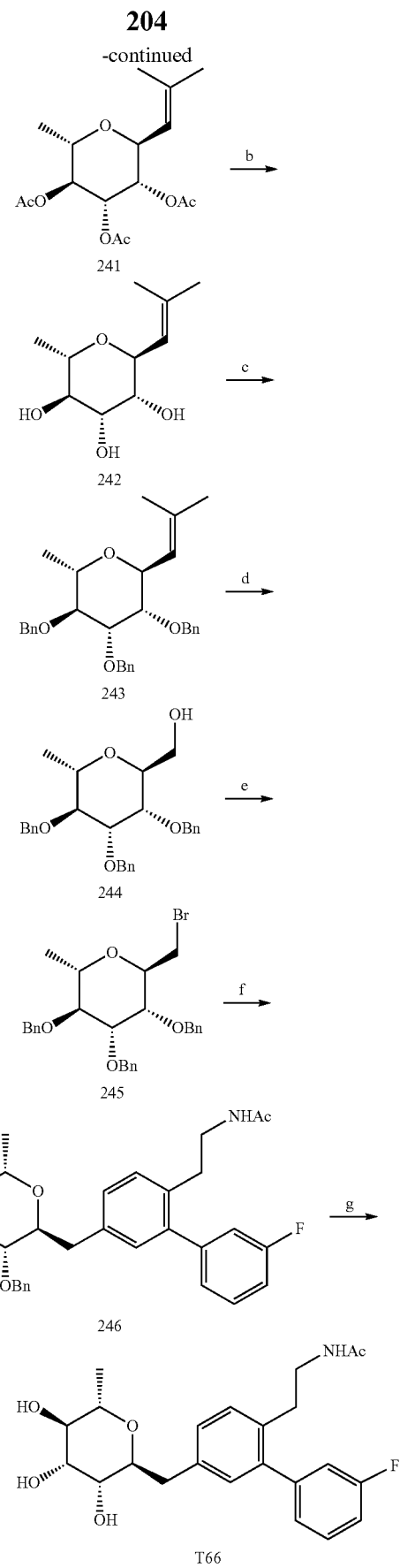

Reagents and conditions: a) Co(acac)₃, TMEDA, 2-methyl-1-propenylmagnesium bromide, THF, 0° C.-rt, 26%; b) 1 N aq. NaOH, MeOH, 0° C.-rt, 77%; c) NaH, BnBr, DMF, 0° C.-rt, 88%; d) i) O3, MeOH, CH₂Cl₂, −78° C.; ii) NaBH₄, 0° C.-rt, 68%; e) CBr₄, PPh₃, pyridine, rt—65° C., 88%; f) 239, Nib, trans-2-aminocyclohexanol hydrochloride, NaHMDS, 2-BuOH, 60° C., 54%; g) H₂, 10% Pd/C, THF, rt, 95%;

Scheme 61

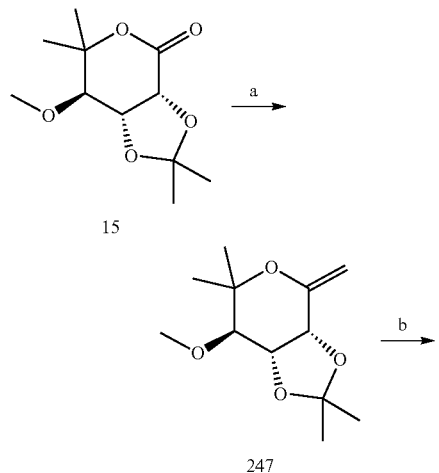

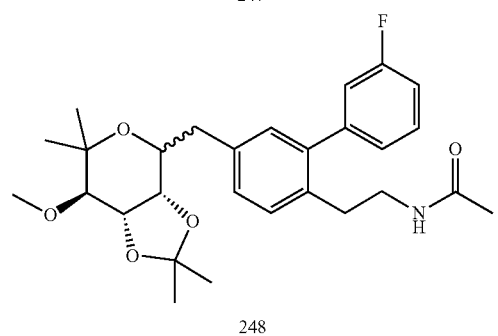

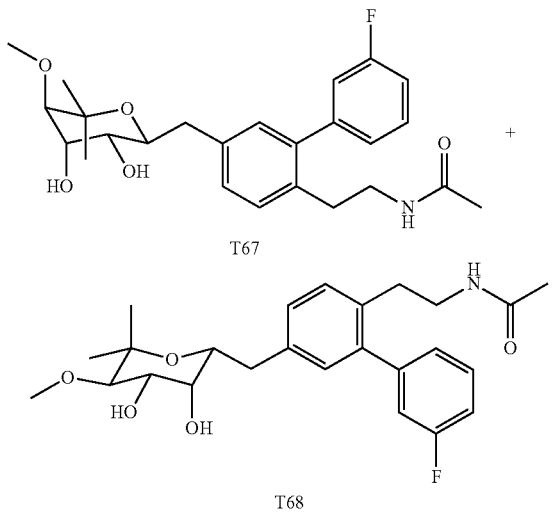

Reagents and conditions: a) Tebbe's reagent, pyridine, toluene, THF, −45° C. to 0° C., 53%; b) i) 9-BBN, THF, 0° C. to rt; ii) NaHCO₃, water, rt; iii) 237, Pd(dppf)Cl₂, DMF, rt—60° C.; c) 6 M aq. HCl, MeOH, rt, 8% for T67 from 247; 15% for T68 from 247.

Scheme 62

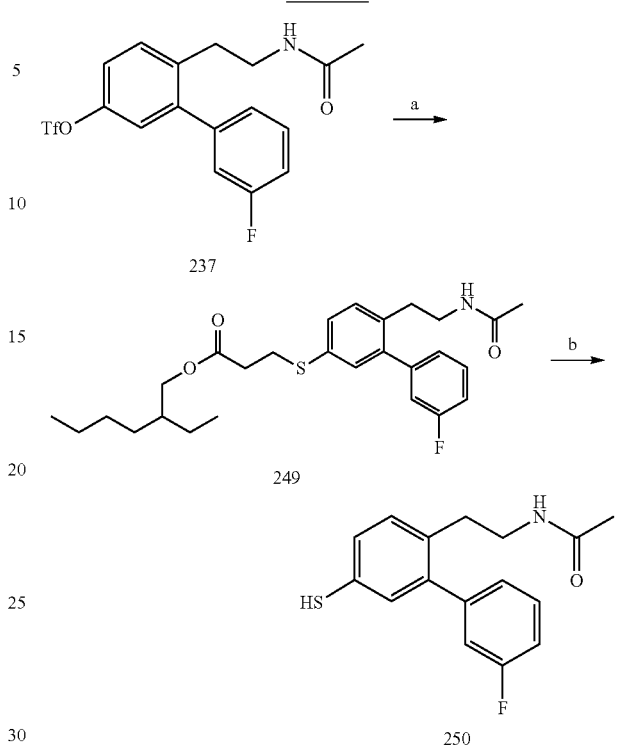

Reagents and conditions: a) Pd₂(dba)₃, Xantphos, i-Pr₂EtN, 2-ethylhexyl 3-mercaptopropanoate, 1,4-dioxane, reflux, 92%; b) NaOMe, MeOH, r.t., 50%.

Scheme 63

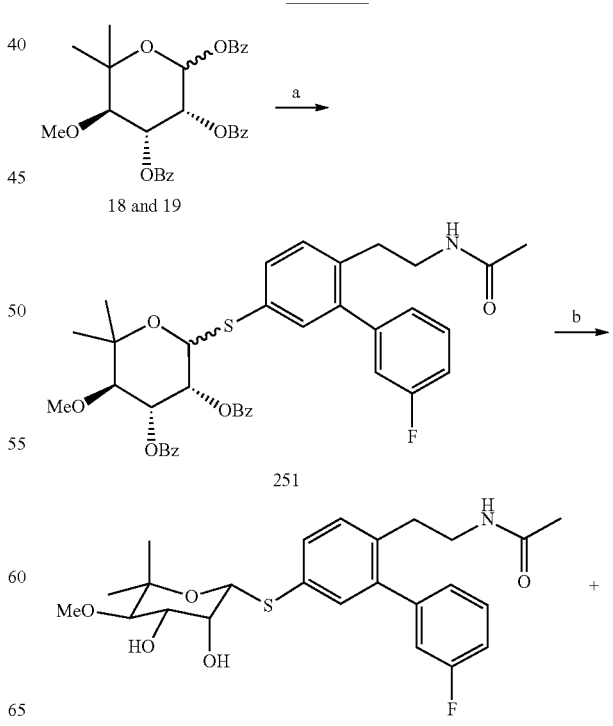

207
-continued

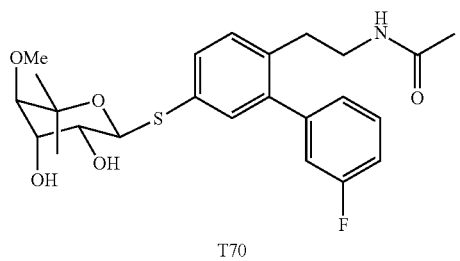

T70

Reagents and conditions: a) 250, BF$_3$·OEt$_2$, CH$_2$Cl$_2$, 0° C., 80%; b) K$_2$CO$_3$, MeOH, rt, 68% for T69; 9% for T70.

Scheme 64

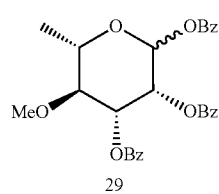

29

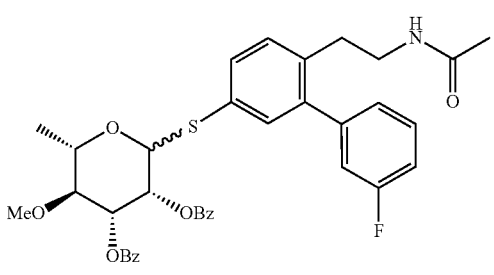

252

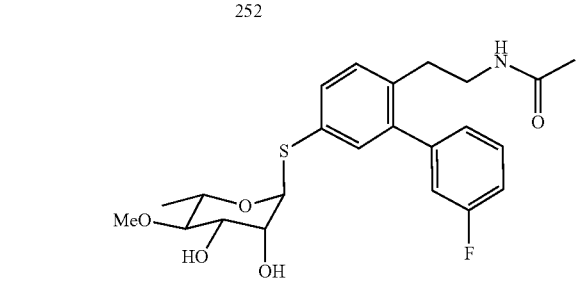

T71

Reagents and conditions: a) 250, BF$_3$·OEt$_2$, CH$_2$Cl$_2$, 0° C.-rt, 55% for major anomer; b) K$_2$CO$_3$, MeOH, rt, 95%.

Scheme 65

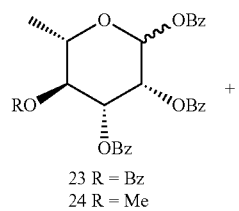

23 R = Bz
24 R = Me

208
-continued

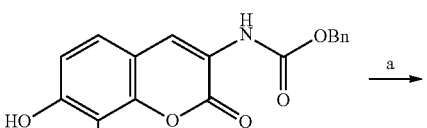

A12

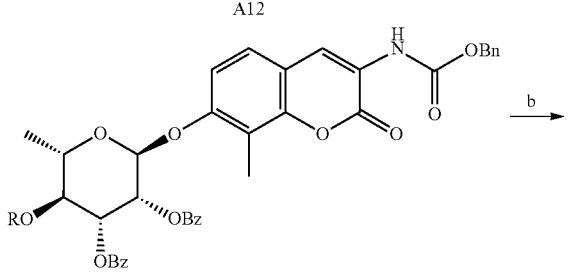

253 R = Bz
254 R = Me

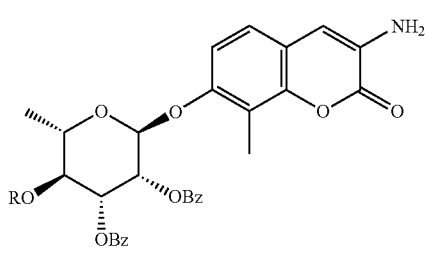

255 R = Bz
256 R = Me

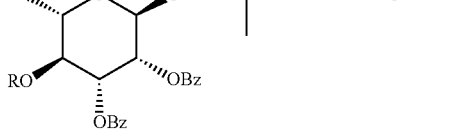

257 R = Bz
258 R = Me

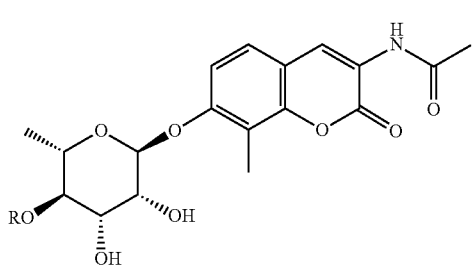

T72 R = H
T73 R = Me

Reagents and conditions: a) BF$_3$·OEt$_2$, CH$_2$Cl$_2$, 0° C.-rt, 59% for 253; 73% for 254; b) H$_2$, 10% Pd/C, EtOAc, rt, 76% for 255; 61% for 256; c) Ac$_2$O, NaOAc, rt, quantitative for 257; 95% for 258; d) K$_2$CO$_3$, THF, MeOH, rt, 10% for T72; 23% for T73.

Scheme 66
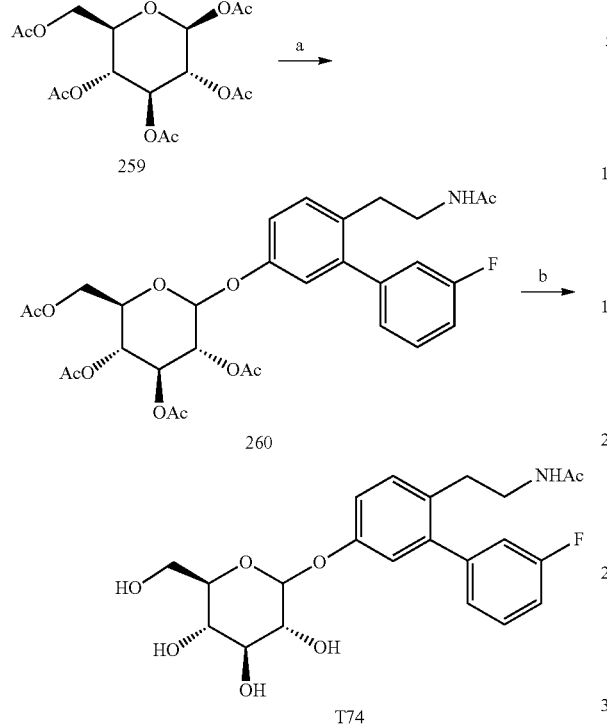
Reagents and conditions: a) A1, BF$_3$·OEt$_2$, CH$_2$Cl$_2$, 0° C.-rt; c) NaOH, MeOH, H$_2$O, rt, 50% from 259.
Scheme 67
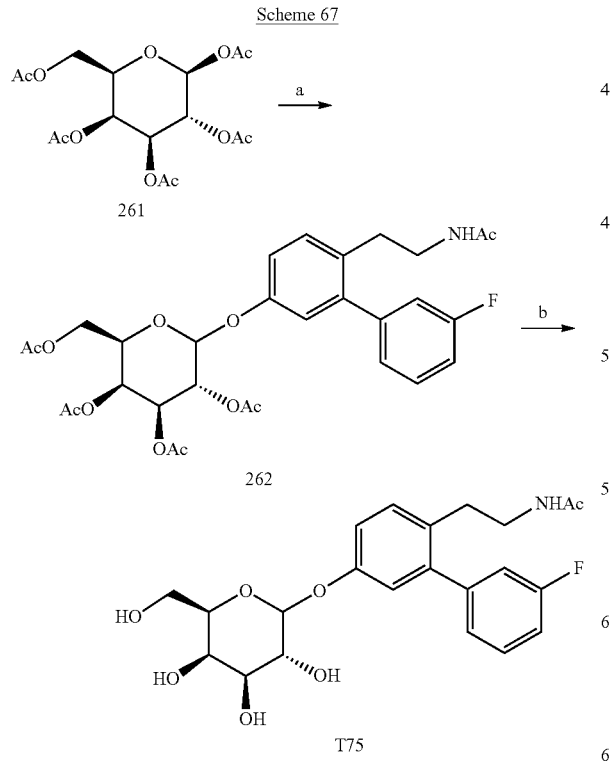
Reagents and conditions: a) A1, BF$_3$·OEt$_2$, CH$_2$Cl$_2$, 0° C.-rt, 64%; c) NaOH, MeOH, THF, H$_2$O, rt, 71%.
Scheme 68
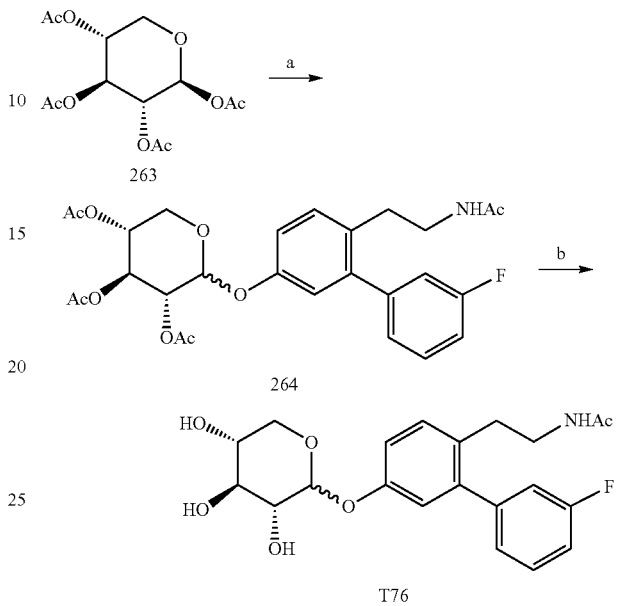
Reagents and conditions: a) A1, BF$_3$·OEt$_2$, CH$_2$Cl$_2$, 0° C.-rt, 56%; c) NaOH, MeOH, THF, H$_2$O, rt, 75%.
Scheme 69
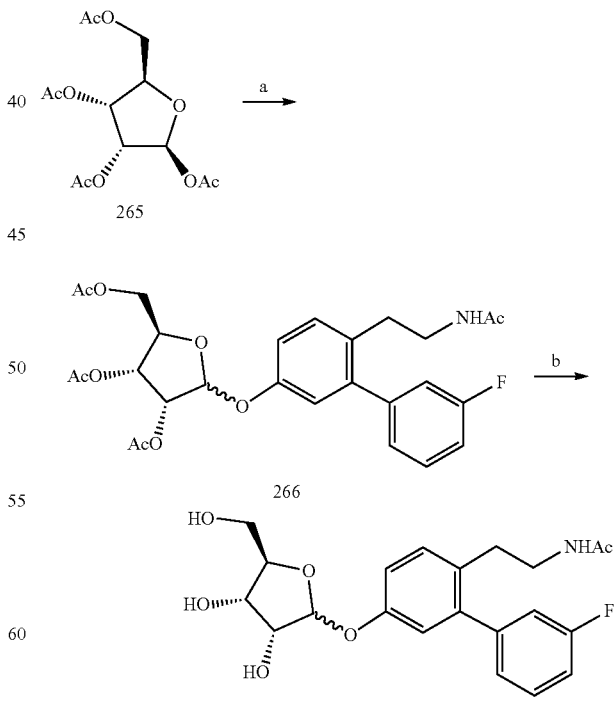
Reagents and conditions: a) A1, BF$_3$·OEt$_2$, CH$_2$Cl$_2$, 0° C.-rt, 35%; c) NaOH, MeOH, THF, H$_2$O, rt, 49%.

Scheme 70
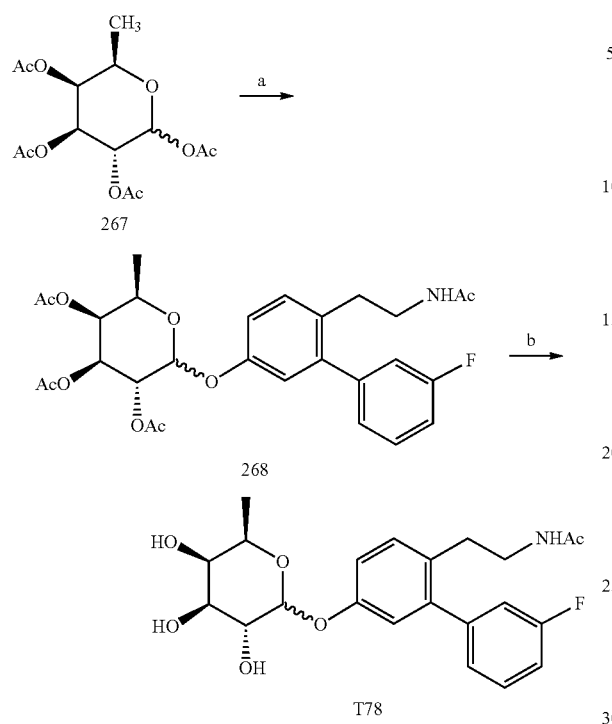
Reagents and conditions: a) A1, BF$_3$·OEt$_2$, CH$_2$Cl$_2$, 0° C.-rt, 76%; c) NaOH, MeOH, THF, H$_2$O, rt, 77%.
Scheme 71
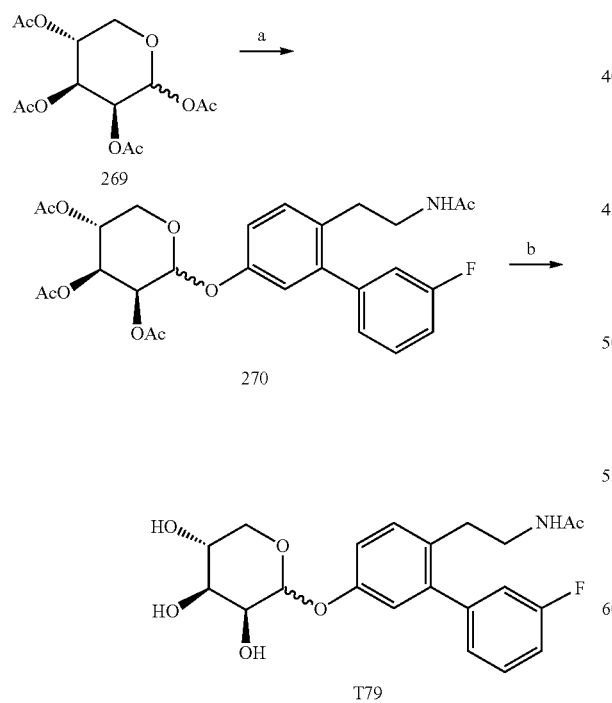
Reagents and conditions: a) A1, BF$_3$·OEt$_2$, CH$_2$Cl$_2$, 0° C.-rt, 74%; c) NaOH, MeOH, THF, H$_2$O, rt, 58%.
Scheme 72
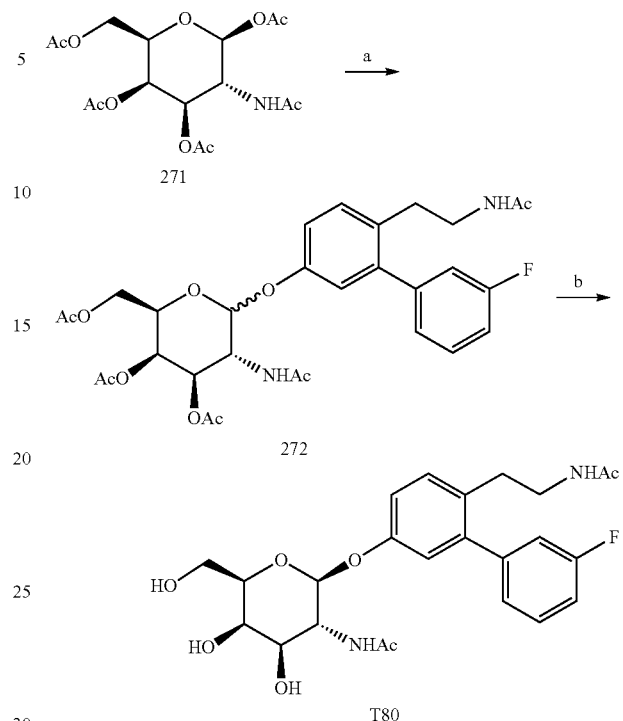
Reagents and conditions: a) A1, BF$_3$·OEt$_2$, CH$_2$Cl$_2$, 0° C.-rt, 15%; c) NaOH, MeOH, THF, H$_2$O, rt, 12%.
Scheme 73
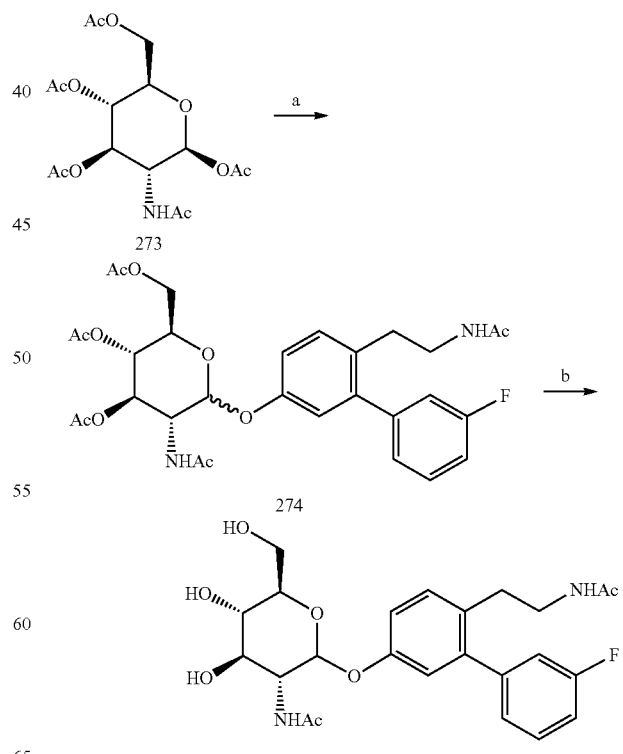

Reagents and conditions: a) A1, BF$_3$·OEt$_2$, CH$_2$Cl$_2$, 0° C.-reflux, 19%; c) NaOH, MeOH, THF, H$_2$O, rt, 29%.

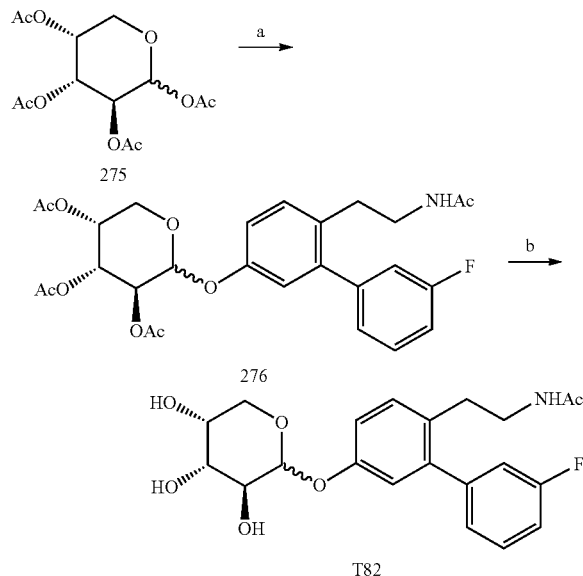

Scheme 74

T82

Reagents and conditions: a) A1, BF$_3$·OEt$_2$, CH$_2$Cl$_2$, 0° C.-rt, 41%; c) NaOH, MeOH, THF, H$_2$O, rt, 15%.

B. Characterization

Unless otherwise stated, commercially reagents were used as received, and all reactions were run under nitrogen atmosphere. Unless otherwise stated, the carboximidamides were prepared from the corresponding nitriles or carboxylic esters using the literature reported procedure (Garigipati, 1990). All solvents were of HPLC or ACS grade. Nuclear magnetic resonance (NMR) spectra were recorded on a Varian Inova-400 spectrometer at operating frequencies of 400 MHz ($^1$H NMR) or 100 MHz ($^{13}$C NMR). Chemical shifts (δ) are given in ppm relative to residual solvent (usually chloroform δ 7.26 ppm for $^1$H NMR), and coupling constants (J) in Hz. Multiplicity is tabulated as s for singlet, d for doublet, t for triplet, q for quadruplet, and m for multiplet. Mass spectra were recorded on Waters Micromass ZQ or Agilent 6120 mass spectrometer.

Compound 2: A flask charged with compound 1 (2818 g, 10.71 mol), (3-fluorophenyl)boronic acid (1574 g, 11.25 mol), and Na$_2$CO$_3$ (1135.1 g, 10.71 mol, 1 equiv) was evacuated and refilled with Ar for three times. Deionized water (5.6 L), DME (14 L) and Pd(PPh$_3$)$_4$ (123.8 g, 0.107 mol) were added sequentially. The resulting mixture was degassed and refilled with Ar for three times and then refluxed for 7 h. The suspension was filtered through Celite® (500 g) plug. The filtrate was a two-phase mixture. The organic phase was separated. The aqueous phase was extracted with EtOAc (10 L). The combined organic extracts was dried over Na$_2$SO$_4$ (3 kg), filtered and concentrated. Half of the crude product was purified by column chromatography (silica gel, eluting with 20% CH$_2$Cl$_2$ in hexanes) to give compound 2 (1040 g, 70% yield) as a white solid.

Compound 3: To a solution of 2 (1020 g, 3.67 mol) in CH$_2$Cl$_2$ (6.12 L, 6 vol) and chloroform (510 mL) was added NBS (717.8 g, 4.04 mol) in one portion. The mixture was stirred at room temperature for 38 h. HPLC indicated that the reaction proceeded to completion. The mixture was washed with 10% aq. Na$_2$SO$_3$ (6 L) and water (3×6 L). The organic phase was dried over Na$_2$SO$_4$ (650 g), filtered and concentrated. The residue was recrystallized from hexane (3 L), filtered, and washed with hexane (500 mL) to give compound 3 (980.4 g, 75% yield) as a white solid. $^1$H NMR (400 MHz, CDCl$_3$) δ 7.54 (d, J=8.8 Hz, 1H), 7.45-7.32 (m, 6H), 7.17 (ddd, J=7.7, 1.7, 1.0 Hz, 1H), 7.15-7.04 (m, 2H), 6.95 (d, J=3.1 Hz, 1H), 6.86 (dd, J=8.8, 3.1 Hz, 1H), 5.07 (s, 2H).

Compound 4: A flask charged was with compound 3 (104.6 g, 292.82 mmol), Pd(OAc)$_2$ (658 mg, 2.93 mmol, 1 mol %), P(o-Tol)$_3$ (1.79 g, 5.88 mmol) and DMF (520 mL). The stirring mixture was evacuated and refilled with Ar for 4 times. Acrylamide (24.98 g, 351.44 mmol) and N,N-diisopropylethylamine (45.42 g, 351.44 mmol) were then added. The resulting mixture was heated at ~130-135° C. for 16 h. The mixture was cooled to room temperature and then passed through a Celite® (26 g) plug. The Celite® was washed with DMF (100 mL). The filtrate was vigorously stirred while water (2.6 L) was added dropwise. The precipitated solid was filtered and washed with water (520 mL) and hexane (100 mL). The solid was triturated in EtOAc (320 mL) for 1 h and then filtered. The filter cake was washed with EtOAc (100 mL) and dried at 60° C. to afford 4 (81.9 g, 81% yield) as a yellow solid. m/z=348.1 (M+1).

Compound 5: To the solution of compound 4 (530 g, 1.53 mol) in THF (6.90 L) was added 10% Pd/C (25 g). The mixture was stirred under H$_2$ (1 atm) at room temperature for 28 h. Additional amount of 10% Pd/C (7.4 g) was added. The mixture was hydrogenated for another 8 h. The mixture was filtered through Celite® (100 g) plug, and the filter cake was washed with THF (500 mL). The filtrate was concentrated to give compound 5 (377.9 g, 95% yield) as a viscous oil, which solidified upon standing. m/z=260.1 (M+1).

Compound 6: Compound 5 (388.7 g, 1.50 mol) was suspended in THF (2.33 L), and cooled to 0° C. The solution of NaOH (390 g, 9.75 mol) in water (1.17 L) was added while maintaining the reaction mixture below 15° C. The mixture was then cooled to 0° C., and PhI(OAc)$_2$ (531.5 g, 1.65 mol) was added portionwise. The reaction mixture was stirred at ~0-5° C. for 2.5 h, and then quenched by dropwise addition of HCl (12 N aq., 570 mL, 6.84 mol) while maintaining the reaction temperature at ~0-5° C. After the addition was complete, the pH of the reaction mixture was ~8-9. The mixture was allowed standing for 10 min. The resultant two phases were separated. The aqueous phase was extracted with EtOAc (2×2 L). The combined organic phases were washed with brine (2 L) and concentrated to dryness. The residue was suspended in EtOAc (2 L) and treated with HCl (4 M in EtOAc, 2 L). The mixture was vigorously stirred for 5 h and filtered. The filter cake was washed with EtOAc (1 L) and dried at 50° C. to give compound 6 (309.2 g, 77% yield) as a brown solid. m/z=232.1 (M of free amine +1).

A1: Compound 6 (348.1 g, 1.30 mol) suspended in EtOH (2.09 L) was cooled to 0° C. The solution of NaOH (57.2 g, 1.43 mol) in water (700 mL) was added. During the addition, the temperature inside was maintained below 15° C. The mixture was stirred at 0-5° C. for 0.5 h. Then NaHCO$_3$ (229.3 g, 2.73 mmol) was added and the mixture was stirred for 0.5 h. Ac$_2$O (139.4 g, 1.37 mol) was added dropwise at ~0-5° C. and the resulting suspension was stirred for 0.5 h. HPLC analysis indicated that compound 6 was consumed to give a mixture of compound A1 (95.1%) and compound 7 (3.6%). NaOH (130 g, 3.25 mol) was then added portionwise at ~0-5° C. The mixture was stirred for 0.5 h. HCl (12 M, 300 mL, 3.6 mol) was added dropwise. The mixture was concentrated to remove most of EtOH. The residue was diluted with water (700 mL), and extracted with ethyl acetate (1.7 L, then 2×350 mL). The combined organic extracts were dried over $Na_2SO_4$, filtered and concentrated to give compound A1 (346.5 g, 97% yield) as a brown oil. m/z=274.1 (M+1); $^1H$ NMR (400 MHz, CD3CN) δ 7.35 (td, J=8.0, 6.0 Hz, 1H), 7.12 (d, J=8.3 Hz, 1H), 7.09-7.00 (m, 2H), 6.97 (ddd, J=9.6, 2.6, 1.6 Hz, 1H), 6.80 (dd, J=8.3, 2.7 Hz, 1H), 6.71 (d, J=2.7 Hz, 1H), 6.35 (s, 1H), 5.36 (m, 1H), 3.27 (td, J=7.3, 6.0 Hz, 2H), 2.71 (t, J=7.2 Hz, 2H), 1.88 (s, 3H).

Compound 9: A 20 L flask was charged with benzyl alcohol (2.5 L) at 10-15° C. under $N_2$. Acetyl chloride (393 g, 5.01 mol) was added at 10-15° C. over 30 min. The mixture was heated to 30° C. and stirred at for 1 h. Compound 8 (500 g, 3.33 mol) was added. The mixture was stirred at 30° C. for 18 h. MTBE (5 L) was added. The mixture was stirred at 30° C. for 18 h, and then filtered. The filter cake was transferred to a 20 L flask and slurried with MTBE (5 L) at 30° C. for 18 h and filtered. The filter cake obtained was slurried with MTBE (5 L) at 30° C. for 18 h again and filtered. The filter cake was dried under vacuum at 35° C. for 20 h to give compound 9 (730 g, 91% yield) as a white solid.

Compound 10: A reaction flask equipped with overhead stirring and temperature probe was charged with compound 9 (500 g, 2.08 mol) and acetone (2.5 L) at 15° C. The mixture was stirred for 5 min, and p-toluenesulfonic acid monohydrate (19.76 g, 0.10 mol) and 2,2-dimethoxypropane (1.08 Kg, 10.37 mol) were added sequentially at 20-25° C. The mixture was stirred for 2.5 h, and was added to 5% aq. $NaHCO_3$ aqueous (2.5 L) over 30 min CPME (5 L) was added, and the mixture was stirred for 20 min. The organic layer was separated; and washed with water (3.75 L+1.5 L) and 10% aq. NaCl (2.5 L). The solution containing compound 10 (498.6 g, 85% yield) was used in the next step directly. $^1H$ NMR (400 MHz, $CDCl_3$) δ 7.46-7.28 (m, 5H), 4.93 (d, J=3.6 Hz, 1H), 4.79 (d, J=11.7 Hz, 1H), 4.55 (d, J=11.7 Hz, 1H), 4.27-4.17 (m, 2H), 4.01 (dd, J=13.2, 2.6 Hz, 1H), 3.93 (dd, J=13.2, 1.3 Hz, 1H), 3.80 (ddd, J=7.4, 6.3, 3.6 Hz, 1H), 2.21 (d, J=7.7 Hz, 1H), 1.53 (s, 3H), 1.36 (s, 3H).

Compound 11: A reaction flask equipped with overhead stirring and temperature probe was charged with compound 10 (344 g, 1.23 mol) in CPME obtained from the last step at room temperature. 40% aq. NaOH (1.72 L), tetrabutylammonium bromide (39.65 g, 0.12 mol) and dimethyl sulfate (264 g, 2.09 mol) were added sequentially at 20-30° C. The mixture was stirred at 20-25° C. for 20 h. Aq ammonia (~25%-28 w %, 689 g, 4.92 mol) was added. The mixture was stirred for 1 h; cooled to 0-5° C.; and washed with water (1.72 L), 10% aq. citric acid (1.03 L), 5% aq. $NaHCO_3$ (1.03 L), and 10% aq. NaCl (1.03 L) sequentially. The organic layer was mixed with $Na_2SO_4$ (344 g) and activated charcoal (3.44 g), and stirred for 10 h at 20-30° C. The mixture was filtered, and the filter cake was washed with CPME. The combined filtrate and wash contains compound 11 (380.6 g, quantitative yield). The solution was used in the next step directly.

Compound 12: An autoclave was charged with compound 11 (706 g, 2.40 mol) in CPME, and 10% Pd/C (70.6 g) at room temperature. The autoclave was purged with $N_2$, followed by $H_2$. The mixture was hydrogenated at 0.5 MPa at 30° C. for 1.5 h and then filtered under $N_2$. The filtrate was concentrated to 700 mL, and heptane (700 mL) was added. The mixture was stirred at 30-50° C. for 30 min; cooled to 5-10° C. over 1 h; and stirred at 5-10° C. for 1-2 h. The mixture was filtered. The filter cake was washed with heptane (350 mL); and dried under vacuum at 50° C. for 6 h to give compound 12 (416 g, 85% yield) as a white solid.

Compound 13: A 10 L three neck flask equipped with overhead stirring and temperature probe was charged with compound 12 (396 g, 1.94 mol) and $CH_2Cl_2$ (2 L). After the mixture was stirred for 5 min, water (500 mL), NaBr (155.5 g, 1.51 mol), NaOAc (238.7 g, 2.91 mol), and TEMPO (30.3 g, 0.19 mol) were added sequentially. The mixture was treated with NaClO (12.6 w %, 1.72 kg, 2.91 mol) at 20-30° C. over 2 h. After the addition was complete, the mixture was stirred at 20-30° C. for another 1 h. 1 M aq. $Na_2SO_3$ (1.5 L) was added over 15 min at 20-30° C., and the mixture was stirred for 30 min. The organic layer was separated. The aqueous layer was extracted with $CH_2Cl_2$ (800 mL). The combined organic extract was washed with 10% aq. NaCl (800 mL) and concentrated to give compound 13 (289.5 g by assay, 73% yield) as an oil. m/z=203.1 (M+1). $^1H$ NMR (400 MHz, $CDCl_3$) δ 4.63 (dd, J=12.1, 2.4 Hz, 1H), 4.53 (dd, J=7.5, 3.2 Hz, 1H), 4.47 (dt, J=7.5, 2.5 Hz, 1H), 4.32 (dd, J=12.1, 2.6 Hz, 1H), 3.94 (d, J=3.2 Hz, 1H), 3.48 (s, 3H), 1.45 (s, 3H), 1.34 (s, 3H). Compound 13 was used in the next step without further purification.

Compound 14: A 1 L three neck flask equipped with overhead stirring and temperature probe was charged with compound 13 (20 g, 98.91 mmol) and CPME (140 mL) at room temperature under $N_2$. The mixture was stirred for 5 min. The solution obtained was added to a solution of methylmagnesium bromide (2.5 M in diethyl ether, 98.9 mL, 247.25 mmol) in CPME (60 mL) in a 1 L three neck flask at 20-35° C. over 2-3 h under $N_2$. After the addition was complete, the mixture was stirred at 20-30° C. for 1 h. Water (17.8 mL, 987.8 mmol) was added slowly while maintaining the reaction mixture below 25° C. The mixture was stirred at 20-25° C. for another 3 h; and then filtered. The filter cake was washed with $CH_2Cl_2$ (25 mL); and slurried with EtOAc (200 mL) for 10-15 h. After filtration, the filter cake was washed with EtOAc (25 mL); and then slurried again with $CH_2Cl_2$ (200 mL) at 30° C. for 5 h. The mixture was filtered; and the filter cake was washed with $CH_2Cl_2$ (25 mL). The combined filtrate and washes were concentrated to give compound 14 (20.39 g by assay, 88% yield) as an oil. 41 NMR (400 MHz, $CDCl_3$) δ 4.36 (dd, J=7.9, 5.5 Hz, 1H), 4.20 (q, J=5.7 Hz, 1H), 3.74 (dd, J=11.1, 6.2 Hz, 1H), 3.63 (dd, J=11.1, 5.5 Hz, 1H), 3.58 (s, 3H), 3.22 (d, J=7.9 Hz, 1H), 1.47 (s, 3H), 1.38 (s, 3H), 1.29 (s, 3H), 1.24 (s, 3H). Compound 14 was used in the next step without further purification.

Compound 15: A 10 L three neck flask equipped with overhead stirring and temperature probe was charged with compound 14 (246.9 g, 1.05 mol) and $CH_2Cl_2$ (1.23 L). After the mixture was stirred for 5 min, water (370 mL), NaBr (84.2 g, 0.82 mol), NaOAc (129.2 g, 1.58 mol), and TEMPO (16.4 g, 0.11 mol) were added sequentially. The mixture was treated with NaClO (12.6 w %, 1.985 Kg, 3.36 mol) at 20-30° C. over 2 h. After the addition was complete, the mixture was stirred at 20-30° C. for another 1 h. 1 M aq. $Na_2SO_3$ (1 L) was added, and the mixture was stirred for 30 min. The organic layer was separated. The aqueous layer was extracted with $CH_2Cl_2$ (2×740 mL). The combined organic extract was washed with 10% aq. NaCl (1 L); dried with $Na_2SO_4$; filtered; and concentrated. The crude product was dissolved in MTBE (250 mL). The mixture was stirred at 20-30° C. for 1 h. Heptane (750 mL) was added. The mixture was stirred at 20-30° C. for 2 h, and then cooled to 0-5° C. The product was collected by filtration; washed with MTBE/heptane (1/3, 100 mL); and dried under vacuum to give compound 15 (182 g, 75% yield) as a white solid.

m/z=231.1 (M+1); $^1$H NMR (400 MHz, CDCl$_3$) δ 4.73 (d, J=8.4 Hz, 1H), 4.47 (dd, J=8.4, 6.3 Hz, 1H), 3.55 (s, 3H), 3.24 (d, J=6.3 Hz, 1H), 1.49 (s, 3H), 1.45 (s, 3H), 1.40 (s, 3H), 1.34 (s, 3H).

Compound 16: A 5 L three neck flask equipped with overhead stirring and temperature probe was charged with compound 15 (182 g, 0.79 mol) and CH$_2$Cl$_2$ (1.8 L) at room temperature under N$_2$. The solution was cooled to −25° C. and treated with diisobutylaluminum hydride (1.49 M, 637.7 mL, 0.948 mol) dropwise over 1 h at ~−35° C. to ~−25° C. After the addition was complete, the mixture was stirred at −25° C. to ~−5° C. for 1 h. Sat. aq. Rochelle's salt (900 mL) was added over 45 min while maintaining the reaction mixture below 10° C. The mixture was stirred at 20-30° C. for 18 h to give a clear solution. The organic layer was separated; and the aqueous layer was extracted with CH$_2$Cl$_2$ (910 mL+550 mL). The combined organic extract was washed with 10% aq. NaCl (910 mL); dried with Na$_2$SO$_4$; filtered; and concentrated to give compound 16 (1/1 mixture of two anomers, 177.07 g, 97% yield) as an oil. $^1$H NMR (400 MHz, CDCl$_3$) δ 5.12-5.06 (m, 1H), 4.37 (t, J=6.8 Hz, 0.5H), 4.29 (t, J=6.6 Hz, 0.5H), 4.22 (dd, J=6.6, 2.7 Hz, 0.5H), 4.15 (dd, J=7.1, 3.7 Hz, 0.5H), 3.55 (s, 1.5H), 3.52 (s, 1.5H), 3.33 (dd, J=9.7, 0.6 Hz, 0.5H), 3.27 (d, J=6.6 Hz, 0.5H), 3.19 (d, J=6.5 Hz, 0.5H), 3.10 (dd, J=6.4, 1.0 Hz, 0.5H), 1.57 (s, 1.5H), 1.53 (s, 1.5H), 1.38 (s, 1.5H), 1.36 (s, 1.5H), 1.34 (s, 3H), 1.26 (s, 1.5H), 1.15 (s, 1.5H).

Compound 17: A 100 mL flask was charged with compound 16 (9 g, 38.75 mmol), water (36 mL) and 732 ion exchange resin (4.5 g) at room temperature. The mixture was heated at 40° C. overnight and filtered. The resin was rinsed with water (9 mL). The filtrate was treated with Amberlite IRA96RF (0.9 g), and stirred for 2 h. The pH of the reaction mixture was 5.3. Additional amount of Amberlite IRA96RF (0.45 g) was added, and the mixture was stirred for 1 h. The pH of the reaction mixture was 6.8. Additional amount of Amberlite IRA96RF (0.35 g) was added, and the mixture was stirred for another 1 h. The pH of the reaction mixture was 7.3. The resin was removed by filtration and washed with water (9 mL). The combined filtrate was concentrated under vacuum to remove acetone, and the aqueous solution was dried in a air-dry oven at 50° C. to give compound 17 (6.97 g, 93% yield) as a white solid. $^1$H NMR (400 MHz, CDCl$_3$) of the major anomer δ 4.93 (dd, J=10.1, 1.7 Hz, 1H), 3.98 (m, 1H), 3.75 (dt, J=8.9, 4.3 Hz, 1H), 3.59 (s, 3H), 3.17 (dd, J=9.7, 1.3 Hz, 1H), 2.58 (d, J=3.5 Hz, 1H), 2.50 (d, J=5.3 Hz, 1H), 1.36 (s, 3H), 1.17 (s, 3H).

Compound 18 and 19: To a solution of compound 17 (1.6 g, 8.32 mmol) in pyridine (16 mL) at 0° C. under N$_2$ was added benzoyl chloride (4.9 mL, 42.21 mmol). The mixture was stirred at ambient temperature overnight. Additional amount of benzoyl chloride (1 mL, 8.61 mmol) was added, and the mixture was continued stirring for 4 h. EtOAc was added. The mixture was washed with 1 N aq. HCl to remove pyridine. The organic extract was cooled to 0° C.; treated with ethylenediamine (4 mL, 59.83 mmol); and stirred for 10 min. The precipitated solid was removed by filtration and washed with EtOAc. The combined filtrate and wash was washed with 1 N aq. HCl, and sat. aq. NaHCO$_3$. The organic extract was dried with Na$_2$SO$_4$; filtered and concentrated. The residue was purified by column chromatography (silica gel, eluting with 0% to 25% EtOAc in hexanes) to give a mixture of compound 18 and compound 19 (6.6/1 ratio, 2.4 g, 57% yield) as a white foam. Re-crystallization of the mixture from heptane gave compound 18 as a single anomer. 18: m/z=383.1 (M-OBz); 19: m/z=383.1 (M-OBz).

Compound 21: To a solution of compound 20 (Klemer and Waldmann, 1986) (7 g, 39.29 mmol) in pyridine (300 mL) was added benzoyl chloride (16.57 g, 117.86 mmol) at 15° C. The mixture was stirred at 15° C. for 16 h. Additional amount of benzoyl chloride (11.04 g, 78.57 mmol) was added, and the mixture was stirred at 15° C. for another 20 h. The mixture was concentrated; and the residue was purified by column chromatography (silica gel, eluting with 20/1 petroleum ether/EtOAc) to give compound 21 (3.7/1 mixture of anomers, 14.4 g, 62% yield) as a white foam. m/z=473 (M-OBz).

Compound 23: To a solution of L-rhamnose monohydrate 22 (5.00 g, 27.45 mmol) in pyridine (100 mL) was added benzoyl chloride (34.25 g, 253.68 mmol) at 0° C. The mixture was stirred at 15° C. for 2 h. Water (100 mL) was added. The mixture was extracted with CH$_2$Cl$_2$ (2×500 mL). The combined organic extracts were dried with Na$_2$SO$_4$, and concentrated. The residue was purified by column chromatography (silica gel, eluting with 3% to 16% ethyl acetate in petroleum ether) to give compound 23 as a 10:1 mixture of two anomers (16.50 g, 93% yield) as white foams. Both isomers m/z=459 (M-OBz).

Compound 24: Compound 23 (3.19 g, 5.49 mmol) and compound A1 (1.37 g, 5.01 mmol) was dissolved in CH$_2$Cl$_2$ (25 mL) and cooled to 0° C. Boron trifluoride diethyl etherate (3.10 mL, 25.12 mmol) was added. The mixture was stirred at ambient temperature for 20 h, and then cooled to 0° C. Sat. aq. NaHCO$_3$ (20 mL) and 1 N aq. NaOH (50 mL) were added sequentially. The organic phase was separated. The aqeuous phase was extracted with CH$_2$Cl$_2$ (50 mL). The combined organic extracts were washed with 1 N aq. NaOH (50 mL); dried with Na$_2$SO$_4$; filtered and concentrated to give a mixture of compound 24 and compound 23 (~3/1 ratio, determined by $^1$H NMR) as a white foam. The mixture was used in the next step without further purification. Compound 24: m/z=732 (M+1).

T1: To a mixture of compound 24 (all from the last step) in MeOH (28 mL) and THF (28 mL) was added aq. 1 N NaOH (55 mL, 55 mmol) at room temperature. After stirring at room temperature for 16 h, the mixture was concentrated. The residue was extracted with EtOAc (2×50 mL, and then 4×25 mL). The combined organic extracts were dried with Na$_2$SO$_4$, and concentrated. The residue was purified by column chromatography (silica gel, eluting with 0% to 30% MeOH in CH$_2$Cl$_2$) to give compound T1 (1.702 g, 81% yield from 23) as a white foam. m/z=420 (M+1); $^1$H NMR (400 MHz, CD$_3$CN) δ 7.44 (dt, J=6.1, 8.0 Hz, 1H), 7.25 (d, J=8.5 Hz, 1H), 7.10 (m, 4H), 6.90 (d, J=2.6 Hz, 1H), 6.24 (br s, 1H), 5.45 (d, J=1.7 Hz, 1H), 3.95 (m, 1H), 3.73 (ddd, J=3.5, 6.4, 9.7 Hz, 1H), 3.61 (qd, J=6.2, 9.5 Hz, 1H), 3.33 (dt, J=5.1, 9.4 Hz, 1H), 3.28 (d, J=4.3 Hz, 1H), 3.15 (m, 4H), 2.65 (dd, J=6.7, 8.2 Hz, 2H), 1.73 (s, 3H), 1.15 (d, J=6.2 Hz, 3H).

Compound 26: To a solution of methyl α-L-rhamnopyranoside 25 (49.50 g, 277.81 mmol) in acetone (500 mL) were added 2,2-dimethoxypropane (144.67 g, 1.39 mol) and TsOH·H$_2$O (2.64 g, 13.89 mmol) at 10° C. After stirring for 2 h at 10° C., the mixture was concentrated. The residue was purified by column chromatography (silica gel, eluting with 33% ethyl acetate in petroleum ether) to give compound 26 (50.50 g, 83% yield) as a yellow oil.

Compound 27: To a solution of compound 26 (20.00 g, 91.64 mmol) in THF (200 mL) was added NaH (60% in mineral oil, 5.50 g, 137.46 mmol) at 0° C. After stirring for 0.5 h, iodomethane (39.02 g, 274.92 mmol) was added to the mixture and stirred at 15° C. for 16 h. The reaction was quenched by adding EtOH (10 mL), and the mixture was partitioned between EtOAc (600 mL) and water (300 mL). The organic extract was dried with $Na_2SO_4$, and concentrated. The residue was purified by column chromatography to give compound 27 (18.20 g, 86% yield) as a yellow oil.

Compound 28: A solution of compound 27 (18.20 g, 78.36 mmol) in aq. $H_2SO_4$ (0.2 M in water, 100 mL) was heated at 80° C. for 40 h. The mixture was cooled to 0° C. $Na_2CO_3$ (10 g) was added slowly. The mixture was concentrated, and the residue was mixed with $CH_2Cl_2$ and MeOH (4/1 v/v, 250 mL), and stirred for 30 min. The mixture was filtered, and the filtrate was concentrated. The residue was purified by column chromatography (silica gel, eluting with 0% to 16% ethyl acetate in MeOH) to give compound 28 (12.60 g, 90% yield) as a brown viscous oil. m/z=201 (M+Na).

Compound 29: To a solution of compound 28 (2.00 g, 11.22 mmol) in pyridine (50 mL) was added benzoyl chloride (7.89 g, 56.10 mmol) at 0° C. The mixture was stirred at 15° C. for 16 h, and concentrated. The residue was purified by column chromatography (silica gel, eluting with 10% ethyl acetate in petroleum ether) to give partially purified product, which was further purified by reverse phase column chromatography (C18, eluting with 5% to 20% MeCN in aq. 0.1% $HCO_2H$) to give compound 29 (3.74 g, 1.4/1 mixture of anomers, 68% yield) as a white solid. Both isomers m/z=369 (M-OBz).

Compound 30: Compound 29 (1.00 g, 2.04 mmol) and compound A1 (614 mg, 2.24 mmol) was dissolved in $CH_2Cl_2$ (10 mL), and cooled to 0° C. Boron trifluoride diethyl etherate (0.75 mL, 6.07 mmol) was added. After the mixture was stirred at 0° C. for 22 h, sat. aq. $NaHCO_3$ (10 mL) was added. The mixture was stirred at room temperature for 15 min and extracted twice with $CH_2Cl_2$. The combined organic extracts were washed with sat. aq. $NaHCO_3$, dried with $Na_2SO_4$, and concentrated. The residue was purified by column chromatography (silica gel, eluting with 0% to 60% acetone in hexanes) to give compound 30 (900 mg, 69% yield) as a white foam. m/z=642 (M+1). Compound 30 contains 5% compound A1 and was used in the next step without further purification.

T2: To a mixture of compound 30 (895 mg, 1.39 mmol) in MeOH (7 mL) and THF (7 mL) was added aq. 1 N NaOH (7 mL, 7 mmol) at room temperature. After stirring at room temperature for 3 h, the mixture was concentrated. Water (10 mL) was added, and the mixture was extracted 3 times with $CH_2Cl_2$. The combined organic extracts were washed with aq. 1 N NaOH (5 mL) and water (5 mL). The aqueous washes were extracted twice with $CH_2Cl_2$. The combined organic extracts were dried with $Na_2SO_4$ and concentrated. The residue was purified by column chromatography (silica gel, eluting with 0% to 10% MeOH in $CH_2Cl_2$) to give compound T2 (540 mg, 89% yield) as a white foam. m/z=456 (M+Na); $^1H$ NMR (400 MHz, $CDCl_3$) δ 7.38 (dt, J=5.9, 8.0 Hz, 1H), 7.21 (d, J=8.5 Hz, 1H), 7.01 (m, 4H), 6.90 (d, J=2.7 Hz, 1H), 5.49 (d, J=1.7 Hz, 1H), 5.30 (br s, 1H), 4.13 (dt, J=1.7, 3.5 Hz, 1H), 4.04 (ddd, J=3.4, 5.1, 8.8 Hz, 1H), 3.76 (qd, J=6.2, 9.5 Hz, 1H), 3.58 (s, 3H), 3.27 (m, 2H), 3.16 (t, J=9.4 Hz, 1H), 2.74 (t, J=7.2 Hz, 2H), 2.64 (m, 2H), 1.87 (s, 3H), 1.29 (d, J=6.3 Hz, 3H).

Compound 31 and 32: $BF_3 \cdot OEt_2$ (0.76 mL, 6.2 mmol) was added dropwise to a 0° C. solution of compound 21 (1.002 g, 1.685 mmol) and compound A1 (425.5 mg, 1.557 mmol) in $CH_2Cl_2$ (7.0 mL), and stirred overnight at 0° C. The reaction was quenched with sat. aq. $NaHCO_3$ (40 mL) and extracted with EtOAc (3×50 mL). The combined organic fractions were dried ($Na_2SO_4$) and concentrated, and the resultant residue purified by column chromatography (silica gel, eluting with 0% to 30% acetone in $CH_2Cl_2$) to give compound 31 (704.2 mg, 61% yield) as a white foam solid, and a mixture containing compound 31 and compound 32 (31:32=17:82, ~60 mg). Compound 31: m/z=746.3 (M+1).

Mixed fractions from three synthetic preparations of compound 31 and 32 were combined to give a mixture containing compound 31 and compound 32 (31:32=39:59, 203 mg), which was purified by column chromatography (silica gel, eluting with 0% to 20% acetone in $CH_2Cl_2$) to give compound 32 (65.3 mg, 3% yield based on theoretical yield of three reactions) as a white foam solid: m/z=746.2 (M+1).

T3: A solution of compound 31 (565 mg, 0.758 mmol) and $K_2CO_3$ (563 mg, 4.07 mmol) in MeOH (10 mL) was stirred at room temperature for 3 h. The resultant reaction was filtered, and the solids washed with EtOAc (30 mL). The combined organic fractions were concentrated, dissolved in EtOAc (125 ml), washed with saturated $NaHCO_3$ (30 mL), dried ($Na_2SO_4$), concentrated and the resultant residue purified by column chromatography (silica gel, eluting with 0% to 10% MeOH in $CH_2Cl_2$) to give compound T3 (321.5 mg, 98% yield) as a white foam solid: $^1H$ NMR (400 MHz, $CDCl_3$) δ 7.38 (q, J=7.6 Hz, 1H), 7.22 (d, J=8.5 Hz, 1H), 7.04 (m, 4H), 6.89 (d, J=2.6 Hz, 1H), 5.58 (d, J=1.7 Hz, 1H), 5.26 (br s, 1H), 4.14 (m, 2H), 3.77 (dd, J=4.3, 9.3 Hz, 1H), 3.28 (q, J=6.8 Hz, 2H), 2.75 (t, J=7.2 Hz, 2H), 2.46 (d, J=5.2, 1H), 2.40 (d, J=3.4 Hz, 1H), 2.12 (d, J=4.4 Hz, 1H), 1.87 (s, 3H), 1.35 (s, 3H), 1.25 (s, 3H); m/z 434.1 (M+1).

T4: A solution of compound 32 (53.9 mg, 0.0723 mmol) and $K_2CO_3$ (53 mg, 0.38 mmol) in MeOH (2 mL) was stirred at room temperature for 3 h. The resultant reaction was concentrated, dissolved in EtOAc (50 mL), washed with saturated $NaHCO_3$ (10 mL), dried ($Na_2SO_4$), concentrated and the resultant residue purified by column chromatography (silica gel, eluting with 0% to 15% MeOH in $CH_2Cl_2$) to give compound T4 (25.0 mg, 80% yield) as a glassy solid: $^1H$ NMR (400 MHz, DMSO-$d_6$) δ 7.82 (t, J=5.6 Hz, 1H), 7.49 (ddd, J=6.0, 7.3, 8.8 Hz, 1H), 7.19 (m, 4H), 6.95 (dd, J=2.7, 8.5 Hz, 1H), 6.79 (d, J=2.7 Hz, 1H), 5.38 (s, 1H), 4.86 (d, J=5.1 Hz, 1H), 4.69 (d, J=4.9 Hz, 1H), 4.57 (d, J=6.2 Hz, 1H), 3.83 (ddd, J=1.0, 3.2, 4.5 Hz, 1H), 3.51 (ddd, J=3.1, 6.2, 9.5 Hz, 1H), 3.40 (dd, J=5.1, 9.9 Hz, 1H), 3.07 (td, J=5.7, 7.5 Hz, 2H), 2.59 (m, 2H), 1.70 (s, 3H), 1.16 (s, 6H); m/z 274.1 (aglycone+1).

Compound 33: To a solution of compound T1 (238 mg, 0.57 mmol) in acetone (5.6 mL) was added 2,2-dimethoxypropane (0.56 mL, 4.55 mmol) and (1S)-(+)-camphor-10-sulfonic acid (23 mg, 0.099 mmol). The mixture was stirred at room temperature for 16 h; diluted with EtOAc; quenched with triethylamine (0.5 mL, 3.59 mmol); and washed with sat. aq. $NaHCO_3$. The organic extract was dried with $Na_2SO_4$; filtered; and concentrated. The residue was purified by column chromatography (silica gel, eluting with 0% to 100% EtOAc in hexanes) to give compound 33 (255 mg, 98% yield). m/z=274.1 (M-$C_9H_{13}O_4$).

Compound 34: A vial charged with a solution of compound 33 (165 mg, 0.36 mmol) and MeCN (3.3 mL) was purged with $N_2$ for 5 min CuI (13 mg, 0.068 mmol) was added. The vial was sealed, and heated to 60° C. 2,2-Difluoro-2-(fluorosulfonyl)acetic acid (109 µL, 1.06 mmol) was added dropwise via syringe. The mixture was heated at 60° C. for 30 min; cooled to room temperature; diluted with EtOAc; and washed with sat. aq. $NaHCO_3$ and water. The organic extract was dried with $Na_2SO_4$; filtered; and concentrated. The residue was purified by column chromatography (silica gel, eluting with 0% to 50% acetone in hexanes) to give compound 34 (52 mg, 28% yield) as a white foam. m/z=510.2 (M+1)

T5: To a solution of compound 34 (50 mg, 0.098 mmol) in MeOH (2.5 mL) was added 6 N aq. HCl (0.5 mL, 3 mmol) at 0° C. The reaction mixture was stirred at 0° C. for 2 h; treated with sat. aq. NaHCO$_3$; and extracted twice with EtOAc. The combined organic extracts were dried with Na$_2$SO$_4$; filtered; and concentrated. The residue was purified by column chromatography (silica gel, eluting with 0% to 10% MeOH in CH$_2$Cl$_2$) to give T5 (35 mg, 76% yield) as a white foam. m/z=470.2 (M+1); $^1$H NMR (400 MHz, CDCl$_3$) δ 7.39 (dt, J=5.9, 7.7 Hz, 1H), 7.23 (d, J=8.5, 1H), 7.03 (m, 4H), 6.91 (d, J=2.7 Hz, 1H), 6.42 (dd, $J_{F-H}$=73.7, 77.6 Hz, 1H), 5.53 (d, J=1.7 Hz, 1H), 5.30 (br s, 1H), 4.12 (m, 2H), 3.99 (t, J=9.3 Hz, 1H), 3.88 (m, 1H), 3.28 (m, 2H), 2.75 (t, J=7.3 Hz, 2H), 2.69 (m, 2H), 1.88 (s, 3H), 1.28 (d, J=6.2 Hz, 3H).

Compound 35: To a solution of compound T3 (500 mg, 1.15 mmol) in acetone (11.5 mL) was added 2,2-dimethoxypropane (1.15 mL, 9.35 mmol) and (1S)-(+)-camphor-10-sulfonic acid (50 mg, 0.22 mmol). The mixture was stirred at room temperature for 3 h; diluted with EtOAc; and washed with sat. aq. NaHCO$_3$. The organic extract was dried with Na$_2$SO$_4$; filtered; and concentrated. The residue was purified by column chromatography (silica gel, eluting with 0% to 100% EtOAc in hexanes) to give compound 35 (530 mg, 97% yield) as a white foam. m/z=274.1 (M-C$_{10}$H$_{15}$O$_4$)

Compound 36: A vial charged with a solution of compound 35 (105 mg, 0.22 mmol) and MeCN (2 mL) was purged with N$_2$ for 5 min. CuI (10 mg, 0.052 mmol) was added. The vial was sealed, and heated to 60° C. After 5 min, 2,2-difluoro-2-(fluorosulfonyl)acetic acid (73 μL, 0.71 mmol) was added dropwise via syringe. The mixture was heated at 60° C. for 30 min; cooled to room temperature; diluted with EtOAc; and washed with sat. aq. NaHCO$_3$ and water. The organic extract was dried with Na$_2$SO$_4$; filtered; and concentrated. The residue was purified by column chromatography (silica gel, eluting with 0% to 50% acetone in hexanes) to give compound 36 (59 mg, 51% yield) as a white foam. m/z=524.2 (M+1)

T6: To a solution of compound 36 (59 mg, 0.11 mmol) in MeOH (3 mL) was added 6 N aq. HCl (0.6 mL, 3.6 mmol). The reaction mixture was stirred at room temperature for 2.5 h. Sat. aq. NaHCO$_3$ was added to adjust pH>7. The mixture was concentrated. The residue was extracted twice with CH$_2$Cl$_2$. The combined organic extracts were washed with 1 N aq. NaOH and water. The organic extract was dried with Na$_2$SO$_4$; filtered; and concentrated. The residue was purified by column chromatography (silica gel, eluting with 0% to 10% MeOH in CH$_2$Cl$_2$) to give T6 (36 mg, 66% yield) as a white foam. m/z=484.1 (M+1); $^1$H NMR (400 MHz, CDCl$_3$) δ 7.38 (dt, J=6.0, 8.0 Hz, 1H), 7.22 (d, J=8.5 Hz, 1H), 7.04 (m, 4H), 6.89 (d, J=2.7 Hz, 1H), 6.40 (dd, $J_{F-H}$=73.9, 77.3 Hz, 1H), 5.58 (d, J=2.4 Hz, 1H), 5.27 (br s, 1H), 4.32 (ddd, J=3.5, 4.5, 8.2 Hz, 1H), 4.20 (q, J=2.8 Hz, 1H), 4.15 (d, J=9.0 Hz, 1H), 3.28 (m, 2H), 2.75 (t, J=7.3 Hz, 2H), 2.64 (d, J=2.8 Hz, 1H), 2.59 (dd, J=2.2, 4.4 Hz, 1H), 1.88 (s, 3H), 1.37 (s, 3H), 1.27 (s, 3H).

Compound 37: To a solution of compound 35 (45 mg, 0.095 mmol) in DMF (0.5 mL) was added sodium hydride (60% in mineral oil, 4.6 mg, 0.12 mmol) at 0° C. under N$_2$. Benzyl bromide (17 μL, 0.14 mmol) was added dropwise. The mixture was stirred at room temperature for 1 h; diluted with EtOAc; and washed with water. The organic extract was dried with Na$_2$SO$_4$; filtered; and concentrated. The residue was purified by column chromatography (silica gel, eluting with 0% to 100% EtOAc in hexanes) to give compound 37 (40 mg, 75% yield) as a white foam. m/z=586.2 (M+Na).

T7: To a solution of compound 37 (40 mg, 0.071 mmol) in MeOH (0.7 mL) was added 6 N aq. HCl (0.14 mL, 0.84 mmol) at room temperature. The reaction was stirred at room temperature for 30 min Sat. aq. NaHCO$_3$ was added to adjust pH>7. The mixture was extracted twice with CH$_2$Cl$_2$. The combined organic extracts were washed twice with 1 N aq. NaOH; dried with Na$_2$SO$_4$; filtered; and concentrated. The residue was purified by column chromatography (silica gel, eluting with 0% to 70% acetone in hexanes) to give compound T7 (19 mg, 51% yield) as a white foam. m/z=524.3 (M+1); $^1$H NMR (400 MHz, CDCl$_3$) δ 7.37 (m, 6H), 7.21 (d, J=8.5 Hz, 1H), 7.04 (m, 4H), 6.89 (d, J=2.7 Hz, 1H), 5.56 (d, J=2.3 Hz, 1H), 5.26 (br s, 1H), 4.78 (d, J=11.6 Hz, 1H), 4.72 (d, J=11.6 Hz, 1H), 4.24 (td, J=3.5, 9.1 Hz, 1H), 4.17 (q, J=2.7 Hz, 1H), 3.61 (d, J=9.0 Hz, 1H), 3.28 (q, J=6.8 Hz, 2H), 2.74 (t, J=7.2 Hz, 2H), 2.54 (d, J=2.6 Hz, 1H), 2.37 (d, J=3.5 Hz, 1H), 1.87 (s, 3H), 1.39 (s, 3H), 1.28 (s, 3H).

Compound 38: To a solution of compound 35 (79 mg, 0.17 mmol) in DMF (1 mL) was added sodium hydride (60% in mineral oil, 123 mg, 3.08 mmol) at room temperature under N$_2$. Isopropyl iodide (307 μL, 3.08 mmol) in DMF (1 mL) was added. The mixture was heated at 65° C. for 1 h and cooled to room temperature. Additional amount of sodium hydride (60% in mineral oil, 100 mg, 2.50 mmol) and isopropyl iodide (250 μL, 2.50 mmol) were added sequentially. The mixture was heated at 65° C. for another 1 h; cooled to 0° C.; quenched with carefully addition of water; and extracted with EtOAc. The organic extract was washed three times with water and 10% aq. Na$_2$SO$_3$; dried with Na$_2$SO$_4$; filtered; and concentrated. The residue was dissolved in MTBE and washed 5 times with water to remove residual DMF. The organic extract was dried with Na$_2$SO$_4$; filtered; and concentrated. The residue was purified by column chromatography (silica gel, eluting with 0% to 100% EtOAc in hexanes) to give compound 38 (32 mg, 37% yield) as a white foam. m/z=516 (M+1).

T8: A solution of compound 38 (37 mg, 0.072 mmol) in acetic acid (70% aq., 0.5 mL) was stirred at room temperature for 16 h; 40° C. for 8 h; room temperature for 14 h; and 40° C. for 3 h. The mixture was diluted with toluene, and the solvent was evaporated. The residue was dissolved in CH$_2$Cl$_2$ and washed with two times with 1 N aq. NaOH. The organic extract was dried with Na$_2$SO$_4$; filtered; and concentrated. The residue was purified by column chromatography (silica gel, eluting with 0% to 10% MeOH in CH$_2$Cl$_2$) to give compound T8 (16 mg, 47% yield) as a white foam. m/z=498 (M+Na); $^1$H NMR (400 MHz, CDCl$_3$) δ 7.38 (dt, J=6.0, 8.0 Hz, 1H), 7.20 (d, J=8.5 Hz, 1H), 7.04 (m, 4H), 6.89 (d, J=2.7 Hz, 1H), 5.55 (d, J=2.6 Hz, 1H), 5.25 (br s, 1H), 4.15 (m, 2H), 3.78 (hept, J=6.2 Hz, 1H), 3.51 (d, J=8.7 Hz, 1H), 3.28 (q, J=6.9 Hz, 2H), 2.74 (t, J=7.2 Hz, 2H), 2.53 (d, J=2.3 Hz, 1H), 2.45 (d, J=2.7 Hz, 1H), 1.87 (s, 3H), 1.35 (s, 3H), 1.23 (s, 3H), 1.22 (d, J=6.1 Hz, 3H), 1.19 (d, J=6.1 Hz, 3H).

T9: A solution of compound 35 (100 mg, 0.21 mmol) in CH$_2$Cl$_2$ (2.1 mL) was cooled to 0° C. DAST (31 μL, 0.23 mmol) was added. The mixture was stirred at 0° C. for 1 h. Sat. aq. NaHCO$_3$ was added. The mixture was stirred for 5 min, and extracted 3 times with CH$_2$Cl$_2$. The organic extract was dried with Na$_2$SO$_4$; filtered; and concentrated. The residue was purified by column chromatography (silica gel, eluting with 0% to 60% acetone in hexanes) to give partially purified product, which was purified again by chromatography (C18, eluting with 10% to 80% acetonitrile in water). The fractions containing the product were combined, and concentrated. The residue was extracted with CH$_2$Cl$_2$. The organic extract was dried with Na$_2$SO$_4$; filtered; and concentrated. The residue was purified again by chromatography (silica gel, eluting with 0% to 50% EtOAc in CH$_2$Cl$_2$) to give the impure product (23 mg, 23% yield) as a white foam. m/z=476.2 (M+1). The compound (23 mg, 0.048 mmol) in MeOH (0.5 mL) was treated with 6 N aq. HCl (0.1 mL, 0.6 mmol) at room temperature. The reaction mixture was stirred at room temperature for 5-6 h; diluted with EtOAc; and washed with water. The organic extract was dried with Na$_2$SO$_4$; filtered; and concentrated. The residue was purified by column chromatography (silica gel, eluting with 0% to 10% MeOH in CH$_2$Cl$_2$) to give 3/1 mixture of two compounds (14 mg, 67% yield) as a white foam. The major compound was T9. m/z=436.1 (M+1); $^1$H NMR (400 MHz, CDCl$_3$, 3:1 mixture of isomers) δ 7.37 (dt, J=5.9, 7.9 Hz, 1H), 7.19 (m, 1H), 7.03 (m, 4H), [6.88 (d, J=2.7 Hz), 6.87 (d, J=2.7 Hz); 1:3; 1H], [5.64 (s), 5.59 (s); 1:3; 1H], 5.29 (br s, 1H), 4.44 (m, 2H), 3.96 (dd, J=6.9, 16.8 Hz, 1H), 3.27 (q, J=6.8 Hz, 2H), [2.87 (d, J=3.3 Hz), 2.78 (d, J=3.4 Hz); 3:1; 1H], 2.74 (t, J=7.2 Hz, 2H), [2.51 (d, J=6.4 Hz), 2.43 (d, J=6.4 Hz); 3:1; 1H], 1.87 (s, 3H), 1.40 (d, J=15.2 Hz, 3H), 1.33 (d, J=15.3 Hz, 3H).

Compound 40: To a mixture of methylamine hydrochloride (10 g, 0.148 mol) in CH$_2$Cl$_2$ (100 mL) at 0° C. was added Et$_3$N (62 mL, 0.446 mmol). The mixture was stirred for 10 min, and then treated with acryloyl chloride 39 (12 mL, 0.148 mmol) dropwise. After the addition was complete, the mixture was continued stirring at 0° C. for 30 min; diluted with hexanes (100 mL); stirred for 5 min; and filtered through a pad of Celite®. The Celite® pad was eluted with CH$_2$Cl$_2$/hexanes (1/1 v/v, 100 mL). The filtrate was concentrated. The residue was purified by column chromatography (silica gel, eluting with 0% to 100% EtOAc in hexanes) to give compound 40 (1.10 g, 12% yield) as a colorless oil.

Compound 41: Compound 3 (1.749 g, 4.90 mmol), Pd(OAc)$_2$ (17 mg, 0.076 mmol) and tri(o-tolyl)phosphine (45 mg, 0.15 mmol) in DMF (8 mL) was purged with N$_2$ at room temperature for 5 min Compound 40 (500 mg, 5.88 mmol) and DIPEA (1.02 mL, 5.87 mmol) were added, and the mixture was purged with N$_2$ at room temperature for another 2 min. The flask was sealed and heated at 135° C. for 16 h. After cooled to room temperature, the mixture was poured into water. EtOAc (100 mL) and water (50 mL) were added. The mixture was stirred until a two-phase solution was obtained. The organic extract was separated; washed with water; dried with Na$_2$SO$_4$; filtered; and concentrated. The residue was purified by column chromatography (silica gel, eluting with 0% to 100% EtOAc in CH$_2$Cl$_2$) to give compound 41 (1.48 g, 84% yield). Compound 41: m/z=362.1 (M+1).

A2: A mixture of compound 41 (2.92 g, 8.08 mmol) and 10% Pd/C (730 mg) in THF (75 mL) was hydrogenated under H$_2$ balloon at room temperature for 4 h. The catalyst was removed by filtered through a pad of Celite®. The filter cake was washed with EtOAc. The filtrate was concentrated. The residue was purified by column chromatography (silica gel, eluting with 0% to 50% EtOAc in CH$_2$Cl$_2$) to give compound A2 (2.06 g, 93% yield) as a white foam. m/z=274.1 (M+1); $^1$H NMR (400 MHz, CDCl$_3$) δ 7.35 (td, J=7.9, 6.0 Hz, 1H), 7.11 (d, J=8.3 Hz, 1H), 7.07-7.01 (m, 2H), 6.98 (ddd, J=9.7, 2.6, 1.6 Hz, 1H), 6.74 (dd, J=8.3, 2.7 Hz, 1H), 6.68 (d, J=2.7 Hz, 1H), 5.93 (bs, 1H), 5.21 (bs, 1H), 2.85 (dd, J=8.6, 6.9 Hz, 2H), 2.71 (d, J=4.8 Hz, 3H), 2.21 (dd, J=8.6, 6.9 Hz, 2H).

Compound 42: A mixture of compound 23 (2.12 g, 3.65 mmol) and compound A2 (1.00 g, 3.66 mmol) in CH$_2$Cl$_2$ (18 mL) was cooled to 0° C. under N$_2$. Boron trifluoride diethyl etherate (1.88 mL, 15.23 mmol) was added. The mixture was stirred at 0° C. for 1 h, and then at room temperature for 20 h; poured into sat. aq. NaHCO$_3$; stirred for 10 min; and extracted twice with CH$_2$Cl$_2$. The combined organic extract was washed 3 times with 1 N aq. NaOH; dried with Na$_2$SO$_4$; filtered; and concentrated to give impure compound 42 (2.50 g) as a yellow foam. m/z=732.2 (M+1).

T10: To a solution of compound 42 (2.50 g, <3.65 mmol) in THF (18 mL) and MeOH (18 mL) was added 1 N aq. NaOH (21.6 mL, 21.6 mmol). The mixture was stirred at room temperature for 6 h; and concentrated. The residue was diluted with water (30 mL) and extracted with EtOAc (3×30 mL). The combined organic extracts were dried with Na$_2$SO$_4$; filtered; and concentrated. The residue was dissolved in MeOH; absorbed on silica gel; and purified by column chromatography (silica gel, eluting with 0% to 15% MeOH in CH$_2$Cl$_2$) to give T10 (925 mg, 60% yield from compound 23) as a white foam. m/z=420.2 (M+1); $^1$H NMR (400 MHz, CDCl$_3$) δ 7.37 (dt. 6.0, 8.0 Hz, 1H), 7.20 (d, J=8.5 Hz, 1H), 7.02 (m, 4H), 6.88 (d, J=2.7 Hz, 1H), 5.50 (d, J=1.7 Hz, 1H), 5.22 (br q, J=5.6 Hz, 1H), 4.13 (ddd, J=1.7, 3.5, 4.8 Hz, 1H), 3.97 (ddd, J=3.5, 6.3, 9.6 Hz, 1H), 3.78 (qd, J=6.2, 9.4 Hz, 1H), 3.51 (dt, J=3.8, 9.4 Hz, 1H), 2.88 (m, 2H), 2.81 (d, J=6.4 Hz, 1H), 2.72 (d, J=4.8 Hz, 3H), 2.66 (d, J=4.4 Hz, 1H), 2.44 (d, J=4.8 Hz, 1H), 2.22 (m, 2H), 1.28 (d, J=6.2 Hz, 3H).

Compound 43: A mixture of compound 29 (2.00 g, 4.08 mmol) and compound A2 (1.228 g, 4.50 mmol) in CH$_2$Cl$_2$ (25 mL) was cooled to 0° C. under N$_2$. Boron trifluoride diethyl etherate (1.89 mL, 15.31 mmol) was added. The mixture was stirred at 0-5° C. for 24 h; poured into sat. aq. NaHCO$_3$; and extracted with CH$_2$Cl$_2$. The organic extract was washed with 1 N aq. NaOH, and water; dried with Na$_2$SO$_4$; filtered; and concentrated. The residue was purified by column chromatography (silica gel, eluting with 0% to 40% EtOAc in CH$_2$Cl$_2$) to give compound 43 (1.628 g, 62% yield) as a white foam. m/z=642.2 (M+1).

T11: To a solution of compound 43 (1.818 g, 2.83 mmol) in THF (7 mL) and MeOH (14 mL) was added 1 N aq. NaOH (14 mL, 14 mmol). The mixture was stirred at room temperature for 2 h; and concentrated. The residue was diluted with water (30 mL), and extracted with CH$_2$Cl$_2$ (3×30 mL). The combined organic extracts were dried with Na$_2$SO$_4$; filtered; and concentrated. The residue was purified by column chromatography (silica gel, eluting with 0% to 50% acetone in CH$_2$Cl$_2$) to give T11 (1.173 g, 95% yield) as a white foam. m/z=434.2 (M+1); $^1$H NMR (400 MHz, CDCl$_3$) δ 7.37 (m, 1H), 7.21 (d, J=8.5 Hz, 1H), 7.03 (m, 4H), 6.88 (d, J=2.7 Hz, 1H), 5.48 (d, J=1.7 Hz, 1H), 5.14 (br s, 1H), 4.13 (dt, J=1.8, 3.5 Hz, 1H), 4.04 (m, 1H), 3.76 (qd, J=6.2, 9.5 Hz, 1H), 3.58 (s, 3H), 3.15 (t, J=9.4 Hz, 1H), 2.89 (m, 2H), 2.72 (d, J=4.8 Hz, 3H), 2.52 (d, J=4.9 Hz, 1H), 2.46 (d, J=3.6 Hz, 1H), 2.21 (m, 2H), 1.29 (d, J=6.3 Hz, 3H).

Compound 44: To a solution of compound 3 (1.79 g, 5.01 mmol) in THF (25 mL) at −78° C. under N$_2$ was added n-BuLi (2.5 M solution in hexanes, 2.2 mL, 5.5 mmol). The mixture was stirred for 1.5 h at −78° C. Dimethyl oxalate (887 mg, 7.51 mmol) in THF (10 mL) was added at −78° C. through cannulation. The mixture was stirred at −78° C. for 2 h; quenched with sat. aq. NH$_4$Cl; and extracted with EtOAc. The organic extract was washed with water; dried with Na$_2$SO$_4$; filtered; and concentrated. The residue was purified by column chromatography (silica gel, eluting with 0% to 20% EtOAc in hexanes) to give compound 44 (315 mg, 17% yield) as a yellow viscous oil.

Compound 45: To a solution of compound 44 (980 mg, 2.69 mmol) in 1,2-dichloroethane (20 mL) was added DAST (1.79 mL, 13.55 mmol) at room temperature. The mixture was heated at 60° C. for overnight; cooled to room temperature; and added to sat. aq. NaHCO$_3$. The mixture was stirred for 10 min, and extracted with CH$_2$Cl$_2$. The organic extract was washed with sat. aq. NaHCO$_3$; dried with Na$_2$SO$_4$; filtered; and concentrated. The residue was purified by column chromatography (silica gel, eluting with 0% to 50% CH$_2$Cl$_2$ in hexanes) to give compound 45 (605 mg, 58% yield) as an orange oil.

Compound 46: To a solution of compound 45 (137 mg, 0.35 mmol) in EtOH (3.6 mL) at 0° C. under N$_2$ was added NaBH$_4$ (27 mg, 0.71 mmol). The mixture was stirred at room temperature for 1 h; quenched with sat. aq. NH$_4$Cl; and extracted with EtOAc. The organic extract was washed with water; dried with Na$_2$SO$_4$; filtered; and concentrated. The residue was purified by column chromatography (silica gel, eluting with 0% to 40% EtOAc in hexanes) to give compound 46 (123 mg, 97% yield) as a viscous oil, and solidified upon standing. m/z=359.1 (M+1).

Compound 47: To a solution of compound 46 (168 mg, 0.47 mmol) in MeCN (2.4 mL) at 0° C. under N$_2$ was added pyridine (64 µL, 0.79 mmol) and trifluoromethanesulfonic anhydride (99 µL, 0.59 mmol) sequentially. The mixture was stirred at 0° C. for 1 h. Ammonium hydroxide (28-30 weight % aq. NH$_3$, 1.50 mL, 23.03 mmol) was added. The mixture was stirred at room temperature for overnight and concentrated to give crude compound 47. m/z=358.1 (M+1).

Compound 48: To a solution of compound 47 (all from the last step, <0.47 mmol) in CH$_2$Cl$_2$ (4 mL) at 0° C. under N$_2$ was added pyridine (0.4 mL, 4.95 mmol) and acetic anhydride (48 µL, 0.51 mmol) sequentially, and the mixture was stirred for 30 min Sat. aq. NaHCO$_3$ was added. The mixture was extracted with EtOAc. The organic extract was washed with 1 N aq. HCl; dried with Na$_2$SO$_4$; filtered; and concentrated. The residue was purified by column chromatography (silica gel, eluting with 0% to 100% EtOAc in hexanes) to give compound 48 (147 mg, 79% yield from 46) as a yellow oil. m/z=380.1 (M-F).

A3: A mixture of compound 48 (78 mg, 0.20 mmol) and 10% Pd/C (25 mg) in THF (6 mL) was hydrogenated under H$_2$ balloon at room temperature for 1 h. The catalyst was removed by filtration and washed with EtOAc. The filtrate was concentrated to give compound A3 (63 mg, quantitative yield) as a white foam. m/z=310 (M+1); $^1$H NMR (400 MHz, CDCl$_3$) δ 7.46 (d, J=8.7 Hz, 1H), 7.32 (m, 1H), 7.14-7.02 (m, 3H), 6.84 (dd, J=8.6, 2.7 Hz, 1H), 6.68 (d, J=2.7 Hz, 1H), 6.24 (bs, 1H), 5.61 (m, 1H), 3.66 (td, J=14.5, 6.2 Hz, 2H), 1.94 (s, 3H).

Compound 49: A mixture of compound 18 and 19 (103 mg, 0.20 mmol) and compound A3 (63 mg, 0.20 mmol) in CH$_2$Cl$_2$ (1 mL) was cooled to 0° C. under N$_2$. Boron trifluoride diethyl etherate (76 µL, 0.62 mmol) was added. The mixture was stirred at 0° C. for 5 h; poured into sat. aq. NaHCO$_3$; and extracted 3 times with CH$_2$Cl$_2$. The organic extract was dried with Na$_2$SO$_4$; filtered; and concentrated to give crude compound 49. m/z=692.2 (M+1).

T12: To a solution of compound 49 (all from the last step, ≤0.20 mmol) in THF (1 mL) and MeOH (1 mL) was added 1 N aq. NaOH (1 mL, 1 mmol) at room temperature. The mixture was stirred at room temperature for 1 h; and concentrated. The residue was diluted with water, and extracted 3 times with CH$_2$Cl$_2$. The combined organic extracts were dried with Na$_2$SO$_4$; filtered; and concentrated. The residue was purified by column chromatography (silica gel, eluting with 0% to 10% MeOH in CH$_2$Cl$_2$) to give T12 (40 mg, 42% yield from 18 and 19) as a white foam. m/z=484 (M+1); $^1$H NMR (400 MHz, CDCl$_3$) δ 7.55 (d, J=8.8 Hz, 1H), 7.34 (m, 1H), 7.10 (m, 4H), 6.86 (d, J=2.6 Hz, 1H), 5.58 (d, J=1.9 Hz, 1H), 5.53 (br t, J=6.2 Hz, 1H), 4.18 (m, 2H), 3.64 (m, 2H), 3.59 (s, 3H), 3.34 (d, J=8.6 Hz, 1H), 2.54 (m, 2H), 1.93 (s, 3H), 1.36 (s, 3H), 1.17 (s, 3H).

Compound 50: A mixture of compound 29 (1.74 g, 3.55 mmol) and compound A3 (1.00 g, 3.24 mmol) in CH$_2$Cl$_2$ (16 mL) was cooled to 0° C. under N$_2$. Boron trifluoride diethyl etherate (1.20 mL, 9.73 mmol) was added. The mixture was stirred at 0° C. for 16 h; poured into sat. aq. NaHCO$_3$; and extracted 2 times with CH$_2$Cl$_2$. The organic extract was washed 2 times with 1 N aq. NaOH and water; dried with Na$_2$SO$_4$; filtered; and concentrated. The residue was purified by column chromatography (silica gel, eluting with 0% to 100% EtOAc in hexanes) to give compound 50 (924 mg, 42% yield). m/z=678.2 (M+1).

T13: To a solution of compound 50 (950 mg, 1.40 mmol) in THF (7 mL) and MeOH (7 mL) was added 1 N aq. NaOH (8.4 mL, 8.4 mmol) at room temperature. The mixture was stirred at room temperature for 1 h; and concentrated. The residue was diluted with water (10 mL) and extracted 3 times with CH$_2$Cl$_2$. The combined organic extracts were dried with Na$_2$SO$_4$; filtered; and concentrated. The residue was purified by column chromatography (silica gel, eluting with 0% to 10% MeOH in CH$_2$Cl$_2$) to give T13 (570 mg, 87% yield) as a white foam. m/z=470.1 (M+1); $^1$H NMR (400 MHz, CDCl$_3$) δ 7.55 (d, J=8.8 Hz, 1H), 7.34 (m, 1H), 7.09 (m, 4H), 6.89 (d, J=2.6 Hz, 1H), 5.56 (t, J=6.5 Hz, 1H), 5.53 (d, J=1.7 Hz, 1H), 4.14 (dt, J=1.7, 3.4 Hz, 1H), 4.02 (ddd, J=3.5, 4.8, 9.3 Hz, 1H), 3.67 (m, 3H), 3.58 (s, 3H), 3.16 (t, J=9.4 Hz, 1H), 2.61 (dd, J=3.3, 4.1 Hz, 2H), 1.93 (s, 3H), 1.29 (d, J=6.2 Hz, 3H).

A4: To a solution of compound 45 (270 mg, 0.70 mmol) in CH$_2$Cl$_2$ (7 mL) at 0° C. under N$_2$ was added boron tribromide (101 µL, 1.05 mmol). The mixture was stirred at 0° C. for 30 min; quenched with sat. aq. NaHCO$_3$; stirred for 5 min; and extracted twice with CH$_2$Cl$_2$. The combined organic extracts were dried with Na$_2$SO$_4$; filtered; and concentrated. The residue was purified by column chromatography (silica gel, eluting with 0% to 35% EtOAc in hexanes) to give compound A4 (187 mg, 90% yield) as a brown oil. $^1$H NMR (400 MHz, CDCl$_3$) δ 7.68 (d, J=8.7 Hz, 1H), 7.34 (ddd, J=8.3, 7.7, 5.9 Hz, 1H), 7.13-7.02 (m, 2H), 7.01-6.88 (m, 2H), 6.72 (d, J=2.7 Hz, 1H), 5.09 (m, 1H), 3.52 (s, 3H).

Compound 51: A mixture of compound 23 (401 mg, 0.69 mmol) and compound A4 (186 mg, 0.63 mmol) in CH$_2$Cl$_2$ (3 mL) was cooled to 0° C. under N$_2$. Boron trifluoride diethyl etherate (0.31 mL, 2.51 mmol) was added. The mixture was stirred at 0° C. for overnight and at room temperature for 3 h; quenched with sat. aq. NaHCO$_3$; stirred for 5 min; and extracted 2 times with CH$_2$Cl$_2$. The organic extract was washed with 1 N aq. NaOH and water; dried with Na$_2$SO$_4$; filtered; and concentrated. The residue was purified by column chromatography (silica gel, eluting with 0% to 30% MTBE in hexanes) to give compound 51 (353 mg, 75% yield). m/z=459.1 (M-OAr).

Compound 52: To a solution of compound 51 (353 mg, 0.47 mmol) in EtOH (4.6 mL) at 0° C. under N$_2$ was added NaBH$_4$ (36 mg, 0.95 mmol). The cold bath was removed. The mixture was gradually warmed to room temperature over 1 h; diluted with EtOAc; and washed with water. The organic phase was dried with Na$_2$SO$_4$; filtered; and concentrated. The residue was purified by column chromatography (silica gel, eluting with 0% to 100% EtOAc in hexanes) to give compound 52 (250 mg, 74% yield) as a white foam. m/z=459.1 (M-OAr).

Compound 53: To a solution of compound 52 (50 mg, 0.069 mmol) in MeCN (0.35 mL) at 0° C. under $N_2$ was added pyridine (9 μL, 0.11 mmol) and trifluoromethane-sulfonic anhydride (14 μL, 0.083 mmol) sequentially. The mixture was stirred at 0° C. for 1 h. Ammonium hydroxide (28-30 weight % aq. $NH_3$, 0.24 mL, 0.37 mmol) was added. The mixture was stirred at room temperature for 24 h and concentrated to give crude compound 53.

Compound 54: To a solution of compound 53 (all from the last step, <0.069 mmol) in EtOAc (0.35 mL) at 0° C. under $N_2$ was added pyridine (50 μL, 0.62 mmol) and acetic anhydride (7 μL, 0.074 mmol) sequentially, and the mixture was stirred for 30 min Sat. aq. $NaHCO_3$ was added. The mixture was extracted with EtOAc. The organic extract was washed with 1 N aq. HCl; dried with $Na_2SO_4$; filtered; and concentrated. The residue was purified by column chromatography (silica gel, eluting with 0% to 100% EtOAc in hexanes) to give compound 54 (21 mg, 40% yield from 52) as a white foam. m/z=768.2 (M+1).

T14: To a solution of compound 54 (20 mg, 0.026 mmol) in THF (0.26 mL) and MeOH (0.26 mL) was added 1 N aq. NaOH (0.16 mL, 0.16 mmol) at room temperature. The mixture was stirred at room temperature for 1 h; and concentrated. The residue was diluted with water and extracted 3 times with EtOAc. The combined organic extracts were dried with $Na_2SO_4$; filtered; and concentrated. The residue was purified by column chromatography (silica gel, eluting with 0% to 15% MeOH in $CH_2Cl_2$) to give T14 (9 mg, 76% yield) as a glass. m/z=456.2 (M+1); $^1$H NMR (400 MHz, $CD_3OD$) δ 7.55 (d, J=8.9 Hz, 1H), 7.40 (m, 1H), 7.14 (m, 4H), 6.89 (d, J=2.6 Hz, 1H), 5.49 (m, 2H), 3.99 (dd, J=1.9, 3.9 Hz, 1H), 3.82 (dd, J=3.5, 9.5 Hz, 1H), 3.60 (m, 3H), 3.45 (t, J=9.5 Hz, 1H), 1.85 (s, 3H), 1.22 (d, J=6.2 Hz, 3H).

Compound 56: To a solution of L-fucose 55 (1.0 g, 6.09 mmol) in pyridine (12 mL) was added acetic anhydride (5.8 mL, 61.41 mmol) and 4-(dimethylamino)pyridine (100 mg, 0.82 mmol) at 0° C. under $N_2$. The mixture was stirred at ambient temperature for overnight; poured into sat. aq. $NaHCO_3$; stirred for 20 min; and extracted twice with toluene. The combined organic extracts were dried with $Na_2SO_4$; filtered; and concentrated to give compound 56 (2.14 g, quantitative yield) as a yellow viscous oil. m/z=273.1 (M-OAc).

Compound 57: A mixture of compound 56 (1.300 g, 3.91 mmol) and compound A1 (1.287 g, 4.71 mmol) in $CH_2Cl_2$ (18 mL) was cooled to 0° C. under $N_2$. Boron trifluoride diethyl etherate (2.90 mL, 23.50 mmol) was added. The mixture was stirred at 0° C. for 10 min, and then at room temperature for 60 h. Sat. aq. $NaHCO_3$ was added. The mixture was extracted 2 times with $CH_2Cl_2$. The combined organic extracts were washed 2 times with 1 N aq. NaOH and water; dried with $Na_2SO_4$; filtered; and concentrated. The residue was purified by column chromatography (silica gel, eluting with 0% to 100% acetone in hexanes) to give compound 57 as 23/1 α-anomer/β-anomer (1.50 g, 70% yield) as a white foam. m/z=546.2 (M+1).

T15: To a solution of compound 57 (1.50 g, 2.75 mmol) in MeOH (28 mL) was added 10% aq. NaOH (6.6 mL, 16.5 mmol) at room temperature. The mixture was stirred at room temperature for 2 h; and concentrated. The residue was extracted repeatedly with EtOAc. The combined organic extracts were dried with $Na_2SO_4$; filtered; and concentrated to give a mixture of anomers. The residue was absorbed on Celite®, and purified by column chromatography (C18, eluting with 0% to 40% acetonitrile in water) to give the major anomer T15 (480 mg, 42% yield) as a white foam. m/z=420.1 (M+1); $^1$H NMR (400 MHz, $CDCl_3$) δ 7.36 (dt, J=6.0, 8.0 Hz, 1H), 7.20 (d, J=8.5 Hz, 1H), 7.05 (m, 3H), 6.97 (m, 1H), 6.93 (d, J=2.7 Hz, 1H), 5.54 (d, J=3.1 Hz, 1H), 5.44 (br t, J=5.9 Hz, 1H), 4.08 (q, J=6.6 Hz, 1H), 3.98 (m, 2H), 3.85 (m, 1H), 3.33 (d, J=3.6 Hz, 1H), 3.26 (m, 2H), 2.81 (d, J=3.3 Hz, 1H), 2.72 (m, 3H), 1.86 (s, 3H), 1.25 (d, J=6.6 Hz, 3H).

Compound 59: To a solution of L-ribose 58 (785 mg, 5.23 mmol) in pyridine (7.9 mL) was added benzoyl chloride (3.6 mL, 31.01 mmol) at 0° C. under $N_2$. The mixture was stirred at ambient temperature for overnight; diluted with EtOAc; and washed with water. The organic extract was treated with 1,2-ethanediamine (2.1 mL, 31.5 mmol). After 15 min, the mixture was washed with water, 1 N aq. HCl, and water. The organic extract was dried with $Na_2SO_4$; filtered; and concentrated. The residue was purified by column chromatography (silica gel, eluting with 0% to 50% EtOAc in hexanes) to give compound 59 (2.78 g, 94% yield) as a white foam. m/z=445.1 (M-OBz).

Compound 60: A mixture of compound 59 (1.42 g, 2.51 mmol) and compound A1 (882 mg, 3.23 mmol) in $CH_2Cl_2$ (14 mL) was cooled to 0° C. under $N_2$. Boron trifluoride diethyl etherate (1.98 mL, 16.04 mmol) was added. The mixture was stirred at 0° C. for 1 h, and then at room temperature for 40 h. The mixture was cooled to 0° C.; treated with sat. aq. $NaHCO_3$; stirred for 10 min; and extracted with $CH_2Cl_2$. The organic extract was washed with 1 N aq. NaOH and water; dried with $Na_2SO_4$; filtered; and concentrated. The residue was purified by column chromatography (silica gel, eluting with 0% to 90% EtOAc in hexanes) to give compound 60 (mixture of anomers in 88/7 ratio, 1.516 g, 84% yield) as a white foam. Compound 60 was further purified by column chromatography (silica gel, eluting with 0% to 15% acetone in $CH_2Cl_2$), followed by (C18, eluting with 0% to 90% MeCN in water) to give compound 60 (mixture of anomers in 94/5 ratio, 1.017 g, 57% yield) as a white foam. m/z=718.2 (M+1).

T16: To a solution of compound 60 (1.42 g, 1.98 mmol) in MeOH (10 mL) and THF (10 mL) was added 1 N aq. NaOH (12 mL, 12 mmol) at room temperature. The mixture was stirred at room temperature for 6 h; and concentrated. The residue was extracted repeatedly with EtOAc. The combined organic extracts were dried with $Na_2SO_4$; filtered; and concentrated. The residue was purified by column chromatography (silica gel, eluting with 0% to 15% MeOH in $CH_2Cl_2$) to give compound T16 (single anomer, 570 mg, 71% yield) as a white foam. m/z=406.1 (M+1); $^1$H NMR (400 MHz, $CD_3OD$) δ 7.95 (br t, J=5.4 Hz, 1H), 7.44 (dt, J=6.0, 7.9 Hz, 1H), 7.26 (d, J=8.5 Hz, 1H), 7.08 (m, 4H), 6.89 (d, J=2.6 Hz, 1H), 5.43 (d, J=4.0 Hz, 1H), 4.01 (t, J=3.1 Hz, 1H), 3.84 (m, 2H), 3.76 (m, 2H), 3.18 (m, 2H), 2.71 (dd, J=6.6, 8.2 Hz, 2H), 1.83 (s, 3H).

Compound 62: To a solution of L-lyxose 61 (1.00 g, 6.66 mmol) in pyridine (10 mL) was added benzoyl chloride (4.6 mL, 39.62 mmol) at 0° C. under $N_2$. The mixture was stirred at ambient temperature for overnight; diluted with EtOAc; and washed with water. The organic extract was treated with 1,2-ethanediamine (2.7 mL, 40.5 mmol). After 15 min, the mixture was washed with water, 1 N aq. HCl, and water. The organic extract was dried with $Na_2SO_4$; filtered; and concentrated. The residue was purified by column chromatography (silica gel, eluting with 0% to 35% EtOAc in hexanes) to give compound 62 (3.60 g, 95% yield) as a white foam. m/z=445.1 (M-OBz).

Compound 63: A mixture of compound 62 (1.58 g, 2.79 mmol) and compound A1 (762 mg, 2.78 mmol) in $CH_2Cl_2$ (14 mL) was cooled to 0° C. under $N_2$. Boron trifluoride diethyl etherate (1.4 mL, 11.34 mmol) was added. The mixture was stirred at 0° C. for 3 h, and then at room temperature for 14 h. The mixture was treated with sat. aq. NaHCO$_3$; stirred for 10 min; and extracted twice with CH$_2$Cl$_2$. The combined organic extracts were washed with 1 N aq. NaOH and water; dried with Na$_2$SO$_4$; filtered; and concentrated. The residue was purified by column chromatography (silica gel, eluting with 0% to 100% EtOAc in hexanes) to give partially purified compound 63 (major anomer 81% pure, 1.60 g, 80% yield) as a white foam. Compound 63 was purified again by column chromatography (C18, eluting with 10% to 95% MeCN in water) to give compound 63 (major anomer 92% pure, 998 mg, 50% yield) as a white foam. m/z=718.2 (M+1).

T17: To a solution of compound 63 (1.50 g, 2.09 mmol) in MeOH (10 mL) and THF (10 mL) was added 1 N aq. NaOH (12 mL, 12 mmol) at room temperature. The mixture was stirred at room temperature for 2 h; and concentrated. The residue was extracted for 4 times with EtOAc. The combined organic extracts were dried with Na$_2$SO$_4$; filtered; and concentrated. The residue was purified by column chromatography (C18, eluting with 0% to 40% MeCN in water) to give partially purified product, which was purified again by column chromatography (C18, eluting with 0% to 40% MeCN in water) to give compound T17 (523 mg, 62% yield) as a white foam. m/z=406.1 (M+1); $^1$H NMR (400 MHz, CD$_3$OD) δ 7.44 (m, 1H), 7.26 (d, J=8.5 Hz, 1H), 7.09 (m, 4H), 6.89 (d, J=2.7 Hz, 1H), 5.39 (d, J=3.1 Hz, 1H), 3.97 (m, 1H), 3.86 (m, 2H), 3.73 (m, 1H), 3.52 (m, 1H), 3.18 (dd, J=6.6, 8.2 Hz, 2H), 2.71 (dd, J=6.6, 8.2 Hz, 2H), 1.82 (s, 3H).

Compound 65: A mixture of compound 64 (960 mg, 3.96 mmol), N-phenyl-bis(trifluoromethanesulfonimide) (2.13 g, 5.96 mmol) and K$_2$CO$_3$ (3.28 g, 23.77 mmol) in THF (15 mL) was heated in a Biotage microwave at 120° C. for 20 min After cooled to room temperature, the mixture was diluted with EtOAc; and washed twice with water and brine. The organic extract was dried with Na$_2$SO$_4$; filtered; and concentrated. The residue was purified by column chromatography (silica gel, eluting with 0% to 25% EtOAc in hexanes) to give compound 65 (924 mg, 62% yield) as a yellow oil. m/z=375.0 (M+1).

Compound 66: A mixture of compound 65 (924 mg, 2.47 mmol), K$_2$CO$_3$ (990 mg, 7.17 mmol), and 3-fluorophenylboronic acid (610 mg, 4.36 mmol) in DMF (40 mL) was sparged with N$_2$ for 5 min [1,1'-bis(diphenylphosphino)ferrocene]dichloropalladium(II) (290 mg, 0.40 mmol) was added. The mixture was sparged with N$_2$ for another 5 min; and then heated at 75° C. for 14 h. The mixture was cooled to room temperature; diluted with water; and extracted with EtOAc. The organic extract was dried with Na$_2$SO$_4$; filtered; and concentrated. The residue was purified by column chromatography (silica gel, eluting with 0% to 12% EtOAc in hexanes) to give compound 66 (768 mg, 97% yield) as a viscous oil. m/z=321.1 (M+1).

Compound 67: To a solution of potassium tert-butoxide (280 mg, 2.50 mmol) in t-butanol (12 mL) at room temperature under N$_2$ was added a solution of compound 66 (668 mg, 2.09 mmol) in THF (6 mL). The mixture was stirred at room temperature for 30 min. Isopentyl nitrite (419 μL, 3.12 mmol) was added. The mixture was stirred at room temperature for 3 h; diluted with EtOAc; and washed with 1 N aq. HCl and water. The organic extract was dried with Na$_2$SO$_4$; filtered; and concentrated. The residue was purified by column chromatography (silica gel, eluting with 0% to 30% acetone in hexanes) to give partially purified compound 67 (460 mg, 75% purity, 47% yield) as a viscous yellow oil. m/z=350.1 (M+1).

Compound 68: To a solution of compound 67 (309 mg, 75% pure, 0.66 mmol) in THF (5 mL) was added indium (410 mg, 3.57 mmol), AcOH (200 μL, 3.49 mmol) and Ac$_2$O (200 μL, 2.12 mmol). The mixture was heated at 70° C. for 2 h; cooled to room temperature; and filtered through a pad of cilite. The filter cake was washed with EtOAc. The filtrate was concentered. The residue was mixed with toluene and concentrated again. The residue was purified by column chromatography (silica gel, eluting with 0% to 30% acetone in hexanes) to give compound 68 (210 mg, 84% yield) as an off-white solid. m/z=378.1 (M+1).

Compound A5: A mixture of compound 68 (50 mg, 0.13 mmol) and 10% Pd/C (10 mg) in EtOAc (2 mL) was hydrogenated under H$_2$ balloon at room temperature for 80 min. The catalyst was removed by filtered through a pad of silica gel. The filterer cake was washed with EtOAc. The filtrate was concentrated. The residue was purified by column chromatography (silica gel, eluting with 0% to 30% acetone in CH$_2$Cl$_2$) to give compound A5 (34 mg, 89% yield) as a white foam. m/z=288.1 (M+1); $^1$H NMR (400 MHz, CDCl$_3$) δ 7.61 (d, J=8.5 Hz, 1H), 7.35 (td, J=7.9, 5.9 Hz, 1H), 7.12 (bs, 1H), 7.08 (m, 1H), 7.00 (m, 1H), 6.94 (m, 1H), 6.91 (dd, J=8.5, 2.5 Hz, 1H), 6.80 (d, J=2.5 Hz, 1H), 6.39 (m, 1H), 4.27 (d, J=4.6 Hz, 2H), 2.02 (s, 3H).

Compound 69: To a mixture of compound 18 and 19 (84 mg, 0.17 mmol), compound A5 (32 mg, 0.11 mmol) and small amount of 4 Å molecular sieves in CH$_2$Cl$_2$ (1.1 mL) at room temperature under N$_2$ was added boron trifluoride diethyl etherate (41 μL, 0.33 mmol). The mixture was stirred at room temperature for 2 h; quenched with sat. aq. NaHCO$_3$; and extracted with EtOAc. The organic extract was dried with Na$_2$SO$_4$; filtered and concentrated. The crude product was purified by column chromatography (silica gel, eluting with 0% to 70% EtOAc in hexanes) to give compound 69 (34 mg, 46% yield) as a white foam. m/z=670 (M+1).

Compound 70: To a solution of compound 69 (32 mg, 0.046 mmol) in EtOH (1 mL) at 0° C. under N$_2$ was added NaBH$_4$ (2 mg, 0.053 mmol). The mixture was stirred at 0° C., and additional amount of NaBH$_4$ (2 mg, 0.053 mmol) was added at 1 h and 1.5 h. The mixture was stirred at 0° C. for another 30 min. EtOAc and 1 N aq. HCl were added. The organic phase was separated. The aqueous phase was extracted with EtOAc. The combined organic extracts were dried with Na$_2$SO$_4$; filtered and concentrated. The residue was purified by column chromatography (silica gel, eluting with 0% to 100% EtOAc in hexanes) to give compound 70 (30 mg, 94% yield) as a white foam. Compound 70 was a 92/4 mixture of amoners. m/z=672.3 (M+1).

T18: To a mixture of compound 70 (27 mg, 0.040 mmol) in EtOH (0.8 mL) was added aq. 1 N NaOH (0.2 mL, 0.2 mmol) at room temperature. The mixture was stirred at room temperature for 1 h; diluted with water; and extracted 3 times with EtOAc. The combined organic extracts were washed with sat. aq. NaHCO$_3$; dried with Na$_2$SO$_4$, and concentrated. The residue was purified by column chromatography (silica gel, eluting with 0% to 20% MeOH in CH$_2$Cl$_2$) to give compound T18 (15 mg, 81% yield) as a white foam. m/z=446.2 (M-OH); $^1$H NMR (400 MHz, CDCl$_3$) δ 7.56 (dd, J=1.9, 8.6 Hz, 1H), 7.38 (dt, J=6.0, 8.0 Hz, 1H), 7.07 (m, 4H), 6.86 (dd, J=2.6, 9.9 Hz, 1H), 5.77 (m, 1H), 5.56 (dd, J=2.2, 4.2 Hz, 1H), 4.83 (m, 1H), 4.18 (m, 2H), 3.59 (s, 3H), 3.36 (m, 4H), 2.56 (t, J=2.0 Hz, 1H), 2.53 (dd, J=1.2, 3.7 Hz, 1H), 1.96 (s, 3H), 1.36 (s, 3H), 1.19 (d, J=2.8 Hz, 3H).

Compound 71: To a mixture of compound 21 (55 mg, 0.092 mmol) and compound A5 (24 mg, 0.083 mmol) in $CH_2Cl_2$ (0.4 mL) at 0° C. under $N_2$ was added boron trifluoride diethyl etherate (42 µL, 0.34 mmol). The mixture was stirred at 0° C. for 6 h; quenched with sat. aq. $NaHCO_3$; and extracted with EtOAc. The organic extract was dried with $Na_2SO_4$; filtered and concentrated. The residue was purified by column chromatography (silica gel, eluting with 0% to 30% acetone in $CH_2Cl_2$) to give compound 71 (15 mg, 24% yield) as a white foam. Compound 71 was a 89/8 mixture of amomers. m/z=760.2 (M+1).

Compound 72: To a solution of compound 71 (34 mg, 0.045 mmol) in MeOH (1 mL) at 0° C. under $N_2$ was added $NaBH_4$ (1.7 mg, 0.045 mmol). The mixture was stirred at 0° C. for 1 h; diluted with EtOAc; and washed sequentially with water, 1 N aq. HCl and water. The organic phase was dried with $Na_2SO_4$; filtered and concentrated. The crude product was purified by column chromatography (silica gel, eluting with 0% to 40% acetone in $CH_2Cl_2$) to give compound 72 (28 mg, 82% yield) as a white foam. m/z=784.2 (M+Na).

T19: To a mixture of compound 72 (28 mg, 0.037 mmol) in MeOH (1.4 mL) was added aq. 1 N NaOH (0.36 mL, 0.36 mmol) at room temperature. The mixture was stirred at room temperature for 3 h; diluted with water; and extracted 3 times with EtOAc. The combined organic extracts were dried with $Na_2SO_4$, filtered and concentrated. The residue was purified by column chromatography (silica gel, eluting with 0% to 20% MeOH in $CH_2Cl_2$) to give compound T19 (11 mg, 67% yield) as a white foam. m/z=432.2 (M-OH); $^1$H NMR (400 MHz, $CD_3CN$) δ 7.52 (d, J=8.7 Hz, 1H), 7.44 (dt, J=6.1, 7.9 Hz, 1H), 7.12 (m, 4H), 6.84 (t, J=2.8 Hz, 1H), 6.47 (br s, 1H), 5.53 (d, J=1.9 Hz, 1H), 4.64 (td, J=4.2, 7.8 Hz, 1H), 3.95 (m, 2H), 3.87 (dd, J=0.9, 4.0 Hz, 1H), 3.59 (dd, J=4.9, 9.2 Hz, 1H), 3.37 (d, J=4.1 Hz, 1H), 3.22 (m, 4H), 1.78 (s, 3H), 1.23 (d, J=2.7 Hz, 3H), 1.14 (s, 3H).

Compound 73: Compound 18 and 19 (695 mg, 1.38 mmol) and compound A1 (250 mg, 0.92 mmol) was dissolved in toluene (7 mL) and cooled to 0° C. Boron trifluoride diethyl etherate (510 µL, 4.13 mmol) was added. The mixture was stirred at 0° C. for 3.5 h; quenched with sat. aq. $NaHCO_3$; stirred for 5 min; and extracted with EtOAc. The organic extracts was dried with $Na_2SO_4$; filtered and concentrated. The residue was purified by column chromatography (silica gel, eluting with 0% to 100% EtOAc in hexanes) to give compound 73 (478 mg, 79% yield) as a white foam. Compound 73 was a mixture of anomers. The α-anomer/β-anomer ratio was 14/1. m/z=656.3 (M+1).

T0 and T20: To a solution of compound 73 (390 mg, 0.59 mmol) in MeOH (6 mL) at room temperature under $N_2$ was added $K_2CO_3$ (411 mg, 2.98 mmol). The mixture was stirred at room temperature for 2 h. EtOAc was added. The mixture was washed with water. The organic extract was dried with $Na_2SO_4$; filtered and concentrated. The residue was purified by column chromatography (silica gel, eluting with 0% to 10% MeOH in $CH_2Cl_2$) to give compound T0 (170 mg, 64% yield) as a white foam. m/z=448.2 (M+1). After the column chromatography, the fractions containing the mixture of T0 and T20 were combined, and concentrated. The mixture was used for the isolation of compound T20 in the next step.

A mixture of compound T0 and T20 (5/1 ratio, 290 mg) was obtained from the combination of the mix fractions from several reactions. The mixture was purified by column chromatography (C18, eluting with 0% to 90% MeCN in water) to give partially purified compound T20, which was purified again by column chromatography (silica gel, eluting with 0% to 10% MeOH in $CH_2Cl_2$) to give compound T20 (20 mg) as a white foam. m/z=448.2 (M+1); $^1$H NMR (400 MHz, DMSO-$d_6$) δ 7.81 (t, J=5.6 Hz, 1H), 7.48 (m, 1H), 7.22 (m, 2H), 7.14 (m, 2H), 6.95 (dd, J=2.7, 8.5 Hz, 1H), 6.78 (d, J=2.7 Hz, 1H), 5.37 (s, 1H), 4.86 (d, J=5.0 Hz, 1H), 4.80 (d, J=7.2 Hz, 1H), 3.81 (ddd, J=1.1, 3.2, 4.7 Hz, 1H), 3.64 (ddd, J=3.1, 7.2, 10.1 Hz, 1H), 3.47 (s, 3H), 3.12 (d, J=9.8 Hz, 1H), 3.07 (m, 2H), 2.59 (dd, J=6.5, 8.8 Hz, 2H), 1.70 (s, 3H), 1.19 (s, 3H), 1.15 (s, 3H).

T21: A mixture of compound T0 (64 mg, 0.14 mmol) and $NH_4Br$ (55 mg, 0.56 mmol) in ethylenediamine (0.5 mL) was heated in a Biotage microwave at 130° C. for 6 h. The mixture was cooled to room temperature; diluted with EtOH (10 mL); and concentrated. The residue was partitioned between EtOAc and water. The aqueous phase was extracted twice with EtOAc. The combined organic extracts were dried with $Na_2SO_4$, filtered and concentrated to give compound T21 (56 mg, 97% yield) as a white foam. m/z=406.2 (M+1); $^1$H NMR (400 MHz, $CDCl_3$) δ 7.36 (dt, J=6.0, 7.9 Hz, 1H), 7.20 (d, J=8.5 Hz, 1H), 7.06 (m, 4H), 6.87 (d, J=2.7 Hz, 1H), 5.54 (d, J=2.3 Hz, 1H), 4.20 (dd, J=3.3, 9.1 Hz, 1H), 4.15 (dd, J=2.0, 3.1 Hz, 1H), 3.59 (s, 3H), 3.33 (d, J=9.0 Hz, 1H), 2.71 (m, 4H), 1.58 (m, 4H), 1.36 (s, 3H), 1.22 (s, 3H).

Compound 75: To a solution of compound 74 (105 mg, 0.26 mmol) and compound A1 (60 mg, 0.22 mmol) in $CH_2Cl_2$ (2 mL) was added 4 Å molecular serves (5 beads) at room temperature. After the mixture was stirred for 10 min, AgOTf (70 mg, 0.27 mmol) was added. The mixture was stirred at room temperature for 2 h; and purified by column chromatography (silica gel, eluting with 0% to 60% EtOAc in hexanes) to give compound 75 (130 mg, quantitative yield) as an off-white foam. m/z=590.2 (M+1).

T22: To a solution of compound 75 (68 mg, 0.12 mmol) in EtOH (1.2 mL) was added aq. 1 N NaOH (1.2 mL, 1.2 mmol) at room temperature. The mixture was stirred at room temperature for 2 h. 1 N aq. HCl (1.5 mL, 1.5 mmol) was added. The mixture was extracted 3 times with EtOAc. The combined organic extracts were dried with $Na_2SO_4$, filtered and concentrated. The residue was purified by column chromatography (C18, eluting with 0% to 50% MeCN in water) to give compound T22 (18.4 mg, 36% yield) as a white foam. Compound T22 was 4/1 mixture of anomers. m/z=450.1 (M+1); $^1$H NMR (400 MHz, $CD_3CN$) δ 7.44 (dt, J=6.2, 8.0 Hz, 1H), 7.26 (d, J=8.5 Hz, 1H), 7.12 (m, 3H), 7.02 (dd, J=2.7, 8.5 Hz, 1H), 6.87 (d, J=2.7 Hz, 1H), 6.40 (br s, 1H), 5.03 (m, 1H), 3.95 (d, J=9.7 Hz, 1H), 3.54 (m, 1H), 3.43 (m, 2H), 3.13 (m, 2H), 2.56 (m, 2H), 1.73 (m, 3H).

Compound 77: A solution of compound 76 (5.00 g, 20.35 mmol) in $CH_2Cl_2$ (40 mL) at 0° C. under $N_2$ was treated with dropwise addition of a solution of boron tribromide (4.8 mL, 50.9 mmol) in $CH_2Cl_2$ (25 mL). The resulting suspension was allowed to warm to room temperature; stirred overnight; cooled to 0° C.; and then poured onto ice (~300 mL). Once all the ice had melted, the mixture was extracted with $CH_2Cl_2$ (400 mL). The organic extract was washed with sat. aq. NaCl (100 mL); dried with $MgSO_4$; filtered and concentrated to give compound 77 (85% pure, contained 15% of monomethyl ether, 3.96 g, ≤85% yield) as a tan solid. Compound 77 was used in the next step without further purification.

Compound 78: A mixture of compound 77 (0.39 g, 1.78 mmol), pyridinium p-toluenesulfonate (90 mg, 0.36 mmol) and 3,4-dihydro-2H-pyran (0.25 mL, 2.73 mmol) in $CH_2Cl_2$ (20 mL) was stirred at room temperature under $N_2$ for 2 h.

The sample was washed with sat. aq. NaHCO₃ (50 mL). The organic extract was dried with MgSO₄; filtered, and concentrated. The residue was purified by column chromatography (silica gel, eluting with 10% EtOAc in hexanes) to give partially purified compound 78 (85% pure, 0.30 g, 56% yield) as light-yellow oil. m/z=217/219 (M-THP+2). Compound 78 was used in the next step without further purification.

Compound 79: A solution of compound 78 (0.30 g, 1.00 mmol) in DMF (2 mL) at 0° C. under N₂ was treated with K₂CO₃ (0.27 g, 1.95 mmol), followed by dropwise addition of benzyl bromide (0.14 mL, 1.18 mmol). After addition, the sample was stirred at room temperature for 2 h; carefully acidified with sat. aq. KH₂PO₄ solution (30 mL); and then extracted with EtOAc (30 mL). The organic extract was washed with sat. aq. NaHCO₃ solution (30 mL); dried with MgSO₄; filtered and concentrated to give an oily solid. The sample was triturated with hexanes. The solid was collected by filtration and dried under vacuum to give compound 79 (0.26 g, 66% yield) as a white solid.

Compound 80: In a sealable vial, a mixture of compound 79 (0.23 g, 0.59 mmol), 3-fluorophenylboronic acid (0.12 g, 0.86 mmol) and K₂CO₃ (0.24 g, 1.74 mmol) in 1,4-dioxane (10 mL) was purged with N₂. [1,1'-bis(diphenylphosphino) ferrocene]dichloropalladium(II) (43 mg, 0.059 mmol) was added. The vial was purged with N₂, sealed and heated at 90° C. for overnight. The sample was cooled; diluted with EtOAc (40 mL); stirred at room temperature for 1 h; and filtered through a pad of Celite®. The filtrate was concentrated. The residue was purified by column chromatography (silica gel, eluting with 20% EtOAc in hexanes) to give compound 80 (0.16 g, 67% yield) as light-yellow oil. m/z=407 (M+1).

Compound 81: A mixture of compound 80 (0.16 g, 0.39 mmol) and ammonium acetate (91 mg, 1.18 mmol) in nitromethane (0.13 mL, 2.40 mmol) was heated at 65° C. under N₂ for 1 h. The sample was cooled to room temperature then partitioned between sat. aq. KH₂PO₄ (10 mL) and EtOAc (10 mL). The organic extract was washed with sat. aq. NaCl (10 mL); dried with MgSO₄; filtered and concentrated to give crude compound 81 (0.28 g) as yellow oil. m/z=366 (M-THP+2). Compound 81 was used in the next step without purification.

Compound 82: A solution of compound 81 (0.28 g, ≤0.39 mmol) in THF (10 mL) at 0° C. under N₂ was treated with lithium aluminum hydride (2.4 M in THF, 0.33 mL, 0.79 mmol). After stirring at 0° C. for 1 h, the reaction was quenched with dropwise addition of 2 N aq. NaOH solution. The mixture was extracted with EtOAc (50 mL). The organic extract was washed with sat. aq. NaCl (50 mL); dried with MgSO₄; filtered and concentrated to give compound 82 (0.24 g) as yellow oil. m/z=422 (M+1).

Compound 83: A mixture of compound 82 (0.24 g, ≤0.39 mmol) and sodium acetate (0.16 g, 1.95 mmol) in acetic anhydride (1 mL, 10.59 mmol) was stirred at room temperature under N₂ overnight. The mixture was diluted with CH₂Cl₂ (10 mL) and filtered. The filtrate was concentrated, and the residue was purified by column chromatography (silica gel, eluting with 75% EtOAc in hexanes) to give compound 83 (61 mg, 33% yield from 80) as a light yellow waxy solid. m/z=464 (M+1).

A7: A mixture of compound 83 (61 mg, 0.13 mmol) and pyridinium p-toluenesulfonate (10 mg, 0.042 mmol) in EtOH (10 mL) was heated at 65° C. under N₂. After 2 h, the sample was cooled to room temperature, and concentrated. The residue was partitioned between sat. aq. KH₂PO₄ (10 mL) and EtOAc (10 mL). The organic extract was washed with sat. aq. NaCl (10 mL); dried with MgSO₄; filtered and concentrated to give compound A7 (43 mg, 86% yield) as a tan foamy solid. m/z=380 (M+1); ¹H NMR (400 MHz, CDCl₃) δ 7.55-7.29 (m, 6H), 7.12-6.95 (m, 2H), 6.92 (d, J=9.4 Hz, 1H), 6.54 (d, J=2.3 Hz, 1H), 6.32 (d, J=2.3 Hz, 1H), 5.78 (bs, 1H), 5.67 (bs, 1H), 5.06 (s, 2H), 3.26 (q, J=6.2 Hz, 2H), 2.72 (t, J=6.6 Hz, 2H), 1.69 (s, 3H).

Compound 84: A mixture of compound A7 (43 mg, 0.11 mmol), compound 18 and 19 (86 mg, 0.17 mmol) and 3 Å molecular sieves (0.2 g) in dry CH₂Cl₂ (10 mL) was stirred at room temperature under N₂ for 1 h. A solution of boron trifluoride etherate (48 mg, 0.34 mmol) in dry CH₂Cl₂ (2 mL) was added. After 2 h, the mixture was cooled; quenched with sat. aq. NaHCO₃ (25 mL); and filtered. The organic phase was washed with sat. aq. NaCl (25 mL); dried with MgSO₄; filtered, and concentrated. The residue was purified by column chromatography (silica gel, eluting with 70% EtOAc in hexanes) to give compound 84 (52 mg, 62% yield) as a light-yellow oil. m/z=762 (M+1).

Compound 85: A mixture of compound 84 (0.11 g, 0.15 mmol) and 1 N aq. NaOH (1.5 mL, 1.5 mmol) in EtOH (5 mL) was stirred at room temperature under N₂. After 2 h, the sample was concentrated, and the residue was partitioned between sat. aq. KH₂PO₄ (25 mL) and EtOAc (25 mL). The organic extract was washed with sat. aq. NaCl (25 mL); dried with MgSO₄; filtered and concentrated. The residue was purified by column chromatography (silica gel, eluting with 5% MeOH in CHCl₃) to give compound 85 (66 mg, 82% yield) as off-white foamy solid. m/z=554 (M+1).

T23: A solution of compound 85 (66 mg, 0.12 mmol) in EtOAc (10 mL) was treated with 10% Pd/C (10 mg). The mixture was hydrogenated under H₂ balloon at room temperature overnight. The mixture was filtered and concentrated to give T23 (46 mg, 83% yield) as a tan foamy solid. m/z=464 (M+1); ¹H NMR (400 MHz, CDCl₃) δ 8.50 (br s, 1H), 7.34 (m, 1H), 7.00 (m, 3H), 6.71 (d, J=2.5 Hz, 1H), 6.42 (d, J=2.5 Hz, 1H), 5.96 (m, 1H), 5.51 (d, J=2.2 Hz, 1H), 4.15 (m, 2H), 3.59 (s, 3H), 3.31 (d, J=9.1 Hz, 1H), 3.20 (m, 2H), 2.66 (dd, J=6.4, 9.2 Hz, 2H), 2.49 (br s, 2H), 2.00 (s, 3H), 1.36 (s, 3H), 1.23 (s, 3H).

Compound 87: Compound 86 (0.5 g, 2.16 mmol) was dissolved in DMF (5 mL). K₂CO₃ (450 mg, 3.25 mmol) and benzyl bromide (470 mg, 2.74 mmol) were added. The reaction mixture was stirred at room temperature overnight. The mixture was neutralized by the addition of sat. aq. KH₂PO₄; and extracted with EtOAc. The organic extract was washed with water; dried with MgSO₄, and concentrated to give compound 87 (695 mg, quantitative yield) as a solid. m/z=321, 323 (M+1).

Compound 88: Compound 87 (500 mg, 1.55 mmol) was taken up in 1,4-dioxane (6 mL). K₂CO₃ (540 mg, 3.91 mmol), Pd(dppf))Cl₂ (115 mg, 0.16 mmol) and 3-fluorophenylboronic acid (275 mg, 1.97 mmol) were added. The mixture was sparged with N₂ for 10 min; stirred at 90° C. for 16 h; cooled to room temperature; and filtered. The filtrate was concentrated. The crude residue was purified by column chromatography (silica gel, eluting with 0 to 30% EtOAc in hexanes) to give compound 88 (500 mg, 95% yield) as a foam. m/z=337 (M+1).

Compound 89: Compound 88 (890 mg, 2.64 mmol) was taken up in DMF (9 mL). Pyridine hydrochloride salt (765 mg, 6.62 mmol) was added and heated in Biotage Initiator microwave synthesizer at 200° C. for 45 min. The reaction was poured into water and extracted with ethyl acetate. The organic extract was washed with brine, dried with MgSO₄, and concentrated. The crude residue was purified by column chromatography (silica gel, eluting with 0% to 30% EtOAc in hexanes) to give compound 89 (200 mg, 23% yield) as a solid. m/z=323 (M+1).

Compound 90: Compound 89 (650 mg, 2.02 mmol) was taken up in $CH_2Cl_2$ (10 mL) at 0° C. N,N-Diisopropylethylamine (2.6 g, 20.11 mmol) and chloromethyl methyl ether (815 mg, 10.12 mmol) were added. The reaction was stirred at room temperature for 16 h; and concentrated. The crude residue was purified by column chromatography (silica gel, eluting with 0% to 35% EtOAc in hexanes) to give compound 90 (700 mg, 95% yield) as an oil. m/z=367 (M+1).

Compound 91: Compound 90 (700 mg, 1.91 mmol) was dissolved in nitromethane (5 mL). Ammonium acetate (300 mg, 3.89 mmol) was added. The mixture was heated at 65° C. for 1 h; cooled to room temperature; and concentrated. The residue was taken up in ethyl acetate and washed with aq. $NaHCO_3$. The organic extract was dried with $MgSO_4$, and concentrated to give compound 91 (755 mg, 97% yield) as an oil. m/z=410 (M+1).

Compound 92: Compound 91 (755 mg, 1.84 mmol) was taken up in THF (5 mL) at 0° C. $LiAlH_4$ (2.4 M in THF, 2.5 mL, 6.0 mmol) was added. The reaction was stirred at 45° C. for 2 h; cooled to 0° C.; and quenched with 2 M aq. NaOH (1 mL) and EtOAc (3 mL). The mixture was filtered; and the filter cake was washed with EtOAc. The filtrate was washed with brine; dried with $MgSO_4$; filtered and concentrated to give compound 92 (660 mg, 94% yield) as an oil. m/z=382 (M+1).

Compound 93: Compound 92 (660 mg, 1.73 mmol) was taken up in acetic anhydride (5 mL). Sodium acetate (750 mg, 9.14 mmol) was added. The mixture was stirred at room temperature overnight; and concentrated. The residue was purified by column chromatography (silica gel, eluting with 0% to 100% EtOAc in hexanes) to give compound 93 (230 mg, 31% yield) as a foam. m/z=424 (M+1).

Compound A8: Compound 93 (300 mg, 0.71 mmol) was taken up in THF (5 mL). 3 N aq. HCl (2 mL) was added. The mixture was stirred overnight at room temperature; and concentrated. The residue was neutralized with sat. aq. $NaHCO_3$ and extracted with ethyl acetate. The organic extract was washed with water; dried with $MgSO_4$; filtered and concentrated to give compound A8 (180 mg, 67% yield) as a solid. m/z=380 (M+1); $^1H$ NMR (400 MHz, $CDCl_3$) δ 7.45 (m, 1H), 7.29 (m, 3H), 7.18-7.06 (m, 2H), 7.05-6.88 (m, 5H), 5.56 (s, 1H), 5.25 (bs, 1H), 4.38 (s, 2H), 3.23 (d, J=7.4 Hz, 2H), 2.64 (t, J=7.1 Hz, 2H), 1.88 (s, 3H).

Compound 94: Compound A8 (65 mg, 0.17 mmol), compound 18 and 19 (125 mg, 0.25 mmol) and 4 Å molecular sieve (210 mg) in anhydrous $CH_2Cl_2$ (5 mL) were stirred at room temperature for 15 min. $BF_3 \cdot OEt_2$ (75 mg, 0.52 mmol) was added dropwise and stirred at room temperature for 2 h. The mixture was cooled to 0° C.; quenched with sat. aq. $NaHCO_3$ (5 mL); stirred for 5 min; and extracted with EtOAc. The organic extract was dried with $MgSO_4$, filtered and concentrated. The residue was purified by column chromatography (silica gel, eluting with 0% to 75% EtOAc in hexanes) to give compound 94 (20 mg, 15% yield) as a foam. m/z=762 (M+1).

Compound 95: Compound 94 (75 mg, 0.098 mmol) was dissolved in EtOH (2 mL). 1 N aq. NaOH (1 mL, 1 mmol) was added. The reaction was stirred at room temperature for 2 h; and diluted with EtOAc. The mixture was washed with water. The organic extract was dried with $MgSO_4$, filtered, and concentrated. The residue was purified by column chromatography (silica gel, eluting with 0% to 10% MeOH in $CH_2Cl_2$) to give compound 95 (30 mg, 56% yield) as a foam. m/z=554 (M+1).

T24: A mixture of compound 95 (30 mg, 0.054 mmol) and 10% Pd/C (10 mg) in EtOAc (2 mL) was hydrogenated at atmospheric pressure over for 16 h at room temperature. The reaction mixture was filtered through a Celite® pad. The filtrate was concentrated to give compound T24 (25 mg, quantitative yield) as a white foam. m/z=464 (M+1); $^1H$ NMR (400 MHz, $CDCl_3$) δ 7.41 (ddd, J=6.0, 7.8, 8.5 Hz, 1H), 7.14 (d, J=8.3 Hz, 1H), 7.07 (ddt, J=1.0, 2.6, 8.6 Hz, 1H), 7.03 (d, J=7.6 Hz, 1H), 6.97 (d, J=9.5 Hz, 1H), 6.76 (d, J=8.3 Hz, 1H), 6.24 (br s, 1H), 5.35 (d, J=4.2 Hz, 1H), 5.29 (m, 1H), 4.23 (td, J=3.3, 6.9 Hz, 1H), 4.13 (m, 1H), 3.55 (s, 3H), 3.27 (d, J=7.3 Hz, 1H), 3.23 (m, 2H), 2.96 (br d, J=3.4 Hz, 1H), 2.66 (br d, J=3.2 Hz, 1H), 2.58 (t, J=7.2 Hz, 2H), 1.88 (s, 3H), 1.43 (s, 3H), 1.29 (s, 3H).

Compound 97: Compound 96 (1 g, 4.32 mmol) was dissolved in DMF (5 mL). $K_2CO_3$ (900 mg, 6.52 mmol) and benzyl bromide (940 mg, 5.50 mmol) were added. The reaction mixture was stirred at room temperature overnight; neutralized by the addition of sat. aq. $KH_2PO_4$; and extracted with ethyl acetate. The organic extract was washed with water; dried with $MgSO_4$, filtered and concentrated to give compound 97 (695 mg, 50% yield) as a solid. m/z=321, 323 (M+1).

Compound 98: To a solution of compound 97 (425 mg, 1.32 mmol) in DMF (3 mL) was added pyridine hydrochloride (410 g, 3.55 mmol). The mixture was heated in Biotage Initiator microwave synthesizer at 200° C. for 45 min; cooled to room temperature; poured into water; and extracted with ethyl acetate. The organic extract was washed with brine; dried with $MgSO_4$, filtered and concentrated. The residue was purified by column chromatography (silica gel, eluting with 0% to 30% EtOAc in hexanes) to give a compound 98 (200 mg, 49% yield) as a solid. m/z=307, 309 (M+1).

Compound 99: To a solution of compound 98 (340 mg, 1.10 mmol) in 1,4-dioxane (6 mL) was added $K_2CO_3$ (380 mg, 2.75 mmol), Pd(dppf)$Cl_2$ (45 mg, 0.061 mmol) and 3-fluorophenylboronic acid (195 mg, 1.39 mmol). The mixture was sparged with $N_2$ for 10 min; stirred at 90° C. for 9 h; cooled to room temperature; and filtered. The filtrate was concentrated. The residue was purified by column chromatography (silica gel, eluting with 0% to 30% EtOAc in hexanes) to give a compound 99 (280 mg, 79% yield) as a solid. m/z=323 (M+1).

Compound 100: To a solution of compound 99 (390 mg, 1.21 mmol) in $CH_2Cl_2$ (10 mL) at 0° C. was added N,N-diisopropylethylamine (1.6 g, 12.38 mmol) and chloromethyl methyl ether (500 mg, 6.21 mmol). The reaction was stirred at room temperature for 16 h; and concentrated. The crude residue was purified by column chromatography (silica gel, 0% to 35% EtOAc in hexanes) to give compound 100 (445 mg, quantitative yield) as an oil. m/z=367 (M+1).

Compound 101: To a mixture of compound 100 (445 mg, 1.21 mmol) in nitromethane (5 mL) was added ammonium acetate (190 mg, 2.46 mmol) at room temperature. The mixture was heated at 65° C. for 1 h; cooled to room temperature; and concentrated. The residue was taken up in ethyl acetate, and washed with aq. $NaHCO_3$. The organic extract was dried with $MgSO_4$; filtered and concentrated to give compound 101 (495 mg, 99% yield) as a solid. m/z=410 (M+1).

Compound 102: Compound 101 (495 mg, 1.21 mmol) was taken up in THF (5 mL) at 0° C. $LiAlH_4$ (2.4 M in THF, 1.5 mL, 3.6 mmol) was added. The reaction was stirred at 45° C. for 2 h; cooled to 0° C.; and quenched with 2 M aq. NaOH (1 mL) and EtOAc (3 mL). The mixture was filtered; and the filter cake was washed with EtOAc. The filtrate was washed with brine; dried with MgSO$_4$; filtered and concentrated to give compound 102 (440 mg, 95% yield) as an oil. m/z=382 (M+1).

Compound 103: Compound 102 (440 mg, 1.15 mmol) was taken up in acetic anhydride (5 mL). Sodium acetate (500 mg, 6.10 mmol) was added. The mixture was stirred at room temperature overnight; and then concentrated. The residue was purified by column chromatography (silica gel, 0% to 100% EtOAc in hexanes) to give compound 103 (195 mg, 40% yield) as an oil. m/z=424 (M+1).

A9: Compound 103 (195 mg, 0.46 mmol) was taken up in THF (3 mL), and 3 N aq. HCl (1 mL) was added. The mixture was stirred overnight at room temperature; and then concentrated. The residue was neutralized with sat. aq. NaHCO$_3$ and extracted with ethyl acetate. The organic extract was washed with water; dried with MgSO$_4$; filtered and concentrated to give compound A9 (115 mg, 66% yield) as a foam. m/z=380 (M+1); $^1$H NMR (400 MHz, CDCl$_3$) δ 7.49-7.31 (m, 5H), 7.09-6.93 (m, 4H), 6.87 (s, 1H), 6.82 (s, 1H), 5.62 (s, 1H), 5.23 (bs, 1H), 5.15 (s, 2H), 3.27 (q, J=6.8 Hz, 2H), 2.73 (t, J=7.3 Hz, 2H), 1.85 (s, 3H).

A10: A mixture of compound A9 (180 mg, 0.47 mmol) and 10% Pd/C (20 mg) in EtOAc (2 mL) was hydrogenated at atmospheric pressure for 16 h at room temperature. The reaction mixture was filtered using a Celite® pad. The filtrate was concentrated to give compound A10 (140 mg, quantitative yield) as a foam. m/z=290 (M+1).

Compound 104 and 105: A mixture of compound A10 (140 mg, 0.48 mmol), compound 18 and 19 (365 mg, 0.72 mmol) and 4 Å molecular sieve (300 mg) in anhydrous CH$_2$Cl$_2$ (5 mL) was stirred at room temperature for 15 min Boron trifluoride diethyl etherate (205 mg, 1.44 mmol) was added dropwise. The mixture was stirred at room temperature for 2 h; cooled to 0° C.; quenched with sat. aq. NaHCO$_3$ (aq, 5 mL); stirred for 5 min; and extracted with EtOAc. The organic extract was dried with MgSO$_4$; filtered and concentrated. The residue was purified by column chromatography (silica gel, eluting with 0% to 75% EtOAc in hexanes) to give compound 104 (50 mg, 15% yield) and compound 105 (70 mg, 22% yield) as foamy solid. 104: m/z=672 (M+1); 105: m/z=672 (M+1).

T25: Compound 104 (50 mg, 0.074 mmol) was dissolved in EtOH (2 mL). 1 N aq. NaOH (0.7 mL, 0.7 mmol) was added. After the reaction was stirred at room temperature for 2 h, EtOAc was added. The mixture was washed with water. The organic extract was dried with MgSO$_4$, filtered and concentrated. The residue was purified by column chromatography (silica gel, eluting with 0% to 7.5% MeOH in EtOAc) to give compound T25 (19 mg, 55% yield) as a white foam. m/z=464 (M+1); $^1$H NMR (400 MHz, CDCl$_3$) δ 7.36 (m, 1H), 7.08 (s, 1H), 7.04 (m, 2H), 6.98 (m, 1H), 6.88 (m, 1H), 6.80 (s, 1H), 5.36 (m, 1H), 5.33 (d, J=5.1 Hz, 1H), 4.26 (m, 1H), 4.10 (m, 1H), 3.55 (s, 3H), 3.52 (m, 1H), 3.31 (m, 2H), 3.25 (d, J=6.4 Hz, 1H), 2.89 (m, 1H), 2.70 (t, J=7.1 Hz, 2H), 1.88 (s, 3H), 1.47 (s, 3H), 1.34 (s, 3H).

T26: Compound 105 (70 mg, 0.10 mmol) was dissolved in EtOH (2 mL). 1 N aq. NaOH (1 mL, 1 mmol) was added. After the reaction was stirred at room temperature for 2 h, EtOAc (50 mL) was added. The mixture was washed with water. The organic layer was dried with MgSO$_4$, filtered and concentrated. The residue was purified by column chromatography (silica gel, eluting with 0% to 7.5% MeOH in EtOAc) to give compound T26 (17 mg, 35% yield) as a white foam. m/z=464 (M+1); $^1$H NMR (400 MHz, CDCl$_3$) δ 7.35 (dt, J=6.0, 8.0 Hz, 1H), 7.01 (m, 5H), 6.91 (s, 1H), 5.35 (br s, 1H), 5.27 (d, J=5.1 Hz, 1H), 4.26 (dd, J=3.7, 6.3 Hz, 1H), 4.09 (br t, J=4.3 Hz, 1H), 3.54 (s, 3H), 3.30 (dt, J=5.8, 7.2 Hz, 2H), 3.23 (d, J=6.4 Hz, 1H), 3.15 (m, 1H), 2.725 (m, 3H), 1.88 (s, 3H), 1.42 (s, 3H), 1.32 (s, 3H).

Compounds 106 and 107: To a stirring solution of phenylmagnesium bromide (3 M solution in diethyl ether, 4.4 mL, 13.2 mmol) in THF (35 mL) at 0° C. under N$_2$ was added dropwise a solution of compound 13 (0.88 g, 4.35 mmol) in THF (10 mL). After 2 h, the cold solution was quenched by dropwise addition of sat. aq. KH$_2$PO$_4$ (25 mL). The sample was concentrated, and the residue was extracted with EtOAc (50 mL). The organic extract was washed with sat. aq. NaCl (50 mL), dried with MgSO$_4$, filtered, and concentrated. The residue was purified by column chromatography (silica gel, eluting with 10% EtOAc in CH$_2$Cl$_2$) to give compound 106 (0.57 g, 37% yield) and compound 107 (0.61 g, 50% yield). 106: m/z=359 (M+1); 107: m/z=262 (M-OH).

Compound 108: A mixture of compound 106 (1.18 g, 3.30 mmol), MgSO$_4$ (0.4 g, 3.32 mmol) and pyridinium dichromate (7.4 g, 19.67 mmol) in CH$_2$Cl$_2$ (35 mL) was stirred at room temperature under N$_2$ for 48 h. The sample was concentrated. The residue was diluted with diethyl ether (100 mL); stirred for 30 min; and then filtered through a pad of Celite®. The filtrate was concentrated. The residue was purified by column chromatography (silica gel, eluting with 30% EtOAc in hexanes) to give compound 108 (0.68 g, 59% yield) as a white gummy solid.

Compound 109: Diisobutylaluminum hydride (1.2 M in toluene, 1.75 mL, 2.10 mmol) was added dropwise to a stirring solution of compound 108 (0.68 g, 1.91 mmol) in CH$_2$Cl$_2$ (19 mL) at 0° C. under N$_2$. After 2 h, the cold solution was quenched by dropwise addition of sat. aq. potassium sodium tartrate solution (25 mL). The ice bath was removed. The sample was stirred at room temperature for 1 h, and concentrated. The residue was extracted with EtOAc (50 mL). The organic extract was washed with sat. aq. NaCl solution (50 mL); dried with MgSO$_4$; filtered and concentrated to give compound 109 (0.65 g, 96% yield) as a white foamy solid. m/z=339 (M-OH).

Compound 110: To a solution of compound 109 (0.36 g, 1.01 mmol), compound A1 (0.35 g, 1.28 mmol) and triphenylphosphine (0.40 g, 1.52 mmol) in THF (10 mL) at room temperature under N$_2$ was added dropwise diisopropyl azodicarboxylate (0.30 mL, 1.52 mmol). The resultant yellow solution was stirred at room temperature for 16 h, and concentrated. The residue was partitioned between sat. aq. NaHCO$_3$ (50 mL) and EtOAc (50 mL). The organic extract was washed with sat. aq. NaCl (50 mL); dried with MgSO$_4$, filtered and concentrated. The crude sample was purified by column chromatography (silica gel, eluting with 75% EtOAc in hexanes) to give partially purified compound 110, which was purified again by column chromatography (silica gel, eluting with 10% acetone in CH$_2$Cl$_2$) to give compound 110 (0.34 g, 55% yield) as an off-white foamy solid. m/z=612 (M+1). Compound 110 was a mixture of anomers in 1:2 ratio.

T27 and T28: A solution of compound 110 (0.34 g, 0.56 mmol) in HOAc:water (4:1 v/v, 5 mL) was heated at 40° C. under N$_2$ for 48 h. The sample was concentrated, and the residue was purified by column chromatography (silica gel, eluting with 100% EtOAc) to give compound T27 (0.14 g, 44% yield) and T28 (47 mg, 15% yield). T27: off-white foamy solid, m/z=572 (M+1); $^1$H NMR (400 MHz, CDCl$_3$) δ 7.35 (m, 5H), 7.19 (m, 3H), 7.04 (m, 6H), 6.92 (m, 1H), 6.82 (dd, J=2.7, 8.5 Hz, 1H), 6.55 (d, J=2.7 Hz, 1H), 5.67 (d, J=4.1 Hz, 1H), 5.25 (br s, 1H), 4.67 (td, J=3.0, 7.9 Hz, 1H), 4.23 (q, J=3.5 Hz, 1H), 4.09 (d, J=7.8 Hz, 1H), 3.25 (d, J=5.6, 7.1 Hz, 2H), 3.02 (s, 3H), 2.71 (m, 4H), 1.86 (s, 3H);

T28: light yellow foamy solid, m/z=572 (M+1); $^1$H NMR (400 MHz, CDCl$_3$) δ 7.64 (d, J=7.2 Hz, 2H), 7.24 (m, 7H), 7.10 (m, 3H), 6.97 (m, 4H), 6.81 (d, J=2.7 Hz, 1H), 5.27 (br s, 1H), 5.09 (d, J=1.3 Hz, 1H), 4.26 (m, 2H), 3.80 (d, J=10.2 Hz, 1H), 3.25 (m, 2H), 3.05 (s, 3H), 2.84 (br s, 1H), 2.71 (m, 3H), 1.85 (s, 3H).

Compound 111: To a stirring solution of compound 107 (0.97 g, 3.45 mmol) in MeOH (35 mL) at 0° C. under N$_2$ was added portionwise sodium borohydride (0.13 g, 3.44 mmol). The mixture was slowly warm to room temperature overnight; quenched with sat. aq. KH$_2$PO$_4$ (50 mL); and concentrated. The residue was extracted with EtOAc (50 mL). The organic extract was washed with sat. aq. NaCl solution (50 mL); dried with MgSO$_4$; filtered and concentrated to give compound 111 (1.00 g, quantitative yield) as a yellow oil. Compound 111 was a mixture of 2 diastereomers.

Compounds 112 and 113: A mixture of compound 111 (1.00 g, ≤3.45 mmol), triethylamine (1.4 mL, 10.06 mmol), DMAP (42 mg, 0.34 mmol) and tert-butyldimethylsilyl chloride (0.62 g, 4.11 mmol) in CH$_2$Cl$_2$ (35 mL) was stirred at room temperature under N$_2$ overnight. The sample was washed with sat. aq. KH$_2$PO$_4$ (50 mL) and sat. aq. NaCl (50 mL). The organic extract was dried with MgSO$_4$; filtered, and concentrated. The residue was purified by column chromatography (silica gel, eluting with 20% EtOAc in hexanes) to give compound 112 (0.51 g, 36% yield) and compound 113 (0.49 g, 35% yield). Both compounds are yellow oil. 112: $^1$H NMR (400 MHz, CDCl$_3$) δ 7.41-7.24 (m, 5H), 5.03 (dd, J=7.4, 5.0 Hz, 1H), 4.16-4.09 (m, 2H), 3.90 (d, J=7.4 Hz, 1H), 3.87-3.75 (m, 2H), 3.60 (dd, J=4.8, 2.8 Hz, 1H), 3.45 (s, 3H), 1.51 (s, 3H), 1.32 (s, 3H), 0.87 (s, 9H), 0.10 (s, 3H), 0.09 (s, 3H). 113: m/z=397 (M+1); $^1$H NMR (400 MHz, CDCl$_3$) δ 7.46-7.41 (m, 2H), 7.34 (m, 2H), 7.27 (m, 1H), 4.90 (dd, J=6.6, 3.1 Hz, 1H), 4.35 (t, J=6.3 Hz, 1H), 4.15 (m, 1H), 3.85 (dd, J=10.8, 7.6 Hz, 1H), 3.77 (dd, J=6.5, 3.2 Hz, 1H), 3.70 (dd, J=10.8, 4.2 Hz, 1H), 3.33 (s, 3H), 3.11 (d, J=6.6 Hz, 1H), 1.47 (s, 3H), 1.34 (s, 3H), 0.89 (s, 9H), 0.08 (s, 3H), 0.06 (s, 3H).

Compound 114: To a stirring solution of compound 112 (0.51 g, 1.28 mmol) in THF (13 mL) at 0° C. under N$_2$ was added TBAF (1 M solution in THF, 1.4 mL, 1.4 mmol) dropwise. After 1 h, the cold sample was treated with sat. aq. KH$_2$PO$_4$ (50 mL), and concentrated. The residue was extracted with EtOAc (50 mL). The organic extract was washed with sat. aq. NaCl (50 mL); dried with MgSO$_4$; filtered, and concentrated. The residue was purified by column chromatography (silica gel, eluting with 50% EtOAc in hexanes) to give compound 114 (0.28 g, 77% yield) as light yellow oil. m/z=283 (M+1).

Compound 115: A mixture of compound 114 (0.28 g, 0.99 mmol), (diacetoxyiodo)benzene (0.97 g, 3.01 mmol) and TEMPO (31 mg, 0.20 mmol) in CH$_2$Cl$_2$ (10 mL) was stirred at room temperature under N$_2$ for 16 h. The sample was concentrated. The residue was partitioned between sat. aq. Na$_2$S$_2$O$_3$ (50 mL) and EtOAc (50 mL). The organic extract was washed with sat. aq. NaHCO$_3$ (50 mL) and sat. aq. NaCl (50 mL); dried with MgSO$_4$; filtered; and concentrated. The residue was purified by column chromatography (silica gel, eluting with 50% EtOAc in hexanes) to give compound 115 (0.23 g, 83% yield) as a white solid. $^1$H NMR (400 MHz, CDCl$_3$) δ 7.40 (s, 5H), 5.03 (d, J=10.0 Hz, 1H), 4.83 (d, J=8.0 Hz, 1H), 4.63 (dd, J=8.0, 5.2 Hz, 1H), 3.52 (dd, J=10.0, 5.2 Hz, 1H), 3.16 (s, 3H), 1.56 (s, 3H), 1.46 (s, 3H).

Compound 116: To a stirring solution of compound 115 (0.23 g, 0.81 mmol) in CH$_2$Cl$_2$ (8 mL) at 0° C. under N$_2$ was added diisobutylaluminum hydride (1.2 M in toluene, 0.82 mL, 0.98 mmol) dropwise. The mixture was stirred at 0° C. for 2 h; and quenched by dropwise addition of sat. aq. potassium sodium tartrate (25 mL). The ice bath was removed. The sample was stirred at room temperature for 1 h; and concentrated. The residue was extracted with EtOAc (50 mL). The organic extract was washed with sat. aq. NaCl (50 mL); dried with MgSO$_4$; filtered; and concentrated to give compound 116 (0.21 g, 92% yield) as a tan foamy solid. m/z=263 (M-OH).

Compound 117: A mixture of compound 116 (0.21 g, 0.75 mmol) and Dowex® 50W X$_2$ hydrogen resin (0.50 g) in acetonitrile and water (4/1 v/v, 8 mL) was stirred at 40° C. under N$_2$ for 48 h. The sample was cooled; filtered; and concentrated to give compound 117 (0.18 g, quantitative yield) as an off-white solid.

Compound 118: A solution of compound 117 (0.18 g, 0.75 mmol) and DMAP (9 mg, 0.074 mmol) in pyridine (5 mL) was treated with benzoyl chloride (0.42 mL, 3.62 mmol). After stirring at room temperature under N$_2$ overnight, the sample was concentrated. The residue was partitioned between sat. aq. KH$_2$PO$_4$ (50 mL) and EtOAc (50 mL). The organic extract was washed with sat. aq. NaCl (50 mL); dried with MgSO$_4$; filtered, and concentrated. The residue was purified by column chromatography (silica gel, eluting with 20% EtOAc in hexanes) to give compound 118 (0.29 g, 70% yield) as a white foamy solid. m/z=431 (M-OBz). Compound 118 was a mixture of anomers in 2:1 ratio.

Compound 119: A mixture of compound 118 (0.29 g, 0.52 mmol), compound A1 (0.14 g, 0.51 mmol) and 3 Å molecular sieves (1.4 g) in dry CH$_2$Cl$_2$ (5 mL) was stirred at room temperature under N$_2$ for 1 h. A solution of boron trifluoride etherate (0.26 mL, 2.11 mmol) in dry CH$_2$Cl$_2$ (5 mL) was added. The mixture was stirred at room temperature for 16 h; cooled; quenched with sat. aq. NaHCO$_3$ (50 mL); and filtered. The organic layer from the filtrate was washed with sat. aq. NaCl (50 mL); dried with MgSO$_4$; filtered; and concentrated. The residue was purified by column chromatography (silica gel, eluting with 70% EtOAc in hexanes) to give compound 119 (0.24 g, 65% yield) as a light yellow foamy solid. m/z=704 (M+1).

T29: A solution of compound 119 (0.24 g, 0.34 mmol) in EtOH (5 mL) was treated with 1 N aq. NaOH (1.7 mL, 1.7 mmol). The sample was stirred at room temperature under N$_2$ for 1 h; and concentrated. The residue was partitioned between EtOAc (25 mL) and sat. aq. KH$_2$PO$_4$ (25 mL). The organic extract was washed with sat. aq. NaCl (25 mL); dried with MgSO$_4$; filtered; and concentrated. The residue was purified by column chromatography (silica gel, eluting with 100% EtOAc) to give compound T29 (0.13 g, 77% yield) as an off-white foamy solid. m/z=496 (M+1); $^1$H NMR (400 MHz, CDCl$_3$) δ 7.44 (m, 2H), 7.35 (m, 4H), 7.15 (d, J=8.5 Hz, 1H), 7.03 (m, 3H), 6.94 (td, J=2.1, 9.6 Hz, 1H), 6.90 (d, J=2.7 Hz, 1H), 5.66 (d, J=1.7 Hz, 1H), 5.25 (br s, 1H), 4.60 (d, J=9.6 Hz, 1H), 4.26 (m, 1H), 4.18 (m, 1H), 3.49 (t, J=9.5 Hz, 1H), 3.24 (q, J=6.8 Hz, 2H), 2.95 (s, 3H), 2.71 (m, 4H), 1.84 (s, 3H).

Compound 120: To a stirring solution of compound 113 (0.49 g, 1.22 mmol) in THF (13 mL) at 0° C. under N$_2$ was added dropwise TBAF (1 M solution in THF, 1.35 mL, 1.35 mmol). The mixture was stirred at 0° C. for 1 h; treated with sat. KH$_2$PO$_4$ solution (50 mL); and concentrated. The residue was extracted with EtOAc (50 mL). The organic extract was washed with sat. aq. NaCl (50 mL); dried with MgSO$_4$; filtered; concentrated; and vacuum dried to give compound 120 (0.44 g, quantitative yield) as light-yellow oil. m/z=283 (M+1).

Compound 121: A mixture of compound 120 (0.44 g, ≤1.22 mmol), (diacetoxyiodo)benzene (1.18 g, 3.66 mmol)

and TEMPO (19 mg, 0.12 mmol) in $CH_2Cl_2$ (12 mL) was stirred at room temperature under $N_2$. The mixture was stirred at room temperature for 16 h; and then concentrated. The residue was partitioned between sat. aq. $Na_2S_2O_3$ (50 mL) and EtOAc (50 mL). The organic extract was washed with sat. aq. $NaHCO_3$ (50 mL) and sat. aq. NaCl (50 mL); dried with $MgSO_4$; filtered; and concentrated. The residue was purified by column chromatography (silica gel, eluting with 50% EtOAc in hexanes) to give compound 121 (0.25 g, 74% yield from 113) as light-yellow oil. m/z=279 (M+1).

Compound 122: To a stirring solution at 0° C. under $N_2$ of compound 121 (0.25 g, 0.90 mmol) in $CH_2Cl_2$ (9 mL) was added diisobutylaluminum hydride (1.2 M solution in toluene, 0.90 mL, 1.08 mmol) dropwise. The mixture was stirred at 0° C. for 2 h; quenched by dropwise addition of sat. aq. potassium sodium tartrate; stirred at room temperature for 1 h; and concentrated. The residue was extracted with EtOAc (50 mL). The organic extract was washed with sat. aq. NaCl (50 mL); dried with $MgSO_4$; filtered; and concentrated to give compound 122 (0.23 g, 93% yield) as a light yellow waxy solid. m/z=263 (M-OH).

Compound 123: A mixture of compound 122 (0.22 g, 0.78 mmol) and Dowex® 50W $X_2$ hydrogen resin (0.25 g) in acetonitrile:water (4:1 v/v, 8 mL) was stirred at 40° C. under $N_2$ for 16 h. The sample was cooled; and filtered. The filtrate was concentrated to give compound 123 (0.19 g, quantitative yield) as yellow oil.

Compound 124: A solution of compound 123 (0.19 g, ≤0.78 mmol) and DMAP (10 mg, 0.082 mmol) in pyridine (5 mL) was treated with benzoyl chloride (0.46 mL, 3.96 mmol). The mixture was stirred at room temperature under $N_2$ overnight; and concentrated. The residue was partitioned between sat. aq. $KH_2PO_4$ (50 mL) and EtOAc (50 mL). The organic extract was washed with sat. aq. NaCl solution (50 mL); dried with $MgSO_4$; filtered; and concentrated. The residue was purified by column chromatography (silica gel, eluting with 20% EtOAc in hexanes) to give compound 124 (0.33 g, 77% yield) as an off-white foamy solid. m/z=431 (M-OBz). Compound 124 was a mixture of anomers in 4/1 ratio.

Compound 125: A mixture of compound 124 (0.33 g, 0.60 mmol), compound A1 (0.17 g, 0.62 mmol) and dried 3 Å molecular sieves (1.7 g) in dry $CH_2Cl_2$ (6 mL) was stirred at room temperature under $N_2$ for 1 h; and was then treated with a solution of boron trifluoride etherate (0.30 mL, 2.43 mmol) in dry $CH_2Cl_2$ (5 mL). The mixture was stirred at room temperature for 16 h; cooled; and quenched with sat. aq. $NaHCO_3$ (50 mL). The mixture was filtered. The organic layer of the filtrate was washed with sat. aq. NaCl (50 mL); dried with $MgSO_4$; filtered; and concentrated. The residue was purified by column chromatography (silica gel, eluting 100% EtOAc) to give compound 125 (0.21 g, 50% yield) as a light yellow foamy solid. m/z=704 (M+1). Compound 125 was a mixture of anomers.

T30 and T31: A solution of compound 125 (0.21 g, 0.30 mmol) in EtOH (3 mL) was treated with 1 N aq. NaOH (1.5 mL, 1.5 mmol). The sample was stirred at room temperature under $N_2$ for 1 h; and concentrated. The residue was partitioned between EtOAc (25 mL) and sat. aq. $NaHCO_3$ (25 mL). The organic extract was washed with sat. aq. NaCl (25 mL); dried with $MgSO_4$; filtered; and concentrated. The residue was purified repeatedly by column chromatography (silica gel, eluting with 5% MeOH in $CHCl_3$) to give compound T30 (35 mg, 24% yield) and T31 (64 mg, 44% yield) as off-white foamy solid. T30: =496 (M+1); $^1$H NMR (400 MHz, $CDCl_3$) δ 7.35 (m, 6H), 7.19 (d, J=8.5 Hz, 1H), 7.02 (m, 5H), 5.73 (d, J=3.9 Hz, 1H), 5.29 (d, J=1.5 Hz, 1H), 5.25 (br s, 1H), 4.27 (td, J=3.7, 8.4 Hz, 1H), 4.20 (td, J=3.9, 10.4 Hz, 1H), 3.65 (dd, J=1.5, 3.8 Hz, 1H), 3.24 (q, J=7.0 Hz, 2H), 3.18 (d, J=9.2 Hz, 1H), 2.90 (s, 3H), 3.24 (m, 3H), 1.84 (s, 3H); T31: =496 (M+1); $^1$H NMR (400 MHz, $CDCl_3$) δ 7.36 (m, 6H), 7.17 (d, J=8.4 Hz, 1H), 7.04 (m, 3H), 6.96 (m, 1H), 6.93 (d, J=2.6 Hz, 1H), 5.38 (d, J=8.0 Hz, 1H), 5.26 (br s, 1H), 5.14 (s, 1H), 4.41 (t, J=3.4 Hz, 1H), 4.08 (dd, J=3.3, 8.0 Hz, 1H), 3.57 (dd, J=1.5, 3.6 Hz, 1H), 3.25 (q, J=6.7 Hz, 2H), 3.11 (s, 3H), 2.80 (br s, 1H), 2.72 (t, J=7.1 Hz, 2H), 2.66 (br s, 1H), 1.85 (s, 3H).

Compound 126: To a stirring solution of allylmagnesium bromide (1 M solution in diethyl ether, 23.7 mL, 23.7 mmol) in tert-butyl methyl ether (75 mL) at room temperature under $N_2$ was added dropwise a solution of compound 13 (0.88 g, 4.36 mmol) in tert-butyl methyl ether (25 mL). The resulting suspension was stirred at room temperature for 16 h; cooled; quenched by dropwise addition of sat. aq. $KH_2PO_4$ (50 mL); and stirred for 1 h at room temperature. The organic extract was separated; washed with sat. aq. NaCl (50 mL); dried with $MgSO_4$; filtered; and concentrated to give compound 126 (1.87 g) as light-yellow oil. Compound 126 was used in the next step without further purification.

Compound 127: A mixture of compound 126 (1.87 g, ≤4.36 mmol), $MgSO_4$ (0.7 g, 5.82 mmol) and pyridinium dichromate (13.4 g, 35.62 mmol) in $CH_2Cl_2$ (100 mL) was stirred at room temperature under $N_2$ for 48 h. The sample was concentrated; diluted with diethyl ether (100 mL); stirred for 1 h; and then filtered through a pad of Celite®. The filtrate was concentrated. The residue was purified by column chromatography (silica gel, eluting with 25% EtOAc in hexanes) to give compound 127 (1.44 g, quantitative yield) as light-yellow liquid. m/z=283 (M+1).

Compound 128: To a stirring solution of compound 127 (1.44 g, ≤4.36 mmol) in $CH_2Cl_2$ (50 mL) at 0° C. under $N_2$ was added diisobutylaluminum hydride (1.2 M in toluene, 5.6 mL, 6.72 mmol) dropwise. The mixture was stirred at 0° C. for 2 h; quenched by dropwise addition of sat. aq. potassium sodium tartrate (50 mL); stirred at room temperature for 1 h; and concentrated. The residue was extracted with EtOAc (50 mL). The organic extract was washed with sat. aq. NaCl solution (50 mL); dried with $MgSO_4$; filtered; and concentrated to give compound 128 (1.44 g, quantitative yield) as light-yellow liquid. m/z=267 (M-OH). Compound 128 was a mixture of anomers in 1.5/1 ratio.

Compound 129: To a solution of compound 128 (0.59 g, 2.07 mmol), compound A1 (0.71 g, 2.60 mmol) and triphenylphosphine (0.81 g, 3.09 mmol) in THF (21 mL) at room temperature under $N_2$ was added dropwise diisopropyl azodicarboxylate (0.61 mL, 3.08 mmol). The resultant yellow solution was stirred at room temperature for 16 h, and concentrated. The residue was partitioned between sat. aq. $NaHCO_3$ (50 mL) and EtOAc (50 mL). The organic extract was washed with sat. aq. NaCl solution (50 mL); dried with $MgSO_4$; filtered; and concentrated. The residue was purified by column chromatography (silica gel, eluting with 70% EtOAc in hexanes) to give compound 129 (0.54 g, 48% yield) as an off-white foamy solid. m/z=540 (M+1). Compound 129 was a mixture of anomers.

T32 and T33: A solution of compound 129 (0.54 g, 1.00 mmol) in HOAc:water (4:1 v/v, 5 mL) was heated at 40° C. under $N_2$ for 48 h. The sample was concentrated. The residue was purified by column chromatography (silica gel, eluting with 5% MeOH in $CHCl_3$). The product obtained was purified twice more by column chromatography (silica gel, eluting with 4% MeOH/48% EtOAc/48% $CH_2Cl_2$) to give T32 (89 mg, 18% yield) and T33 (75 mg, 15% yield). T32:

light yellow foamy solid, m/z=500 (M+1); $^1$H NMR (400 MHz, CDCl$_3$) δ 7.38 (dt, J=5.9, 8.0 Hz, 1H), 7.21 (d, J=8.5 Hz, 1H), 7.03 (m, 5H), 5.89 (m, 2H), 5.32 (d, J=1.5 Hz, 1H), 5.29 (br s, 1H), 5.09 (m, 3H), 4.90 (m, 1H), 4.16 (m, 1H), 3.91 (dt, J=3.3, 8.2 Hz, 1H), 3.58 (s, 3H), 3.54 (d, J=9.3 Hz, 1H), 3.28 (q, J=7.1 Hz, 2H), 2.74 (t, J=7.2 Hz, 2H), 2.58 (m, 3H), 2.38 (m, 3H), 1.87 (s, 3H); T33: off-white foamy solid, m/z=500 (M+1); $^1$H NMR (400 MHz, CDCl$_3$) δ 7.38 (dt, J=6.0, 8.0 Hz, 1H), 7.20 (d, J=8.5 Hz, 1H), 7.02 (m, 4H), 6.89 (d, J=2.7 Hz, 1H), 5.93 (dddd, J=5.4, 8.6, 11.4, 16.6 Hz, 1H), 5.61 (m, 1H), 5.57 (d, J=3.3 Hz, 1H), 5.25 (br s, 1H), 5.11 (m, 2H), 4.93 (m, 2H), 4.29 (td, J=3.2, 7.9 Hz, 1H), 4.11 (q, J=3.1 Hz, 1H), 3.54 (s, 3H), 3.53 (d, J=7.9 Hz, 1H), 3.26 (m, 2H), 2.74 (t, J=7.2 Hz, 2H), 2.57 (m, 4H), 2.39 (t, J=8.6, 15.4 Hz, 2H), 1.87 (s, 3H).

T34: A mixture of T32 (59 mg, 0.12 mmol) and 10% Pd/C (5 mg) in EtOAc (5 mL) was hydrogenated under H$_2$ balloon pressure at room temperature overnight. The sample was filtered; and the filtrate was concentrated to give T34 (47 mg, 79% yield) as an off-white foamy solid. m/z=504 (M+1); $^1$H NMR (400 MHz, CDCl$_3$) δ 7.38 (dt, J=5.9, 8.0 Hz, 1H), 7.22 (d, J=8.5 Hz, 1H), 7.05 (m, 3H), 6.97 (m, 2H), 5.27 (d, J=1.6 Hz, 1H), 5.26 (br s, 1H), 3.91 (m, 1H), 3.59 (s, 3H), 3.50 (d, J=9.2 Hz, 1H), 3.28 (m, 2H), 2.75 (t, J=7.2 Hz, 2H), 2.59 (br s, 1H), 2.52 (br d, J=7.9 Hz, 1H), 1.87 (s, 3H), 1.47 (m, 8H), 0.88 (t, J=7.1 Hz, 3H), 0.82 (t, J=7.1 Hz, 3H).

T35: A mixture of T33 (41 mg, 0.082 mmol) and 10% Pd/C (10 mg) in EtOAc (5 mL) was hydrogenated under H$_2$ balloon at room temperature overnight. The sample was filtered; and the filtrate was concentrated to give T35 (37 mg, 90% yield) as an off-white foamy solid. m/z=504 (M+1); $^1$H NMR (400 MHz, CDCl$_3$) δ 7.38 (dt, J=6.0, 8.0 Hz, 1H), 7.19 (d, J=8.5 Hz, 1H), 7.02 (m, 4H), 6.88 (d, J=2.7 Hz, 1H), 5.55 (d, J=3.5 Hz, 1H), 5.22 (br s, 1H), 4.29 (m, 1H), 4.09 (m, 1H), 3.54 (s, 3H), 3.50 (d, J=8.0 Hz, 1H), 3.26 (q, J=6.7 Hz, 2H), 2.74 (t, J=7.2 Hz, 2H), 2.51 (br s, 1H), 2.49 (br s, 1H), 1.86 (s, 3H), 1.40 (m, 6H), 0.90 (t, J=7.3H, 3H), 0.83 (m, 2H), 0.66 (t, J=7.3 Hz, 3H).

Compound 130: A solution of compound 128 (0.84 g, 2.95 mmol) in CH$_2$Cl$_2$ (30 mL) at room temperature under N$_2$ was treated with Grubbs Catalyst™ 2$^{nd}$ Generation (0.12 g, 0.14 mmol). The mixture was stirred at room temperature for 4 h and concentrated. The residue was purified by column chromatography (silica gel, eluting with 30% EtOAc in hexanes) to give compound 130 (0.61 g, 81% yield) as dark green-brown oil.

Compound 131: A mixture of compound 130 (0.61 g, 2.38 mmol) and Dowex® 50W X$_2$ hydrogen resin (0.65 g) in acetonitrile:water (4:1 v/v, 10 mL) was stirred at room temperature under N$_2$ for 48 h. The sample was filtered and concentrated to give compound 131 (0.48 g, 93% yield) as a tan foamy solid. The compound is a mixture of lactol anomers.

Compound 132: A solution of compound 131 (0.48 g, 2.22 mmol) and DMAP (55 mg, 0.45 mmol) in pyridine (5 mL) was treated with benzoyl chloride (1.30 mL, 11.20 mmol) at room temperature. The mixture was stirred at room temperature under N$_2$ overnight; and concentrated. The residue was partitioned between sat. aq. KH$_2$PO$_4$ (50 mL) and EtOAc (50 mL). The organic extract was washed with sat. aq. NaCl (50 mL); dried with MgSO$_4$; filtered; and concentrated. The residue was purified by column chromatography (silica gel, eluting with 20% EtOAc in hexanes) to give compound 132 (1.00 g, 85% yield) as light-yellow oil. m/z=407 (M-OBz). The compound is a mixture of anomers.

Compound 133: A mixture of compound 132 (1.00 g, 1.89 mmol), compound A1 (0.52 g, 1.90 mmol) and 3 Å molecular sieves (1.4 g) in dry CH$_2$Cl$_2$ (19 mL) was stirred at room temperature under N$_2$ for 1 h, and then treated with a solution of boron trifluoride etherate (0.95 mL, 7.56 mmol) in dry CH$_2$Cl$_2$ (5 mL) dropwise. The mixture was stirred at room temperature for 16 h; cooled; quenched with sat. aq. NaHCO$_3$ (50 mL); and filtered. The organic extract from the filtrate was washed with sat. aq. NaCl (50 mL; dried with MgSO$_4$; filtered; and concentrated. The residue was purified by column chromatography (silica gel, eluting with 75% EtOAc in hexanes) to give compound 133 (0.41 g, 32% yield) as light yellow foamy solid. m/z=680 (M+1). $^1$H NMR spectrum is consistent with the structure as one major anomer.

T36: A solution of compound 133 (0.41 g, 0.60 mmol) in EtOH (6 mL) was treated with 1 N aq. NaOH (3 mL, 3 mmol). The sample was stirred at room temperature under N$_2$ for 1 h, and concentrated. The residue was partitioned between EtOAc (25 mL) and sat. aq. KH$_2$PO$_4$ (25 mL). The organic extract was washed with sat. aq. NaCl (25 mL); dried with MgSO$_4$; filtered; and concentrated. The residue was purified by column chromatography (silica gel, eluting with 100% EtOAc) to give compound T36 (0.14 g, 49% yield) as an off-white foamy solid. m/z=472 (M+1); $^1$H NMR (400 MHz, CDCl$_3$) δ 7.37 (dt, J=5.9, 8.0 Hz, 1H), 7.18 (d, J=8.5 Hz, 1H), 7.02 (m, 4H), 6.88 (d, J=2.7 Hz, 1H), 5.61 (s, 2H), 5.50 (d, J=4.4 Hz, 1H), 5.26 (br s, 1H), 4.25 (td, J=2.9, 6.6 Hz, 1H), 4.12 (m, 1H), 3.54 (s, 3H), 3.49 (d, J=7.0 Hz, 1H), 3.26 (q, J=7.0 Hz, 2H), 2.68 (m, 8H), 1.86 (s, 3H).

T37: A mixture of T36 (0.10 g, 0.21 mmol) and 10% Pd/C (25 mg) in EtOAc (10 mL) was hydrogenated under H$_2$ balloon at room temperature overnight. The sample was filtered. The filtrate was concentrated. The residue was purified by column chromatography (silica gel, eluting with 100% EtOAc) to give compound T37 (66 mg, 63% yield) as an off-white foamy solid. m/z=474 (M+1); $^1$H NMR (400 MHz, CDCl$_3$) δ 7.37 (dt, J=6.0, 8.0 Hz, 1H), 7.19 (d, J=8.5 Hz, 1H), 7.02 (m, 4H), 6.90 (d, J=2.6 Hz, 1H), 5.48 (d, J=3.9 Hz, 1H), 5.25 (br s, 1H), 4.20 (td, J=3.0, 6.9 Hz, 1H), 4.12 (m, 1H), 3.56 (s, 3H), 3.42 (d, J=7.5 Hz, 1H), 3.27 (td, J=5.7, 7.2 Hz, 2H), 2.73 (m, 2H), 2.58 (m, 2H), 1.95 (m, 2H), 1.86 (s, 3H), 1.59 (m, 6H).

Compound 134: To a stirring solution of compound 13 (2.00 g, 9.89 mmol) in THF (20 mL) at 0° C. under N$_2$ was added a solution of allylmagnesium bromide (1 M in diethyl ether, 10.9 mL, 10.9 mmol) dropwise. The resulting suspension was stirred at room temperature for 16 h; cooled and quenched by dropwise addition of sat. aq. KH$_2$PO$_4$ (50 mL). The mixture was stirred at room temperature for 1 h; and concentrated. The residue was extracted with EtOAc (50 mL). The organic extract was washed with sat. aq. NaCl; dried with MgSO$_4$; filtered; and concentrated. The residue was purified by column chromatography (silica gel, eluting with 20% EtOAc in CH$_2$Cl$_2$) to give compound 134 (1.60 g, 66% yield) as light yellow oil. m/z=227 (M-OH).

Compound 135: To a stirring solution of compound 134 (1.60 g, 6.55 mmol) in MeOH (65 mL) at 0° C. under N$_2$ was added NaBH$_4$ (0.25 g, 6.61 mmol) portionwise over 15 min After addition, the ice-bath was removed. The sample was stirred at room temperature for 16 h; and concentrated. The residue was partitioned between sat. aq. KH$_2$PO$_4$ (50 mL) and CHCl$_3$ (50 mL). The organic extract was washed with sat. aq. NaCl solution (50 mL); dried with MgSO$_4$; filtered; and concentrated to give compound 135 (1.85 g, quantitative yield) as light yellow oil.

Compounds 136 and 137: A mixture of compound 135 (1.85 g, ≤6.55 mmol), (diacetoxyiodo)benzene (6.33 g, 19.65 mmol) and TEMPO (0.21 g, 1.34 mmol) in $CH_2Cl_2$ (70 mL) was stirred at room temperature under $N_2$ for 48 h. The sample was concentrated, and the residue was partitioned between sat. aq. $Na_2S_2O_3$ (50 mL) and EtOAc (50 mL). The organic extract was washed with sat. aq. $NaHCO_3$ (50 mL) and sat. aq. NaCl (50 mL); dried with $MgSO_4$; filtered; and concentrated. The residue was purified by column chromatography (silica gel, eluting with 4% EtOAc/ 48% $CH_2Cl_2$/48% hexanes) to give compound 136 (colorless oil, 0.45 g, 28% yield) and compound 137 (off-white waxy solid, 0.38 g, 24% yield). 136: m/z=243 (M+1); 137: m/z=243 (M+1).

Compound 138: To a stirring solution of compound 136 (0.45 g, 1.86 mmol) in $CH_2Cl_2$ (18 mL) at 0° C. under $N_2$ was added diisobutylaluminum hydride (1.2 M in toluene, 1.90 mL, 2.28 mmol) dropwise. The reaction mixture was stirred at 0° C. for –30 min; and then, quenched by dropwise addition of sat. aq. potassium sodium tartrate (25 mL). The ice bath was removed; the sample was stirred at room temperature for 1 h, and then concentrated. The residue was extracted with EtOAc (50 mL). The organic extract was washed with sat. aq. NaCl (50 mL); dried with $MgSO_4$; filtered; and concentrated to give compound 138 (0.42 g, 92% yield) as an off-white waxy solid. m/z=267 (M+Na).

Compound 139: A mixture of compound 138 (0.42 g, 1.72 mmol) and Dowex® 50W $X_2$ hydrogen resin (0.50 g) in acetonitrile:water (4:1 v/v, 17 mL) was stirred at 40° C. under $N_2$ for 16 h. The sample was cooled, filtered and concentrated to give compound 139 (0.32 g, 91% yield) as dark yellow oil. m/z=227 (M+Na).

Compound 140: A solution of compound 139 (0.32 g, 1.58 mmol) and DMAP (19 mg, 0.16 mmol) in pyridine (5 mL) was treated with benzoyl chloride (0.92 mL, 7.92 mmol). After stirring at room temperature under $N_2$ overnight, the sample was concentrated. The residue was then partitioned between sat. aq. $KH_2PO_4$ (50 mL) and EtOAc (50 mL). The organic extract was washed with sat. aq. NaCl (50 mL); dried with $MgSO_4$; filtered; and concentrated. The residue was purified by column chromatography (silica gel, eluting with 20% EtOAc in hexanes) to give compound 140 (0.62 g, 76% yield) as a white foamy solid.

Compound 141: A solution of compound 140 (1.18 g, 2.29 mmol) in EtOAc (25 mL) was treated with 10% Pd/C (0.24 g). The sample was hydrogenated under $H_2$ balloon at room temperature for 16 h. After filtration, the filtrate was concentrated to give compound 141 (1.06 g, 89%) as colorless oil. $^1$H NMR (400 MHz, $CDCl_3$) δ 8.15-7.25 (m, 15H), 6.48 (d, J=8.7 Hz, 1H), 6.00 (t, J=3.6 Hz, 1H), 5.76 (dd, J=8.7, 3.5 Hz, 1H), 4.16 (m, 1H), 3.67 (s, 3H), 3.46 (dd, J=3.7, 1.4 Hz, 1H), 1.86 (m, 1H), 1.67-1.33 (m, 3H), 0.95 (t, J=7.3 Hz, 3H).

Compound 142: A mixture of compound 141 (1.06 g, 2.04 mmol), compound A1 (0.56 g, 2.05 mmol) and 3 Å molecular sieves (5 g) in dry $CH_2Cl_2$ (20 mL) was stirred at room temperature under $N_2$ for 1 h. A solution of boron trifluoride etherate (1.0 mL, 8.10 mmol) in dry $CH_2Cl_2$ (5 mL) was added. The mixture was stirred at room temperature for 16 h; cooled; quenched with sat. aq. $NaHCO_3$ (50 mL); and filtered. The organic extract from the filtrate was washed with sat. aq. NaCl (50 mL); dried with $MgSO_4$; filtered; and concentrated. The residue was purified by column chromatography (silica gel, eluting with 100% EtOAc) to give compound 142 (0.77 g, 56% yield) as an off-white foamy solid. m/z=670 (M+1). $^1$H NMR spectrum is consistent with the structure as a mixture of anomers.

T38 and T39: A solution of compound 142 (0.77 g, 1.15 mmol) in EtOH (15 mL) was treated with 1 N aq. NaOH solution (5.7 mL, 5.7 mmol). The sample was stirred at room temperature under $N_2$ for 1 h, and concentrated. The residue was then partitioned between EtOAc (25 mL) and sat. aq. $NaHCO_3$ (25 mL). The organic extract was washed with sat. aq. NaCl solution (25 mL); dried with $MgSO_4$; filtered; and concentrated. The residue was purified repeatedly by column chromatography (silica gel, eluting with 5% MeOH in $CHCl_3$) to give T38 (off-white foamy solid, 162 mg, 30% yield) and T39 (off-white foamy solid, 66 mg, 12% yield). T38: m/z=462 (M+1); $^1$H NMR (400 MHz, $CDCl_3$) δ 7.37 (dt, J=5.9, 7.9 Hz, 1H), 7.20 (d, J=8.5 Hz, 1H), 7.06 (m, 2H), 6.98 (m, 2H), 6.89 (d, J=2.6 Hz, 1H), 5.27 (br s, 1H), 5.19 (d, J=7.9 Hz, 1H), 4.34 (t, J=3.5 Hz, 1H), 3.96 (m, 2H), 3.48 (s, 3H), 3.26 (m, 3H), 2.74 (dt, J=2.3, 7.1 Hz, 2H), 2.65 (br s, 1H), 2.59 (br s, 1H), 1.87 (s, 3H), 1.87 (m, 1H), 1.38 (m, 3H), 0.90 (t, J=7.2 Hz, 3H); T39: m/z=462 (M+1); $^1$H NMR (400 MHz, $CDCl_3$) δ 7.38 (dt, J=5.9, 8.0 Hz, 1H), 7.24 (d, J=8.5 Hz, 1H), 7.06 (m, 3H), 6.97 (m, 2H), 5.53 (d, J=3.8 Hz, 1H), 5.26 (br s, 1H), 4.20 (m, 1H), 4.05 (m, 2H), 3.50 (s, 3H), 3.34 (dd, J=1.3, 3.9 Hz, 1H), 3.28 (dt, J=5.9, 7.2 Hz, 2H), 3.00 (d, J=9.7 Hz, 1H), 2.75 (t, J=7.2 Hz, 2H), 2.68 (d, J=11.1 Hz, 1H), 1.87 (s, 3H), 1.73 (m, 1H), 1.37 (m, 3H), 0.85 (t, J=7.2 Hz, 3H).

Compound 144: A solution of D-Mannose 143 (4.00 g, 22.20 mmol) in pyridine (40 mL) was treated with dropwise addition of acetic anhydride (40 mL, 424 mmol). After stirring at room temperature under $N_2$ for 16 h, the solution was concentrated. The residue was partitioned between 10% aq. HCl (10 mL) and EtOAc (100 mL). The organic extract was washed with sat. aq. NaCl solution (100 mL); dried with $MgSO_4$; filtered; and concentrated to give compound 144 (9.42 g) as light yellow viscous oil. The compound 144 was used in the next step without further purification.

Compound 145: A mixture of compound 144 (3.77 g, ≤8.88 mmol), compound A1 (2.90 g, 10.61 mmol) and 3 Å molecular sieves (19 g) in dry $CH_2Cl_2$ (50 mL) was stirred at room temperature under $N_2$ for 1 h. A solution of boron trifluoride etherate (9.7 mL, 79.60 mmol) in dry $CH_2Cl_2$ (20 mL) was added. After 16 h, the sample was filtered through a pad of Celite®. The filtrate was concentrated. The residue was cooled; carefully quenched with sat. aq. $NaHCO_3$ (200 mL); and extracted with EtOAc (100 mL). The organic extract was washed with sat. aq. NaCl (100 mL); dried with $MgSO_4$; filtered; and concentrated. The residue was purified by column chromatography (silica gel, eluting with 100% $CHCl_3$ until all unreacted starting material had eluted then 2.5% MeOH in $CHCl_3$) to give compound 145 (3.56, 66% yield from 143) as an off-white foamy solid. m/z=604 (M+1). $^1$H NMR ($CDCl_3$) spectrum is consistent with the structure, mainly as one anomer.

T42: A solution of compound 145 (3.04 g, 5.04 mmol) in MeOH (25 mL) was treated with NaOMe (30 wt % in MeOH, 0.25 mL, 1.33 mmol). The sample was heated at 50° C. under $N_2$ for 4 h; cooled to room temperature; and treated with Amberlite CG-50 ion-exchange weakly acidic (10 meq/g dry) resin (0.75 g, 7.5 meq). The sample was stirred at room temperature for 5 min, and then filtered through a pad of Celite®. The filtrate was concentrated. The residue was purified by column chromatography (silica gel, eluting with 20% MeOH in $CHCl_3$) to give compound T42 (1.38 g, 63% yield) as an off-white solid. m/z=436 (M+1); $^1$H NMR (400 MHz, DMSO-$d_6$) δ 7.82 (t, J=5.6 Hz, 1H), 7.47 (dt, J=6.2, 8.1 Hz, 1H), 7.18 (m, 4H), 7.07 (dd, J=2.7, 8.5 Hz, 1H), 6.89 (d, J=2.7 Hz, 1H), 5.36 (d, J=1.8 Hz, 1H), 5.00 (d, J=4.4 Hz, 1H), 4.83 (d, J=5.5 Hz, 1H), 4.76 (d, J=6.0 Hz, 1H), 4.47 (t, J=5.8 Hz, 1H), 3.81 (ddd, J=1.8, 3.4, 5.0 Hz, 1H), 3.66 (m, 1H), 3.59 (m, 1H), 3.45 (m, 3H), 3.08 (td, J=6.2, 8.1 Hz, 2H), 2.59 (dd, J=6.5, 8.8 Hz, 2H), 1.71 (s, 3H).

Compound 147: A solution of compound 146 (Lin and Kasko, 2013) (1.36 g, 3.90 mmol) and pyridine (0.50 mL, 6.18 mmol) in $CH_2Cl_2$ (40 mL) at −0° C. under $N_2$ was treated with dropwise addition of trifluoromethanesulfonic anhydride (1.0 M in $CH_2Cl_2$, 4.3 mL, 4.3 mmol). The mixture was stirred at 0° C. for 1 h; quenched with sat. aq. $KH_2PO_4$ (50 mL); and stirred at room temperature for 30 min. The organic layer was separated; washed with sat. aq. NaCl (50 mL); dried with $MgSO_4$; filtered; and concentrated. The residue was purified by column chromatography (silica gel, eluting with 25% EtOAc in hexanes) to give compound 147 (1.33 g, 71% yield) as a tan foamy solid.

Compound 148: To a stirring solution of compound 147 (1.33 g, 2.77 mmol) in tert-amyl alcohol (10 mL) was added in one portion solid cesium fluoride (1.26 g, 8.29 mmol). The mixture was heated at 110° C. for 1 h, and then allowed to cool to room temperature. The sample was concentrated. The residue was diluted with EtOAc (50 mL); stirred for 30 min; and then filtered through a pad of Celite®. The filtrate was concentrated, and the residue was purified by column chromatography (silica gel, eluting with 50% EtOAc in hexanes) to give compound 148 (mixture of anomers, 0.55 g, 57% yield) as light-yellow liquid. $^1H$ NMR for major anomer (400 MHz, $CDCl_3$) δ 6.10 (d, J=1.9 Hz, 1H), 5.41-5.33 (m, 2H), 5.26 (t, J=2.3 Hz, 1H), 4.60-4.33 (m, 2H), 4.02 (m, 1H), 2.17 (s, 3H), 2.17 (s, 3H), 2.07 (s, 3H), 2.01 (s, 3H).

Compound 149: A mixture of compound 148 (0.51 g, 1.45 mmol), compound A1 (0.44 g, 1.61 mmol) and 3 Å molecular sieves (2.5 g) in dry $CH_2Cl_2$ (8 mL) was stirred at room temperature under $N_2$ for 1 h. A solution of boron trifluoride etherate (1.5 mL, 12.15 mmol) in dry $CH_2Cl_2$ (5 mL) was added. The mixture was stirred at room temperature for 16 h; cooled; quenched with sat. aq. $NaHCO_3$ (50 mL); and filtered. The organic layer from the filtrate was washed with sat. aq. NaCl (50 mL); dried with $MgSO_4$; filtered; and concentrated. The residue was purified by column chromatography (silica gel, eluting with 2.5% MeOH in $CHCl_3$) to give compound 149 (0.68 g, 83% yield) as a tan foamy solid. m/z=564 (M+1).

T43: A solution of compound 149 (0.66 g, 1.17 mmol) in MeOH (12 mL) was treated with NaOMe (30 wt % solution in MeOH, 53 mg, 0.29 mmol). The sample was stirred at room temperature under $N_2$ for 16 h and concentrated. The residue was purified by column chromatography (silica gel, eluting with 10% MeOH in $CHCl_3$) to give compound T43 (0.30 g, 58% yield) as an off-white foamy solid. m/z=438 (M+1); $^1H$ NMR (400 MHz, DMSO-$d_6$) δ 7.82 (t, J=5.6 Hz, 1H), 7.47 (m, 1H), 7.18 (m, 4H), 7.05 (dd, J=2.7, 8.5 Hz, 1H), 6.87 (d, J=2.6 Hz, 1H), 5.43 (d, J=1.8 Hz, 1H), 5.13 (m, 2H), 4.90 (d, J=6.1 Hz, 1H), 4.57 (m, 1H), 4.45 (m, 1H), 3.83 (ddd, J=1.8, 3.3, 4.4 Hz, 1H), 3.63 (m, 3H), 3.08 (dt, J=5.8, 7.6, 8.3 Hz, 2H), 2.59 (dd, J=6.5, 8.8 Hz, 2H), 1.71 (s, 3H).

Compound 150: A mixture of L-Rhamnose 22 (5.00 g, 30.46 mmol) and scandium(III) trifluoromethanesulfonate (0.15 g, 0.30 mmol) in allyl alcohol (17 mL, 249 mmol) was heated at 100° C. under $N_2$ overnight. The sample was cooled, and concentrated. The residue was purified by column chromatography (silica gel, eluting with 10% MeOH in $CHCl_3$) to give compound 150 (3.14 g, 50% yield) as dark yellow oil.

Compound 151: A solution of compound 150 (3.14 g, 15.40 mmol), 2,2-dimethoxypropane (29 mL, 236 mmol), acetone (3.4 mL, 46.3 mmol) and p-toluenesulfonic acid monohydrate (0.29 g, 1.52 mmol) in $CH_2Cl_2$ (10 mL) was stirred at room temperature under $N_2$ overnight. The sample was concentrated, and the residue was partitioned between sat. aq. $NaHCO_3$ (50 mL) and EtOAc (50 mL). The organic extract was washed with sat. aq. NaCl (50 mL); dried with $MgSO_4$; filtered; and concentrated. The residue was purified by column chromatography (silica gel, eluting with 25% EtOAc in hexanes) to give compound 151 (3.57 g, 95% yield) as dark yellow liquid. $^1H$ NMR (400 MHz, $CDCl_3$) of major anomer δ 5.90 (dddd, J=16.8, 10.4, 6.2, 5.2 Hz, 1H), 5.31 (dq, J=17.2, 1.6 Hz, 1H), 5.22 (dq, J=10.4, 1.3 Hz, 1H), 5.00 (s, 1H), 4.23-4.15 (m, 2H), 4.10 (dd, J=7.2, 5.8 Hz, 1H), 4.00 (ddt, J=12.8, 6.3, 1.3 Hz, 1H), 3.69 (dq, J=9.1, 6.2 Hz, 1H), 3.40 (m, 1H), 2.39 (d, J=4.5 Hz, 1H), 1.52 (s, 3H), 1.35 (s, 3H), 1.29 (d, J=6.3 Hz, 3H). The $^1H$ NMR is consistent with the reported data (Hanaya et al., 2009)

Compound 152: To a stirring solution of compound 151 (3.57 g, 14.61 mmol) in DMF (30 mL) at 0° C. under $N_2$ was added sodium hydride (60% dispersion in mineral oil, 1.75 g, 43.75 mmol) portionwise (over 30 min). After addition, the sample was stirred at room temperature for 1 h; cooled to 0° C.; and then treated with dropwise addition of benzyl chloride (3.4 mL, 29.52 mmol). The sample was stirred at room temperature for 2 h; cooled; and carefully poured into cold sat. aq. $KH_2PO_4$ (100 mL). The mixture was extracted with EtOAc (100 mL). The organic extract was washed with sat. aq. NaCl (100 mL); dried with $MgSO_4$; filtered; and concentrated. The residue was purified by column chromatography (silica gel, eluting with 10% EtOAc in hexanes) to give compound 152 (4.32 g, 89% yield) as dark yellow liquid. $^1H$ NMR (400 MHz, $CDCl_3$) of major anomer δ 7.40-7.27 (m, 5H), 5.90 (dddd, J=16.9, 10.3, 6.2, 5.2 Hz, 1H), 5.29 (dq, J=17.2, 1.6 Hz, 1H), 5.20 (dq, J=10.4, 1.4 Hz, 1H), 5.01 (s, 1H), 4.90 (d, J=11.6 Hz, 1H), 4.62 (d, J=11.6 Hz, 1H), 4.28 (dd, J=7.1, 5.8 Hz, 1H), 4.22-4.13 (m, 2H), 3.98 (ddt, J=12.7, 6.3, 1.3 Hz, 1H), 3.71 (dq, J=9.8, 6.2 Hz, 1H), 3.22 (dd, J=9.9, 7.1 Hz, 1H), 1.51 (s, 3H), 1.37 (s, 3H), 1.28 (d, J=6.2 Hz, 3H).

Compound 153: A mixture of compound 152 (3.71 g, 11.09 mmol) and Dowex® 50W $X_2$ hydrogen resin (6.5 g) in acetronitrile:water (4:1 v/v, 50 mL) was stirred at 45° C. under $N_2$ for 48 h. The sample was cooled, filtered and concentrated to give compound 153 (3.21 g, 98% yield) as a light yellow waxy solid. $^1H$ NMR (400 MHz, $CDCl_3$) of major anomer δ 7.43-7.28 (m, 5H), 5.88 (dddd, J=16.6, 10.5, 6.1, 5.1 Hz, 1H), 5.28 (dq, J=17.2, 1.6 Hz, 1H), 5.18 (dq, J=10.4, 1.4 Hz, 1H), 4.81 (s, 1H), 4.74 (s, 2H), 4.16 (ddt, J=13.0, 5.1, 1.5 Hz, 1H), 4.04-3.86 (m, 3H), 3.75 (m, 1H), 3.35 (m, 1H), 2.34 (m, 2H), 1.35 (d, J=6.3 Hz, 3H).

Compound 154: Step 1. A mixture of compound 153 (3.21 g, 10.90 mmol), tris(triphenylphosphine)rhodium (I) chloride (Wilkinson catalyst; 0.90 g, 0.97 mmol) and 1,4-diazabicyclo[2.2.2]octane (0.55 g, 4.90 mmol) in EtOH: benzene:water (8:3:1 v/v/v, 100 mL) was heated at 80° C. under $N_2$ overnight. The sample was cooled, and concentrated. The residue was partitioned between 1 N aq. HCl (50 mL) and EtOAc (50 mL). The organic extract was washed with sat. aq. NaCl (50 mL); dried with $MgSO_4$; filtered; and concentrated to give a dark yellow-brown oil. Step 2. A mixture of the crude product from Step 1 and 1 N aq. HCl (25 mL) in acetone (100 mL) was heated at 60° C. under $N_2$ for 2 h. The mixture was cooled, and concentrated. The residue was extracted with EtOAc (50 mL). The organic extract was washed with sat. aq. NaCl (50 mL); dried with MgSO$_4$; filtered; and concentrated. The residue was purified by column chromatography (silica gel, eluting with 100% EtOAc) to give compound 154 (2.37 g, 85% yield) as a yellow-orange waxy solid.

Compound 155: A solution of compound 154 (2.32 g, 9.12 mmol) in pyridine (20 mL) was treated with acetic anhydride (13 mL, 138 mmol) at room temperature. After stirring at room temperature under N$_2$ overnight, the sample was concentrated. The residue was partitioned between cold water (50 mL) and EtOAc (50 mL). The organic extract was washed with sat. aq. NaCl (50 mL); dried with MgSO$_4$; filtered; and concentrated. The residue was purified by column chromatography (silica gel, eluting with 50% EtOAc in hexanes) to give compound 155 (2.40 g, 69% yield) as yellow oil. $^1$H NMR (400 MHz, CDCl$_3$) mixture of anomers in 1.6/1 ratio δ 7.41-7.19 (m, 5H), 5.98 (d, J=2.0 Hz, 0.38H), 5.82 (d, J=1.2 Hz, 0.62H), 5.47 (dd, J=3.3, 1.2 Hz, 0.62H), 5.31 (dd, J=9.6, 3.5 Hz, 0.38H), 5.25 (dd, J=3.5, 2.0 Hz, 0.38H), 5.07 (dd, J=9.6, 3.2 Hz, 0.62H), 4.77-4.60 (m, 2H), 3.88 (m, 0.38H), 3.61 (m, 0.38H), 3.53 (m, 1.24H), 2.20 (s, 1.86H), 2.16 (s, 1.14H), 2.13 (s, 1.14H), 2.08 (s, 1.86H), 1.99 (d, 1.14H), 1.97 (s, 1.86H), 1.40 (d, J=6.0 Hz, 1.86H), 1.35 (d, J=6.2 Hz, 1.14H).

Compound 156: A mixture of compound 155 (1.89 g, 4.97 mmol), compound A1 (1.50 g, 5.49 mmol) and 3 Å molecular sieves (~9.5 g) in dry CH$_2$Cl$_2$ (25 mL) was stirred at room temperature under N$_2$ for 1 h. Boron trifluoride etherate (5.0 mL, 40.51 mmol) was added dropwise. The mixture was stirred at room temperature for 16 h; cooled; quenched with sat. aq. NaHCO$_3$ (200 mL); and filtered. The organic extract from the filtrate was washed with sat. aq. NaCl (50 mL); dried with MgSO$_4$; filtered; and concentrated. The residue was purified by column chromatography (silica gel, eluting with 2.5% MeOH in CHCl$_3$) to give compound 156 (1.68 g, 57% yield) as a light yellow foamy solid. m/z=594 (M+1).

T44: A solution of compound 156 (1.41 g, 2.37 mmol) in MeOH (25 mL) was treated with NaOMe (30 wt. % in MeOH, 0.11 mL, 0.59 mmol). The sample was stirred at room temperature under N$_2$ for 16 h, and concentrated. The residue was partitioned between EtOAc (50 mL) and sat. aq. KH$_2$PO$_4$ (50 mL). The organic extract was washed with sat. aq. NaCl (50 mL); dried with MgSO$_4$; filtered; and concentrated. The residue was purified by column chromatography (silica gel, eluting with 5% MeOH in CHCl$_3$) to give compound T44 (0.96 g, 79% yield) as an off-white foamy solid. m/z=510 (M+1); $^1$H NMR (400 MHz, DMSO-d$_6$) δ 7.81 (t, J=5.6 Hz, 1H), 7.47 (dt, J=6.2, 8.1 Hz, 1H), 7.25 (m, 9H), 7.03 (dd, J=2.7, 8.5 Hz, 1H), 6.83 (d, J=2.7 Hz, 1H), 5.39 (m, 1H), 5.23 (d, J=4.3 Hz, 1H), 5.00 (d, J=4.3 Hz, 1H), 4.88 (d, J=11.4 Hz, 1H), 4.59 (d, J=11.5 Hz, 1H), 3.84 (m, 2H), 3.58 (qd, J=6.2, 9.3 Hz, 1H), 3.35 (t, J=9.1 Hz, 1H), 3.08 (td, J=6.1, 8.2 Hz, 2H), 2.59 (dd, J=6.5, 8.8 Hz, 2H), 1.70 (s, 3H), 1.10 (d, J=6.2 Hz, 3H).

Compound 157: Compound 13 (1 g, 4.95 mmol) was dissolved in THF (10 mL). Isobutyl magnesium bromide (2M in ether, 3.15 mL, 6.30 mmol) was added dropwise at room temperature, and stirred for 16 h. The reaction was neutralized by addition of sat. aq. NH$_4$Cl and was extracted with ethyl acetate. The organic extract was washed with water; dried with MgSO$_4$; filtered and concentrated. The residue was purified by column chromatography (silica gel, eluting with 0% to 30% EtOAc in hexanes) to give compound 157 (0.8 g, 62% yield) as an oil. m/z=243 (M-OH).

Compound 158: A solution of NaBH$_4$ (200 mg, 5.16 mmol) in MeOH (5 mL) was added to a solution of compound 157 (1.3 g, 4.99 mmol) in EtOH (15 mL) at 0° C. The reaction was stirred at room temperature overnight; quenched with acetic acid (310 mg, 5.16 mmol); and concentrated. The residue was extracted with ethyl acetate. The organic extract was washed with water; dried with MgSO$_4$; filtered and concentrated to give compound 158 (1.1 g, 84% yield) as an oil. m/z=263 (M+1).

Compound 159 and 160: Compound 158 (920 mg, 3.51 mmol) was taken up in CH$_2$Cl$_2$ (15 mL) at 0° C. Et$_3$N (1.1 g, 10.5 mmol) was added, followed by tert-butyldimethylsilyl chloride (530 mg, 3.52 mmol) and DMAP (15 mg, 0.12 mmol). The reaction was stirred at room temperature overnight; and quenched with sat. aq. NaHCO$_3$ (25 mL). The mixture was extracted with EtOAc. The organic extract was washed with brine; dried with MgSO$_4$; filtered and concentrated. The residue was purified by column chromatography (silica gel, eluting with 0% to 30% EtOAc in hexanes) to give compound 159 (0.51 g, 39% yield) and compound 160 (0.46 g, 35% yield). 159: m/z=319 (M-t-Bu); 160: m/z=319 (M-t-Bu).

Compound 161: Compound 159 (0.51 g, 1.35 mmol) was dissolved in THF (5 mL). TBAF (1M in THF, 1.5 mL, 1.5 mmol) was added dropwise at room temperature. The mixture was stirred at room temperature overnight; quenched by addition of sat. aq. NH$_4$Cl; and extracted with ethyl acetate. The organic extract was washed with water; dried with MgSO$_4$; filtered and concentrated. The residue was purified by column chromatography (silica gel, eluting with 0% to 50% EtOAc in hexanes) to give compound 161 (0.36 g, quantitative yield) as an oil. m/z=245 (M-OH).

Compound 162: Compound 161 (0.37 g, 1.41 mmol) was taken up in CH$_2$Cl$_2$ (5 mL). PhI(OAc)$_2$ (1.4 g, 4.35 mmol) and TEMPO (45 mg, 0.29 mmol) were added at room temperature. After stirring at room temperature for 6 h, the reaction was quenched by addition of sat. aq. Na$_2$S$_2$O$_3$ (25 mL) and extracted with ethyl acetate. The organic extract was washed with water; dried with MgSO$_4$; filtered and concentrated. The residue was purified by column chromatography (silica gel, eluting with 0% to 30% EtOAc in hexanes) to give compound 162 (0.32 g, 88% yield) as an oil. m/z=259 (M+1).

Compound 163: Compound 162 (320 mg, 1.24 mmol) was taken up in CH$_2$Cl$_2$ (5 mL) and cooled to 0° C. DIBAL-H (1.2 M in toluene, 1.3 mL, 1.56 mmol) was added dropwise. The reaction was stirred at room temperature for 5 h; quenched with sat. aq. potassium sodium tartrate (25 mL); and extracted with EtOAc. The organic extract was washed with brine; dried with MgSO$_4$; filtered and concentrated to give compound 163 (315 mg, 98% yield) as a solid. m/z=243 (M-OH).

Compound 164: Compound 163 (0.31 g, 1.19 mmol) was taken up in MeCN (4 mL) and water (1 mL). AG50X-W2 (H+ resin, 350 mg) was added. The mixture was stirred at 40° C. for 16 h; and filtered. The resin was washed with acetonitrile/water (4:1 v/v, 25 mL). The combined filtrate and wash were concentrated and dried under a high vacuum pump at 40° C. to give compound 164 (0.26 g, quantitative yield) as a foam. m/z=203 (M-OH).

Compound 165: Compound 164 (0.25 g, 1.13 mmol) was dissolved in pyridine (5 mL) and cooled to 0° C. BzCl (800 mg, 5.69 mmol) was added dropwise and stirred at room temperature overnight. EtOAc (50 mL) was added. The mixture was washed with 1 N aq. HCl. The organic layer was washed with water; dried with MgSO$_4$; filtered and concentrated. The residue was purified by column chromatography (silica gel, eluting with 0% to 20% EtOAc in hexanes) to give compound 165 (0.52 g, 86% yield) as a foam. m/z=411 (M-OBz).

Compound 166: Compound 165 (520 mg, 0.98 mmol), compound A1 (270 mg, 0.99 mmol) and 4 Å molecular sieve (500 mg) in anhydrous $CH_2Cl_2$ (10 mL) were stirred at room temperature for 15 min Boron trifluoride etherate (430 mg, 3.03 mmol) was added dropwise. The mixture was stirred at room temperature for 2 h; cooled to 0° C.; quenched with sat. aq. $NaHCO_3$ (10 mL); stirred for 5 min; and extracted with EtOAc. The organic extract was dried with $MgSO_4$; filtered and concentrated. The residue was purified by column chromatography (silica gel, eluting with 0%-75% EtOAc in hexanes) to give compound 166 (410 mg, 62% yield) as a foam. m/z=684 (M+1).

T45 and T46: Compound 166 (410 mg, 0.60 mmol) was dissolved in EtOH (2 mL). 1N aq. NaOH (6 mL, 6 mmol) was added at room temperature. After the reaction was stirred at room temperature for 2 h, EtOAc (50 mL) was added. The mixture was washed with water. The organic layer was dried with $MgSO_4$, filtered and concentrated. The residue was purified by column chromatography (silica gel, eluting with 0% to 5% MeOH in $CHCl_3$) to give compound T45 (white foam, 75 mg, 26% yield) and T46 (white foam, 100 mg, 35% yield). T45: =476 (M+1); $^1$H NMR (400 MHz, $CDCl_3$) δ 7.38 (dt, J=5.9, 8.0 Hz, 1H), 7.23 (m, 1H), 7.05 (m, 3H), 6.97 (m, 2H), 5.56 (d, J=3.8 Hz, 1H), 5.25 (br s, 1H), 4.18 (m, 2H), 4.04 (td, J=3.8, 10.8 Hz, 1H), 3.49 (s, 3H), 3.28 (m, 3H), 3.02 (d, J=9.7 Hz, 1H), 2.75 (m, 2H), 2.66 (d, J=10.8 Hz, 1H), 1.87 (s, 3H), 1.78 (ddd, J=5.0, 9.8, 14.2, 1H), 1.68 (m, 1H), 1.17 (m, 1H), 0.88 (d, J=6.6 Hz, 3H), 0.69 (d, J=6.5 Hz, 3H); T46: =476 (M+1); $^1$H NMR (400 MHz, $CDCl_3$) δ 7.37 (dt, J=5.9, 7.9 Hz, 1H), 7.19 (d, J=8.4 Hz, 1H), 7.06 (m, 2H), 6.97 (m, 2H), 6.90 (d, J=2.7 Hz, 1H), 5.26 (br s, 1H), 5.19 (d, J=8.0 Hz, 1H), 4.34 (dt, J=1.2 3.4 Hz, 1H), 4.04 (ddd, J=1.4, 3.5, 10.4 Hz, 1H), 3.94 (td, J=3.2, 8.0 Hz, 1H), 3.48 (s, 3H), 3.27 (q, J=7.2 Hz, 2H), 3.20 (dd, J=1.3, 3.5 Hz, 1H), 2.74 (dt, J=1.7, 7.1 Hz, 2H), 2.63 (br s, 1H), 2.56 (br s, 1H), 1.88 (m, 1H), 1.87 (s, 3H), 1.74 (m, 1H), 1.15 (ddd, J=3.4, 9.3, 14.0 Hz, 1H), 0.89 (d, J=6.7 Hz, 3H), 0.81 (d, J=6.5 Hz, 3H).

Compound 167: Compound 160 (1.46 g, 3.87 mmol) was dissolved in THF (15 mL). TBAF (1M in THF, 4 mL, 4 mmol) was added dropwise. The mixture was stirred at room temperature overnight. Sat. aq. $NH_4Cl$ was added, and the mixture was extracted with ethyl acetate. The organic extract was washed with water; dried with $MgSO_4$; filtered and concentrated. The residue was purified by column chromatography (silica gel, eluting with 0% to 50% EtOAc in hexanes) to give compound 167 (1.02 g, quantitative yield) as an oil. m/z=245 (M-OH).

Compound 168: Compound 167 (1.02 g, ≤3.87 mmol) was taken up in $CH_2Cl_2$ (10 mL). $PhI(OAc)_2$ (3.75 g, 11.65 mmol) and TEMPO (125 mg, 0.80 mmol) were added. The mixture was stirred at room temperature for 6 h; quenched by addition of sat. aq. $Na_2S_2O_3$ (35 mL); and extracted with ethyl acetate. The organic extract was washed with water; dried with $MgSO_4$; filtered and concentrated. The residue was purified by column chromatography (silica gel, eluting with 0% to 30% EtOAc in hexanes) to give compound 168 (0.69 g, 69% yield) as an oil. m/z=259 (M+1).

Compound 169: Compound 168 (690 mg, 2.67 mmol) was taken up in $CH_2Cl_2$ (10 mL) at 0° C. DIBAL-H (1.2 M in toluene, 2.7 mL, 3.24 mmol) was added dropwise. The reaction was stirred at room temperature for 5 h; quenched with sat. aq. potassium sodium tartrate (Rochelle's salt, 35 mL); and extracted with EtOAc. The organic extract was washed with brine; dried with $MgSO_4$; filtered and concentrated to give compound 169 (680 mg, 98% yield) as a solid. m/z=243 (M-OH).

Compound 170: Compound 169 (0.68 g, 2.61 mmol) was taken up in MeCN (4 mL) and water (1 mL). AG50X-W2 (H+ resin, 700 mg) was added. The mixture was stirred at 40° C. for 16 h and filtered. The resin was washed with acetonitrile/water (4:1 v/v, 25 mL). The filtrates was concentrated and dried under high vacuum at 40° C. to give compound 170 (0.57 g, 99% yield) as a foam. m/z=221 (M+1).

Compound 171: Compound 170 (0.57 g, 2.59 mmol) was dissolved in pyridine (10 mL) and cooled to 0° C. Benzoyl chloride (1.8 g, 12.81 mmol) was added dropwise and stirred at room temperature overnight. The reaction solvent was removed by distillation under vacuo. The residue was diluted with EtOAc (50 mL), and the mixture was washed with 1 N aq. HCl. The organic layer was washed with water; dried with $MgSO_4$; filtered and concentrated. The residue was purified by column chromatography (silica gel, eluting with 0% to 20% EtOAc in hexanes) to give compound 171 (1.3 g, 93% yield) as a foam. m/z=411 (M-OBz).

Compound 172: A mixture of compound 171 (1.29 g, 2.42 mmol), compound A1 (665 mg, 2.40 mmol) and 4 Å molecular sieve (1.5 g) in anhydrous $CH_2Cl_2$ (15 mL) was stirred at room temperature for 15 min. Boron trifluoride diethyl etherate (1.1 g, 7.75 mmol) was added dropwise at room temperature. The mixture was stirred at room temperature for 2 h; cooled to 0° C.; quenched with sat. aq. $NaHCO_3$ (15 mL); stirred for 5 min; and extracted with EtOAc. The organic extract was dried with $MgSO_4$; filtered and concentrated. The residue was purified by column chromatography (silica gel, eluting with 0% to 75% EtOAc in hexanes) to give compound 172 (1.01 g, 61% yield) as a foam. m/z=684 (M+1).

T47: Compound 172 (1.01 g, 1.47 mmol) was dissolved in EtOH (10 mL). 1N aq. NaOH (7 mL, 7 mmol) was added at room temperature. The mixture was stirred at room temperature for 2 h. EtOAc (100 mL) was added. The mixture was washed with water. The organic layer was dried with $MgSO_4$; filtered and concentrated. The residue was purified by column chromatography (silica gel, eluting with 0% to 5% MeOH in $CHCl_3$) to give compound T47 (605 mg, 86% yield) as a white foam. m/z=476 (M+1); $^1$H NMR (400 MHz, $CDCl_3$) δ 7.37 (dt, J=5.9, 8.0 Hz, 1H), 7.20 (d, J=8.5 Hz, 1H), 7.03 (m, 3H), 6.95 (ddd, J=1.7, 2.6, 9.6 Hz, 1H), 6.91 (d, J=2.7 Hz, 1H), 5.54 (d, J=1.7 Hz, 1H), 5.24 (br s, 1H), 4.14 (m, 1H), 4.06 (m, 1H), 3.64 (dt, J=3.3, 9.7 Hz, 1H), 3.57 (s, 3H), 3.26 (dt, J=5.8, 7.2 Hz, 2H), 3.15 (t, J=9.4 Hz, 1H), 2.73 (dt, J=1.7, 7.1 Hz, 2H), 2.56 (m, 2H), 1.86 (s, 3H), 1.72 (m, 1H), 1.48 (m, 2H), 0.85 (d, J=6.7 Hz, 3H), 0.52 (d, J=6.5 Hz, 3H).

Compound 173: Compound 157 (1.8 g, 6.91 mmol) was taken up in $CH_2Cl_2$ (15 mL) at 0° C. $Et_3N$ (2.1 g, 20.79 mmol), tert-butyldimethylsilyl chloride (1.15 g, 7.63 mmol) and DMAP (25 mg, 0.20 mmol) were added sequentially. The reaction was stirred at room temperature overnight; quenched with sat. aq. $NaHCO_3$ (35 mL); and extracted with EtOAc. The organic extract was washed with brine; dried with $MgSO_4$; filtered and concentrated. The residue was purified by column chromatography (silica gel, eluting with 0% to 30% EtOAc in hexanes) to give compound 173 (1.58 g, 61% yield). m/z=375 (M+1).

Compound 174: Compound 173 (1.58 g, 4.21 mmol) was dissolved in THF (10 mL). Isobutyl magnesium bromide (2M in ether, 3.5 mL, 7 mmol) was added dropwise at room temperature. The mixture was stirred for 16 h; neutralized by addition of sat. aq. $NH_4Cl$; and was extracted with ethyl acetate. The organic extract was washed with water; dried with MgSO$_4$; filtered and concentrated to give compound 174 (1.68 g, 92% yield) as an oil.

Compound 175: Compound 174 (1.68 g, 3.88 mmol) was dissolved in THF (15 mL). TBAF (1M in THF, 5 mL, 5 mmol) was added dropwise at room temperature. The mixture was stirred at room temperature overnight. Sat. aq. NH$_4$Cl was added; and the mixture was extracted with ethyl acetate. The organic extract was washed with water; dried with MgSO$_4$; filtered and concentrated. The residue was purified by column chromatography (silica gel, eluting with 0% to 50% EtOAc in hexanes) to give a compound 175 (0.83 g, 67% yield) as a solid.

Compound 176: Compound 175 (0.79 g, 2.48 mmol) was taken up in CH$_2$Cl$_2$ (10 mL). PhI(OAc)$_2$ (2.4 g, 7.5 mmol) and TEMPO (80 mg, 0.5 mmol) were added, stirred at room temperature for 16 h. The reaction was quenched by addition of sat. Na$_2$S$_2$O$_3$ (35 mL) and extracted with ethyl acetate. The organic extracts were washed with water, then dried with MgSO$_4$, concentrated, and purified by column chromatography (silica gel, 0 to 30% EtOAc in hexanes) to give compound 176 (0.58 g, 74% yield) as a solid. m/z=315 (M+1).

Compound 177: Compound 176 (580 mg, 1.84 mmol) was taken up in CH$_2$Cl$_2$ (10 mL) at 0° C. DIBAL-H (1.2 M in toluene, 2 mL, 2.4 mmol) was added dropwise. The reaction was stirred at room temperature for 5 h; quenched with sat. aq. potassium sodium tartrate (Rochelle's salt, 35 mL); and extracted with EtOAc. The organic extract was washed with brine; dried with MgSO$_4$; filtered and concentrated to give compound 177 (580 mg, quantitative yield) as an oil. m/z=299 (M-OH).

Compound 178: Compound 177 (0.58 g, 1.83 mmol) was taken up in MeCN (4 mL) and water (1 mL). AG50X-W2 (H+ resin, 650 mg) was added. The mixture was stirred at 40° C. for 16 h; cooled; and filtered. The resin was washed with acetonitrile/water (4:1 v/v, 25 mL). The filtrate was concentrated and dried under high vacuum at 40° C. to give compound 178 (0.51 g, quantitative yield) as a foam. m/z=241 (M-2H$_2$O+1).

Compound 179: Compound 178 (0.51 g, 1.83 mmol) was dissolved in pyridine (10 mL) and cooled to 0° C. Benzoyl chloride (1.3 g, 9.25 mmol) was added dropwise. The mixture was stirred at room temperature overnight, and concentrated. The residue was diluted with EtOAc (50 mL); and washed with 1 N aq. HCl and water. The organic extract was dried with MgSO$_4$; filtered and concentrated. The residue was purified by column chromatography (silica gel, eluting with 0% to 20% EtOAc in hexanes) to give compound 179 (1 g, 93% yield) as a foam. m/z=467 (M-OBz).

Compound 180: A mixture of compound 179 (1 g, 1.70 mmol), compound A1 (465 mg, 1.70 mmol) and 4 Å molecular sieve (1.5 g) in anhydrous CH$_2$Cl$_2$ (15 mL) was stirred at room temperature for 15 min Boron trifluoride diethyl etherate (950 mg, 6.69 mmol) was added dropwise. The mixture was stirred at room temperature for 2 h; cooled to 0° C.; quenched with sat. aq. NaHCO$_3$ (15 mL); stirred for 5 min; and extracted with EtOAc. The organic extract was dried with MgSO$_4$; filtered and concentrated. The residue was purified by column chromatography (silica gel, eluting with 0% to 75% EtOAc in hexanes) to give compound 180 (0.25 g, 20% yield) as a foam. m/z=740 (M+1).

T48: Compound 180 (0.25 g, 0.33 mmol) was dissolved in EtOH (2 mL). 1 N aq. NaOH (2 mL, 2 mmol) was added at room temperature. The mixture was stirred for 2 h at room temperature. EtOAc (50 mL) was added. The mixture was washed with water. The organic layer was dried with MgSO$_4$; filtered and concentrated. The residue was purified by column chromatography [silica gel, eluting with 0% to 5% MeOH in CH$_2$Cl$_2$/EtOAc (1/1, v/v)] to give compound T48 (60 mg, 34% yield) as a white foam. m/z=532 (M+1); $^1$H NMR (400 MHz, CDCl$_3$) δ 7.38 (dt, J=6.0, 8.0 Hz, 1H), 7.19 (d, J=8.5 Hz, 1H), 7.03 (m, 4H), 6.86 (d, J=2.6 Hz, 1H), 5.50 (d, J=3.2 Hz, 1H), 5.22 (br s, 1H), 4.27 (td, J=3.3, 8.2 Hz, 1H), 4.10 (q, J=3.1 Hz, 1H), 3.60 (d, J=8.3 Hz, 1H), 3.54 (s, 3H), 3.26 (dt, J=5.8, 7.2 Hz, 2H), 2.74 (t, J=7.2 Hz, 2H), 2.54 (m, 2H), 1.86 (s, 3H), 1.71 (m, 6H), 1.03 (d, J=6.4 Hz, 3H), 0.93 (d, J=6.6 Hz, 3H), 0.87 (d, J=6.2 Hz, 3H), 0.63 (d, J=6.3 Hz, 3H).

Compound 181: Compound 13 (2 g, 9.89 mmol) was dissolved in THF (15 mL). Allyl magnesium bromide (1 M in ether, 10.25 mL, 10.25 mmol) was added dropwise at room temperature. The mixture was stirred at room temperature for 16 h; quenched by addition of sat. aq. NH$_4$Cl; and was extracted with ethyl acetate. The organic extract was washed with water; dried with MgSO$_4$; filtered and concentrated to give compound 181 (2.27 g, 93% yield) as an oil. m/z=227 (M-OH).

Compound 182: A solution of NaBH$_4$ (360 mg, 9.51 mmol) in MeOH (5 mL) was added to a 0° C. solution of compound 181 (2.27 g, 9.29 mmol) in EtOH (15 mL). The reaction was stirred at room temperature overnight; quenched with acetic acid (550 mg, 9.16 mmol); and concentrated. The residue was diluted with ethyl acetate; washed with water; dried with MgSO$_4$; filtered and concentrated to give compound 182 (2.3 g, quantitative yield) as an oil. m/z=229 (M-OH).

Compound 183 and 184: Compound 182 (2.3 g, ≤9.29 mmol) was taken up in CH$_2$Cl$_2$ (15 mL) at 0° C. Et$_3$N (2.8 g, 27.65 mmol), tert-butyldimethylsilyl chloride (1.55 g, 10.28 mmol) and DMAP (25 mg, 0.20 mmol) were added sequentially. The reaction was stirred at room temperature overnight; quenched with sat. aq. NaHCO$_3$ (25 mL); and extracted with EtOAc. The organic extract was washed with brine; dried with MgSO$_4$; filtered and concentrated. The residue was purified by column chromatography (silica gel, eluting with 0% to 30% EtOAc in hexanes) to give compound 183 (1.1 g, 33% yield) and compound 184 (1.4 g, 42% yield). 183: m/z=303 (M-t-Bu); 184: m/z=303 (M-t-Bu).

Compound 185: Compound 183 (1.1 g, 3.05 mmol) was dissolved in THF (10 mL). TBAF (1 M in THF, 3 mL, 3 mmol) was added dropwise. The mixture was stirred at room temperature overnight. Sat. aq. NH$_4$Cl and extracted with ethyl acetate. The organic extract was washed with water; dried with MgSO$_4$; filtered and concentrated to give compound 185 (0.74 g, quantitative yield) as an oil. m/z=229 (M-OH).

Compound 186: Compound 185 (0.74 g, 3.01 mmol) was taken up in CH$_2$Cl$_2$ (10 mL). PhI(OAc)$_2$ (3 g, 9.31 mmol) and TEMPO (100 mg, 0.64 mmol) were added. The mixture was stirred at room temperature for 16 h; quenched by addition of sat. aq. Na$_2$S$_2$O$_3$ (25 mL); and extracted with ethyl acetate. The organic extract was washed with water; dried with MgSO$_4$;

filtered and concentrated. The residue was purified by column chromatography (silica gel, eluting with 0% to 30% EtOAc in hexanes) to give compound 186 (0.48 g, 66% yield) as an oil. m/z=243 (M+1).

Compound 187: Compound 186 (480 mg, 1.98 mmol) was taken up in CH$_2$Cl$_2$ (10 mL) at 0° C. DIBAL-H (1.2 M in toluene, 2 mL, 2.4 mmol) was added dropwise. The reaction was stirred at room temperature for 5 h; quenched with sat. aq. potassium sodium tartrate (25 mL); and extracted with EtOAc. The organic extract was washed with brine; dried with MgSO$_4$; filtered and concentrated to give compound 187 (470 mg, 97% yield) as a solid. m/z=227 (M-OH).

Compound 188: Compound 187 (0.47 g, 1.92 mmol) was taken up in MeCN (4 mL) and water (1 mL). AG50X-W2 (H+ resin, 500 mg) was added. The mixture was stirred at 40° C. for 16 h; cooled; and filtered. The resin was washed with acetonitrile/water (4:1 v/v, 25 mL). The filtrate was concentrated and dried under high vacuum at 40° C. to give compound 188 (0.34 g, 87% yield) as a foam. m/z=187 (M-OH).

Compound 189: Compound 188 (0.34 g, 1.67 mmol) was dissolved in pyridine (5 mL) and cooled to 0° C. Benzoyl chloride (800 mg, 5.65 mmol) were added dropwise and stirred at room temperature overnight. The reaction solvent was removed by distillation under vacuo. EtOAc (50 mL) was added, the mixture was washed with 1 N aq. HCl. The organic layer was washed with water; dried with MgSO$_4$; filtered and concentrated. The residue was purified by column chromatography (silica gel, eluting with 0% to 20% EtOAc in hexanes) to give compound 189 (0.6 g, 70% yield) as a foam. m/z=395 (M-OBz).

Compound 190: Compound 189 (600 mg, 1.16 mmol), compound A1 (315 mg, 1.15 mmol) and 4 Å molecular sieve (800 mg) in anhydrous CH$_2$Cl$_2$ (10 mL) were stirred at room temperature for 15 min Boron trifluoride diethyl etherate (660 mg, 4.65 mmol) was added dropwise. The mixture was stirred at room temperature for 2 h; cooled to 0° C.; quenched with sat. aq. NaHCO$_3$ (15 mL); stirred for 5 min; and extracted with EtOAc. The organic extract was dried with MgSO$_4$; filtered and concentrated. The residue was purified by column chromatography (silica gel, eluting with 0% to 75% EtOAc in hexanes) to give compound 190 (300 mg, 39% yield) as a foam. m/z=668 (M+1).

T49 and T50: Compound 190 (300 mg, 0.45 mmol) was dissolved in EtOH (2 mL). 1 N aq. NaOH (2.5 mL, 2.5 mmol) was added at room temperature. After the reaction was stirred at room temperature for 2 h, EtOAc (50 mL) was added. The mixture was washed with water. The organic layer was dried with MgSO$_4$; filtered and concentrated. The residue was purified by column chromatography (silica gel, eluting with 0% to 5% MeOH in CHCl$_3$) to give compound T49 (white foam, 60 mg, 29% yield) and T50 (white foam, 40 mg, 20% yield). T49: m/z=460 (M+1); $^1$H NMR (400 MHz, CDCl$_3$) δ 7.38 (dt, J=5.9, 7.9 Hz, 1H), 7.20 (d, J=8.5 Hz, 1H), 7.01 (m, 4H), 6.91 (d, J=2.7 Hz, 1H), 5.79 (m, 1H), 5.27 (br s, 1H), 5.18 (d, J=8.0 Hz, 1H), 5.11 (m, 1H), 5.00 (m, 1H), 4.35 (t, J=3.4 Hz, 1H), 4.02 (m, 1H), 3.95 (dd, J=3.3, 8.0 Hz, 1H), 3.48 (s, 3H), 3.28 (m, 3H), 2.74 (m, 2H), 2.56 (m, 3H), 2.33 (m, 1H), 1.87 (s, 3H); T50: =460 (M+1); $^1$H NMR (400 MHz, CDCl$_3$) δ 7.38 (dt, J=6.0, 8.0 Hz, 1H), 7.24 (d, J=8.5 Hz, 1H), 7.07 (m, 3H), 6.98 (m, 2H), 5.70 (m, 1H), 5.50 (d, J=3.8 Hz, 1H), 5.28 (br s, 1H), 5.10 (m, 1H), 5.00 (m, 1H), 4.18 (m, 2H), 4.04 (td, J=3.8, 10.9 Hz, 1H), 3.49 (s, 3H), 3.38 (dd, J=1.5, 3.7 Hz, 1H), 3.27 (m, 2H), 2.98 (d, J=9.7 Hz, 1H), 2.75 (t, J=7.2 Hz, 2H), 2.69 (d, J=10.9 Hz, 1H), 2.47 (ddd, J=6.5, 8.0, 14.4 Hz, 1H), 2.35 (ddd, J=6.3, 7.6, 14.1 Hz, 1H), 1.88 (s, 3H).

T40: Ozone gas was bubbled through a solution of compound T50 (97 mg, 0.21 mmol) in CH$_2$Cl$_2$:MeOH (1:1 v/v, 15 mL) at −78° C. until a blue color remained (15 min). N$_2$ was bubbled through the solution until the blue color disappeared. Sodium borohydride (20 mg, 0.53 mmol) was added in one portion. The cold bath was removed. The sample was stirred at room temperature under N$_2$ for 1 h and then concentrated. The residue was partitioned between EtOAc (25 mL) and sat. aq. KH$_2$PO$_4$ (25 mL). The organic extract was washed with sat. aq. NaCl solution (25 mL); dried with MgSO$_4$; filtered; and concentrated. The residue was purified by column chromatography (silica gel, eluting with 10% MeOH in CHCl$_3$) to give compound T40 (45 mg, 45% yield) as an off-white solid. m/z=464 (M+1); $^1$H NMR (400 MHz, CDCl$_3$) δ 7.38 (dt, J=6.0, 8.0 Hz, 1H), 7.22 (d, J=8.4 Hz, 1H), 7.04 (m, 4H), 6.93 (d, J=2.7 Hz, 1H), 5.66 (d, J=3.8 Hz, 1H), 5.47 (br s, 1H), 4.32 (m, 1H), 4.22 (br s, 1H), 4.06 (br s, 1H), 3.62 (dd, J=4.5, 6.8 Hz, 2H), 3.50 (s, 3H), 3.48 (d, J=14.2 Hz, 1H), 3.35 (m, 1H), 3.31 (m, 1H), 3.20 (qd, J=6.3, 13.0 Hz, 1H), 3.02 (br d, J=9.4 Hz, 1H), 2.75 (m, 3H), 2.00 (m, 1H), 1.84 (s, 3H), 1.66 (m, 1H).

T41: Ozone gas was bubbled through a solution of compound T49 (146 mg, 0.32 mmol) in CH$_2$Cl$_2$:MeOH (1:1 v/v, 20 mL) at ca. −78° C. until a blue color remained (15 min). N$_2$ was bubbled through the solution until the blue color disappeared. Solid sodium borohydride (30 mg, 0.79 mmol) was added in one portion. The dry ice-acetone bath was removed. The sample was stirred at room temperature under N$_2$ for 1 h, and concentrated. The residue was partitioned between EtOAc (25 mL) and sat. aq. KH$_2$PO$_4$ (25 mL). The organic extract was washed with sat. aq. NaCl solution (25 mL); dried with MgSO$_4$; filtered; and concentrated. The residue was purified by column chromatography (silica gel, eluting with 10% MeOH in CHCl$_3$) to give compound T41 (69 mg, 47% yield) as an off-white foamy solid. m/z=464 (M+1); $^1$H NMR (400 MHz, CDCl$_3$) δ 7.37 (dt, J=6.0, 8.0 Hz, 1H), 7.19 (d, J=8.4 Hz, 1H), 7.03 (m, 4H), 6.89 (d, J=2.6 Hz, 1H), 5.50 (br s, 1H), 5.28 (d, J=8.0 Hz, 1H), 4.35 (t, J=3.4 Hz, 1H), 4.22 (ddd, J=1.4, 3.4, 10.3 Hz, 1H), 3.94 (m, 1H), 3.74 (t, J=5.6 Hz, 2H), 3.49 (s, 3H), 3.26 (m, 3H), 2.83 (br s, 2H), 2.74 (t, J=6.9 Hz, 2H), 2.13 (tdd, J=5.6, 10.8, 15.6 Hz, 1H), 1.96 (br s, 1H), 1.85 (s, 3H), 1.69 (m, 1H).

Compound 191: Compound 184 (1.4 g, 3.88 mmol) was dissolved in THF (15 mL). TBAF (1 M in THF, 4 mL, 4 mmol) was added dropwise at room temperature. The mixture was stirred at room temperature overnight. Sat. aq. NH$_4$Cl was added. The mixture was extracted with ethyl acetate. The organic extract was washed with water; dried with MgSO$_4$; filtered and concentrated to give compound 191 (0.96 g, quantitative yield) as an oil. m/z=229 (M-OH).

Compound 192: Compound 191 (0.96 g, 3.88 mmol) was taken up in CH$_2$Cl$_2$ (10 mL). PhI(OAc)$_2$ (3.75 g, 11.65 mmol) and TEMPO (125 mg, 0.80 mmol) were added. The mixture was stirred at room temperature for 6 h; quenched by addition of sat. aq. Na$_2$S$_2$O$_3$ (35 mL); and extracted with ethyl acetate. The organic extract was washed with water; dried with MgSO$_4$, filtered and concentrated. The residue was purified by column chromatography (silica gel, eluting with 0% to 30% EtOAc in hexanes) to give compound 192 (0.59 g, 63% yield) as a soft solid. m/z=243 (M+1).

Compound 193: Compound 192 (590 mg, 2.43 mmol) was taken up in CH$_2$Cl$_2$ (10 mL) at 0° C. DIBAL-H (1.2 M in toluene, 2.5 mL, 3.0 mmol) was added dropwise. The reaction was stirred at room temperature for 5 h; quenched with sat. aq. potassium sodium tartrate (Rochelle's salt, 35 mL); and extracted with EtOAc. The organic extract was washed with brine; dried with MgSO$_4$; filtered and concentrated to give compound 193 (590 mg, quantitative yield) as a solid. m/z=227 (M-OH).

Compound 194: Compound 193 (0.59 g, 2.41 mmol) was taken up in MeCN (4 mL) and water (1 mL). AG50X-W2 (H+ resin, 700 mg) was added. The mixture was stirred at 40° C. for 16 h; cooled; and filtered. The resin was washed with acetonitrile/water (4:1 v/v, 25 mL). The filtrate was concentrated and dried under high vacuum at 40° C. to give compound 194 (0.46 g, 93% yield) as a foam. m/z=187 (M-OH).

Compound 195: Compound 194 (0.46 g, 2.25 mmol) was dissolved in pyridine (10 mL) and cooled to 0° C. Benzoyl chloride (1.6 g, 11.38 mmol) was added dropwise. The mixture was stirred at room temperature overnight; and concentrated under vacuo. The residue was diluted with EtOAc (50 mL); and washed with 1 N aq. HCl and water. The residue was dried with $MgSO_4$; filtered and concentrated. The residue was purified by column chromatography (silica gel, eluting with 0% to 20% EtOAc in hexanes) to give compound 195 (0.9 g, 78% yield) as a foam. m/z=395 (M-OBz).

Compound 196: A mixture of compound 195 (0.9 g, 1.74 mmol), compound A1 (500 mg, 1.83 mmol) and 4 Å molecular sieve (1.2 g) in anhydrous $CH_2Cl_2$ (15 mL) were stirred at room temperature for 15 min Boron trifluoride diethyl etherate (1 g, 7.05 mmol) was added dropwise at room temperature. The mixture was stirred at room temperature for 2 h; cooled to 0° C.; quenched with sat. aq. $NaHCO_3$ (15 mL); stirred for 5 min; and extracted with EtOAc. The organic extract was dried with $MgSO_4$; filtered and concentrated. The residue was purified by column chromatography (silica gel, eluting with 0% to 75% EtOAc in hexanes) to give compound 196 (0.68 g, 59% yield) as a foam. m/z=668 (M+1).

T51: Compound 196 (0.68 g, 1.02 mmol) was dissolved in EtOH (10 mL). 1 N aq. NaOH (5 mL, 5 mmol) was added at room temperature. After the reaction was stirred at room temperature for 2 h, EtOAc (100 mL) was added. The mixture was washed with water. The organic layer was dried with $MgSO_4$; filtered and concentrated. The residue was purified by column chromatography (silica gel, eluting with 0% to 5% MeOH in $CHCl_3$) to give compound T51 (460 mg, 98% yield) as a white foam. m/z=460 (M+1); $^1$H NMR (400 MHz, $CDCl_3$) δ 7.38 (dt, J=6.0, 7.9 Hz, 1H), 7.20 (d, J=8.4 Hz, 1H), 7.01 (m, 4H), 6.93 (d, J=2.7 Hz, 1H), 5.73 (dddd, J=6.1, 7.5, 10.2, 17.6 Hz, 1H), 5.48 (d, J=1.7 Hz, 1H), 5.27 (br s, 1H), 5.05 (qd, J=1.6, 17.2 Hz, 1H), 4.97 (qd, J=1.4, 10.3 Hz, 1H), 4.13 (m, 1H), 4.06 (ddd, J=3.4, 5.4, 9.0 Hz, 1H), 3.69 (dt, J=3.1, 9.1 Hz, 1H), 3.58 (s, 3H), 3.26 (m, 3H), 2.74 (m, 2H), 2.53 (m, 3H), 2.30 (td, J=8.2, 15.3 Hz, 1H), 1.87 (s, 3H).

T52: A mixture of compound T51 (60 mg, 0.13 mmol) and 10% Pd/C (50 mg) in EtOAc (10 mL) was hydrogenated at atmospheric pressure for 16 h at room temperature. The reaction mixture was filtered through a Celite® pad. The filtrate was concentrated to give compound T52 (55 mg, 92% yield) as a white foam. m/z=462 (M+1); $^1$H NMR (400 MHz, $CDCl_3$) δ 7.38 (ddd, J=5.9, 7.5, 8.4 Hz, 1H), 7.20 (d, J=8.5 Hz, 1H), 7.02 (m, 4H), 6.92 (d, 1H), 5.51 (d, J=1.7 Hz, 1H), 5.25 (br s, 1H), 4.14 (m, 1H), 4.04 (ddd, J=3.5, 5.1, 8.8 Hz, 1H), 3.59 (m, 1H), 3.57 (s, 3H), 3.27 (dt, J=5.8, 7.2 Hz, 2H), 3.18 (t, J=9.4 Hz, 1H), 2.74 (dt, J=1.1, 7.2 Hz, 2H), 2.53 (m, 2H), 1.87 (s, 3H), 1.70 (m, 1H), 1.48 (m, 2H), 1.19 (m, 1H), 0.77 (t, J=7.3 Hz, 3H).

T53: Compound T51 (100 mg, 0.22 mmol) was dissolved in $CH_2Cl_2$/MeOH (1:1 v/v, 15 mL). The solution was cooled to −78° C. in a dry ice/acetone bath, and $O_3$ was bubbled through until the solution turned blue. $N_2$ was bubbled through for 15 min. $NaBH_4$ (20 mg, 0.52 mmol) was added and the dry ice bath was removed. The reaction was stirred at room temperature for 1 h; quenched with sat. aq. $NaHCO_3$ (15 mL); and extracted with EtOAc. The organic extract was dried with $MgSO_4$; filtered and concentrated. The residue was purified by column chromatography (silica gel, eluting with 0% to 15% MeOH in $CHCl_3$) to give compound T53 (45 mg, 44% yield) as a white foam. m/z=464 (M+1); $^1$H NMR (400 MHz, $CDCl_3$) δ 7.37 (m, 1H), 7.20 (d, J=8.5 Hz, 1H), 7.03 (m, 4H), 6.90 (d, J=2.6 Hz, 1H), 5.63 (m, 2H), 4.18 (s, 1H), 4.07 (m, 1H), 3.74 (dt, J=2.4, 10.1 Hz, 1H), 3.58 (s, 3H), 3.55 (m, 1H), 3.23 (m, 3H), 2.76 (m, 4H), 2.03 (m, 1H), 1.83 (s, 3H), 1.70 (m, 3H).

Compound 197: D-Mannose 143 (1 g, 5.55 mmol) was dissolved in pyridine (10 mL) and cooled to 0° C. p-Toluenesulfonyl chloride (1.21 g, 6.35 mmol) was added. The mixture was stirred at room temperature overnight. Acetic anhydride (6.1 g, 59.80 mmol) was added, and the mixture was stirred for another day. The solvent was removed under vacuo. The residue was diluted with EtOAc (100 mL). The mixture was washed with 1 N aq. HCl and water. The organic extract was dried with $MgSO_4$; filtered and concentrated. The residue was purified by column chromatography (silica gel, eluting with 0% to 30% EtOAc in hexanes) to give compound 197 (2.7 g, 97% yield) as a foam. m/z=443 (M-OAc).

Compound 198: Compound 197 (4.04 g, 8.04 mmol) was dissolved in acetone (50 mL). NaI (5 g, 33.35 mmol) was added. The mixture was reflux overnight; and concentrated. The residue was diluted with EtOAc (50 mL), and the mixture was washed with water. The organic extract was dried with $MgSO_4$; filtered and concentrated. The residue was purified by column chromatography (silica gel, eluting with 0% to 30% EtOAc in hexanes) to give compound 198 (3.4 g, 92% yield) as a foam. m/z=399 (M-OAc).

Compound 199: A mixture of compound 198 (4.4 g, 9.60 mmol) and 10% Pd/C (250 mg) in MeOH (50 mL) was hydrogenated at atmospheric pressure for 16 h at room temperature. The reaction mixture was filtered through a Celite® pad. The filtrate was concentrated. The oily residue was taken up in pyridine (35 mL) and acetic anhydride (10 g, 0.098 mol), and the mixture was stirred at room temperature overnight. The solvent was removed under vacuo. The residue was diluted with EtOAc (100 mL), and the mixture was washed with 1 N aq. HCl and water. The organic layer was dried with $MgSO_4$; filtered and concentrated. The residue was purified by column chromatography (silica gel, eluting with 0 to 30% EtOAc in hexanes) to give compound 199 (1 g, 31% yield) as a foam. m/z=273 (M-OAc).

Compound 200: A mixture of compound 199 (120 mg, 0.36 mmol), compound A1 (100 mg, 0.37 mmol) and 4 Å molecular sieve (0.5 g) in anhydrous $CH_2Cl_2$ (5 mL) was stirred at room temperature for 15 min. Boron trifluoride diethyl etherate (310 mg, 2.18 mmol) was added dropwise. The mixture was stirred at room temperature for 16 h; cooled to 0° C.; quenched with sat. aq. $NaHCO_3$ (2 mL); stirred for 5 min; and extracted with EtOAc. The organic extract was dried with $MgSO_4$; filtered and concentrated. The residue was purified by column chromatography (silica gel, eluting with 0% to 75% EtOAc in hexanes) to give compound 200 (135 mg, 69% yield) as a foam. m/z=546 (M+1).

T54: Compound 200 (1.25 g, 2.29 mmol) was dissolved in MeOH (10 mL). NaOMe (30 w % in MeOH, 85 mg, 0.47 mmol) was added. The reaction was stirred at room temperature for 16 h and concentrated. The residue was purified by column chromatography (silica gel, eluting with 0% to 5% MeOH in $CHCl_3$) to give compound T54 (685 mg, 71% yield) as a white foam. m/z=420 (M+1); $^1$H NMR (400 MHz, DMSO-$d_6$) δ 7.81 (t, J=5.7 Hz, 1H), 7.47 (dt, J=6.2, 8.1 Hz, 1H), 7.17 (m, 4H), 7.03 (dd, J=2.7, 8.5 Hz, 1H), 6.82 (d, J=2.7 Hz, 1H), 5.36 (d, J=1.8 Hz, 1H), 5.02 (d, J=4.4 Hz, 1H), 4.86 (d, J=5.7 Hz, 1H), 4.73 (d, J=5.9 Hz, 1H), 3.81 (ddd, J=1.8, 3.4, 4.6 Hz, 1H), 3.62 (ddd, J=3.4, 6.0, 9.3 Hz, 1H), 3.48 (qd, J=6.1, 9.3 Hz, 1H), 3.27 (dt, J=5.8, 9.4 Hz, 1H), 3.08 (m, 2H), 2.59 (dd, J=6.5, 8.8 Hz, 2H), 1.71 (s, 3H), 1.10 (d, J=6.2 Hz, 3H).

Compound 201: Compound 146 (1.67 g, 4.79 mmol) was dissolved in benzene (25 mL). Benzyl bromide (3.4 g, 19.88 mmol) and Ag$_2$O (4.4 g, 18.99 mmol) were added. The mixture was stirred at room temperature for 16 h and filtered. The filtrate was concentrated, and the residue was purified by column chromatography (silica gel, eluting with 0% to 30% EtOAc in hexanes) to give compound 201 (0.5 g, 24% yield) as a foam. m/z=379 (M-OAc).

Compound 202: A mixture of compound 201 (150 mg, 0.34 mmol), compound A1 (94 mg, 0.34 mmol) and 4 Å molecular sieve (0.5 g) in anhydrous CH$_2$Cl$_2$ (5 mL) was stirred at room temperature for 15 min Boron trifluoride diethyl etherate (385 mg, 2.71 mmol) was added dropwise. The mixture was stirred at room temperature for 16 h; cooled to 0° C.; quenched with sat. aq. NaHCO$_3$ (2 mL); stirred for 5 min; and extracted with EtOAc. The organic extract was dried with MgSO$_4$; filtered and concentrated. The residue was purified by column chromatography (silica gel, eluting with 0% to 5% MeOH in CHCl$_3$) to give compound 202 (170 mg, 76% yield) as a foam. m/z=652 (M+1).

T55: Compound 202 (170 mg, 0.26 mmol) was dissolved in MeOH (2 mL). NaOMe (30 w % in MeOH, 10 mg, 0.056 mmol) was added. The reaction was stirred at room temperature for 16 h and concentrated. The residue was purified by column chromatography (silica gel, eluting with 0% to 10% MeOH in CHCl$_3$) to give compound T55 (70 mg, 51% yield) as a white foam. m/z=526 (M+1); $^1$H NMR (400 MHz, DMSO-d$_6$) δ 7.32 (m, 6H), 7.20 (d, J=8.5 Hz, 1H), 7.04 (m, 3H), 6.96 (ddd, J=1.6, 2.6, 9.6 Hz, 1H), 6.92 (d, J=2.7 Hz, 1H), 5.56 (d, J=1.7 Hz, 1H), 5.30 (br t, J=5.4 Hz, 1H), 4.57 (d, J=11.9 Hz, 1H), 4.51 (d, J=11.9 Hz, 1H), 4.11 (m, 1H), 4.02 (m, 1H), 3.93 (t, J=9.3 Hz, 1H), 3.83 (td, J=4.4, 9.3 Hz, 1H), 3.75 (dd, J=4.3, 10.2 Hz, 1H), 3.68 (dd, J=4.7, 10.2 Hz, 1H), 3.26 (m, 2H), 3.03 (br s, 1H), 2.97 (m, 1H), 2.87 (br s, 1H), 2.73 (t, J=7.2 Hz, 2H), 1.86 (s, 3H).

Compound 204: In a vial, a mixture of compound 203 (110 mg, 0.45 mmol), Ba(OH)$_2$.8H$_2$O (389 mg, 1.23 mmol) and 3-fluorophenyl-boronic acid (70 mg, 0.50 mmol) in 1,4-dioxane (2.4 mL) and water (0.6 mL) was sparged with N$_2$ for 3 min [1,1'-bis(diphenylphosphino)ferrocene]dichloropalladium(II) (290 mg, 0.40 mmol) was added. The mixture was sparged with N$_2$ for another 3 min. The vial was sealed. The mixture was heated at 80° C. for 4 h. The mixture was cooled to room temperature; filtered through a pad of Celite®; and the filter cake was washed with EtOAc. The filtrate was concentrated. The residue was purified by column chromatography (silica gel, eluting with 0% to 25% acetone in CH$_2$Cl$_2$) to give compound 204 (32 mg, 27% yield) as a white solid. m/z=260.1 (M+1).

Compound 205: To a solution of compound 204 (32 mg, 0.12 mmol) in toluene (2 mL) was added Zn(BD$_4$)$_2$ (~0.65 M in THF, prepared in situ, 0.47 mL, 0.30 mmol) under N$_2$. The mixture was heated at reflux for 30 min; cooled to 0° C.; quenched with MeOH (1 mL); and filtered through a pad of Celite®. The filter cake was washed with EtOAc. The filtrate was concentrated. The residue was dissolved in EtOAc (2 mL), and cooled to 0° C. Sat. aq. NaHCO$_3$ (2 mL) and Ac$_2$O (13 µL, 0.14 mmol) were added. The mixture was stirred at 0° C. for 30 min; and extracted with EtOAc. The organic extract was dried with Na$_2$SO$_4$, filtered and concentrated. The residue was purified by column chromatography (silica gel, eluting with 0% to 65% EtOAc in hexanes) to give partially purified compound 205, which was purified again by column chromatography (silica gel, eluting with 0% to 35% acetone in hexanes) to give compound 84 (18 mg, 50% yield) as viscous oil. m/z=290.1 (M+1).

A6: To a solution of compound 205 (18 mg, 0.062 mmol) in CH$_2$Cl$_2$ (1 mL) at 0° C. under N$_2$ was added boron tribromide (12 µL, 0.12 mmol). The mixture was stirred at 0° C. for 1 h; quenched with sat. aq. NaHCO$_3$; stirred for 5 min; and extracted twice with EtOAc. The organic extract was dried with Na$_2$SO$_4$; filtered; and concentrated. The residue was purified by column chromatography (silica gel, eluting with 0% to 50% EtOAc in CH$_2$Cl$_2$) to give compound A6 (13 mg, 76% yield) as a brown oil. m/z=276.1 (M+1); $^1$H NMR (400 MHz, CDCl$_3$) δ 7.36 (m, 1H), 7.13 (t, J=8.5 Hz, 1H), 7.09-7.01 (m, 2H), 6.98 (m, 1H), 6.80 (dt, J=8.3, 2.7 Hz, 1H), 6.71 (d, J=2.7 Hz, 1H), 5.32 (m, J=18.9 Hz, 1H), 2.70 (s, 2H), 1.88 (s, 3H).

Compound 206: To a solution of compound A6 (13 mg, 0.047 mmol) and compound 18 (27 mg, 0.053 mmol) in CH$_2$Cl$_2$ (0.25 mL) at 0° C. under N$_2$ was added boron trifluoride diethyl etherate (12 µL, 0.097 mmol). The mixture was stirred at 0° C. for 16 h; quenched with sat. aq. NaHCO$_3$; and extracted with EtOAc. The organic extract was dried with Na$_2$SO$_4$, filtered and concentrated. The residue was purified by column chromatography (silica gel, eluting with 0% to 100% EtOAc in hexanes) to give compound 206 (23 mg, 74% yield) as a white foam. m/z=658 (M+1). Compound 206 was 88/9 mixture of α- and β-anomers.

T56: A mixture of compound 206 (23 mg, 0.035 mmol) and K$_2$CO$_3$ (24 mg, 0.17 mmol) in MeOH (1 mL) was stirred at room temperature for 1 h. The mixture was diluted with EtOAc; and washed with water. The organic extract was dried with Na$_2$SO$_4$, filtered and concentrated. The residue was purified by column chromatography (silica gel, eluting with 0% to 10% MeOH in CH$_2$Cl$_2$) to give compound T56 (12 mg, 76% yield) as a white foam. m/z=450.2 (M+1); $^1$H NMR (400 MHz, CDCl$_3$) δ 7.38 (dt, J=5.9, 8.0 Hz, 1H), 7.20 (d, J=8.5 Hz, 1H), 7.03 (m, 4H), 6.88 (d, J=2.7 Hz, 1H), 5.54 (d, J=2.3 Hz, 1H), 5.28 (br s, 1H), 4.19 (dd, J=3.4, 9.0 Hz, 1H), 4.15 (dd, J=2.3, 3.4 Hz, 1H), 3.59 (s, 3H), 3.33 (d, J=9.0 Hz, 1H), 2.73 (s, 2H), 1.87 (s, 3H), 1.36 (s, 3H), 1.21 (s, 3H).

Compound 207: A mixture of compound 3 (410 mg, 1.15 mmol), benzyl acrylate (0.21 mL, 1.38 mmol), Pd(OAc)$_2$ (2.6 mg, 0.012 mmol), tri(o-tolyl)phosphine (6.98 mg, 0.023 mmol) and DMF (2 mL) in a vial was degassed with N$_2$ for 5 min at rt. The vial was sealed and N,N-diisopropylethylamine (0.24 mL, 1.38 mmol) was added. The mixture was stirred at 130° C. overnight; cooled to rt; diluted with EtOAc (30 mL); and washed with water (3×30 mL). The organic extract was dried with Na$_2$SO$_4$, filtered and concentrated. The residue was purified by chromatography (silica gel, eluting with 0% to 50% acetone in hexanes) to give compound 207 (460 mg, 91% yield) as a pale-yellow oil. m/z=439.1 (M+1).

Compound A11: A solution of compound 207 (560 mg, 1.28 mmol) in EtOAc (20 mL) was flushed with N$_2$ for 10 min. 10% Pd/C (100 mg) was added. The flask was purged with H$_2$, and then hydrogenated at room temperature under H$_2$ balloon for 6 h. The mixture was filtered through a Celite® pad, and the filtrate was concentrated. The residue was purified by column chromatography (silica gel, eluting with 0% to 50% EtOAc in hexanes) to give compound A11 (320 mg, 96% yield) as a colorless oil. m/z=260.9 (M+1); $^1$H NMR (400 MHz, CDCl$_3$) δ 7.36 (m, 1H), 7.18 (d, J=8.4 Hz, 1H), 7.06-6.96 (m, 3H), 6.79 (dd, J=8.0, 2.8 Hz, 1H), 6.67 (d, J=2.8 Hz, 1H), 2.85 (dd, J=8.4, 7.2 Hz, 2H), 2.41 (dd, J=8.4, 7.6 Hz, 2H).

Compound 208: A mixture of compound A11 (97 mg, 0.37 mmol) and compound 18 (188 mg, 0.37 mmol) in CH$_2$Cl$_2$ (4 mL) was cooled to 0° C. under N$_2$. Boron trifluoride diethyl etherate (0.142 mL, 1.15 mmol) was added. The mixture was stirred at 0° C. overnight. Sat. aq. NaHCO$_3$ was added. The mixture was extracted 2 times with CH$_2$Cl$_2$. The combined organic extracts were washed 2 times with water; dried with Na$_2$SO$_4$; filtered; and concentrated. The residue was purified by column chromatography (silica gel, eluting with 0% to 40% EtOAc in hexanes) to give compound 208 (136 mg, 57% yield) as a light yellow foam. m/z=665.2 (M+Na).

Compound 209: A solution of compound 208 (135 mg, 0.21 mmol) in CH$_2$Cl$_2$ (4 mL) was cooled to 0° C. under N$_2$. DMF (2 drops) and oxalyl chloride (0.054 mL, 0.64 mmol) were added sequentially. The mixture was allowed to warm to rt and stirred for 2 h; and then concentrated. The residue was diluted with toluene and concentrated to remove excess oxalyl chloride to give crude acid chloride. The acid chloride was dissolved in CH$_2$Cl$_2$ (2 mL), and the solution was added dropwise to a stirring suspension of methylamine hydrochloride (35.5 mg, 0.53 mmol) and Et$_3$N (0.146 mL, 1.05 mmol) in CH$_2$Cl$_2$ (4 mL) at room temperature under N$_2$. The mixture was stirred at room temperature for 1 h and concentrated. The residue was diluted with EtOAc; and washed with sat. aq. NaHCO$_3$. The organic extract was dried over Na$_2$SO$_4$, filtered and concentrated. The residue was purified by column chromatography (silica gel, eluting with 0% to 30% EtOAc in CH$_2$Cl$_2$) to give compound 209 (105 mg, 76% yield) as a pale yellow foam. m/z=678.2 (M+Na).

T57: To a solution of compound 209 (90 mg, 0.137 mmol) in MeOH (1.5 mL) was added K$_2$CO$_3$ (95 mg, 0.686 mmol) at room temperature. After stirring at room temperature for 2 h, the mixture was filtered, and the solid was washed with EtOAc. The combined filtrate and wash was dried with Na$_2$SO$_4$; filtered; and concentrated. The residue was purified by column chromatography (silica gel, eluting with 0% to 30% MeOH in CH$_2$Cl$_2$) to give partially purified product, which was purified again by column chromatography (silica gel, eluting 0% to 100% EtOAc in CH$_2$Cl$_2$) to give compound T57 (white foam, 30 mg, 49% yield) as mainly a single anomer. m/z=448.2 (M+1); $^1$H NMR (400 MHz, CDCl$_3$) δ 7.37 (dt, J=6.0, 8.0, 1H), 7.20 (d, J=8.5 Hz, 1H), 7.03 (m, 4H), 6.86 (d, J=2.7 Hz, 1H), 5.53 (d, J=2.3 Hz, 1H), 5.13 (br s, 1H), 4.20 (td, J=3.5, 8.9 Hz, 1H), 4.15 (m, 1H), 3.59 (s, 3H), 3.33 (d, J=9.0 Hz, 1H), 2.88 (dd, J=6.8, 9.1 Hz, 2H), 2.72 (d, J=4.8 Hz, 3H), 2.50 (m, 2H), 2.21 (dd, J=6.8, 9.0 Hz, 2H), 1.36 (s, 3H), 1.21 (s, 3H).

Compound 211: To a solution of L-(−)-Xylose 210 (1.2 g, 7.99 mmol) in pyridine (12 mL) was added acetic anhydride (7.6 mL, 79.93 mmol) and 4-(dimethylamino)pyridine (146.5 mg, 1.20 mmol) at 0° C. under N$_2$. The mixture was stirred at ambient temperature overnight; poured into sat. aq. NaHCO$_3$; stirred for 20 min; and extracted twice with EtOAc. The combined organic extracts were washed with sat. aq. NaHCO$_3$, and water; dried with Na$_2$SO$_4$; and concentrated. The residual pyridine was removed by azeotropic evaporation with toluene. The residue was purified by chromatography (silica gel, eluting with 0% to 40% acetone in hexanes) to give compound 211 (2.0 g, 79% yield) as a clear viscous oil. m/z=259.0 (M-OAc).

Compound 212: A mixture of compound 211 (2.0 g, 6.28 mmol) and compound A1 (2.06 g, 7.54 mmol) in CH$_2$Cl$_2$ (20 mL) was cooled to 0° C. under N$_2$. Boron trifluoride diethyl etherate (3.10 mL, 25.12 mmol) was added. The mixture was stirred at 0° C. for 10 min, and then at room temperature for 60 h. Sat. aq. NaHCO$_3$ was added. The mixture was extracted 2 times with CH$_2$Cl$_2$. The combined organic extracts were washed 2 times with 1 N aq. NaOH and water; dried with Na$_2$SO$_4$; filtered; and concentrated. The residue was purified by column chromatography (silica gel, eluting with 0% to 30% acetone in CH$_2$Cl$_2$) and a second column chromatography (silica gel, eluting with 0% to 20% acetone in CH$_2$Cl$_2$) to give compound 212 as a mixture of α- and β-anomers (1.80 g, 54% yield) as a white foam. m/z=532.2 (M+1).

T58: To a solution of compound 212 (1.50 g, 2.82 mmol) in MeOH (20 mL) and THF (20 mL) was added 1 N aq. NaOH (20.0 mL, 20.0 mmol) at room temperature. The mixture was stirred at room temperature for 4 h; and concentrated. The residue was extracted repeatedly with EtOAc. The combined organic extracts were dried with Na$_2$SO$_4$; filtered; and concentrated. The residue was purified by column chromatography (silica gel, eluting with 0% to 20% MeOH in CH$_2$Cl$_2$) to give compound T58 as a 2/1 mixture of anomers (590 mg, 52% yield) as a white foam. m/z=406.1 (M+1); $^1$H NMR (400 MHz, acetone-d$_6$, 2:1 mixture of isomers) δ 7.47 (s, 1H), 7.27 (m, 1H), 7.13 (m, 5H), [6.93 (d, J=2.6 Hz), 6.87 (d, J=2.6 Hz); 2:1; 1H], [5.50 (d, J=3.6 Hz), 4.99 (m); 2:1; 1H], 3.99 (m, 6H), 3.22 (m, 2H), 2.86 (br s, 2H), 2.82 (br s, 1H), 2.69 (m, 2H), [1.77 (s), 1.76 (s); 2:1; 3H].

Compound 214: To a solution of L-(−)-Glucose 213 (1.1 g, 6.11 mmol) in pyridine (10 mL) was added acetic anhydride (5.8 mL, 61.36 mmol) and 4-(dimethylamino)pyridine (112 mg, 0.92 mmol) at 0° C. under N$_2$. The mixture was stirred at ambient temperature overnight; poured into sat. aq. NaHCO$_3$; stirred for 30 min; and extracted twice with EtOAc. The combined organic extracts were washed with sat. aq. NaHCO$_3$, 1 N aq. HCl, and water; dried with Na$_2$SO$_4$; filtered; and concentrated. The residue was purified by column chromatography (silica gel, eluting with 0% to 40% acetone in hexanes) to give compound 214 (2.0 g, 84% yield) as a white foam.

Compound 215: A mixture of compound 214 (1.1 g, 2.82 mmol) and compound A1 (847 mg, 3.10 mmol) in CH$_2$Cl$_2$ (10 mL) was cooled to 0° C. under N$_2$. Boron trifluoride diethyl etherate (1.39 mL, 11.27 mmol) was added. The mixture was stirred at 0° C. for 10 min, and then at room temperature for 24 h. Sat. aq. NaHCO$_3$ was added. The mixture was extracted 2 times with CH$_2$Cl$_2$. The combined organic extracts were washed 2 times with sat. aq. NaHCO$_3$, 1N aq. HCl and water; dried with Na$_2$SO$_4$; filtered; and concentrated. The residue was purified by column chromatography (silica gel, eluting with 0% to 35% acetone in CH$_2$Cl$_2$) to give compound 215 (white foam, 760 mg, 45% yield) as a mixture of α- and β-anomer mixture. m/z=604.2 (M+1).

T59: To a solution of compound 215 (1.31 g, 2.17 mmol) in MeOH (20 mL) and THF (20 mL) was added 1 N aq. NaOH (20.0 mL, 20.0 mmol) at room temperature. The mixture was stirred at room temperature for 24 h; and concentrated. The residue was extracted repeatedly with EtOAc. The combined organic extracts were dried with Na$_2$SO$_4$; filtered; and concentrated. The residue was purified by column chromatography (silica gel, eluting with 0% to 30% MeOH in CH$_2$Cl$_2$) to give compound T59 (white foam, 580 mg, 61% yield) as mainly a single anomer. m/z=436.1 (M+1); $^1$H NMR (400 MHz, DMSO-d$_6$) δ 7.80 (t, J=5.7 Hz, 1H), 7.46 (m, 1H), 7.18 (m, 4H), 7.02 (dd, J=2.7, 8.5 Hz, 1H), 6.83 (d, J=2.6 Hz, 1H), 5.29 (d, J=4.8 Hz, 1H), 5.07 (d, J=4.7 Hz, 1H), 5.00 (d, J=5.3 Hz, 1H), 4.88 (d, J=7.3 Hz, 1H), 4.56 (dd, J=5.4, 6.1 Hz, 1H), 3.66 (ddd, J=2.0, 5.4, 11.7

Hz, 1H), 3.43 (td, J=6.1, 11.9 Hz, 1H), 3.19 (m, 6H), 2.59 (dd, J=6.5, 8.5 Hz, 2H), 1.70 (s, 3H).

Compound 217: To a solution of L-(−)-Mannose 216 (1.0 g, 5.55 mmol) in pyridine (12 mL) was added acetic anhydride (5.3 mL, 56.07 mmol) and 4-(dimethylamino)pyridine (102 mg, 0.83 mmol) at 0° C. under $N_2$. The mixture was stirred at ambient temperature for overnight; poured into sat. aq. $NaHCO_3$; stirred for 30 min; and extracted twice with EtOAc. The combined organic extracts were washed with sat. aq. $NaHCO_3$ and water; dried with $Na_2SO_4$; filtered; and concentrated. The residue was purified by column chromatography (silica gel, eluting with 0% to 50% EtOAc in hexanes) to give compound 217 (2.02 g, 94% yield) as a clear viscous oil. m/z=331.0 (M-OAc)

Compound 218: A mixture of compound 217 (872 mg, 2.23 mmol) and compound A1 (916 mg, 3.35 mmol) in $CH_2Cl_2$ (10 mL) was cooled to 0° C. under $N_2$. Boron trifluoride diethyl etherate (1.10 mL, 8.91 mmol) was added. The mixture was stirred at 0° C. for 10 min, and then at room temperature for 24 h. Sat. aq. $NaHCO_3$ was added. The mixture was extracted 2 times with $CH_2Cl_2$. The combined organic extracts were washed 2 times with sat. aq. $NaHCO_3$ and water; dried with $Na_2SO_4$; filtered; and concentrated. The residue was purified by column chromatography (silica gel, eluting with 0% to 20% acetone in $CH_2Cl_2$) to give compound 218 (900 mg, 67% yield) as a white foam. m/z=604.2 (M+1).

T60: To a solution of compound 218 (900 mg, 1.49 mmol) in MeOH (20 mL) was added 1 N aq. NaOH (8.95 mL, 8.95 mmol) at room temperature. The mixture was stirred at room temperature for 24 h; and concentrated. The residue was extracted repeatedly with EtOAc. The combined organic extracts were dried with $Na_2SO_4$; filtered; and concentrated. The residue was purified by column chromatography (silica gel, eluting with 0% to 20% MeOH in $CH_2Cl_2$) to give compound T60 (490 mg, 75% yield) as a white foam. m/z=436.1 (M+1); $^1$H NMR (400 MHz, DMSO-$d_6$) δ 7.82 (t, J=5.6 Hz, 1H), 7.47 (dt, J=6.3, 8.1 Hz, 1H), 7.18 (m, 4H), 7.07 (dd, J=2.7, 8.5 Hz, 1H), 6.89 (d, J=2.7 Hz, 1H), 5.37 (d, J=1.8 Hz, 1H), 5.00 (d, J=4.4 Hz, 1H), 4.83 (d, J=5.5 Hz, 1H), 4.76 (d, J=5.8 Hz, 1H), 4.47 (t, J=5.9 Hz, 1H), 3.81 (ddd, J=1.8, 3.2, 4.9 Hz, 1H), 3.66 (ddd, J=3.3, 5.3, 8.8 Hz, 1H), 3.59 (tq, J=2.8, 5.4 Hz, 1H), 3.44 (s, 3H), 3.08 (m, 2H), 2.59 (dd, J=6.5, 8.8 Hz, 2H), 1.71 (s, 3H).

Compound 219: To a solution of L-(+)-Arabinose 8 (1.2 g, 7.99 mmol) in pyridine (12 mL) was added acetic anhydride (7.6 mL, 80.40 mmol) and 4-(dimethylamino)pyridine (146.5 mg, 1.20 mmol) at 0° C. under $N_2$. The mixture was stirred at ambient temperature overnight; poured into sat. aq. $NaHCO_3$; stirred for 30 min; and extracted twice with EtOAc. The combined organic extracts were washed with sat. aq. $NaHCO_3$ and water. The organic extract was dried with $Na_2SO_4$; filtered; and concentrated. The residue was purified by column chromatography (silica gel, eluting with 0% to 40% acetone in hexanes) to give compound 219 (2.4 g, 94% yield) as a clear viscous oil. m/z=259.1 (M-OAc)

Compound 220 and 221: A mixture of compound 219 (2.4 g, 7.54 mmol) and compound A1 (2.5 g, 9.15 mmol) in $CH_2Cl_2$ (20 mL) was cooled to 0° C. under $N_2$. Boron trifluoride diethyl etherate (3.7 mL, 29.98 mmol) was added. The mixture was stirred at 0° C. for 10 min, and then at room temperature for 24 h. Sat. aq. $NaHCO_3$ was added. The mixture was extracted 2 times with $CH_2Cl_2$. The combined organic extracts were washed 2 times with sat. aq. $NaHCO_3$, and water; dried with $Na_2SO_4$; filtered; and concentrated. The residue was purified by column chromatography (silica gel, eluting with 0% to 20% acetone in $CH_2Cl_2$), followed by a second column chromatography (silica gel, eluting with 0% to 30% acetone in $CH_2Cl_2$) to give compound 220 (970 mg, 24% yield) and compound 221 (800 mg, 20% yield) as a white foam. 220: m/z=532.3 (M+1); 221: m/z=532.3 (M+1).

T61 (isomer 1): To a solution of compound 220 (970 mg, 1.82 mmol) in MeOH (20 mL) and THF (10 mL) was added 1 N aq. NaOH (8.0 mL, 8.0 mmol) at room temperature. The mixture was stirred at room temperature for 24 h; and concentrated. The residue was extracted repeatedly with EtOAc. The combined organic extracts were dried with $Na_2SO_4$; filtered; and concentrated. The residue was purified by column chromatography (silica gel, eluting with 0% to 20% MeOH in $CH_2Cl_2$) to give compound T61 (500 mg, 68% yield) as a white foam. m/z=406.2 (M+1); $^1$H NMR (400 MHz, DMSO-$d_6$) δ 7.81 (t, J=5.6 Hz, 1H), 7.48 (m, 1H), 7.18 (m, 4H), 7.03 (dd, J=2.7, 8.5 Hz, 1H), 6.84 (d, J=2.6 Hz, 1H), 5.45 (d, J=2.5 Hz, 1H), 4.90 (m, 1H), 4.74 (d, J=5.1 Hz, 1H), 4.65 (d, J=3.7 Hz, 1H), 3.74 (m, 4H), 3.50 (dd, J=2.2, 12.0 Hz, 1H), 3.08 (td, J=6.0, 8.2 Hz, 2H), 2.59 (dd, J=6.5, 8.7 Hz, 2H), 1.71 (s, 3H).

T62 (isomer 2): To a solution of compound 221 (800 mg, 1.51 mmol) in MeOH (20 mL) and THF (10 mL) was added 1 N aq. NaOH (10.0 mL, 10.0 mmol) at room temperature. The mixture was stirred at room temperature for 24 h; and concentrated. The residue was extracted repeatedly with EtOAc. The combined organic extracts were dried with $Na_2SO_4$; filtered; and concentrated. The residue was purified by column chromatography (silica gel, eluting with 0% to 20% MeOH in $CH_2Cl_2$) to give compound T62 (490 mg, 80% yield) as a white foam. m/z=406.2 (M+1); $^1$H NMR (400 MHz, DMSO-$d_6$) δ 7.81 (t, J=5.6 Hz, 1H), 7.48 (m, 1H), 7.18 (m, 4H), 7.00 (dd, J=2.7, 8.5 Hz, 1H), 6.80 (d, J=2.7 Hz, 1H), 5.19 (d, J=5.0 Hz, 1H), 4.85 (d, J=13.1 Hz, 1H), 4.83 (d, J=13.1 Hz, 1H), 4.64 (d, J=3.9 Hz, 1H), 3.63 (m, 4H), 3.44 (ddd, J=3.3, 5.6, 8.8 Hz, 1H), 3.07 (m, 2H), 2.58 (m, 2H), 1.70 (s, 3H).

Compound 222: Compound A1 (2.733 g, 10.00 mmol) in THF (50 mL) was cooled to 0° C. under $N_2$. Sodium methoxide (25 weight % in MeOH, 2.17 mL, 9.48 mmol) was added. The mixture was stirred at 0° C. for 30 min; concentrated; and dried under vacuum to give compound 222 (3.336 g, quantitative yield) as a white powder.

Compound 223: To a suspension of sodium hydride (60% in mineral oil, 0.67 g, 16.75 mmol) in DMF (3 mL) was added compound 25 (500 mg, 2.81 nnol) in DMF (2 mL) at 0° C. under $N_2$. The mixture was stirred at room temperature for 5 min, and cooled to 0° C. Benzyl bromide (1.67 mL, 14.06 mmol) was added dropwise. The mixture was stirred at room temperature for overnight; cooled to 0° C.; quenched with water; and partitioned between MTBE and water. The aqueous phase was extracted again with MTBE. The combined organic extracts were washed 3 times with water; dried with $Na_2SO_4$; filtered; and concentrated. The residue was purified by column chromatography (silica gel, eluting with 0% to 25% EtOAc in hexanes) to give compound 223 (1.26 g, quantitative yield) as a colorless oil.

Compound 224: A mixture of compound 223 (5.85 g, 13.04 mmol), acetic acid (74 mL), 2 N aq. HCl (29 mL) and water (18.5 mL) was heated at 95° C. for 5-6 h. Compound 223 was completely consumed. Toluene was added, and the mixture was concentrated. The residue was diluted with EtOAc and washed with water. The organic extract was dried with $Na_2SO_4$; filtered; and concentrated. The residue was purified by column chromatography (silica gel, eluting with 0% to 40% EtOAc in hexanes) to give compound 224 (4.43 g, 78% yield) as a white solid. m/z=417.1 (M-OH).

Compound 225: To a solution of compound 224 (2.60 g, 5.98 mmol) in THF (60 mL) was added methylmagnesium chloride solution (3 M in diethyl ether, 23 mL, 69 mmol) at 0° C. under $N_2$. The mixture was stirred at room temperature for overnight; cooled to 0° C.; quenched by careful addition of water (5 mL); and partitioned between EtOAc and 1 N aq. HCl. The organic phase was separated; the aqueous phase was extracted again with EtOAc. The combined organic extracts were dried with $Na_2SO_4$; filtered; and concentrated to give compound 225 (2.60 g, 97% yield) as a viscous oil. m/z=451 (M+1).

Compound 226: To a solution of DMSO (4.25 mL, 59.83 mmol) in $CH_2Cl_2$ (30 mL) at −78° C. was added a solution of oxalyl chloride (3.04 mL, 35.92 mmol) dropwise under $N_2$. The solution was stirred at −78° C. for 30 min. The solution of compound 225 (2.60 g, 5.78 mmol) in $CH_2Cl_2$ (30 mL) was added. The mixture was stirred at −78° C. for 2 h, and $Et_3N$ (16 mL, 115.01 mmol) was then added. The mixture was stirred at ambient temperature for 1 h; and washed with water. The organic extract was concentrated. The residue was dissolved in MTBE/hexanes (1/1 v/v) and washed 4 times with water. The organic extract was dried with $Na_2SO_4$; filtered; and concentrated. The residue was purified by column chromatography (silica gel, eluting with 0% to 35% EtOAc in hexanes) to give compound 226 (2.58 g, quantitative yield) as a colorless oil. m/z=469.2 (M+Na).

Compound 227 and 228: Compound 226 (2.58 g, 5.78 mmol) was dissolved in THF (193 mL) and cooled to −78° C. under $N_2$. LDA (1 M solution in hexanes and THF, prepared in situ, 9 mL, 9 mmol) was added. The mixture was stirred at −78° C. for 1 h; and then quenched with sat. aq. $NH_4Cl$ (20 mL). The organic phase was separated; washed with brine; dried with $Na_2SO_4$; filtered; and concentrated. The residue was purified by column chromatography (silica gel, eluting with 0% to 35% EtOAc in hexanes) to give compound 227 (955 mg, 37% yield) and a mixture of compound 227 and 228 (1/2 ratio in HPLC, 940 mg, 36% yield) as viscous oil.

Compound 229: Compound 227 (952 mg, 2.13 mmol) in pyridine (7.6 mL) was cooled to 0° C. under $N_2$. Phosphorus (V) oxychloride (0.99 mL, 10.62 mmol) was added. The mixture was stirred at room temperature for 18 h; cooled to 0° C.; and added to sat. aq. $NaHCO_3$. The mixture was extracted with EtOAc. The organic extract was washed with 1 N aq. HCl, and water; dried with $Na_2SO_4$; filtered; and concentrated. The residue was purified by column chromatography (silica gel, eluting with 0% to 25% EtOAc in hexanes) to give compound 229 (610 g, 67% yield) as a viscous oil. m/z=429.2 (M+1).

Compound 230: To a mixture of copper(I) bromide dimethyl sulfide complex (24 mg, 0.12 mmol) in THF (6 mL) at 0° C. under Ar was added $AlMe_3$ (2 M solution in heptane, 0.69 mL, 1.38 mmol). The solution of compound 229 (493 mg, 1.15 mmol) in THF (6 mL) was added. The mixture was stirred at room temperature for 1 h; cooled to 0° C.; and quenched with sat. aq. $NH_4Cl$. The mixture was partitioned between EtOAc and 1 N aq. HCl. The aqueous phase was extracted again with EtOAc. The combined organic extracts were dried with $Na_2SO_4$; filtered; and concentrated. The residue was purified by column chromatography (silica gel, eluting with 0% to 12% EtOAc in hexanes) to give compound 230 (468 mg, 92% yield) as a colorless oil.

Compound 231: Compound 230 (836 mg, 1.88 mmol) in $Et_2O$ (40 mL) was cooled to 0° C. under $N_2$. $Zn(BH_4)_2$ (0.75 M in THF, 5 mL, 3.75 mmol) was added. The mixture was stirred at 0° C. for 30 min; quenched with water; and partitioned between EtOAc and 1 N aq. HCl. The organic extract was dried with $Na_2SO_4$; filtered; and concentrated. The residue was purified by column chromatography (silica gel, eluting with 0% to 35% EtOAc in hexanes) to give compound 231 (811 mg, 96% yield) as a white solid. m/z=447.3 (M+1).

Compound 232: Compound 231 (405 mg, 0.91 mmol) in $CH_2Cl_2$ (9 mL) was cooled to 0° C. under $N_2$. Pyridine (0.37 mL, 4.57 mmol) and trifluoromethanesulfonic anhydride (0.37 mL, 2.20 mmol) were added sequentially. The mixture was stirred at 0° C. for 30 min; quenched with sat. aq. $NaHCO_3$; stirred for 5 min; and extracted 3 times with $CH_2Cl_2$. The combined organic extracts were dried with $Na_2SO_4$; filtered; and concentrated. The residue was purified by column chromatography (silica gel, eluting with 0% to 5% EtOAc in $CH_2Cl_2$) to give compound 232 (465 mg, 88% yield) as a yellow oil.

Compound 233: A mixture of compound 232 (424 mg, 0.73 mmol) and 18-crown-6 (387 mg, 1.46 mmol) in DMF (1.8 mL) were cooled to 0° C. under $N_2$. Compound 222 (489 mg, 1.46 mmol) in DMF (1.8 mL) was added over 5 min via syringe. The syringe was rinsed with DMF (0.9 mL) and added to the reaction mixture. The mixture was stirred at 0° C. for 14 h; diluted with MTBE; and washed with 1 N aq. NaOH and water (2 times) sequentially. The organic extract was dried with $Na_2SO_4$; filtered; and concentrated. The residue was purified by column chromatography (silica gel, eluting with 0% to 100% EtOAc in hexanes) to give compound 233 (123 mg, 24% yield) as a semi-solid. m/z=702.4 (M+1).

T63: A mixture of compound 233 (271 mg, 0.39 mmol) and 10% Pd/C (90 mg) in THF (25 mL) was hydrogenated under $H_2$ balloon at room temperature for 4 h. The catalyst was removed by filtration and washed with EtOAc. The filtrate was concentrated. The residue was purified by column chromatography (silica gel, eluting with 0% to 10% MeOH in $CH_2Cl_2$) to give T63 (151 mg, 91% yield) as a white foam. m/z=432.2 (M+1); $^1$H NMR (400 MHz, $CDCl_3$) δ 7.38 (dt, J=6.0, 8.0 Hz, 1H), 7.20 (d, J=8.5 Hz, 1H), 7.07 (m, 2H), 6.99 (td, J=2.1, 9.5 Hz, 1H), 6.87 (dd, J=2.8, 8.5 Hz, 1H), 6.74 (d, J=2.7 Hz, 1H), 5.27 (br s, 1H), 4.58 (q, J=3.6 Hz, 1H), 4.20 (m, 1H), 4.00 (td, J=3.3, 9.2 Hz, 1H), 3.62 (dd, J=4.8, 9.2 Hz, 1H), 3.27 (q, J=6.9 Hz, 2H), 2.73 (t, J=7.2 Hz, 2H), 2.63 (d, J=3.3 Hz, 1H), 2.61 (d, J=1.9 Hz, 1H), 1.91 (d, J=4.9 Hz, 1H), 1.87 (s, 3H), 1.80 (d, J=3.5 Hz, 2H), 1.08 (s, 3H), 1.06 (s, 3H).

Compound 234: To a solution of compound T63 (56 mg, 0.13 mmol) in acetone (1.3 mL) was added 2,2-dimethoxypropane (0.13 mL, 1.06 mmol) and (1S)-(+)-camphor-10-sulfonic acid (5 mg, 0.022 mmol). The mixture was stirred at room temperature for 2 h; diluted with EtOAc; and washed with sat. aq. $NaHCO_3$. The organic extract was dried with $Na_2SO_4$; filtered; and concentrated. The residue was purified by column chromatography (silica gel, eluting with 0% to 100% EtOAc in hexanes) to give compound 234 (53 mg, 87% yield) as a white foam. m/z=472.2 (M+1).

Compound 235 and 236: To a solution of compound 234 (52 mg, 0.11 mmol) in DMF (0.55 mL) at 0° C. under $N_2$ were added sodium hydride (60% in mineral oil, 5 mg, 0.13 mmol) and iodomethane (10 μL, 0.16 mmol) sequentially. The mixture was stirred at 0° C. for 1 h; quenched with sat. aq. $NaHCO_3$; and extracted with EtOAc. The organic extract was washed with water; dried with $Na_2SO_4$; filtered; and concentrated. The residue was purified by column chromatography (silica gel, eluting with 0% to 40% acetone in hexanes) to give a mixture of compound 235 and 236 (28 mg). Compound 235: m/z=486.3 (M+1); compound 236: m/z=500.3 (M+1).

T64: The mixture of compound 235 and 236 (28 mg) obtained above was dissolved in MeOH (2.5 mL) and treated with 6 N aq. HCl (0.5 mL, 3 mmol). The mixture was stirred at room temperature for 2 h; diluted with EtOAc; and washed with water. The organic extract was dried with $Na_2SO_4$; filtered; and concentrated. The residue was purified by column chromatography (silica gel, eluting with 0% to 10% MeOH in $CH_2Cl_2$) to give compound T64 (18 mg, 37% yield from 234) as a white foam. m/z=446.2 (M+Na); $^1$H NMR (400 MHz, $CD_3OD$) δ 7.95 (br s, 1H), 7.43 (dt, J=6.0, 8.0 Hz, 1H), 7.24 (d, J=8.5 Hz, 1H), 7.08 (m, 3H), 6.91 (dd, J=2.8, 8.5 Hz, 1H), 6.74 (d, J=2.7 Hz, 1H), 4.50 (dt, J=3.8, 5.4 Hz, 1H), 3.98 (m, 2H), 3.53 (s, 3H), 3.18 (m, 2H), 3.10 (d, J=7.4 Hz, 1H), 2.69 (dd, J=6.6, 8.3 Hz, 2H), 1.83 (s, 3H), 1.77 (dd, J=3.8, 14.3 Hz, 1H), 1.63 (dd, J=5.6, 14.3 Hz, 1H), 1.08 (s, 3H), 1.00 (s, 3H).

Compound 236: To a solution of compound 234 (22 mg, 0.046 mmol) in DMF (0.5 mL) at room temperature under $N_2$ were added sodium hydride (60% in mineral oil, 10 mg, 0.25 mmol) and iodomethane (16 μL, 0.25 mmol) sequentially. The mixture was stirred at room temperature for 1 h; quenched with sat. aq. $NaHCO_3$; and extracted with MTBE. The organic extract was washed with water; dried with $Na_2SO_4$; filtered; and concentrated. The residue was purified by column chromatography (silica gel, eluting with 0% to 100% EtOAc in hexanes) to give compound 236 (23 mg, 99% yield). m/z=500.3 (M+1).

T65: The mixture of compound 236 (22 mg, 0.044 mmol) was dissolved in MeOH (1.8 mL), and treated with 6 N aq. HCl (0.36 mL, 2.16 mmol). The mixture was stirred at room temperature for 1 h; diluted with EtOAc; and washed with water. The organic extract was dried with $Na_2SO_4$; filtered; and concentrated. The residue was purified by column chromatography (silica gel, eluting with 0% to 10% MeOH in $CH_2Cl_2$) to give compound T65 (17 mg, 84% yield) as a white foam. m/z=460.2 (M+1); $^1$H NMR (400 MHz, $CDCl_3$, 1:1 mixture of isomers) δ 7.40 (m, 1H), 7.24 (m, 1H), 7.07 (m, 3H), 6.86 (ddd, J=2.8, 4.4, 7.7 Hz, 1H), 6.75 (dd, J=2.7, 6.8 Hz, 1H), 4.55 (m, 1H), 4.12 (m, 2H), 3.53 (s, 3H), 3.32 (m, 1H), 3.14 (m, 2H), 2.76 (m, 2H), [2.70 (s), 2.65 (s); 1:1, 3H], 2.59 (s, 1H), 2.52 (s, 1H), [1.98 (s), 1.65 (s); 1:1, 3H], 1.77 (dd, J=4.0, 14.2 Hz, 1H), 1.67 (m, 1H), 1.12 (s, 3H), 1.03 (s, 3H).

Compound 237: To a solution of compound A1 (549 mg, 2.01 mmol) and N-phenyl-bis(trifluoromethanesulfonimide) (863 mg, 2.42 mmol) in $CH_2Cl_2$ (34 mL) at 0° C. under $N_2$ was added triethylamine (0.56 mL, 4.02 mmol). The mixture was stirred at ambient temperature for 16 h; and concentrated. The residue was purified by column chromatography (silica gel, eluting with 0% to 75% EtOAc in $CH_2Cl_2$) to give compound 237 (890 mg, quantitative yield) as a colorless oil.

Compound 238: To a solution of compound 237 (8.20 g, 20.23 mmol) in DMF (150 mL) was added bis(pinacolato)diboron (6.16 g, 24.28 mmol), KOAc (5.96 g, 60.69 mmol) and [1,1'-bis(diphenylphosphino)ferrocene]dichloropalladium(II) (1.48 g, 2.02 mmol, 0.10 eq) under $N_2$. The mixture was stirred at 130° C. for 2 h; and concentrated under vacuum. The residue was purified by column chromatography (silica gel, eluting with 0% to 100% EtOAc in hexanes) to give compound 238 (4.70 g, 61% yield) as a yellow solid. m/z=384 (M+1).

Compound 239: To a solution of compound 238 (1.0 g, 2.61 mmol) in THF (20 mL) and water (5 mL) was added $NaIO_4$ (1.675 g, 7.83 mmol) at room temperature. After the mixture was stirred at room temperature for 30 min, 1 N aq. HCl (1.83 mL, 1.83 mmol) was added. The mixture was stirred at room temperature for overnight; diluted with EtOAc; and washed twice with water. The organic extract was dried with $Na_2SO_4$; filtered; and concentrated. The residue was purified by column chromatography (silica gel, eluting with 0% to 20% MeOH in $CH_2Cl_2$) to give compound 239 (655 mg, 83% yield) as a tan solid. m/z=302.1 (M+1).

Compound 241: Compound 241 was synthesized using the literature reported procedure (Nicolas et al., 2012). To a solution of compound 240 (2.662 g, 7.54 mmol) in THF (72 mL) was added cobalt(III) acetylacetonate (135 mg, 0.38 mmol) and TMEDA (56 μL, 0.37 mmol) at room temperature under $N_2$. The mixture was cooled to 0° C. 2-Methyl-1-propenylmagnesium bromide (0.5 M in THF, 23 mL, 11.5 mmol) was added dropwise over 1 h. After the addition was complete, the cold bath was removed. The mixture was stirred at ambient temperature for 2 h; cooled to 0° C.; quenched with sat. aq. $NH_4Cl$ (40 mL); stirred for 10 min; and extracted twice with EtOAc. The combined organic extracts were washed with 1 N aq. HCl and water; dried with $Na_2SO_4$; filtered; and concentrated. The residue was purified by column chromatography (silica gel, eluting with 0% to 20% EtOAc in $CH_2Cl_2$) to give compound 241 (633 mg, 26% yield) as a yellow oil. $^1$H NMR (400 MHz, $CDCl_3$) δ 5.41 (dp, J=7.5, 1.4 Hz, 1H), 5.22 (dd, J=9.7, 3.3 Hz, 1H), 5.17 (dd, J=3.3, 2.3 Hz, 1H), 5.07 (t, J=9.4 Hz, 1H), 4.59 (m, 1H), 3.79 (m, 1H), 2.16 (s, 3H), 2.05 (s, 3H), 2.00 (s, 3H), 1.79 (t, J=1.2 Hz, 3H), 1.73 (d, J=1.2 Hz, 3H), 1.20 (d, J=6.2 Hz, 3H).

Compound 242: To a solution of compound 241 (764 mg, 2.33 mmol) in MeOH (12 mL) was added 1 N aq. NaOH (10.5 mL, 10.5 mmol) at 0° C. The mixture was stirred at room temperature for 1 h; and concentrated. The residue was extracted repeatedly with EtOAc. The combined organic extracts were dried with $Na_2SO_4$; filtered; and concentrated. The residue was purified by column chromatography (silica gel, eluting with 0% to 20% MeOH in $CH_2Cl_2$) to give compound 242 (363 mg, 77% yield) as a viscous oil. $^1$H NMR (400 MHz, $CDCl_3$) δ 5.33 (dp, J=7.6, 1.5 Hz, 1H), 4.60 (dd, J=7.5, 1.6 Hz, 1H), 3.82 (m, 1H), 3.69 (ddd, J=9.2, 6.3, 3.1 Hz, 1H), 3.59 (dq, J=9.2, 6.1 Hz, 1H), 3.45 (bt, J=9.3 Hz, 1H), 2.96 (d, J=7.0 Hz, 1H), 2.66 (m, 2H), 1.76 (s, 3H), 1.73 (s, 3H), 1.28 (d, J=6.1 Hz, 3H).

Compound 243: To a solution of compound 242 (301 mg, 1.49 mmol) in DMF (3 mL) at 0° C. under $N_2$ was added sodium hydride (60% in mineral oil, 360 mg, 9.00 mmol). The mixture was stirred for 5 min; and then benzyl bromide (0.90 mL, 7.57 mmol) was added. The mixture was stirred at room temperature for 3 h; and cooled to 0° C. MTBE and water were added. The mixture was stirred for 10 min; diluted with EtOAc; and washed 3 times with water. The organic extract was dried with $Na_2SO_4$; filtered; and concentrated. The residue was purified by column chromatography (silica gel, eluting with 0% to 20% EtOAc in hexanes) to give compound 243 (617 mg, 88% yield) as a viscous oil. m/z=365.2 (M-OBn).

Compound 244: A solution of compound 243 (614 mg, 1.30 mmol) in MeOH (7 mL) and $CH_2Cl_2$ (7 mL) was cooled to −78° C. Ozone was bubbled through the reaction mixture for 30 min; and then $O_2$ was bubbled through the reaction mixture for 5 min. $NaBH_4$ (493 mg, 13.03 mmol) was added. The mixture was stirred at 0° C. for 3 h; at room temperature for 1 h; and concentrated. The residue was diluted with EtOAc; and washed twice with water. The organic extract was dried with $Na_2SO_4$; filtered; and concentrated. The residue was purified by column chromatography (silica gel, eluting with 0% to 50% EtOAc in hexanes)

to give compound 244 (395 mg, 68% yield) as a viscous oil. $^1$H NMR (400 MHz, CDCl$_3$) δ 7.39-7.27 (m, 15H), 4.66-4.47 (m, 6H), 4.05 (td, J=6.6, 4.0 Hz, 1H), 3.95 (td, J=7.0, 3.9 Hz, 1H), 3.83-3.65 (m, 4H), 3.50 (dd, J=4.9, 3.8 Hz, 1H), 1.95 (t, J=6.3 Hz, 1H), 1.37 (d, J=6.9 Hz, 3H). From the column compound 243 (127 mg) was recovered.

Compound 245: To a solution of compound 244 (394 mg, 0.88 mmol) and triphenylphosphine (461 mg, 1.76 mmol) in pyridine (2.2 mL) was added carbon tetrabromide (321 mg, 0.97 mmol) at room temperature. The mixture was heated at 65° C. under N$_2$ for 50 min; and cooled to room temperature. The mixture was partitioned between EtOAc and water. The aqueous phase was extracted twice with EtOAc. The combined organic extracts were washed sequentially with water, 10% aq. Na$_2$SO$_3$, 1 N aq. HCl and water; dried with Na$_2$SO$_4$; filtered; and concentrated. The residue was purified by column chromatography (silica gel, eluting with 0% to 20% EtOAc in hexanes) to give compound 245 (397 mg, 88% yield) as a white semi-solid. $^1$H NMR (400 MHz, CDCl$_3$) δ 7.38-7.26 (m, 15H), 4.66-4.47 (m, 6H), 4.16 (q, J=5.7 Hz, 1H), 3.95-3.84 (m, 2H), 3.75 (dd, J=5.8, 3.1 Hz, 1H), 3.58-3.49 (m, 3H), 1.37 (d, J=6.7 Hz, 3H).

Compound 246: Compound 239 (433 mg, 1.43 mmol), NiI$_2$ (22 mg, 0.070 mmol), trans-2-aminocyclohexanol hydrochloride (11 mg, 0.072 mmol), and sodium bis(trimethylsilyl)amide (263 mg, 1.43 mmol) were weighed in a vial. The vial was purged with Ar. 2-Butanol (sparged with N$_2$ for 5 min, 1.5 mL) was added. The mixture was stirred under Ar for 5 min Compound 245 (293 mmol, 0.57 mmol) was dissolved in 2-butanol (1.4 mL) at 60° C. and added to the reaction mixture. The mixture was heated at 60° C. for 16 h; cooled to room temperature; and partitioned between EtOAc and water. The aqueous phase was extracted twice with EtOAc. The combined organic extracts were dried with Na$_2$SO$_4$; filtered; and concentrated. The residue was purified by column chromatography (silica gel, eluting with 0% to 100% acetone in hexanes) to give compound 246 (212 mg, 54% yield) as a white foam. m/z=688.3.

T66: A mixture of compound 246 (247 mg, 0.36 mmol) and 10% Pd/C (60 mg) in THF (35 mL) was hydrogenated under H$_2$ balloon at room temperature for 4.5 h. The catalyst was removed by filtered through a pad of Celite®. The filter cake was washed with EtOAc. The filtrate was concentrated. The residue was dissolved in minimal amount of EtOAc/CH$_2$Cl$_2$ (1/1 v/v), and purified by column chromatography (silica gel, eluting with 0% to 20% MeOH in CH$_2$Cl$_2$) to give T66 (142 mg, 95% yield) as a white foam. m/z=418.2 (M+1); $^1$H NMR (400 MHz, CD$_3$CN) δ 7.44 (ddd, J=6.1, 7.5, 8.5 Hz, 1H), 7.26 (d, J=7.9 Hz, 1H), 7.21 (dd, J=1.9, 7.9 Hz, 1H), 7.12 (m, 4H), 6.27 (br s, 1H), 3.97 (ddd, J=1.9, 5.8, 9.5 Hz, 1H), 3.73 (td, J=1.9, 3.8 Hz, 1H), 3.64 (m, 2H), 3.28 (m, 1H), 3.17 (m, 3H), 3.10 (d, J=4.8 Hz, 1H), 3.01 (m, 2H), 2.79 (dd, J=5.8, 14.1 Hz, 1H), 2.69 (dd, J=6.6, 8.3 Hz, 2H), 1.73 (s, 3H), 1.13 (d, J=6.1 Hz, 3H).

Compound 247: Tebbe reagent (0.5 M in toluene, 22.0 ml, 11.0 mmol) was added dropwise to a −45° C. solution of compound 15 (2.34 g, 10.2 mmol) and pyridine (0.97 ml, 12.0 mmol) in THF/toluene (1:2, 30 mL). The reaction was stirred at −45° C. for 1.5 h and 0° C. for 1.5 h. The reaction was cooled to −15° C., quenched by the addition of 5.3 mL of NaOH (4 M aqueous, 5.3 mL), stirred 10 min, Et$_2$O (700 mL) was added, vigorously stirred at room temperature for 20 min, filtered through a plug of Celite®, eluted with Et$_2$O (100 mL) added, concentrated and the resultant residue purified by column chromatography (silica gel, eluting with 0% to 60% EtOAc in hexanes) to give compound 247 (1.24 g, 53% yield) as a white, crystalline solid: m/z=229.1 (M+1).

Compound 248: A solution of 9-BBN (0.5 M in THF, 1.32 mL, 0.66 mmol) was added to compound 247 (100.4 mg, 0.4398 mmol) at 0° C., stirred at 0° C. for 30 min and then at room temperature for 2 h. The resultant reaction was quenched with a solution of NaHCO$_3$ (141 mg, 1.68 mmol) in water (1.6 mL), stirred 15 min at room temperature, and a suspension of Pd(dppf)Cl$_2$ (33.3 mg, 0.0455 mmol) and compound 237 (182 mg, 0.450 mmol) in DMF (2.6 mL) was added. The mixture was stirred at room temperature in the dark overnight, then warmed to 60° C. for 1 day. The resultant reaction was diluted with EtOAc (70 mL), washed with water (40 mL) and brine (25 mL), dried (Na$_2$SO$_4$), concentrated and the resultant residue was purified by column chromatography (silica gel, eluting with 0% to 100% EtOAc in hexanes), then by reverse phase chromatography (C18, eluting with 10% to 100% MeCN in water) to give a mixture of compound 248 epimers, and unreacted compound 237 (compound 237:compound 248 epimer 1:compound 248 epimer 2=11:53:33, 79 mg) which was used without further purification.

T67 and T68: A solution containing a mixture of compound 248 epimers and unreacted compound 237 (compound 237:compound 248 epimer 1:compound 248 epimer 2=11:53:33, 79 mg), 6 M aq. HCl (0.6 mL, 3.6 mmol) and MeOH (3 mL) was stirred at room temperature for 2 h. The resultant mixture was diluted with EtOAc (100 mL); washed with water (25 mL), sat. aq. NaHCO$_3$ (25 mL) and brine (25 mL); dried (Na$_2$SO$_4$); concentrated and the resultant residue purified by column chromatography (silica gel, eluting with 0% to 75% Acetone in CH$_2$Cl$_2$), then the partially purified fractions of each epimer were further purified by column chromatography (silica gel, eluting with 0% to 10% MeOH in CH$_2$Cl$_2$) to give compound T67 (15.7 mg, 8% from compound 247) as a colorless glassy solid and compound T68 (29.0 mg, 15% from compound 247) as a colorless glassy solid. T67: $^1$H NMR (400 MHz, CDCl$_3$) δ 7.37 (dt, J=5.9, 7.9 Hz, 1H), 7.28 (d, J=1.9 Hz, 1H), 7.19 (d, J=1.9 Hz, 1H), 7.16 (d, J=1.8 Hz, 1H), 7.03 (m, 3H), 5.30 (br s, 1H), 4.06 (dt, J=2.4, 4.2 Hz, 1H), 3.85 (dt, J=3.4, 8.8 Hz, 1H), 3.71 (ddd, J=4.1, 6.0, 9.6 Hz, 1H), 3.45 (s, 3H), 3.30 (q, J=7.0 Hz, 2H), 3.07 (d, J=4.4 Hz, 1H), 3.04 (dd, J=3.4, 14.4 Hz, 1H), 2.79 (s, 3H), 2.60 (d, J=2.5 Hz, 1H), 2.24 (d, J=6.1 Hz, 1H), 1.86 (s, 3H), 1.32 (s, 3H), 1.19 (s, 3H); =446.2 (M+1). T68: $^1$H NMR (400 MHz, CDCl$_3$) δ 7.38 (m, 1H), 7.24 (m, 2H), 7.07 (m, 4H), 5.28 (br s, 1H), 3.72 (m, 2H), 3.62 (m, 1H), 3.59 (s, 3H), 3.30 (m, 2H), 3.15 (d, J=9.7 Hz, 1H), 2.93 (dq, J=7.2, 13.5 Hz, 2H), 2.78 (t, J=7.2 Hz, 2H), 2.44 (d, J=5.1 Hz, 1H), 2.24 (d, J=4.7 Hz, 1H), 1.87 (s, 3H), 1.34 (s, 3H), 1.12 (s, 3H); =446.2 (M+1).

Compound 249: A mixture of compound 237 (1.19 g, 2.94 mmol), i-Pr$_2$EtN (1.03 mL, 5.91 mmol), Pd$_2$(dba)$_3$ (134.4 mg, 0.1468 mmol), Xantphos (171.8 mg, 0.2969 mmol), and 2-ethylhexyl 3-mercaptopropanoate (0.82 mL, 3.68 mmol) in 1,4-dioxane (22 mL) was brought to reflux under N$_2$ for 2 h. The resultant mixture was concentrated, and the resultant residue purified by column chromatography (silica gel, eluting with 0% to 100% EtOAc in hexanes) to give compound 249 (1.27 g, 92% yield) as a viscous, yellow oil: m/z 474.2 (M+1).

Compound 250: NaOMe (25% w/w in MeOH, 3.8 mL, 16.7 mmol) was added to a room temperature solution of compound 249 (1.27 g, 2.68 mmol) in MeOH (38 mL). The resultant mixture was stirred 5 h at room temperature, diluted with 1 M aq. HCl (20 mL), concentrated to ~25 mL and extracted with EtOAc (100 mL, then 2×50 mL). The combined organic fractions were dried (Na$_2$SO$_4$), concentrated and the resultant residue purified by column chromatography (silica gel, eluting with 0% to 100% EtOAc in hexanes) to give compound 250 (385.9 mg, 50% yield) as a viscous, colorless oil: m/z=290.1 (M+1).

Compound 251: BF$_3$·OEt$_2$ (61 µL, 0.49 mmol) was added dropwise to a 0° C. solution of compound 250 (35.8 mg, 0.124 mmol) and compound 18 and 19 (68.6 mg, 0.136 mmol) in CH$_2$Cl$_2$ (1.2 mL), and stirred overnight at 0° C. The reaction was quenched with sat. aq. NaHCO$_3$ (10 mL), and extracted with EtOAc (3×25 mL). The combined organic fractions were dried (Na$_2$SO$_4$), concentrated and the resultant residue purified by column chromatography (silica gel, eluting with 0% to 40% acetone in CH$_2$Cl$_2$) to give compound 251 (83:16 mixture of epimers, 66.2 mg, 80% yield) as a white foam solid: m/z=672.2 (M+1).

T69 and T70: A solution of compound 251 (66.2 mg, 0.0985 mmol) and K$_2$CO$_3$ (68.8 mg, 0.498 mmol) in MeOH (4 mL) was stirred at room temperature for 3 h. The resultant reaction was concentrated, dissolved in EtOAc (100 mL), washed with sat. aq. NaHCO$_3$ (10 mL), dried (Na$_2$SO$_4$), concentrated and the resultant residue purified by repeated column chromatography (silica gel, eluting with 0% to 15% MeOH in CH$_2$Cl$_2$, 2×) followed by column chromatography (silica gel, eluting with 0% to 10% MeOH in CH$_2$Cl$_2$) to give compound T69 (31.2 mg, 68% yield) as a white, foam solid, and compound T70 (4.3 mg, 9% yield) as a white, foam solid. T69: $^1$H NMR (400 MHz, CDCl$_3$) δ 7.45 (dd, J=2.1, 8.1, 1H), 7.39 (dt, J=6.0, 8.0 Hz, 1H), 7.35 (d, J=2.0 Hz, 1H), 7.24 (d, J=8.1 Hz, 1H), 7.06 (m, 2H), 6.98 (ddd, J=1.6, 2.6, 9.5 Hz, 1H), 5.32 (br s, 1H), 5.06 (d, J=1.2, 1H), 4.14 (br t, J=3.7 Hz, 1H), 3.70 (m, 1H), 3.59 (s, 3H), 3.29 (m, 2H), 3.21 (d, J=9.7 Hz, 1H), 2.78 (t, J=7.2 Hz, 2H), 2.67 (br d, J=4.5 Hz, 1H), 2.59 (br d, J=6.1 Hz, 1H), 1.87 (s, 3H), 1.39 (s, 3H), 1.13 (s, 3H); m/z=290.1 (aglycone+1). T70: $^1$H NMR (400 MHz, CDCl$_3$) δ 7.46 (m, 2H), 7.38 (m, 1H), 7.24 (d, J=7.9 Hz, 1H), 7.04 (m, 3H), 5.31 (br s, 1H), 5.12 (d, J=8.8 Hz, 1H), 4.22 (t, J=4.0 Hz, 1H), 3.80 (dd, J=3.6, 8.8 Hz, 1H), 3.44 (s, 3H), 3.30 (m, 2H), 3.12 (d, J=4.4 Hz, 1H), 2.79 (m, 2H), 2.67 (br s, 1H), 2.61 (br s, 1H), 1.87 (s, 3H), 1.45 (s, 3H), 1.31 (s, 3H); m/z=290.1 (aglycone+1).

Compound 252: BF$_3$·OEt$_2$ (0.27 mL, 2.2 mmol) was added dropwise to a 0° C. solution of compound 250 (156.5 mg, 0.5408 mmol) and compound 29 (291.8 mg, 0.5949 mmol) in CH$_2$Cl$_2$ (5.4 mL), and stirred at 0° C. for 2 h, then warmed to room temperature overnight. The reaction was quenched with sat. aq. NaHCO$_3$ (25 mL) and extracted with EtOAc (100 mL). The organic extract was washed with brine (25 mL), dried (Na$_2$SO$_4$), concentrated and the resultant residue purified by column chromatography (silica gel, eluting with 0% to 10% MeOH in CH$_2$Cl$_2$) to give compound 252 (major isomer, 195.2 mg, 55% yield) as a white solid: m/z=658.2 (M+1).

T71: A solution of compound 252 (194 mg, 0.295 mmol) and K$_2$CO$_3$ (205 mg, 1.48 mmol) in MeOH (12 mL) was stirred at room temperature for 1 h. The resultant reaction was concentrated; dissolved in EtOAc (100 mL); washed with sat. aq. NaHCO$_3$, and brine (25 mL); dried (Na$_2$SO$_4$), concentrated and the resultant residue purified by column chromatography (silica gel, eluting with 0% to 10% MeOH in CH$_2$Cl$_2$) to give compound T71 (126.4 mg, 95% yield) as a white, foam solid: $^1$H NMR (400 MHz, CDCl$_3$) δ 7.40 (m, 2H), 7.31 (d, J=2.0 Hz, 1H), 7.24 (d, J=8.1 Hz, 1H), 7.06 (m, 2H), 6.98 (ddd, J=1.6, 2.6, 9.5 Hz, 1H), 5.48 (d, J=1.6 Hz, 1H), 5.32 (br s, 1H), 4.19 (br s, 1H), 4.11 (m, 1H), 3.85 (td, J=3.7, 8.3 Hz, 1H), 3.58 (s, 3H), 3.29 (m, 2H), 3.16 (t, J=9.3 Hz, 1H), 2.77 (t, J=7.2 Hz, 2H), 2.73 (m, 1H), 2.68 (d, J=5.0 Hz, 1H), 1.87 (s, 3H), 1.32 (d, J=6.3 Hz, 3H); m/z=450.1 (M+1).

Compound 253: To a mixture of compound 23 (356 mg, 0.61 mmol) and compound A12 (133 mg, 0.41 mmol) in CH$_2$Cl$_2$ (15 mL) at 0° C. under N$_2$ was added boron trifluoride diethyl etherate (155 µL, 1.22 mmol). The cold bath was removed. The mixture was stirred at room temperature 30 min. Additional amount of boron trifluoride diethyl etherate (155 µL, 1.22 mmol) was added at room temperature. The mixture was stirred at room temperature for 15 h, and then poured into sat. aq. NaHCO$_3$ (50 mL). The mixture was stirred at room temperature for 5 min, and then extracted with CH$_2$Cl$_2$ (3×20 mL). The combined organic extracts were dried with Na$_2$SO$_4$, filtered and concentrated. The residue was purified by column chromatography (silica gel, eluting with 0% to 40% EtOAc in hexanes) to give partially purified compound 253 (190 mg, 59% yield) as a white foam. Compound 253 was used in the next step without further purification. m/z=459 (M-C$_{18}$H$_{14}$NO$_5$).

Compound 255: A mixture of 253 (187 mg, 0.24 mmol) and 10% palladium on carbon (60 mg) in EtOAc (10 mL) was hydrogenated under H$_2$ balloon at room temperature for 4 h. The mixture was filtered through a pad of Celite® and eluted with EtOAc. The combined filtrate and wash were concentrated. The residue was purified by column chromatography (silica gel, eluting with 0% to 70% EtOAc in hexanes) to give compound 255 (118 mg, 76% yield) as a white foam. m/z=650 (M+1).

Compound 257: The mixture of compound 255 (115 mg, 0.18 mmol) and sodium acetate (87 mg, 1.06 mmol) in acetic anhydride (1.6 mL) was stirred at room temperature under N$_2$ for 3 h. Sat. aq. NaHCO$_3$ (20 mL) was added. The mixture was stirred at room temperature for 10 min; and then extracted with CH$_2$Cl$_2$ (3×20 mL). The combined organic extracts were dried with Na$_2$SO$_4$, filtered and concentrated to give compound 257 (130 mg, quantitative yield) as a tan foamy solid. Compound 257 was used in the next step without further purification. m/z=692 (M+1).

T72: To a solution of compound 257 (130 mg, ≤0.18 mmol) in THF (2 mL) and MeOH (2 mL) was added K$_2$CO$_3$ (245 mg, 1.77 mmol) at room temperature. The mixture was stirred under N$_2$ for 14 h, and then concentrated. The residue was diluted with water (1 mL) and EtOAc (20 mL). 6 N aq. HCl (0.6 mL, 3.6 mmol) and solid NaHCO$_3$ (500 mg) were added sequentially. The organic phase was separated. The aqueous phase was extracted repeated with EtOAc (5×20 mL). The combined organic extracts were dried with Na$_2$SO$_4$, filtered and concentrated. The residue was purified by column chromatography (silica gel, eluting with 0% to 20% MeOH in CH$_2$Cl$_2$) to give compound T72 (7 mg, 10% yield) as a white solid. m/z=380 (M+1); $^1$H NMR (400 MHz, CD$_3$OD) δ 8.55 (s, 1H), 7.38 (d, J=8.7 Hz, 1H), 7.19 (d, J=8.7 Hz, 1H), 5.55 (d, J=1.9 Hz, 1H), 4.07 (dd, J=3.5, 1.8 Hz, 1H), 3.89 (dd, J=9.3, 3.5 Hz, 1H), 3.57 (dq, J=9.5, 6.0 Hz, 1H), 3.48 (t, J=9.4 Hz, 1H), 2.30 (s, 3H), 2.19 (s, 3H), 1.22 (d, J=6.1 Hz, 3H).

Compound 254: To a mixture of compound 24 (301 mg, 0.61 mmol) and compound A12 (133 mg, 0.41 mmol) in CH$_2$Cl$_2$ (15 mL) at 0° C. under N$_2$ was added boron trifluoride diethyl etherate (155 µL, 1.22 mmol). The cold bath was removed. The mixture was stirred at room temperature 30 min. Additional amount of boron trifluoride diethyl etherate (155 µL, 1.22 mmol) was added at room temperature. The mixture was stirred at room temperature for 15 h, and then poured into sat. aq. NaHCO$_3$ (50 mL). The mixture was stirred at room temperature for 5 min, and then extracted with CH$_2$Cl$_2$ (3×20 mL). The combined organic extracts were dried with Na$_2$SO$_4$, filtered and concentrated. The residue was purified by column chromatography (silica gel, eluting with 0% to 40% EtOAc in hexanes) to give partially purified compound 254 (208 mg, 73% yield) as a white foam. Compound 254 was used in the next step without further purification. m/z=369 (M-C$_{18}$H$_{14}$NO$_5$).

Compound 256: A mixture of 254 (205 mg, 0.30 mmol) and 10% palladium on carbon (60 mg) in EtOAc (10 mL) was hydrogenated under H$_2$ balloon at room temperature for 3 h. The mixture was filtered through a pad of Celite® and eluted with EtOAc. The combined filtrate and wash were concentrated. The residue was purified by column chromatography (silica gel, eluting with 0% to 70% EtOAc in hexanes) to give compound 256 (101 mg, 61% yield) as a white foam. m/z=560 (M+1).

Compound 258: The mixture of compound 256 (99 mg, 0.18 mmol) and sodium acetate (87 mg, 1.06 mmol) in acetic anhydride (1.6 mL) was stirred at room temperature under N$_2$ for 3 h. Sat. aq. NaHCO$_3$ (20 mL) was added. The mixture was stirred at room temperature for 10 min; and then extracted with CH$_2$Cl$_2$ (3×20 mL). The combined organic extracts were dried with Na$_2$SO$_4$, filtered and concentrated to give compound 258 (101 mg, 95% yield) as a tan foamy solid. Compound 258 was used in the next step without further purification. m/z=602 (M+1).

T73: To a solution of compound 258 (101 mg, 0.17 mmol) in THF (2 mL) and MeOH (2 mL) was added K$_2$CO$_3$ (245 mg, 1.77 mmol) at room temperature. The mixture was stirred under N$_2$ for 14 h, and then concentrated. The residue was diluted with water (10 mL) and EtOAc (20 mL). 6 N aq. HCl (0.6 mL, 3.6 mmol) and solid NaHCO$_3$ (1 g) were added sequentially. The organic phase was separated. The aqueous phase was extracted repeated with EtOAc (10×20 mL). The combined organic extracts were dried with Na$_2$SO$_4$, filtered and concentrated. The residue was purified by column chromatography (silica gel, eluting with 0% to 20% MeOH in CH$_2$Cl$_2$) to give compound T73 (15 mg, 23% yield) as a white solid. m/z=394 (M+1); $^1$H NMR (400 MHz, DMSO-d$_6$) δ 9.66 (s, 1H), 8.52 (s, 1H), 7.48 (d, J=8.3 Hz, 1H), 7.12 (d, J=8.7 Hz, 1H), 5.49 (d, J=1.9 Hz, 1H), 5.27 (d, J=4.6 Hz, 1H), 4.99 (d, J=6.7 Hz, 1H), 3.86 (m, 1H), 3.78 (ddd, J=9.8, 6.7, 3.3 Hz, 1H), 3.45 (s, 3H), 3.41 (m, 1H), 3.06 (t, J=9.3 Hz, 1H), 2.18 (s, 3H), 2.12 (s, 3H), 1.10 (d, J=6.2 Hz, 3H).

Compound 260: A mixture of β-D-glucose pentaacetate 259 (300 mg, 0.77 mmol) and compound A1 (315 mg, 1.15 mmol) in CH$_2$Cl$_2$ (3 mL) was cooled to 0° C. Boron trifluoride diethyl etherate (0.57 mL, 4.65 mmol) was added. The mixture was stirred at room temperature for 24 h, and then cooled to ° C. 1 N aq. NaOH (1 N, 5 mL) was added. After stirring for 5 min, the mixture was diluted with CH$_2$Cl$_2$ (30 mL); and washed with 1 N aq. NaOH (2×10 mL), water (10 mL) sequentially. The organic extract was dried with Na$_2$SO$_4$, filtered and concentrated to give crude compound 260 (433 mg) as a white foam. m/z=604 (M+1).

T74: Compound 260 (433 mg, 0.72 mmol) was mixed with MeOH (8.6 mL), and treated with 1 N aq. NaOH (7.2 mL, 7.2 mmol) at room temperature. The mixture was stirred at room temperature for 8 h, and then concentrated. The residue was extracted with EtOAc (5×30 mL). The combined organic extracts were dried with Na$_2$SO$_4$, filtered and concentrated. The residue was purified by column chromatography (silica gel, eluting with 0-100% acetone in CH$_2$Cl$_2$) to give compound T74 (167 mg, 50% yield from 259) as a white foam. m/z=436 (M+1); $^1$H NMR (400 MHz, DMSO-d$_6$) δ 7.79 (t, J=5.6 Hz, 1H), 7.45 (td, J=7.9, 6.1 Hz, 1H), 7.10-7.24 (m, 4H), 7.00 (dd, J=8.5, 2.7 Hz, 1H), 6.81 (d, J=2.6 Hz, 1H), 5.28 (d, J=4.8 Hz, 1H), 5.07 (d, J=4.6 Hz, 1H), 4.99 (d, J=5.2 Hz, 1H), 4.86 (d, J=7.3 Hz, 1H), 4.55 (t, J=5.7 Hz, 1H), 3.64 (ddd, J=11.8, 5.4, 1.9 Hz, 1H), 3.42 (dt, J=11.9, 6.1 Hz, 1H), 3.09-3.30 (m, 4H), 3.05 (m, 2H), 2.57 (t, J=7.6 Hz, 2H), 1.69 (s, 3H).

Compound 262: A mixture of β-D-galactose pentaacetate 261 (390.3 mg, 1.00 mmol) and compound A1 (300.6 mg, 1.10 mmol) in CH$_2$Cl$_2$ (5 mL) was cooled to 0° C. under nitrogen. Boron trifluoride etherate (0.49 mL, 4.00 mmol) was added. The reaction mixture was stirred at 0° C. for 15 minutes and then allowed to warm up to room temperature. After stirring for 24 hours, the reaction mixture was quenched by adding sat'd aq. NaHCO$_3$. The mixture was extracted twice with CH$_2$Cl$_2$. The combined organic extracts were washed with sat'd aq. NaHCO$_3$, sat'd aq. KH$_2$PO$_4$, and sat'd aq. NaCl; dried over Na$_2$SO$_4$; filtered and concentrated. The residue was purified by column chromatography (silica gel, eluting with 5% MeOH in CH$_2$Cl$_2$) to give compound 262 (383.6 mg, 64% yield) as a white foam. m/z=604 (M+1).

T75: To a solution of compound 262 (373.6 mg, 0.62 mmol) in MeOH (6 mL) and tetrahydrofuran (6 mL) was added 1.0 N aq. NaOH (6.0 mL, 6.0 mmol) at room temperature. The reaction mixture was stirred for 24 hours, and then concentrated. The residue was extracted three times with EtOAc. The combined organic extracts were dried over Na$_2$SO$_4$, filtered and concentrated. The residue was purified by column chromatography (silica gel, eluting with 12% MeOH in CHCl$_3$) gave compound T75 (192.6 mg, 71% yield) as a white foam. m/z=458 (M+Na); $^1$H NMR (400 MHz, DMSO-d$_6$) δ 7.79 (t, J=5.6 Hz, 1H), 7.45 (td, J=7.9, 6.1 Hz, 1H), 7.10-7.22 (m, 4H), 6.99 (dd, J=8.5, 2.6 Hz, 1H), 6.81 (d, J=2.6 Hz, 1H), 5.12 (d, J=5.1 Hz, 1H), 4.83 (d, J=5.9 Hz, 1H), 4.82 (d, J=8.0 Hz, 1H), 4.61 (m, 1H), 4.47 (d, J=4.6 Hz, 1H), 3.65 (t, J=4.0 Hz, 1H), 3.34-3.56 (m, 4H), 3.14 (d, J=5.2 Hz, 1H), 3.05 (q, J=7.3 Hz, 2H), 2.57 (dd, J=8.6, 6.4 Hz, 2H), 1.68 (s, 3H).

Compound 264: A mixture of 1,2,3,4-tetra-O-acetyl-β-D-xylopyranose 263 (500 mg, 1.57 mmol) and compound A1 (472 mg, 1.73 mmol) in CH$_2$Cl$_2$ (5 mL) was cooled to 0° C. under nitrogen. Boron trifluoride etherate (0.78 mL, 6.32 mmol) was added. The reaction mixture was stirred at 0° C. for 10 minutes, and then at room temperature for 46 hours. The reaction was quenched by slowly dropwise addition of sat'd aq. NaHCO$_3$. The mixture was diluted with CH$_2$Cl$_2$. The organic phase was washed with sat'd aq. NaHCO$_3$, sat'd aq. KH$_2$PO$_4$, H$_2$O, and sat'd aq. NaCl; dried with Na$_2$SO$_4$; filtered and concentrated. The residue was purified by column chromatography (silica gel, eluting with 3% MeOH in CH$_2$Cl$_2$) to give compound 264 (471 mg, 56% yield) as a white glass. m/z=532 (M+1).

T76: A solution of 264 (470 mg, 0.88 mmol) in MeOH (10 mL) and tetrahydrofuran (10 mL) was treated with 1.0 N aq. NaOH (7.96 mL, 7.96 mmol) at room temperature. The reaction mixture was stirred at room temperature for 20 hours, and then concentrated to near dryness. The residue was dissolved in warm EtOAc (~150 mL). The organic phase was dried over Na$_2$SO$_4$, filtered and concentrated. The residue was purified by column chromatography (silica gel, eluting with 12% MeOH in EtOAc) to give compound T76 (269 mg, 75% yield) as a white glass. m/z=406 (M+1); $^1$H NMR (400 MHz, DMSO-d$_6$, 5/1 mixture of anomers) δ 7.79 (t, J=5.5 Hz, 1H), 7.46 (td, J=8.1, 6.2 Hz, 1H), 7.10-7.25 (m, 4H), 7.02 (dd, J=8.5, 2.7 Hz, 0.17H), 6.98 (dd, J=8.5, 2.7 Hz, 0.83H), 6.83 (d, J=2.6 Hz, 0.17H), 6.78 (d, J=2.6 Hz, 0.83H), 5.41 (d, J=3.6 Hz, 0.17H), 5.30 (d, J=4.3 Hz, 0.83H), 5.09 (d, J=3.9 Hz, 0.83H), 5.04 (d, J=4.7 Hz, 1H), 5.01 (d, J=4.6 Hz, 0.17H), 4.96 (d, J=4.9 Hz, 0.17H), 4.86 (d, J=7.2 Hz, 0.83H), 3.69 (dd, J=11.0, 5.0 Hz, 1H), 3.33 (m, 1H), 3.14-3.26 (m, 3H), 3.05 (m, 2H), 2.57 (dd, J=8.7, 6.4 Hz, 2H), 1.69 (s, 3H).

Compound 266: A mixture of β-D-ribofuranose-1,2,3,5-tetraacetate 265 (1.0 g, 3.14 mmol) and compound A1 (944 mg, 3.45 mmol) in $CH_2Cl_2$ (10 mL) was cooled to 0° C. under nitrogen. Boron trifluoride etherate (1.55 mL, 12.56 mmol) was added. The reaction mixture was stirred at 0° C. for 10 minutes, and then at room temperature for 17 hours. The reaction mixture was diluted with $CH_2Cl_2$ and treated with sat'd aq. $NaHCO_3$. The organic phase was separated and washed with sat'd aq. $KH_2PO_4$ and sat'd aq. NaCl; dried with $Na_2SO_4$; filtered and concentrated. The residue was purified by column chromatography (silica gel, eluting with 2% MeOH in $CH_2Cl_2$) to give compound 266 (577 mg, 35% yield) as a clear viscous oil. m/z=532 (M+1).

T77: A solution of compound 266 (577 mg, 1.08 mmol) in MeOH (10 mL) and THF (10 mL) was treated with 1.0 N aq. NaOH (9.72 mL, 9.72 mmol) at room temperature. The reaction mixture was stirred at room temperature for 20 hours, and then concentrated. The residue was extracted repeatedly with EtOAc. The combined organic extracts were dried with $Na_2SO_4$, filtered and concentrated. The residue was purified by column chromatography (silica gel, eluting with 8% MeOH in EtOAc) to give compound T77 (216 mg, 49% yield) as a clear viscous oil. m/z=406 (M+1); $^1H$ NMR (400 MHz, $CD_3OD$, 10/1 mixture of anomers) 6 Major anomer: 7.42 (td, J=7.9, 6.0 Hz, 1H), 7.23 (d, J=8.5 Hz, 1H), 6.96-7.14 (m, 4H), 6.84 (d, J=2.7 Hz, 1H), 5.52 (d, J=1.2 Hz, 1H), 4.18 (dd, J=6.7, 4.7 Hz, 1H), 4.14 (d, J=4.8, 1.2 Hz, 1H), 4.04 (td, J=6.5, 3.6 Hz, 1H), 3.72 (dd, J=11.9, 3.6 Hz, 1H), 3.55 (dd, J=11.8, 6.3 Hz, 1H), 3.16 (m, 2H), 2.70 (dd, J=8.3, 6.6 Hz, 2H), 1.82 (s, 3H).

Compound 268: A mixture of 1,2,3,4-tetra-O-acetyl-D-fucopyranose 267 (726 mg, 2.18 mmol) and compound A1 (657 mg, 2.40 mmol) in $CH_2Cl_2$ (7 mL) was cooled to 0° C. under nitrogen. Boron trifluoride etherate (1.08 mL, 8.75 mmol) was added. The reaction mixture was stirred at 0° C. for 10 minutes, and then at room temperature for 43 h. The reaction was quenched by dropwise addition of sat'd aq. $NaHCO_3$. The mixture was diluted with $CH_2Cl_2$, and washed with sat'd aq. $NaHCO_3$, sat'd aq. $KH_2PO_4$, and sat'd aq. NaCl. The organic extract was dried with $Na_2SO_4$; filtered and concentrated. The residue was purified by column chromatography (silica gel, eluting with 5% MeOH in $CH_2Cl_2$) to give compound 268 (898 mg, 76% yield) as a white glass. m/z=546 (M+1).

T78: A solution of compound 268 (897 mg, 1.64 mmol) in MeOH (20 mL) and tetrahydrofuran (20 mL) was treated with 1.0 N aq. NaOH (14.76 mL, 14.76 mmol). The reaction mixture was stirred at room temperature for 19 hours, and then was concentrated in vacuo to near dryness. The residue was taken up in warm 12% MeOH in EtOAc solution (~150 mL). The organic phase was dried over $Na_2SO_4$, filtered and concentrated. The residue was purified by column chromatography (silica gel, eluting with 12% MeOH in EtOAc) to give compound T78 (530 mg, 77% yield) as a white glass. m/z=420 (M+1); $^1H$ NMR (400 MHz, DMSO-$d_6$, 4/1 mixture of anomers) δ 7.79 (t, J=5.6 Hz, 1H), 7.46 (td, J=8.1, 6.2 Hz, 1H), 7.10-7.24 (m, 4H), 7.01 (dd, J=8.5, 2.6 Hz, 0.8H), 6.97 (dd, J=8.5, 2.7 Hz, 0.2H), 6.82 (d, J=2.6 Hz, 0.8H), 6.77 (d, J=2.6 Hz, 0.2H), 5.36 (d, J=3.2 Hz, 0.8H), 5.09 (d, J=5.0 Hz, 0.2H), 4.83 (d, J=7.6 Hz, 0.2H), 4.78 (d, J=6.0 Hz, 1H), 4.66 (bs, 0.8H), 4.55 (d, J=4.5 Hz, 0.8H), 4.52 (d, J=4.8 Hz, 0.2H), 3.88 (q, J=6.5 Hz, 0.8H), 3.34-3.77 (m, 3.2H), 3.06 (m, 2H), 2.57 (dd, J=8.9, 6.5 Hz, 2H), 1.68 (s, 3H), 1.09 (d, J=6.4 Hz, 0.6H), 1.03 (d, J=6.5 Hz, 2.4H).

Compound 270: A mixture of 1,2,3,4-tetra-O-acetyl-D-lyxose 269 (636.6 mg, 2.00 mmol) and compound A1 (655.9 mg, 2.39 mmol) in $CH_2Cl_2$ (10 mL) was cooled to 0° C. under nitrogen. Boron trifluoride etherate (1.0 mL, 8.10 mmol) was slowly added. The reaction mixture was stirred at 0° C. for 15 minutes, and then at room temperature for 24 hours. The reaction was quenched by adding sat'd aq. $NaHCO_3$. The mixture was extracted twice with $CH_2Cl_2$. The combined organic extracts were washed with sat'd aq. $NaHCO_3$, sat'd aq. $KH_2PO_4$, and sat'd aq. NaCl; dried over $Na_2SO_4$; filtered and concentrated. The residue was purified by column chromatography (silica gel, eluting with 5% MeOH in $CH_2Cl_2$) to give compound 270 (783.9 mg, 74% yield) as a slightly yellow foam. m/z=532 (M+1).

T79: To a solution of compound 270 (531.5 mg, 1.0 mmol) in MeOH (10 mL) and tetrahydrofuran (10 mL) was added 1.0 N aq. NaOH (10.0 mL, 10.0 mmol) at room temperature. The reaction mixture was stirred for 24 hours, and then concentrated to near dryness. The residue was extracted three times with EtOAc. The combined organic extracts were dried over $Na_2SO_4$, filtered and concentrated. The residue was purified by column chromatography (silica gel, eluting with 12% MeOH in $CHCl_3$) to give compound T79 (236.4 mg, 58% yield) as white solid. m/z=428 (M+Na); $^1H$ NMR (400 MHz, $CD_3OD$, 3/1 mixture of anomers) δ 7.43 (m, 1H), 7.25 (d, J=8.5 Hz, 1H), 7.01-7.13 (m, 4H), 6.93 (d, J=2.6 Hz, 0.25H), 6.88 (d, J=2.6 Hz, 0.75H), 5.39 (d, J=3.1 Hz, 0.75H), 5.29 (d, J=2.6 Hz, 0.25H), 3.79-4.05 (m, 3H), 3.73 (m, 1H), 3.51 (m, 0.75H), 3.35 (m, 0.25H), 3.17 (dd, J=6.6, 8.2 Hz, 2H), 2.71 (dd, J=6.6, 8.2 Hz, 2H), 1.82 (s, 3H).

Compound 272: A mixture of β-D-galactosamine pentaacetate 271 (0.30 g, 0.77 mmol) and compound A1 (0.23 g, 0.84 mmol) in $CH_2Cl_2$ (5 mL) was cooled to 0° C. Boron trifluoride diethyl etherate (0.4 mL, 3.24 mmol) was added. The solution was gradually warmed to room temperature and stirred for overnight. The reaction was treated with sat. aq. $NaHCO_3$ (10 mL) and $CH_2Cl_2$ (10 mL). The organic phase was separated; washed with 1N aq. HCl and brine; dried over $Na_2SO_4$; filtered and concentrated. The residue was purified by column chromatography (silica gel, eluting with 5% MeOH in $CH_2Cl_2$) to give compound 272 (0.070 g, 15% yield) as a white foam solid. m/z=603 (M+1).

T80: To a solution of compound 272 (0.070 g, 0.12 mmol) in 1:1 THF/MeOH (10 mL) was added 1N aq. NaOH (1.2 mL, 1.2 mmol). The solution was stirred at room temperature for overnight and then concentrated in vacuo. The residue was dissolved in MeOH, and purified by column chromatography (silica gel, eluting with 10% MeOH in EtOAc) to give partially purified compound T80, which was triturated with 9:1 EtOAc/$CH_3OH$. The solid was collected by filtration to give T80 (0.007 g, 12%) as a white solid. m/z=499 (M+Na); $^1H$ NMR (400 MHz, $CD_3OD$) δ 7.42 (td, J=8.0, 6.0 Hz, 1H), 7.24 (d, J=8.5 Hz, 1H), 6.99-7.13 (m, 4H), 6.86 (d, J=2.6 Hz, 1H), 5.03 (d, J=8.4 Hz, 1H), 4.17 (dd, J=10.7, 8.4 Hz, 1H), 3.88 (d, J=3.3 Hz, 1H), 3.68-3.81 (m, 3H), 3.63 (t, J=4.5 Hz, 1H), 3.16 (t, J=7.4 Hz, 2H), 2.70 (dd, J=8.3, 6.5 Hz, 2H), 1.97 (s, 3H), 1.81 (s, 3H).

Compound 274: A mixture of β-D-glucosamine pentaacetate 273 (389.4 mg, 1.00 mmol) and compound A1 (300.6 mg, 1.10 mmol) in $CH_2Cl_2$ (5 mL) was cooled to 0° C. under nitrogen. Boron trifluoride etherate (0.49 mL, 3.97 mmol) was added slowly. The reaction mixture was stirred at 0° C. for 15 minutes, and then heated at reflux for 6 days. The reaction was quenched by adding sat'd aq. $NaHCO_3$. The mixture was extracted twice with $CH_2Cl_2$. The combined organic extracts were washed with sat'd aq. $NaHCO_3$, sat'd aq. $KH_2PO_4$ and sat'd aq. NaCl; dried over $Na_2SO_4$; filtered and concentrated. The residue was purified by column chromatography (silica gel, eluting with 5% MeOH in $CH_2Cl_2$) to give compound 274 (115.6 mg, 19% yield) as an off-white foam. m/z=603 (M+1).

T81: To a solution of compound 274 (113.0 mg, 0.19 mmol) in MeOH (2 mL) and tetrahydrofuran (2 mL) was added 1.0 N aq. NaOH (2.0 mL, 2.0 mmol) at room temperature. The reaction mixture was stirred for 24 hours, and then concentrated to near dryness. The residue was extracted three times with EtOAc. The combined organic extracts were dried over $Na_2SO_4$, filtered and concentrated. The residue was purified by column chromatography (silica gel, eluting with 12% MeOH in $CHCl_3$) to give compound T81 (25.7 mg, 29% yield) as a white solid. m/z=499 (M+Na); $^1$H NMR (400 MHz, $CD_3OD$) δ 7.42 (td, J=8.0, 6.0 Hz, 1H), 7.24 (d, J=8.5 Hz, 1H), 6.98-7.13 (m, 4H), 6.85 (d, J=2.6 Hz, 1H), 5.05 (d, J=8.4 Hz, 1H), 3.88 (m, 2H), 3.68 (m, 1H), 3.56 (m, 1H), 3.39 (m, 2H), 3.16 (t, J=7.4 Hz, 2H), 2.70 (t, J=7.1 Hz, 2H), 1.97 (s, 3H), 1.81 (s, 3H).

Compound 276: A mixture of 1,2,3,4-tetra-O-acetyl-D-arabinose 275 (0.50 g, 1.57 mmol) and compound A1 (0.47 g, 1.72 mmol) in $CH_2Cl_2$ (15 mL) was cooled to 0° C. under nitrogen. Boron trifluoride etherate (0.80 mL, 6.48 mmol) was added. The reaction mixture was warmed to room temperature and stirred for overnight. The reaction was treated with sat. aq. $NaHCO_3$ (10 mL) and $CH_2Cl_2$ (10 mL). The organic phase was separated; washed with 1N aq. HCl and brine; dried over $Na_2SO_4$; filtered and concentrated. The residue was purified by column chromatography (silica gel, eluting with 5% MeOH in $CH_2Cl_2$) to give compound 276 (0.337 g, 41% yield) as a viscous yellow oil. m/z=532 (M+1).

T82: To a solution of compound 276 (0.337 g, 0.63 mmol) in MeOH (10 mL) and tetrahydrofuran (10 mL) was added 1.0 N aq. NaOH (6.3 mL, 6.3 mmol) at room temperature. The reaction mixture was stirred for overnight, and then concentrated. The residue was washed repeatedly with 9/1 EtOAc/MeOH. The washes were combined and concentrated. The residue was purified by column chromatography (silica gel, eluting with 10% MeOH in EtOAc) to give compound T82 (38 mg, 15% yield) as a white solid. m/z=428 (M+Na); $^1$H NMR (400 MHz, $CD_3OD$, 1.6/1 mixture of anomers) δ 7.43 (td, J=7.9, 6.0 Hz, 1H), 7.25 (d, J=8.5 Hz, 0.38H), 7.25 (d, J=8.5 Hz, 0.62H), 7.01-7.14 (m, 4H), 6.95 (d, J=2.6 Hz, 0.38H), 6.90 (d, J=2.6 Hz, 0.62H), 5.51 (d, J=3.1 Hz, 0.38H), 4.84 (d, J=7.1 Hz, 0.62H), 3.58-4.00 (m, 5H), 3.17 (t, J=7.4 Hz, 2H), 2.70 (m, 2H), 1.82 (s, 3H).

C. Biological Activity

1. Methods

A streptozotocin-induced rat model was used to test the effectiveness of KU-596 (T0) and several of the instant compounds in a model of painful diabetic neuropathy. The study rats were allowed to acclimate to the Von Frey apparatus for one day prior to the initial Von Frey measurement. A baseline Von Frey measurement, a body weight measurement, and blood glucose level measurements were conducted one day before the intravenous administration of streptozotocin to induce diabetes. Rats which exhibited a blood glucose level above 300 mg/dL on Day 3 were included in the study. On day 9 or 10, the sensitivity of the rats to the von Frey filaments was tested and those animals that showed a decrease in withdrawal force threshold were included and assigned to treatment groups. Each of the animals in a treatment group was dosed with either the vehicle or a therapeutic agent orally. Treatment was continued until euthanasia approximately one to two weeks later. Table 2 shows the summary of each of the study groups and days of analyses for evaluation of T0 (FIG. 1A).

TABLE 2

Summary of Treatment Groups and Characteristics for Compound T0.

| Group | N | Test Item | Route | Dose/Volume | Regimen | STZ (IV) | Von Frey Measurements |
|---|---|---|---|---|---|---|---|
| 1 | 10 | Vehicle[a] | PO | 10 mL/lg | PO, QD × 12 d Days 10-21 | 60 mg/kg | Baseline, pre-dose on Day 10 and 2 hours post-dose on Days 11, 17, and 21 |
| 2 | 10 | T0 | PO | 1 mg/kg | PO, QD × 12 d Days 10-21 | 60 mg/kg | |
| 3 | 10 | T0 | PO | 3 mg/kg | PO, QD × 12 d Days 10-21 | 60 mg/kg | |
| 5 | 10 | T0 | PO | 10 mg/kg | PO, QD × 12 d Days 10-21 | 60 mg/kg | |

[a] 0.5% Carboxymethylcellulose (CMC) in distilled water

Figure 1B:
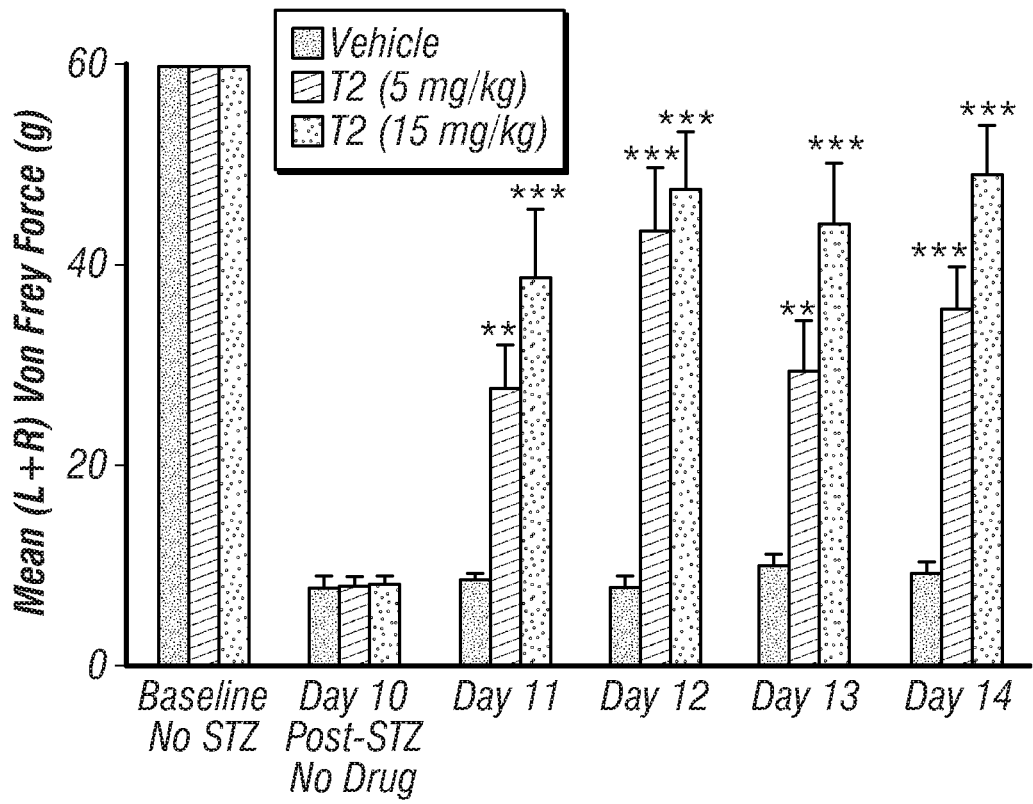

Table 3 shows the summary of each of the study groups and days of analyses for evaluation of T2 (FIG. 1B).

TABLE 3

Summary of Treatment Groups and Characteristics for Compound T2

| Group | N | Test Item | Route | Dose/Volume | Regimen | STZ (IV) | Von Frey Measurements |
|---|---|---|---|---|---|---|---|
| 1 | 10 | Vehicle[a] | PO | 10 mL/lg | PO, QD × 5 d Days 10-14 | 60 mg/kg | Baseline, pre-dose on Day 10 and 2 hours post-dose on Days 11, 12, 13, and 14 |

TABLE 3-continued

Summary of Treatment Groups and Characteristics for Compound T2

| Group | N | Test Item | Route | Dose/Volume | Regimen | STZ (IV) | Von Frey Measurements |
|---|---|---|---|---|---|---|---|
| 2 | 10 | T2 | PO | 5 mg/kg | PO, QD × 5d Days 10-14 | 60 mg/kg | |
| 3 | 10 | T2 | PO | 15 mg/kg | PO, QD × 5d Days 10-14 | 60 mg/kg | |

[a] 0.5% Carboxymethylcellulose (CMC) in distilled water

Figure 1C:
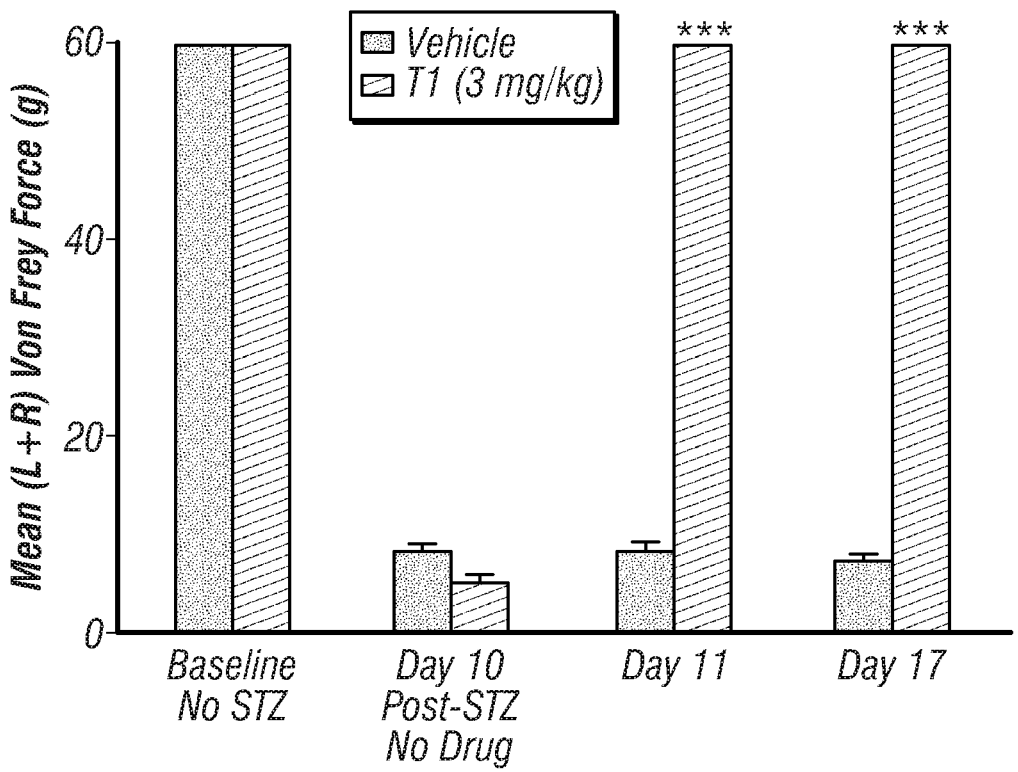

Table 4 shows the summary of each of the study groups and days of analyses for the evaluation of T1 (FIG. 1C).

TABLE 4

Summary of Treatment Groups and Characteristics for Compound T2

| Group | N | Test Item | Route | Dose/Volume | Regimen | STZ (IV) | Von Frey Measurements |
|---|---|---|---|---|---|---|---|
| 1 | 10 | Vehicle[a] | PO | 10 mL/lg | PO, QD × 8d, Days 10-17 | 60 mg/kg | Baseline, pre-dose on Day 10, and 2 hours post-dose on Days 11 and 17 |
| 2 | 10 | T2 | PO | 3 mg/kg | PO, QD × 8d, Days 10-17 | 60 mg/kg | |

[a] 0.5% Carboxymethylcellulose (CMC) in distilled water

Figure 2:
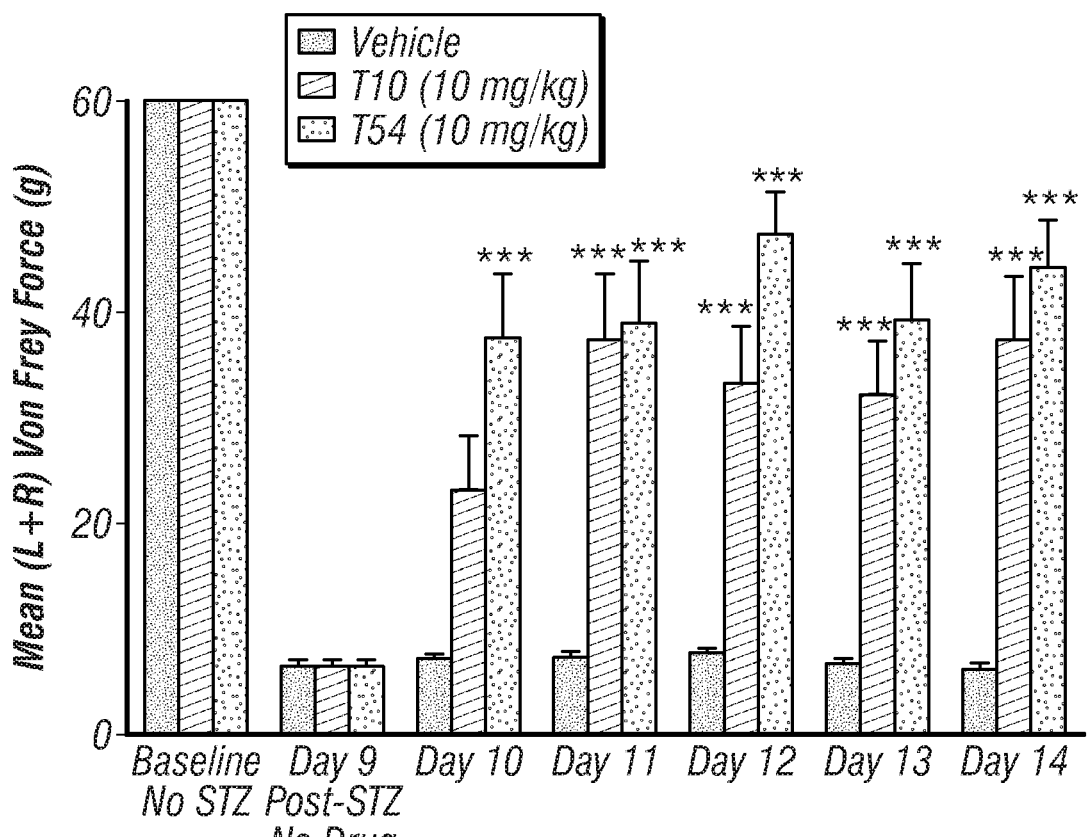
FIG. 2 shows the von Frey measurements of a rat streptozotocin induced diabetes model for painful diabetic neuropathy for compounds T10 and T54.

Table 5 shows the summary of each of the study groups and days of analyses for the evaluation of T10 and T54 (FIG. 2).

TABLE 5

Summary of Treatment Groups and Characteristics for Experimental Groups for Compounds T10 and T54.

| Group | N | Test Item | Route | Dose/Volume | Regimen | STZ (IV) | Von Frey Measurements |
|---|---|---|---|---|---|---|---|
| 1 | 11 | Vehicle[a] | PO | 10 mL/kg | PO, QD × 5 d Days 10-14 | 60 mg/kg | Baseline, pre-dose on Day 9, and 2 hours post-dose on Days 10, 11, 12, 13, and 14 |
| 2 | 11 | T10 | PO | 10 mg/kg | PO, QD × 5 d Days 10-14 | 60 mg/kg | |
| 3 | 11 | T54 | PO | 10 mg/kg | PO, QD × 5 d Days 10-14 | 60 mg/kg | |

[a] 0.5% Carboxymethylcellulose (CMC) in distilled water

2. Results

Streptozotocin was injected into rats to induce diabetes after a baseline Von Frey measurement for allodynia was collected. Oral administration of each test drug (Compound T0 (KU-596), FIG. 1A; Compound T2, FIG. 1B, and Compound T1, FIG. 1C) was started on Day 10 after another Von Frey measurement. Compounds T1 and T2 both demonstrated comparable to slightly better activity to compound T0 (KU-596) in this particular model of painful diabetic neuropathy. FIG. 2 shows the Von Frey measurement for compounds T10 and T54.

D. Stability in Acidic Medium

A sample of a test compound (1.2 mg) was dissolved in 0.1 N aq. HCl/MeOH (2/1 v/v, 4 mL) at room temperature. The degradation of the test compound was monitored by HPLC. The percentage of the test compound remaining was calculated using the peak area % in HPLC. The result is summarized in Table 4.

TABLE 4

Stability of Test Compound in Acidic Medium

| Time (h) | T0 (KU-596) (%) | T1 (%) | T2 (%) | T3 (%) | T6 (%) | T7 (%) | T11 (%) | T12 (%) |
|---|---|---|---|---|---|---|---|---|
| 0 | 100.0 | 100.0 | 100.0 | 100.0 | 100.0 | 100.0 | 100.0 | 100.0 |
| 4 | 96.7 ± 1.4 | 101.1 | 99.9 | 98.1 | 99.1 | 93.3 | 100.2 | 97.2 |
| 8 | 93.4 ± 1.7 | 100.1 | 99.5 | 96.1 | 99.0 | 85.6 | 100.3 | 95.5 |
| 12 | 90.5 ± 2.3 | 100.5 | 99.8 | 94.1 | 97.6 | 78.8 | 100.6 | 93.7 |
| 16 | 87.3 ± 2.9 | 100.4 | 100.2 | 92.2 | 96.6 | 71.5 | 100.9 | 92.3 |
| 20 | 83.9 ± 4.1 | 100.3 | 99.9 | 90.2 | 96.0 | 65.5 | 101.4 | 90.6 |
| 24 | 81.8 ± 4.2 | 100.4 | 100.2* | 88.3 | 95.7 | 61.7 | 102.1 | 89.9* |

| Time (h) | T0 (KU-596) (%) | T13 (%) | T15 (%) | T20 (%) | T54 (%) | T57 (%) | T60 (%) |
|---|---|---|---|---|---|---|---|
| 0 | 100.0 | 100.0 | 100.0 | 100.0 | 100.0 | 100.0 | 100.0 |
| 4 | 96.7 ± 1.4 | 99.3 | 99.9 | 97.7 | 100.4 | 97.9 | 97.6 |
| 8 | 93.4 ± 1.7 | 99.7 | 99.0 | 94.8 | 100.2 | 93.4 | 97.6 |

TABLE 4-continued

| 12 | 90.5 ± 2.3 | 100.3 | 98.5 | 91.9 | 101.0 | 90.3 | 97.5 |
| 16 | 87.3 ± 2.9 | 99.5 | 97.9 | 89.2 | 101.1 | 86.4 | 97.2 |
| 20 | 83.9 ± 4.1 | 99.7 | 97.0 | 86.8 | 101.3 | 82.5 | 98.0 |
| 24 | 81.8 ± 4.2 | 99.3 | 96.5 | 84.4 | 101.2 | 79.3 | 97.4 |

\*These data points were taken at 22 hours.

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 9,422,320
Baylon, et al., *J. Org. Chem.*, 12:121, 1999.
Beaver, et al., *J. Am. Chem. Soc.*, 130:2082-2086, 2008.
Brand and Nicholls, *Biochem. J.*, 435:297, 2011.
Burlison, et al., *J. Am. Chem. Soc.*, 128:15529, 2006.
Burlison and Blagg, *J. Org. Chem.*, 8:4855, 2006.
Burlison, et al., *J. Org. Chem.*, 73:2130, 2008.
Chowdhury, et al., *Brain*, 135:1751, 2012.
Cohen, et al., *Ann. Surg. Oncol.*, 19 (Suppl. 3): 5483, 2012.
Donnelly, et al., *J. Org. Chem.*, 2008, 73:8901.
Hanaya et al., *Tetrahedron*, 65(38):7989-7997, 2009.
*Handbook of Pharmaceutical Salts: Properties, and Use*, Stahl and Wermuth Eds.), Verlag Helvetica Chimica Acta, 2002.
Harbauer, et al., *Cell Metabolism*, 19(3):357-372, 2014.
Klemer and Waldman, *Justus Liebigs Annalen Der Chemie*, 1986(2):221-225, 1986.
Kusuma, et al., *J. Med. Chem.*, 55:5797, 2012.
Lin and Kasko, *Biomacromolecules*, 14(2):350-357, 2013.
Ma, et al., *J. Pharmacol. Exp. Ther.*, 348:281-292, 2014.
Ma et al., *ACS Chem. Neurosci.*, 6(9):1637-1648, 2015.
*March's Advanced Organic Chemistry: Reactions, Mechanisms, and Structure*, 2007.
Marcu, et al., *J. Natl. Cancer Inst.*, 92:242-248, 2000.
Nicolas et al., *Angew. Chem. Int. Ed.*, 51(44):11101-11104, 2012.
Shelton, et al., *Mol. Pharmacol.*, 76:1314, 2009.
Strejan et al., *J. Neuroimmunol.*, 7:27, 1984.
Urban, et al., *ASN Neuro.*, 2:189-199, 2010.
Veves et al., *Pain Med.*, 9:660-674, 2008.
Yu, et al., *J. Am. Chem. Soc.*, 127:12778, 2005a.
Yu, et al., *J. Org. Chem.*, 70:5599-5605, 2005b.
Yun, et al., *Biochemistry*, 43:8217-8229, 2004.
Zhao and Blagg, In: *Inhibitors of Molecular Chaperones. As Therapeutic Agents*, Ed: Timothy Machajewski, RSC Publishing: London, 2014.
Zhao, et al., *J. Med. Chem.*, 54:3839-3853, 2011.

What is claimed is:

1. A compound of the formula:

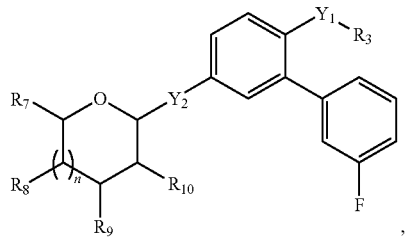

(VII)

wherein:

n is 1;

$Y_1$ is -alkanediyl$_{(C≤6)}$-, —C(O)-alkanediyl$_{(C≤6)}$-, or a substituted version of any of these groups;

$Y_2$ is O;

$R_3$ is —NR$_{11}$R$_{11}$' or —C(O)NR$_{12}$R$_{12}$', wherein:

$R_{11}$ and $R_{11}$' are each independently hydrogen, alkyl$_{(C≤6)}$, substituted alkyl$_{(C≤6)}$, acyl$_{(C≤6)}$, or substituted acyl$_{(C≤6)}$;

$R_{12}$ and $R_{12}$' are each independently hydrogen, alkyl$_{(C≤6)}$, or substituted alkyl$_{(C≤6)}$;

$R_7$ is alkyl$_{(C≤6)}$ or substituted alkyl$_{(C≤6)}$;

$R_8$ is hydroxy, alkoxy$_{(C≤6)}$, or substituted alkoxy$_{(C≤6)}$; and $R_9$ and $R_{10}$ are each hydroxy;

or a pharmaceutically acceptable salt of the formula.

2. The compound of claim 1 further defined as:

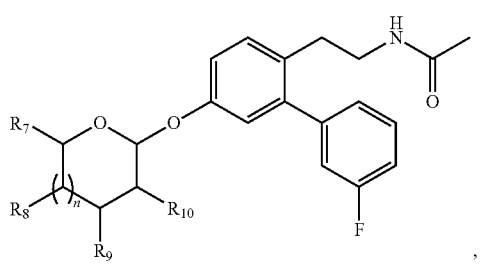

(VIII)

wherein:

n is 1;

$R_7$ is alkyl$_{(C≤6)}$ substituted alkyl$_{(C≤6)}$;

$R_8$ is hydroxy alkoxy$_{(C≤6)}$, or substituted alkoxy$_{(C≤6)}$; and $R_9$ and $R_{10}$ are each hydroxy;

or a pharmaceutically acceptable salt of the formula.

3. The compound of claim 1, wherein $Y_1$ is -alkanediyl$_{(C≤6)}$- or substituted -alkanediyl$_{(C≤6)}$- and $R_3$ is —R$_{11}$R$_{11}$'.

4. The compound of claim 1, wherein $R_8$ is hydroxy.

5. The compound of claim 1, wherein $R_7$ is alkyl$_{(C≤6)}$.

6. A pharmaceutical composition comprising:

(A) a compound of claim 1; and (B) an excipient.

7. The compound of claim 2 further defined as:

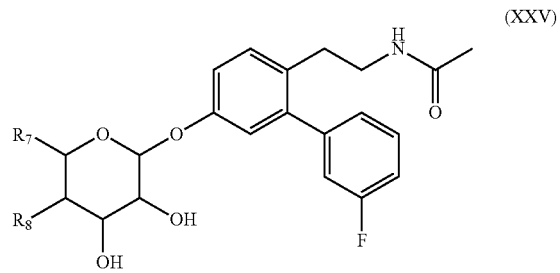

(XXV)

wherein:

$R_7$ is alkyl$_{(C≤6)}$; and $R_8$ is hydroxy, alkoxy$_{(C≤6)}$, or substituted alkoxy$_{(C≤6)}$;

or a pharmaceutically acceptable salt of the formula.

8. The compound of claim 7 further defined as:

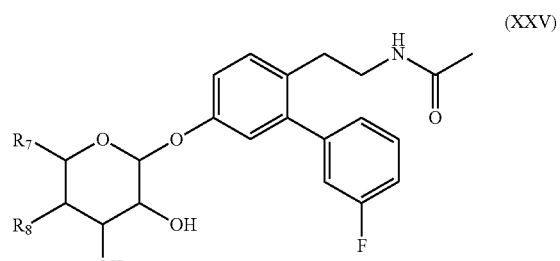

(XXV)

wherein:

$R_7$ is alkyl$_{(C≤6)}$; and $R_8$ is hydroxy or alkoxy$_{(C≤6)}$;

or a pharmaceutically acceptable salt of the formula.

9. The compound of claim 8 further defined as:

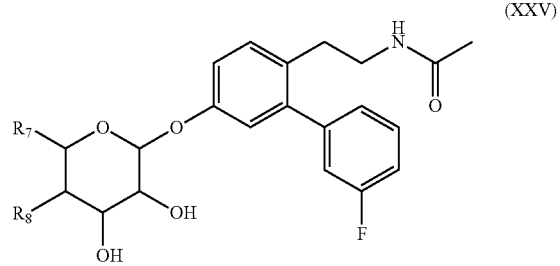

(XXV)

wherein:

$R_7$ is alkyl$_{(C≤6)}$; and $R_8$ is hydroxy;

or a pharmaceutically acceptable salt of the formula.

10. The compound of claim 1, wherein the compound is further defined as:
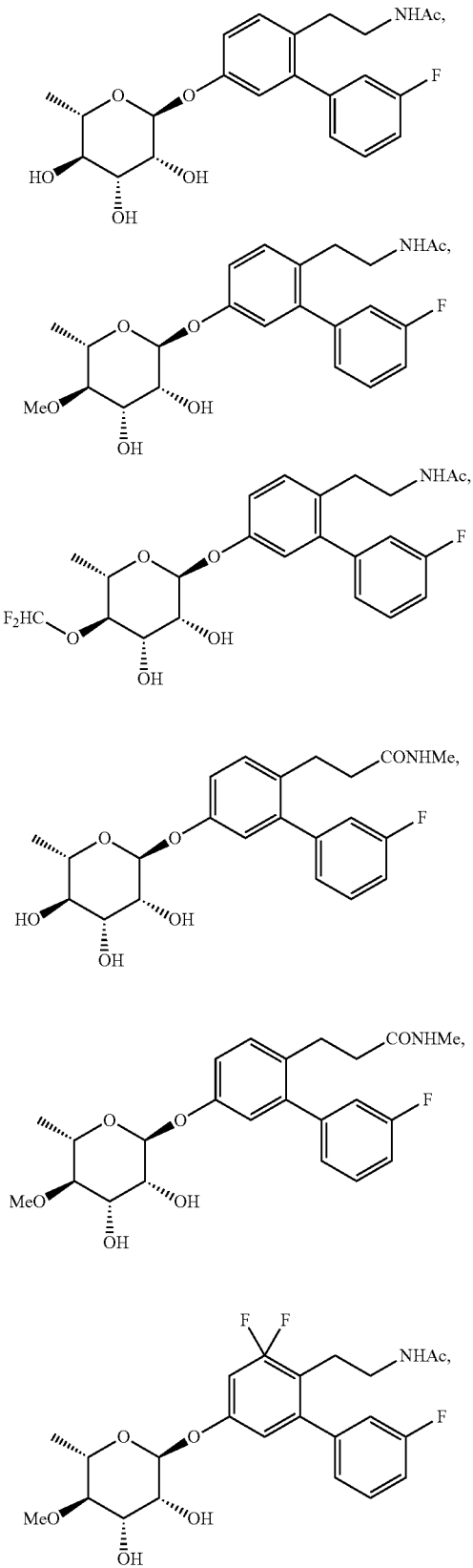
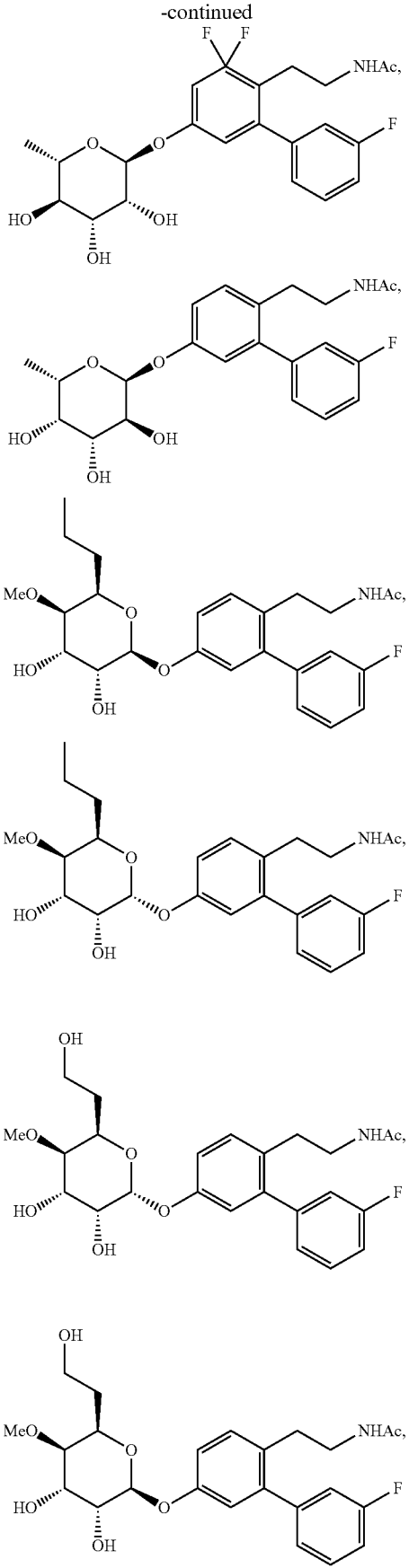

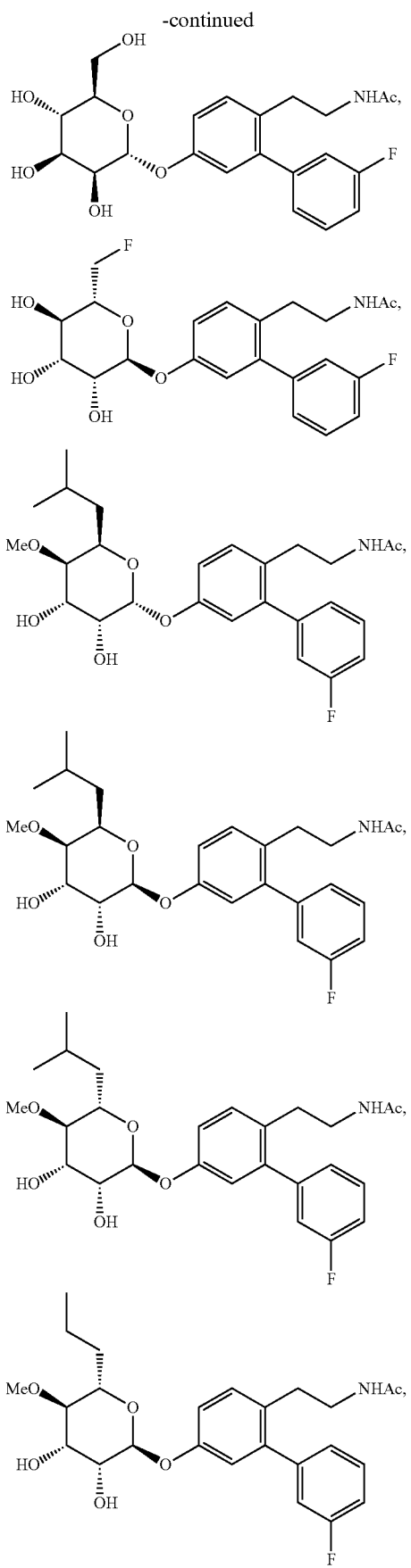
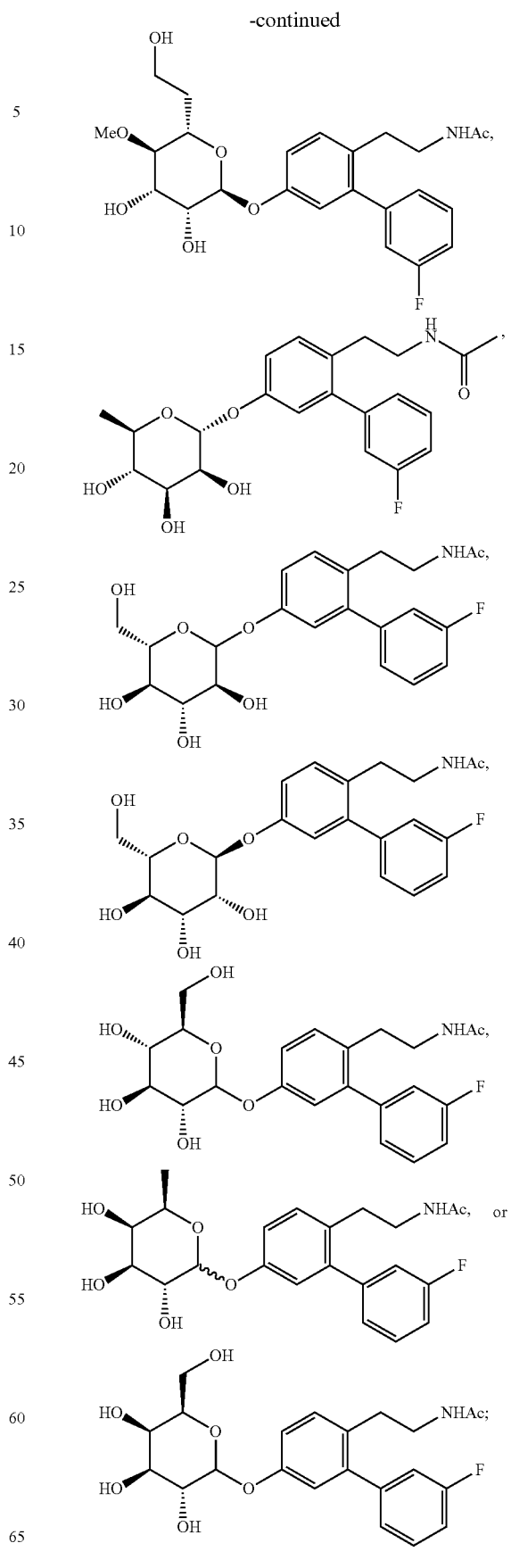

or a pharmaceutically acceptable salt of any of these formulas.
11. The compound of claim 10, wherein the compound is further defined as:
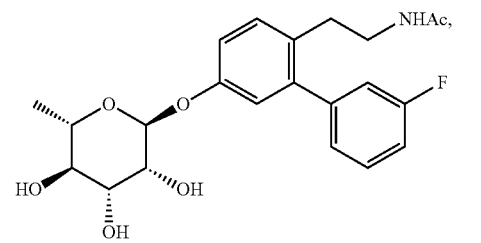
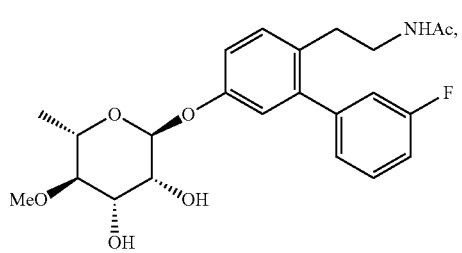
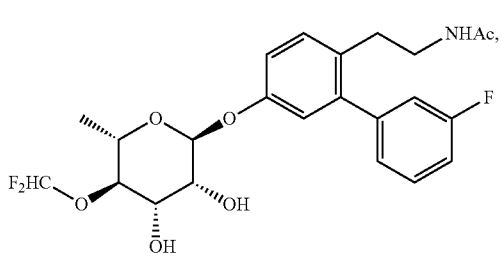
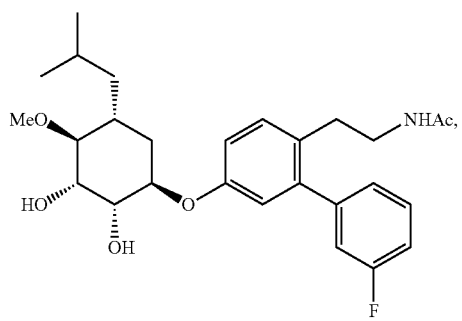
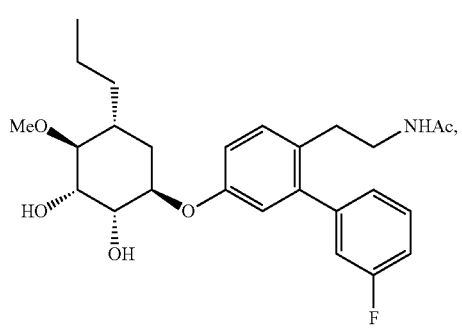
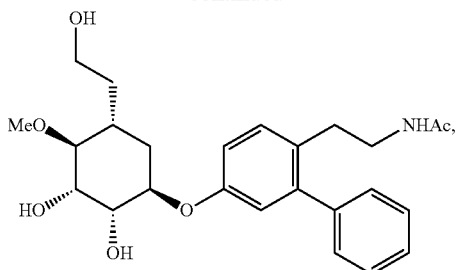
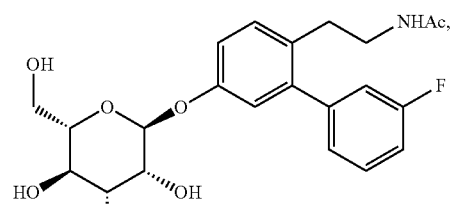
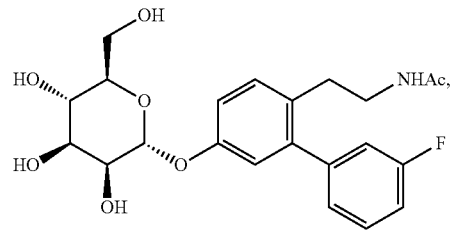
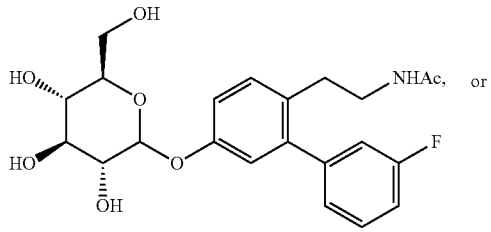
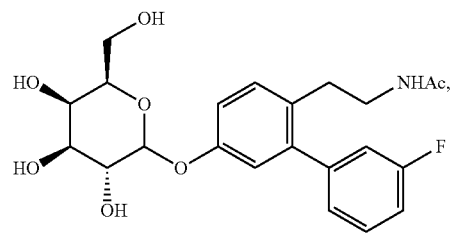
or a pharmaceutically acceptable salt of any of these formulas.
12. The compound of claim 11, wherein the compound is further defined as:
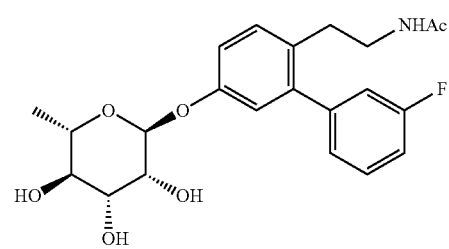 [SMILES: CC(=O)NCCc1ccc(O[C@@H]2O[C@@H](C)[C@H](O)[C@@H](O)[C@H]2O)cc1-c1cccc(F)c1]
or -continued

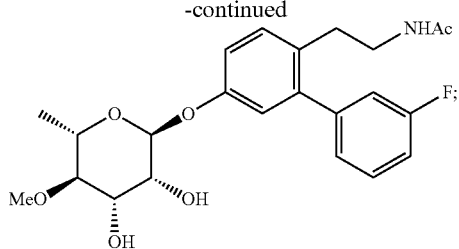

or a pharmaceutically acceptable salt of any of these formulas.

13. The compound of claim 12, wherein the compound is further defined as:

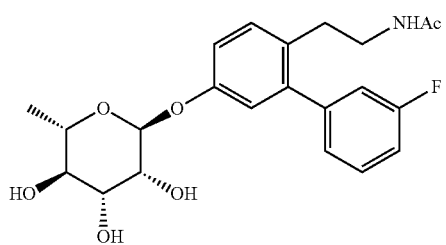

or a pharmaceutically acceptable salt thereof.

14. The compound of claim 1, wherein $R_8$ is alkoxy$_{(C \leq 6)}$.

15. The compound of claim 12, wherein the compound is further defined as:

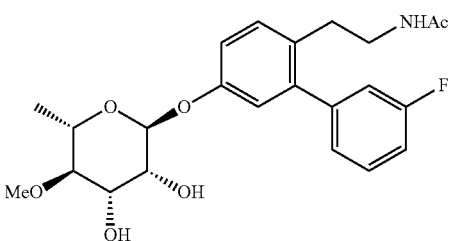 [SMILES: CO[C@@H]1[C@@H](O)[C@@H](O)[C@H](Oc2ccc(CCNC(C)=O)c(-c3cccc(F)c3)c2)O[C@H]1C]

or a pharmaceutically acceptable salt thereof.

16. The compound of claim 1, wherein $R_7$ is substituted alkyl$_{(C \leq 6)}$, wherein the alkyl$_{(C \leq 6)}$ is substituted with an OH, OCH$_3$, F, Cl, or Br group.

17. The compound of claim 16, wherein $R_7$ is substituted alkyl$_{(C \leq 6)}$, wherein the alkyl$_{(C \leq 6)}$ is substituted with an OH group.

* * * * *

UNITED STATES PATENT AND TRADEMARK OFFICE
CERTIFICATE OF CORRECTION

PATENT NO. : 11,827,664 B2
APPLICATION NO. : 17/055331
DATED : November 28, 2023
INVENTOR(S) : Xin Jiang et al.

Page 1 of 2

It is certified that error appears in the above-identified patent and that said Letters Patent is hereby corrected as shown below:

In the Claims

In Claim 1, Line 20, Column 283, delete "-alkanediyl$_{(C\leq6)}$-, –C(O)-alkanediyl$_{(C\leq6)}$-" and insert -- –alkanediyl$_{(C\leq6)}$–, –C(O)–alkanediyl$_{(C\leq6)}$– -- therefor.

In Claim 2, Line 57, Column 283, delete "alkyl$_{(C\leq6)}$ substituted alkyl$_{(C\leq6)}$" and insert -- alkyl$_{(C\leq6)}$ or substituted alkyl$_{(C\leq6)}$ -- therefor.

In Claim 3, Lines 65-66, Column 283, delete "-alkanediyl$_{(C\leq6)}$- or substituted -alkanediyl$_{(C\leq6)}$- and $R_3$ is –$R_{11}R_{11}'$." and insert -- –alkanediyl$_{(C\leq6)}$– or substituted –alkanediyl$_{(C\leq6)}$– and $R_3$ is –$NR_{11}R_{11}'$. -- therefor.

In Claim 10, Lines 56-65, Column 285, delete " 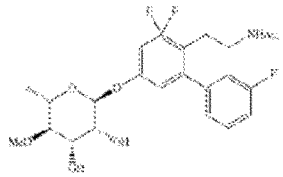 " and insert -- 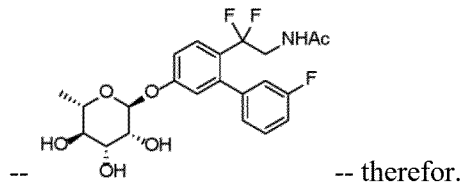 -- therefor.

Signed and Sealed this
Third Day of September, 2024

Katherine Kelly Vidal
*Director of the United States Patent and Trademark Office*

CERTIFICATE OF CORRECTION (continued)
U.S. Pat. No. 11,827,664 B2

In Claim 10, Lines 1-12, Column 286, delete " 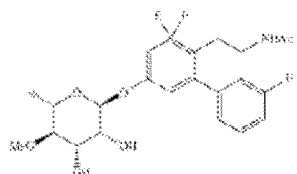 " and insert -- 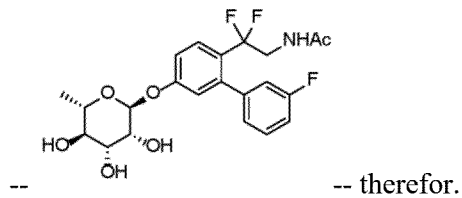 -- therefor.